US006960474B2

(12) United States Patent
Salvati et al.

(10) Patent No.: US 6,960,474 B2
(45) Date of Patent: Nov. 1, 2005

(54) METHOD FOR THE TREATMENT OF A CONDITION REMEDIABLE BY ADMINISTRATION OF A SELECTIVE ANDROGEN RECEPTOR MODULATOR

(75) Inventors: Mark E. Salvati, Lawrenceville, NJ (US); Marco M. Gottardis, Princeton, NJ (US); Ricardo M. Attar, Lawrenceville, NJ (US); Stanley R. Krystek, Jr., Ringoes, NJ (US); John S. Sack, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 183 days.

(21) Appl. No.: 09/885,827

(22) Filed: Jun. 20, 2001

(65) Prior Publication Data

US 2002/0173445 A1 Nov. 21, 2002

Related U.S. Application Data

(60) Provisional application No. 60/284,617, filed on Apr. 18, 2001, provisional application No. 60/284,438, filed on Apr. 18, 2001, provisional application No. 60/284,730, filed on Apr. 18, 2001, provisional application No. 60/233,519, filed on Sep. 19, 2000, and provisional application No. 60/214,392, filed on Jun. 28, 2000.

(51) Int. Cl.[7] ............................................. G01N 33/48
(52) U.S. Cl. .................... 436/64; 514/425; 514/411; 514/387; 514/379; 514/249; 514/169
(58) Field of Search ..................... 436/64; 514/425, 514/411, 387, 379, 249, 169, 2; 530/350

(56) References Cited

U.S. PATENT DOCUMENTS

| | | | |
|---|---|---|---|
| 3,261,845 A | 7/1966 | Bockstahler | |
| 3,343,940 A | 9/1967 | Popoff et al. | |
| 3,428,538 A | 2/1969 | Scheiner | 204/158 |
| 3,821,232 A | 6/1974 | Redmore | 260/294.8 |
| 3,906,102 A | 9/1975 | Tottori et al. | 424/274 |
| 3,923,490 A | 12/1975 | Redmore | 71/67 |
| 3,925,554 A | 12/1975 | Tottori et al. | 424/274 |
| 3,948,933 A | 4/1976 | Fontanella | |
| 3,965,264 A | 6/1976 | Redmore | 424/200 |
| 3,997,293 A | 12/1976 | Redmore | 21/2.5 |
| 3,998,833 A | 12/1976 | Redmore | 260/293.55 |
| 4,089,650 A | 5/1978 | Redmore | 21/2.7 |
| 4,092,413 A | 5/1978 | Arth et al. | 424/241 |
| 4,097,578 A | 6/1978 | Perronnet | 424/273 |
| 4,191,775 A | 3/1980 | Glen | 424/304 |
| 4,234,736 A | 11/1980 | Bernauer et al. | 548/314 |
| 4,239,776 A | 12/1980 | Glen et al. | 424/304 |
| 4,310,523 A | 1/1982 | Neumann | |
| 4,397,857 A | 8/1983 | Vincent et al. | 424/263 |
| 4,472,382 A | 9/1984 | Labrie et al. | 424/177 |
| 4,473,393 A | 9/1984 | Nagpal | 71/92 |
| 4,476,184 A | 10/1984 | Lubowitz et al. | 428/288 |
| 4,507,303 A | 3/1985 | Ishizumi et al. | 514/255 |
| 4,533,737 A | 8/1985 | Ryang | 548/110 |
| 4,536,559 A | 8/1985 | Lubowitz et al. | 528/170 |
| 4,543,355 A | 9/1985 | Ishizumi et al. | 514/253 |
| 4,562,255 A | 12/1985 | Freed et al. | 544/357 |
| 4,582,886 A | 4/1986 | Ryang | |
| 4,584,364 A | 4/1986 | Lubowitz et al. | 528/128 |
| 4,598,072 A | 7/1986 | Schweikert et al. | 514/170 |
| 4,656,235 A | 4/1987 | Tesoro et al. | 526/262 |
| 4,659,695 A | 4/1987 | Labrie | 514/15 |
| 4,666,885 A | 5/1987 | Labrie | 514/15 |
| 4,673,748 A | 6/1987 | Rock et al. | 548/237 |
| 4,739,030 A | 4/1988 | Lubowitz et al. | |
| 4,739,075 A | 4/1988 | Odagiri et al. | 548/431 |
| 4,753,957 A | 6/1988 | Chan | 514/391 |
| 4,760,053 A | 7/1988 | Labrie | 514/15 |
| 4,775,660 A | 10/1988 | Labrie et al. | 514/15 |
| 4,775,661 A | 10/1988 | Labrie | 514/15 |
| 4,851,495 A | 7/1989 | Sheppard et al. | 528/170 |
| 4,873,256 A | 10/1989 | Coussediere et al. | 514/391 |
| 4,892,578 A | 1/1990 | Chang et al. | 71/94 |
| 4,895,715 A | 1/1990 | Neri et al. | |
| 4,944,791 A | 7/1990 | Schroder et al. | 71/92 |
| 4,980,481 A | 12/1990 | Lubowitz et al. | 548/435 |
| 5,084,472 A | 1/1992 | Moguilewsky et al. | 514/389 |
| 5,093,500 A | 3/1992 | Wang | 548/410 |
| 5,098,888 A | 3/1992 | Vincent et al. | 514/18 |
| 5,104,967 A | 4/1992 | Sheppard et al. | 528/322 |
| 5,112,939 A | 5/1992 | Lubowitz et al. | 528/289 |
| 5,114,612 A | 5/1992 | Benicewicz et al. | 252/299.01 |
| 5,116,935 A | 5/1992 | Lubowitz et al. | 528/173 |
| 5,151,487 A | 9/1992 | Lubowitz et al. | 528/170 |
| 5,155,206 A | 10/1992 | Lubowitz et al. | 528/322 |
| 5,210,213 A | 5/1993 | Sheppard et al. | 548/435 |
| 5,239,046 A | 8/1993 | Lubowitz et al. | 528/322 |
| 5,367,083 A | 11/1994 | Sheppard et al. | 548/431 |
| 5,399,725 A | 3/1995 | Poss et al. | |
| 5,403,666 A | 4/1995 | Lubowitz et al. | 428/474.4 |
| 5,434,176 A | 7/1995 | Claussner et al. | 514/391 |
| 5,446,120 A | 8/1995 | Lubowitz et al. | 528/171 |
| 5,455,115 A | 10/1995 | Lubowitz et al. | 428/411.1 |

(Continued)

FOREIGN PATENT DOCUMENTS

| | | |
|---|---|---|
| AU | A-16993-83 | 1/1984 |
| CN | 1050877 | 4/1991 |
| DE | 2365677 | 11/1975 |

(Continued)

OTHER PUBLICATIONS

CA 54: 1480g, 1959.*
CA 65: 15326c, 1966.*

(Continued)

*Primary Examiner*—Ardin H. Marschel
*Assistant Examiner*—Carolyn L. Smith
(74) *Attorney, Agent, or Firm*—Paul D. Golian

(57) ABSTRACT

Selective androgen receptor modulators (SARMs) having antagonist activity in hormone-dependent tumors while exhibiting no activity or agonist activity against other non-tumor tissues containing the androgen receptor as well as methods for identifying, designing and using SARMs are provided.

8 Claims, No Drawings

U.S. PATENT DOCUMENTS

| | | | |
|---|---|---|---|
| 5,463,076 A | 10/1995 | Sheppard et al. | 548/431 |
| 5,482,921 A | 1/1996 | Secking et al. | 504/246 |
| 5,512,676 A | 4/1996 | Sheppard et al. | 544/198 |
| 5,516,876 A | 5/1996 | Lubowitz et al. | 528/170 |
| 5,530,089 A | 6/1996 | Sheppard et al. | 528/321 |
| 5,532,372 A | 7/1996 | Saji et al. | |
| 5,545,634 A | 8/1996 | Labrie | |
| 5,550,107 A | 8/1996 | Labrie | 514/11 |
| 5,556,983 A | 9/1996 | Claussner et al. | 548/300.7 |
| 5,573,854 A | 11/1996 | Sheppard et al. | 428/411.1 |
| 5,587,105 A | 12/1996 | Sheppard et al. | |
| 5,589,497 A | 12/1996 | Claussner et al. | 514/386 |
| 5,594,089 A | 1/1997 | Lubowitz et al. | 528/171 |
| 5,595,985 A | 1/1997 | Labrie | 514/169 |
| 5,605,877 A | 2/1997 | Schafer et al. | |
| 5,610,317 A | 3/1997 | Lubowitz et al. | 548/431 |
| 5,627,201 A | 5/1997 | Gaillard-Kelley et al. | 514/386 |
| 5,643,855 A | 7/1997 | Kilama | 504/224 |
| 5,645,925 A | 7/1997 | Sheppard et al. | 422/128 |
| 5,693,741 A | 12/1997 | Sheppard et al. | 528/183 |
| 5,714,566 A | 2/1998 | Lubowitz et al. | 528/170 |
| 5,750,553 A | 5/1998 | Claussner et al. | 514/392 |
| 5,780,583 A | 7/1998 | Lubowitz et al. | 528/388 |
| 5,817,649 A | 10/1998 | Labrie | 514/169 |
| 5,817,744 A | 10/1998 | Sheppard et al. | |
| RE35,956 E | 11/1998 | Gaillard-Kelly et al. | |
| 5,877,161 A | 3/1999 | Riabowol | 514/44 |
| 5,929,146 A | 7/1999 | Amos et al. | |
| 5,986,055 A | 11/1999 | Yang et al. | 530/350 |
| 6,004,554 A * | 12/1999 | Thorpe et al. | 424/178.1 |
| 6,017,924 A | 1/2000 | Edwards et al. | 514/292 |
| 6,020,327 A | 2/2000 | Messenger | |
| 6,040,136 A * | 3/2000 | Garrard et al. | 435/5 |
| 6,054,487 A | 4/2000 | Sekut et al. | |
| 6,071,957 A | 6/2000 | Miller et al. | |
| 6,075,053 A | 6/2000 | Hausheer | |
| 6,124,460 A | 9/2000 | Tomiyama et al. | |
| 6,162,444 A | 12/2000 | Dubois | |
| 6,200,573 B1 | 3/2001 | Locke | |
| 6,242,611 B1 | 6/2001 | Claussner et al. | |
| 6,358,947 B1 * | 3/2002 | Zhi et al. | 514/229.5 |
| 6,469,024 B2 * | 10/2002 | Li et al. | 514/307 |
| 2001/0012839 A1 | 8/2001 | Miller et al. | |
| 2001/0020002 A1 | 9/2001 | Lederman et al. | |
| 2003/0130273 A1 | 7/2003 | Sheppeck et al. | |

FOREIGN PATENT DOCUMENTS

| | | | |
|---|---|---|---|
| DE | 3227055 A1 * | 7/1982 | |
| EP | 0001813 A1 * | 10/1978 | |
| EP | 0082402 B1 | 6/1982 | |
| EP | 0091596 A2 * | 3/1983 | |
| EP | 051020 B1 | 8/1984 | |
| EP | 0253503 B1 | 6/1987 | |
| EP | 0277476 A2 | 1/1988 | |
| EP | 0436426 A1 * | 12/1990 | |
| EP | 0494819 A1 * | 1/1992 | |
| EP | 0406119 B1 * | 1/1994 | |
| EP | 626384 A1 | 11/1994 | |
| EP | 0678507 | 10/1995 | |
| EP | 1008457 A1 | 6/2000 | |
| FR | 2075751 * | 1/1971 | |
| FR | 2329276 * | 11/1975 | |
| GB | 1039020 | 8/1964 | |
| GB | 2133006 B | 10/1986 | |
| GB | 2133006 B | 10/1986 | |
| GB | 2290296 | 12/1995 | |
| GB | 2290296 A | 12/1995 | |
| JP | 50-13872 | 5/1975 | |
| JP | 51088631 * | 8/1976 | |
| JP | 53-39488 | 4/1978 | |
| JP | 53-86035 | 7/1978 | |
| JP | 54-2257 | 1/1979 | |
| JP | 64-6258 | 1/1989 | |
| JP | 64-38403 | 2/1989 | |
| JP | 1-125381 | 5/1989 | |
| JP | 1-38403 | 8/1989 | |
| JP | 6-114813 | 4/1994 | |
| JP | 7-144477 | 6/1995 | |
| JP | 2000-16004 | 1/2000 | |
| WO | WO 95/18794 * | 7/1995 | |
| WO | WO 96/03875 | 2/1996 | |
| WO | WO96/19458 | 6/1996 | |
| WO | WO97/21994 | 6/1997 | |
| WO | WO97/49709 | 12/1997 | |
| WO | WO 98/11134 | 3/1998 | |
| WO | WO98/16830 | 4/1998 | |
| WO | WO98/ 29495 | 7/1998 | |
| WO | WO98/32439 | 7/1998 | |
| WO | WO 98/39303 | 9/1998 | |
| WO | WO98/49555 | 11/1998 | |
| WO | WO 99/22729 | 5/1999 | |
| WO | WO99/27365 | 6/1999 | |
| WO | WO 99/32463 | 7/1999 | |
| WO | WO 00/01813 | 1/2000 | |
| WO | WO 00/04152 | 1/2000 | |
| WO | WO00/06525 | 2/2000 | |
| WO | WO 00/13508 | 3/2000 | |
| WO | WO 00/15834 | 3/2000 | |
| WO | WO 00/18961 | 4/2000 | |
| WO | WO 00/37430 | 6/2000 | |
| WO | WO 00/69814 | 11/2000 | |
| WO | WO 01/16108 A2 | 3/2001 | |
| WO | WO 01/16133 A2 | 3/2001 | |
| WO | WO 01/16139 A1 | 3/2001 | |
| WO | WO01/19831 | 3/2001 | |
| WO | WO 01/27622 A1 | 4/2001 | |
| WO | WO01/30781 | 5/2001 | |
| WO | WO 01/49294 | 7/2001 | |
| WO | WO 01/66599 | 9/2001 | |
| WO | WO 01/89515 | 11/2001 | |
| WO | WO 01/89516 | 11/2001 | |
| WO | WO02/00617 | 1/2002 | |
| WO | WO 02/00653 A2 | 1/2002 | |
| WO | WO 02/00716 | 1/2002 | |
| WO | WO 02/02099 | 1/2002 | |
| WO | WO 02/02107 | 1/2002 | |
| WO | WO 02/02112 | 1/2002 | |
| WO | WO 02/02113 | 1/2002 | |
| WO | WO 02/16310 A1 | 2/2002 | |
| WO | WO 02/24702 A1 | 3/2002 | |
| WO | WO 02/96426 | 12/2002 | |

OTHER PUBLICATIONS

U.S. Appl. No. 09/855,798, filed Jun. 2001, Salvati et al.*

U.S. Appl. No. 09/855,381, filed Jun. 2001, Salvati et al.*

Drenth, Principles of Protein X–ray Crystallography. 1995, Springer–Verlag, Second Edition, pp. 1–18.*

Krow et al, Tetrahedron, vol. 30, p. 2977–2981 (1974).

Kucharczyk et al., J. Med. Chem., vol. 36, p. 1645–1661 (1993).

Ben–Ishai et al., Tetrahedron, vol. 27, p. 3119–3127 (1971).

Vincent et al., Tetrahedron Letters, vol. 33, No. 48, p. 7369–7372 (1992).

Goldstein et al., Tetrahedron Letters, vol. 31, p. 2631–2634 (1969).

Evnin et al., J. Org. Che., vol. 35, No. 9, p. 3097–3106 (1970).

Kobayashi et al., Bull. Chem. Soc. Jpn., vol. 67, No. 11, p. 3082–3087 (1994).
Kobayashi et al., Bull. Chem. Soc. Jpn., vol. 65, p. 61–65 (1992).
Pons et al., Eur. J. Org. Chem., p. 853–859 (1998).
Pons et al., Pept. Proc. Am. Pept. Symp., 15th p. 176–177 (1999).
Reyniers et al., Bull. Soc. Chim. Belg. vol. 94(6), pp. 413–419 (1985).
Anteunis et al., Tetrahedron Lett., vol. 22(32), p. 3101–3104 (1981).
Mauger et al., J. Chem. Soc., Perkin Trans. 1, vol. 17, p. 2146–2148 (1972).
Mauger, J. Chem. Soc. d, vol. 1, p. 39–40 (1971).
Lee et al., Tetrahedron Lett., vol. 37(34), p. 6053–6056 (1996).
Verbruggen et al., Acta Crystallogr., Sect. C: Cryst. Struct. Commun., vol. C49(6), p. 1113–1116 (1993).
Shalati et al., Journal of Polymer Science: Polrn. Chem. Ed., vol. 22(1), p. 107–120 (1984).
Van Poucke et al., Bull. Soc. Chim. Belg., vol. 91(3), p. 213–218 (1982).
Schrooten et al., Bull. Soc. Chim. Belg., vol. 89(8), p. 615–628 (1980).
Hausler et al., Chem. Ber. vol. 107(9), p. 2804–2815 (1974).
Vicar et al., Collect. Czech. Chem. Commun. vol. 38(7), p. 1940–1956 (1973).
Vicar et al., Collect Czech. Chem. Commun. vol. 37(12), p. 4060–4071 (1972).
Kovtunenko et al., Ulkr. Khim. Zh. (Russ. Ed), vol. 58(11), p 1035–1040 (1992).
Kovtunenko et al., Ukr. Khim. Zh. (Russ. Ed), vol. 58(7), p. 588–592 (1992).
Kreher et al., Chem. Ber., vol. 125(1), p. 183–189 (1992).
Kovtunenko et al., Ukr. Khim. Zh. (Russ. Ed), vol. 57(1), p. 71–77 (1991).
Kovtunenko et al., Khim. Geterotsikl. Soedin., vol. (2), p. 190–202 (1990).
Kreher et al., Chem. Ber., vol. 123(2), p. 381–390 (1990).
Kreher et al., Chem.–Ztg., vol. 112(11), p. 335–342 (1988).
Kovtunenko et al., Ukr. Khim. Zh. (Russ. ed.), vol. 55(1), p. 64–69 (1989).
Kovtunenko et al., Ukr. Khim. Zh. (Russ. ed.), vol. 54(11), p. 1186–1190 (1988).
Kovtunenko et al., Ukr. Khim. Zh., vol. 54(2), p. 186–190 (1988).
Kreher et al., Chem.–Ztg., vol. 111(12), p. 349–356 (1987).
Kreher et al., Chem. Ber., vol. 121(5), p. 927–934 (1988).
Kreher at al., Chem.–Ztg., vol. 110(10), p. 363–367 (1986).
Kovtunenko et al., Khim. Geterotsikl. Soedin., vol. 20(9), p. 1200–1205 (1984).
Kreher et al., Angew. Chem., vol. 96(7), p. 507–508 (1984).
Kovtunenko et al., Ukr. Khim. Zh., vol. 49(12), p. 1287–1293 (1983).
Kreher et al., Angew. Chem., vol. 94(8), p. 634–635 (1982).
Munoz et al., Biotechnol. Bioeng., vol. 71(1), p. 78–84 (2000).
Chen et al., Tetrahedron Lett., vol. 40(18), p. 3491–3494 (1999).
Srivastav et al., Natl. Acad. Sci. Lett., vol. 19(1&2), p. 16–18 (1996).
Tosunyan et al., Khim. Geterotsikl. Soedin., vol. (11), p. 1465–1471 (1992).

Kirby et al., J. Chem. Res., Synop., vol. (9), p. 273 (1985).
Krow et al., J. Heterocycl. Chem., vol. 22(1), p. 131–135 (1985).
Krow et al., J. Org. Chem., vol. 47(11), p. 1989–1993 (1982).
Knaus et al., J. Heterocycl. Chem., vol. 13(3), p. 481–486 (1976).
Lyle et al., J. Org. Chem., vol. 39(25), p. 3708–3711 (1974).
Lin et al., Journal of the Chinese Chemical Society, vol. 48, p. 49–53 (2001).
Kirby et al., J. Chem. Res. Miniprint, vol. 9, p. 3089–3097 (1985).
Xu, Trends in Pharmacological Science, vol. 2 (10), p. 271–272 (1981).
Li et al., J. Pharm. Biomed. Anal. vol. 7(12), p. 1635–1639 (1989).
Cheng et al., Huaxue Shiji, vol. 15(1), p. 1–4 (1993).
Liu et al., Yaoxue Xuebao, vol. 18(10), p. 752–759 (1983).
Bockstahler et al., J. Med. Chem., vol. 11(3), p. 603–606 (1968).
Srivastava et al., Natl. Acad. Sci. Lett., vol. 15(2), p. 41–44 (1992).
Joshi et al., Indian J. Chem., Sect. B, vol. 22B(2), p. 131–135 (1983).
Fisera et al., Chem. Pap., vol. 49(4), p. 186–191 (1995).
Fang et al., Huaxue Tongbao, vol. (1), p. 27–30 (1994).
Wijnberg et al., Tetrahedron, vol. 38, p. 209–217 (1982).
Grogan et al., J. Med. Chem., vol. 6, p. 802–805 (1963).
Gringauz et al., J. Med. Chem., vol. 11, p. 611–612 (1968).
Chem. Abstr., vol. 65 p. 15325h (1966).
Dominianni, J. Med. Chem., vol. 14, No. 2, p. 175 (1971).
Chem. Abstr., vol. 57, p. 16561f (1962).
Jolivet, Ann. Chim., vol. 5, p. 1165–1217 (1960).
Maruyama et al., J. Org. Chem., vol. 46, p. 27–34 (1981).
Chem. Abstr., vol 68, p. 39458j (1964).
Kwart, J. Amer. Chem. Soc., vol. 74 p. 3094–3097 (1952).
Berson et al., J. Amer. Chem. Soc., vol. 76, p. 4060–4067 (1954).
Yur'ev et al., J. Gen. Chem. (Engl. Transl.), vol. 30, p. 869–872 (1960).
Jolivet, C.R. Hebd. Seances Acad. Sci., vol. 243, p. 2085–2086 (1956).
Lin et al., Biorganic Chemistry, vol. 28, p. 266–272 (2000).
Mel'nikow, Zh. Obshch, Khim., vol. 26, p. 227–232 (1956).
Mel'nikow, Zh. Obshch, Khim., vol. 29, p. 968,970 (1956).
Fisera et al., Chem. Pap., vol. 49(4), p. 186–191 (1995).
Warrener et al., Tetrahedron Lett., vol. 36(42), p. 7753–7756 (1995).
Oimin et al., J. Pharm. Biomed. Anal., vol. 7(12), p. 1635–1639 (1989).
Maruyama et al., J. Org. Chem., vol. 46(1), p. 27–34 (1981).
Zawadowski et al., Rocz. Chem., vol. 51(3), p. 557–560 (1977).
Liu et al., Eur. J. Canada, vol. 31A, (6), p. 953–963 (1995).
Lin, Journal of Natural Toxins, vol. 4 (2), p. 147–153 (1995).
Walter et al., Biochemica et Biophysica Acta, 1155, p. 207–0226 (1993).
Walter, J. Pharm. Sci., vol. 78 (1), p. 66–67 (1989).
Yin et al., Chem. Chinese Chemical Society, No. 1, p. 27–30 (1994).
Bockstahler et al., J. Med. Chem., vol. 11 (3), p. 603–606 (1968).

Dominianni et al., J. Med. Chem., vol. 14 (2), p. 175 (1971).
Zhou et al., Acta Pharm. Sinica, vol. 18 (10), p. 725–729 (1983).
Wang, J. Ethnopharm., vol. 26, p. 147–162 (1989).
Honkanen, FEBS Letters, vol. 330 (3), p. 283–286 (1993).
Waller, Toxicol. Appl. Pharmacol., vol. 137 (2), p. 219–227 (1996).
Search Report "A" (Scifinder Jun. 23, 2000).
Search Report "B" (Scifinder Jun. 5, 2001).
Search Report "C" (Scifinder, Jun. 20, 2001).
Search Report "D" (Scifinder, Jun. 20, 2001).
Search Report "E" (Scifinder, Jun. 20, 2001).
Search Report "F" (Scifinder, Aug. 16, 2000).
Search Report "G" (Scifinder, Aug. 22, 2000).
Search Report "H" (Scifinder, Sep. 12, 2000).
Search Report "K" (Scifinder, Sep. 11, 2000).
Search Report "L" (Scifinder, Sep. 11, 2000).
Search Report "M" (Scifinder, Sep. 11, 2000).
Search Report "N" (Scifinder, Sep. 11, 2000).
Search Report "O" (Scifinder, Sep. 11, 2000).
Search Report "P" (Scifinder, Sep. 11, 2000).
Search Report "Q" (Scifinder, Sep. 11, 2000).
Search Report "R" (Scifinder, Sep. 11, 2000).
Search Report "S" (Scifinder, Sep. 11, 2000).
Search Report "T" (Scifinder, Sep. 11, 2000).
Search Report "U" (Scifinder, Sep. 11, 2000).
Search Report "V" (Scifinder, Sep. 11, 2000).
Search Report "Y" (Scifinder, Sep. 11, 2000).
Search Report "BB" (Scifinder, Sep. 11, 2000).
Yanaka et al., Tetrahedron, Elsevier Science Publishers, Amsterdam, NL, vol. 54 (34), p. 10029–10042 (1998).
Rosen et al., J. Med. Chem., vol. 31 (8), p. 1598–1611 (1988).
Remuzon et al., Journal of Medicinal Chemistry, American Chemical Society, vol. 35, (15), p. 2989–2909, 1992.
Evans, American Association for the Advancement of Science, vol. 240, No. 4854, p. 889–895 (1988).
Denison, J. Biol. Chem., vol. 270 (31), p. 18175–18178 (1995).
Negro–Vilar A., "Selective Androgen Receptor Modulators (SARMs): A Novel Approach to Androgen Therapy for the New Millennium", *JCE & M* 1999 54(10):3459–3462.
Reid et al., "Antiandrogenes in prostate cancer", *Investigational New Drugs* 1999 17:271–284.
Hofbauer et al., "The Anti–Androgen Hydroxyflutamide and Androgens Inhibit Interleukin–6 Production by an Androgen–Responsive Human Osteoblastic Cell Line", *J. Bone Miner. Res.* 1999 14:1330–1337.
Peterziel et al., "Rapid Signalling by androgen receptor in prostate cancer cells", *Oncogene* 1999 6322–6329.
Scrip, "Ligand begins clinical trials with first SARM (selective estrogen receptor modulators", *World Pharmaceutical News Filed* 2000.
Hamann et al., Presentation #S39–2, *Endocrine Society 80th Annual Meeting* 1998.
Kousteni et al., "Nongenotropic, Sex–Nonspecific Signaling through the Estrogen or Androgen Receptors:Dissociation from Transcriptional Activity", *Cell* 2000 104:719–730.
Matias et al., "Structural Evidence for Ligand Specificity in the Binding Domain of the Human Androgen Receptor", *J. Biol. Chem.* 2000 275:26164–26171.
Pike et al., "Structure of the ligand–binding domain of oestrogen receptor beta in the presence of a partial agonist and a full antagonist", *EMBO J.* 1999 18(17):4608–4618.

Poujol et al., "Specific Recognition of Androgens by Their Nuclear Receptor", *J. Biol. Chem.* 2000 275(321): 24022–24031.
Sack et al., "Crystallographic structures of the ligand–binding domains of the androgen receptor and its T877A mutant complexed with the natural agonist dihydrotestosterone" *Proc. Natl. Acad. Sci. USA* 2001 98(9):4904–4909.
Furr B.J.A., "The Development of Casodex (Bicalutamide):Preclinical Studies", Eur. Urol. 1996 29(supp 2):83–95.
Avalos et al., "Clay–Catalyzed Solventless Addition Reactions of Furan with α–β–Unsaturated Carbonyl Compounds,[1]", Tetrahedron Letters 1998 39(49):9301–9304.
Tsuchiya et al., "Photochemistry—IX[1] Formation of Cyclopropenyl Ketones and Furans from Pyridazine N–Oxides by Irradiation", Tetrahendron 1973 29:2747–2751.
Shuiquan Z., "A Study on Antitumor Chemotherapeutic Agents–Synthesis of N–Cantharidine Derivatives", Acta Pharmaceutica Sinica 1981 16(10)782–786.
W. G. Walter, Journal of Pharmaceutical Sciences, American Pharmaceutical Association, Washington, D.C., vol. 78, No. 1, pp. 66–67, 1989.
Xu Bin, Trends in Pharmacological Sciences, vol. 2, pp. 271–272, 1981.
Terouanne Beatrice et al., Molecular and Cellular Endocrinology, vol. 160, No. 1–2, pp. 39–49, 2000.
U. Fuhrmann et al., Journal of Steroid Biochemistry and Molecular Biology, vol. 42, No. 8, pp. 787–793, 1992.
W. G. Yarbrough et al., Journal of Biological Chemistry, American Society of Biological Chemists, Baltimore, MD, vol. 265, No. 15, pp. 8893–8990, 1990.
U.S. Appl. No. 10/322,306, filed Dec. 18, 2002, Salvati et al.
U.S. Appl. No. 10/322,077, filed Dec. 18, 2002, Salvati et al.
Alekperov, N.A. et al., "Effect of the Nature of the Groups at the Bridging Carbon Atom on the Formation of Endo, Endo– and Endo–Exo–Anhydrides and Imides of the 3,6–epoxytricyclo[$6.2.1.0^2, ^7$]–undecene Series", Zhumal Organicheskoi Khimii, vol. 16, No. 4, pp. 770–777 (1980) (English translation).
Benitez, A. et al., "Site Selectivty of the Diels–Alder Reactions of 3–'1–(tert–Butyldimethylsilyloxy)vin–1–yl'furan and 3–(Propen–2–yl)furan. Synthesis of 4–Substituted Benzofurans", J. Org. Chem. vol. 61, pp. 1487–1492 (1996).
Chemical Abstracts, vol. 113, p. 440505 (1990).
Cancer Chemotherapy Report, vol. 1, pp. 43–47 (1959).
Chen et al., Gaodeng Xuexiao Huaxue Xuebao, vol. 4, No. 2, pp. 201–206 (1983) (English abstract only).
Gribble, G.W. et al., "Syntheses and Diels–Alder Cycloaddition Reactions of 4H–Furo'3,4–b'indoles. A Regiospecific Diels–Alder Synthesis of Ellipticine", J. Org. Chem., vol. 57, pp. 5878–5891 (1992).
Huang, Z.–T. et al., "Synthesis of Heterocyclic Ketene N,S– and N,O–Acetals with Ester Substituent in the Heterocyclic Ring", Synthetic Communications, vol. 21, No. 10 & 11, pp. 1177–1187 (1991).
Kaplan, F.A. et al., "Annelation of Tricarbonyliron Complexes or Ortho–Disubstituted '4'Annulenes. Synthesis of Tricarbonyliron Complexes of Derivatives of Bicyclo'6.2.0'decapentaene via Wittig Cycloolefination", Journal of the American Chemical Society, vol. 99, No. 2, pp. 513–517 (1977).
Kawashima, T., "Diterpenic Lactones of Mallotus Repandus", Heterocycles, vol. 5, pp. 227–232 (1976).

Kobayashi, T. et al., "Novel Imidazoles and Hydantoins Moderately Strained by Incorporation with 2–Azabicyclo '2.2.1'heptene Skeleton", Bull. Chem. Soc. Jpn., vol. 67, No. 11, pp. 3082–3087 (1994).

Liu, J. et al., "A Study on Antitumor Chemotherapeutic Agents—Synthesis of Cantharidine Derivatives", Yaoxue Xuebao, vol. 15, No. 5, pp. 271–277 (1980) (English abstract).

Mikhailyuchenko, N.G. et al., "Polyfural(aryl)alkanes and Their Derivatives. 9. Polyfury(aryl)methanes in the Diels–Alder Reaction", Khimiya Geterotsiklicheskikh Soedinenil, No. 6, pp. 642–649 (1993) (English translation).

Mitsuhashi, K. et al., "Reactions of 7–Oxa– and –Aza–norbornenes and –dienes with 1,3–Dipolar Compounds", Seikei Daigaku Kogaku Hokoku, vol. 44, pp. 2983–2992 (1987) (English abstract only).

Mueller, R.H. et al., "Diastereoselective Reaction of a Grignard Reagent with Chiral Imides: A Practical Preparation of a Key Intermediate in the Synthesis of Ifetroban Sodium", Organic Process Research & Development, vol. 1, pp. 14–19 (1997).

Napper, A.M. et al., "An Unequivocal Demonstration of the Importance of Nonbonded Contacts In the Electronic Coupling between Electron Donor and Acceptor Units of Donor–Bridge–Acceptor Molecules", J. Am. Chem. Soc., vol. 122, pp. 5220–5221 (2000).

Padwa, A. et al., "Cyclic Carbonyl Ylide Formation from the Rhodium (II) Acetate Catalyzed Reaction of 1–diazoalkanediones", Tetrahedron Letters, vol. 30, No. 3, pp. 301–304 (1989).

Paquette, L.A. et al., "Electronic Control of Stereoselectivity, 27. The Effect of Apical Spirocyclopropane Substitution on the Stereochemical Course of Diels–Alder Cycloadditions to Norbomyl–Fused Diene Systems", J. Am. Chem. Soc., vol. 106, pp. 8232–8240 (1984).

Rice, L.M. et al., "Hypotensive Agents. V. Hydrogenated Bis–isoindole Quaternary Salts", J. Am. Chem. Soc., vol. 77, pp. 616–621 (1955).

Rice, L.M. et al., "Imidothiazoles", J. Med. Chem., vol. 11, pp. 183–185 (1968).

Salakhov, M.S. et al., "Stereochemistry of the Adducts of Some Polychlorocyclopentadienes with the Anhydride and N–phenylimide of 3,6–epoxy–4–cyclohexene–1,2–dicarboxylic Acid", Zhurnal Organicheskoi Khimii, vol. 14, No. 6, pp. 1200–1202 (1978) (English translation).

Zhubanov, B.A., "Synthesis of Polyheterocycles on the Basis of Polyfunctional Monomers and Study of Their Characteristics", Makromol. Chem., Marcomol. Symp., vol. 4, pp. 157–171 (1986).

* cited by examiner

METHOD FOR THE TREATMENT OF A CONDITION REMEDIABLE BY ADMINISTRATION OF A SELECTIVE ANDROGEN RECEPTOR MODULATOR

INTRODUCTION

This application claims priority from U.S. Provisional Application Ser. No. 60/214,392, filed Jun. 28, 2000, from U.S. Provisional Application Ser. No. 60/233,519, filed Sep. 19, 2000, from U.S. Provisional Application Ser. No. 60/284,617, filed Apr. 18, 2001, from U.S. Provisional Application Ser. No. 60/284,438, filed Apr. 18, 2001, and from U.S. Provisional Application Ser. No. 60/284,730, filed Apr. 18, 2001, each of which are incorporated herein by reference in their entirety.

FIELD OF INVENTION

Selective androgen receptor modulators (SARMs) have now been identified which exhibit antagonistic activity against hormone-dependent tumors while exhibiting no activity or more preferably agonist activity against other nontumor tissues containing the androgen receptor. The present invention relates to methods for using these SARMs in the treatment of conditions remediable by administration of an androgen receptor modulator. The present invention also relates to methods for designing and identifying new SARMs that exhibit antagonistic activity against hormone-dependent tumors while exhibiting no activity, or more preferably agonist activity, against other nontumor tissues containing the androgen receptor. This invention also relates to structure coordinates of an androgen receptor ligand binding domain or ligand binding domain complex and method of using these structure coordinates for designing and selecting new SARMs that modulate androgen receptors.

BACKGROUND OF THE INVENTION

The androgen receptor (AR) is a member of the steroid nuclear-receptor superfamily of ligand-dependent transcription factors and is widely distributed among reproductive and nonreproductive tissues, including the prostate and seminal vesicles, male and female genitalia, skin, testis, ovary, cartilage, sebaceous glands, hair follicles, sweat glands, cardiac muscle, skeletal and smooth muscle, gastrointestinal vesicular cells, thyroid follicular cells, adrenal cortex, liver, pineal, and numerous brain cortical and subcortical regions, including spinal motor neurons (Negro-Vilar, A. JCE&M 1999 54(10):3459–62). As with the other members of the steroid receptor family, AR has several functional domains including a DNA binding domain (DBD), and a 261 residue ligand-binding domain (LBD) (Mw=30,245 Da) that contains the androgen binding site, and is responsible for switching on the androgen function. The cDNA and amino acid sequences of human and rat androgen receptors have been described (Proc. Natl. Acad. Sci. U.S.A. 1988 85: 7211–7215).

AR is an important target in multiple areas of drug discovery and patient therapy. In Oncology, for example, inhibitors (antagonists or partial antagonists) of the androgen receptor function are useful for the treatment of androgen dependent prostate cancer while agonists or partial agonists of the AR are applicable to the treatment of breast cancer. For metabolic and endocrine diseases disorders, for example, agonists or partial agonists of the androgen receptor function are useful for the treatment of age-related diseases and conditions of cachexia in several disease states including, but not limited to, AIDS. Functional AR has also been identified in various bone cells and androgen administration has beneficial effects on skeletal development and maintenance in men and women.

Progress of androgen therapy has been limited by the inability to separate desirable androgenic activities from undesirable or dose limiting side effects. However, recent advances in the development of selective estrogen receptor modulators (SERMs), with a great degree of tissue selectivity in targeting the estrogen receptor while eliminating undesired side effects, has resulted in the suggestion of SARMs, selective androgen receptor modulators (Negro-Vilar, A. JCE&M 1999 54(10):3459–62; Reid et al. Investigational New Drugs 1999 17:271–284).

U.S. Pat. No. 6,017,924 discloses non-steroidal compounds characterized as high affinity, high specificity agonists, partial agonists (i.e. partial activators and/or tissue-specific activators) and antagonists for androgen receptors based upon a "cis-trans" or "co-transfection" assays. Non-steroidal compounds characterized as high affinity, high specificity agonists, partial agonists (i.e. partial activators and/or tissue-specific activators) and antagonists for androgen receptors via the "cis-trans" or "co-transfection" assays are also described in WO 01/16108, WO 01/16133, and WO 01/16139. This co-transfection assay (Evans et al. Science 1988 240:889–95) is suggested to provide a method for identifying functional agonists and partial agonists which mimic, or antagonists which inhibit, the effect of native hormones, and quantifying their activity for responsive intracellular receptor proteins.

In addition, hydroxyflutamide, a known AR antagonist in most tissues, has been suggested to function as a selective AR modulator (SARM) for effects on IL-6 production by osteoblasts (Hofbauer et al. J. Bone Miner. Res. 1999 14:1330–1337).

Hydroxyflutamide and Casodex, both known to be full AR antagonists in most tissues, have been shown, in AR-transfected PC3 cells, to activate MAP kinases Erk-1 and Erk-2 in an AR dependent fashion similar to DHT (Peterziel et. al. Oncogene 18, 6322–6329 (1999)).

The compound LGD2226, a non-steroidal AR agonist, has also been characterized as a selective androgen receptor modulator for use in the treatment of androgen-related diseases such as osteoporosis, male hormone replacement, male and female sexual dysfunction and cachexia (SCRIP— World Pharmaceutical New FILED 12 May 2000; WO 01/16108; WO 01/16133; and WO 01/16139).

The compound LG120907, a non-steroidal AR antagonist, has been shown, in rats, to have reduced antagonist effects on the hypothalamic axis and on libido (reproductive rate) as compared to other clinically used AR antagonists, such as Casodex. As such, LG120907 has been characterized as a selective androgen receptor modulator for the treatment of prostate cancer (Wang et. al. Poster # P3-126, Endocrine Society 80$^{th}$ Annual Meeting (1998), Hamann et. al. Presentation # S39-2, Endocrine Society 80$^{th}$ Annual Meeting (1998)).

Recent reports exploring the nogenotropic effects of sex steroid hormones such as DHT and E2 on the AR and ER, clearly show that both receptors regulate functions not specifically involved with transcriptional events (Kousteni et. al., Cell 104, 719–730 (2001)). The antiapoptic effects of ER and AR have been shown to be inducible by ligands that have no effects on transcription. It has also been shown that ligands that have effects on transcription can have no anti-apoptotic effect.

SARMs exhibiting a difference-in-kind of the modulation effected in tumors containing the androgen receptor relative to the modulation effected in other, nontumor tissues containing the androgen receptor (especially, antagonist activity in tumors versus agonist activity in other, nonmalignant tissues containing the androgen receptor), have heretofore been neither disclosed nor suggested. The present invention provides SARMs, and methods for identifying and designing such SARMs, which exhibit antagonist activity in hormone-dependent tumors while exhibiting no activity, or more preferably agonist activity, against other nontumor tissues containing the androgen receptor. As described below, these SARMs can be employed, for example, to treat hormone-dependent tumors such as prostate cancer in patients by both inhibiting the growth of the tumor while mitigating side effects such as muscle wasting/cachexia, loss of libido, osteoporosis and gynecomastia. The term "patient" as used herein denotes an animal, preferably a mammal such as a dog, cat, or, most preferably, a human.

SUMMARY OF THE INVENTION

An object of the present invention is to provide methods for identifying SARMs having antagonist activity against hormone-dependent tumors while exhibiting no activity, or more preferably agonist activity, against other nontumor tissues containing the androgen receptor. In one embodiment, antagonist activity in hormone-dependent tumors is ascertained via screening for inhibition of growth, either in vitro or in vivo, in hormone-dependent tumor cell lines. In this embodiment, the activity of a potential SARM is also assessed in a normal, nontumor cell line. Alternatively, an animal model bearing a hormone-dependent tumor can be used to assess the antagonist activity of a potential SARM against the tumor as well as its activity in nontumor tissues in the animal.

Another object of the present invention is to provide methods for designing SARMs having antagonist activity in hormone-dependent tumors while exhibiting no activity, or more preferably agonist activity, against other nontumor tissues containing the androgen receptor by using information about the AR crystal structure and the estrogen receptor (ER) crystal structure with estradiol, tamoxifen or raloxifen.

Another object of the present invention is to provide molecule or molecular complexes comprising all or any part of a ligand binding site defined by structure coordinates of an androgen-receptor ligand binding domain (AR-LBD) amino acids V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, M894, M895, A896, E897, I898, I899, S900, V901, Q902, V903, P904, K905, I906 and L907 according to Table A as provided herein, or a mutant or homologue of said molecule or molecular complex for use in identifying SARMs.

Another object of the present invention is to provide machine-readable data storage media comprising a data storage material encoded with machine readable data, wherein the data is defined by the structure coordinates of an AR-LBD with an AR-LBD ligand or ligand complex according to Table A or a homologue of said complex, wherein said homologue comprises backbone atoms that have a root mean square deviation from the backbone atoms of the complex of not more than 3.0 Å.

Another object of the present invention is to provide a binding site in AR-LBD for an AR modulator in which a portion of said ligand is in van der Walls contact or hydrogen bonding contact with any portion or all of residues V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904, K905, I906 or L907 of AR-LBD according to Table A. In a preferred embodiment, the binding site is a homologue or mutant with 25%–95% identity to residues V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904, K905, I906 or L907 of AR-LBD according to Table A as provided herein.

Another object of the present invention is to provide SARMs having antagonist activity in hormone-dependent tumors while exhibiting no activity, or more preferably agonist activity, against other nontumor tissues containing the androgen receptor, as well as pharmaceutical compositions comprising at least one such SARM and a pharmaceutically acceptable carrier. In a preferred embodiment, the SARM is identified or designed in accordance with a method of the present invention.

Another object of the present invention is to provide a method for inhibiting the growth of hormone-dependent tumor cells comprising contacting the tumor cells with a SARM having antagonist activity in hormone-dependent tumors while exhibiting no activity, or more preferably agonist activity against other nontumor tissues containing the androgen receptor.

Unless otherwise indicated, SARMs of the present invention having antagonist activity against hormone-dependent tumors while exhibiting no activity, more preferably agonist activity against other nontumor tissues containing the androgen receptor are contemplated as further exhibiting, in all embodiments of the invention, agonist, antagonist or no activity against normal prostate tissue.

Yet another object of the present invention is to provide methods for using these SARMs in the treatment of conditions remediable by administration of an androgen receptor modulator as described herein including, but not limited to, hirsutism, acne, seborrhea, Alzheimer's disease, androgenic alopecia, hypogonadism, hyperpilosity, benign prostate hypertrophia, adenomas and neoplasias of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers, modulation of VEGF expression and the applications therein for use as antiangiogenic agents, osteoporosis, suppressing spermatogenesis, libido, cachexia, endometriosis, polycystic ovary syndrome, anorexia, androgen dependent age-related diseases and conditions, such as androgen supplement for age-related decreased testosterone levels in men, male menopause, male hormone replacement, male and female sexual dysfunction, and inhibition of muscular atrophy in ambulatory patients. Particularly preferred, is the use of SARMs for the treatment of hormone-dependent tumors, particularly early stage prostate cancers, and for chemoprevention of hormone-dependent cancer, particularly prostate cancers.

All documents referred to herein, including but not limited to U.S. patent applications, are incorporated herein by reference in their entirety.

DETAILED DESCRIPTION OF THE INVENTION

Selective androgen receptor modulators (SARMs) have now been identified with antagonist activity against hormone-dependent tumors while exhibiting no activity, or more preferably agonist activity against other (i.e., one or more) nontumor tissues containing the androgen receptor. SARMs of the present invention exhibiting antagonist activity against hormone-dependent tumors and no activity against other nontumor tissues containing the androgen receptor may also be referred to as specific androgen receptor modulators.

For purposes of the present invention by "nontumor", noncancerous" or "nonmalignant" androgen receptor containing tissues it is meant to include, but is not limited to, seminal vesicles, male and female genitalia, skin, testis, ovary, cartilage, sebaceous glands, hair follicles, sweat glands, muscle such as cardiac muscle, skeletal and smooth muscle, gastrointestinal vesicular cells, thyroid follicular cells, adrenal cortex, liver, pineal, bone, stromal cells, kidney tubules, urinary bladder and numerous brain cortical and subcortical regions, including spinal motor neurons.

Unless otherwise indicated, SARMs of the present invention having antagonist activity against hormone-dependent tumors while exhibiting no activity, or more preferably agonist activity, against other nontumor tissues containing the androgen receptor are contemplated as further exhibiting, in all embodiments of the invention, agonist, antagonist or no activity against normal prostate tissue.

As used herein, the phrase "no activity or agonist activity" preferably denotes compounds with an activation effect (greater than 5%) in vivo as compared to control animals on the weights of the ventral prostate, seminal vesicles, levator ani and/or luteinizing hormone serum levels, and most preferably activity which maintains average normal bone density, average normal muscle mass, average normal reproductive function, and/or average normal libido seen in ugonadal warm-blooded male mammals, preferably human males. "No activity or agonist activity" of SARMS of the present invention is preferably exhibited at the same amount or range of amounts that exhibit antagonist activity against hormone-dependent tumors. When administered to a patient, this amount or range of amounts, wherein the SARM exhibits antagonist activity against hormone-dependent tumors while exhibiting no activity or more preferably agonist activity against other nontumor containing tissues, is the preferred therapeutically useful range. As will be understood by those of skill in the art upon reading this disclosure, SARMs of the present invention, when used in amounts outside the preferred therapeutically useful range, may exhibit the same antagonist activity against hormone-dependent tumors and no activity or agonist activity against nontumor containing tissues or may no longer exhibit the same specificity or selectivity. For example, SARMs of the present invention, when used in amounts exceeding the preferred therapeutically useful range may exhibit some antagonist activity in nontumor containing tissues.

The present invention relates to SARMs with these dual activities, methods for identifying these SARMs, pharmaceutical compositions comprising these SARMs, and methods of using these SARMs in the treatment of androgen receptor mediated diseases and disorders.

For example, SARMs of the present invention are useful in selectively inhibiting the growth of hormone-dependent tumors while preferably activating androgen receptor activity in other nontumor, meaning noncancerous or nonmalignant, androgen receptor containing tissues. Accordingly, the SARMs of the present invention are useful in treating tumors including, but not limited to, androgen receptor containing tumors such as prostate, breast, brain, skin, ovarian, bladder, lymphatic, liver and kidney cancers, and pancreatic cancers, while mitigating or eliminating unwanted side effects associated with inhibition of androgen receptor activity in other nontumor androgen receptor containing tissues. Some of the potential unwanted side effects which result from antagonizing the normal function of androgens such as dihydrotestosterone (DHT) seen, for example, with current antiandrogen therapy in the treatment of prostate cancer include, but are not limited to, muscle wasting/cachexia, loss of libido, osteoporosis and gynecomastia.

An additional preferred use of such SARMs is in the area of chemoprevention, particularly as it pertains to prostate cancer. SARMs of the present invention can be administered after radical prostectomy during the period of "watchful waiting" to decrease the incidence of reoccurrence of metastatic prostate cancer.

In addition, these SARMs are useful in the treatment of androgen dependent age-related diseases and conditions including, without limitation, cachexia and osteoporosis. Such agents provide an orally bioavailable androgen replacement therapy that does not suffer from the increased risk of prostate cancer seen with traditional androgen agonists.

The SARMs of the present invention are also expected to be useful in treating other conditions remediable by administration of an androgen receptor modulator such as hirsutism, acne, seborrhea, Alzheimer's disease, androgenic alopecia, hypogonadism, hyperpilosity, benign prostate hypertrophia, modulation of VEGF expression and the applications therein for use as antiangiogenic agents, suppressing spermatogenesis, libido, endometriosis, polycystic ovary syndrome, anorexia, and androgen dependent age-related diseases and conditions, such as androgen supplement for age-related decreased testosterone levels in men, male menopause, male hormone replacement, male and female sexual dysfunction, and inhibition of muscular atrophy in ambulatory patients.

Various methods for identifying SARMs having antagonist activity against hormone-dependent tumors while exhibiting no activity, or more preferably agonist activity against other nontumor tissues containing the androgen receptor can be used. In one embodiment, antagonist activity in hormone-dependent tumors is ascertained via screening for inhibition of growth, either in vitro or in vivo, in hormone-dependent tumor cell lines. Examples of hormone-dependent tumor cell lines which can be used for screening potential SARMs include, but are not limited to, human breast tumor cell line MDA MB453, human breast tumor cell line ZR-75-1, murine breast line Shionogi, rat prostate adenocarcinoma line Dunning R-3327, human prostate tumor cell line MDA PCa 2a and PCa 2b, human prostate cell line LNCap, human prostate tumor cell line CWR22, human prostate tumor cell line LuCaP 35 and LuCaP 23.12, human prostate cell line LAPC-4 and LAPC-9, human prostate tumor cell line PC-295, human prostate tumor cell line PC-310, and human osteosarcoma cell line MG-63. These experimental human and murine prostate and breast cell lines and the tumor model systems derived therein are well accepted by those of skill in the art as indicative of the pharmacology of human hormone-dependent tumors, such as prostate cancer. Examples of the relationship of such models to the human disease state can be found in, but are not limited to, the following references and the references contained therein, Jacques et. al. *Endocrinology* 140, 416–421 (1999); Yeap et. al. *Endocrinology* 140, 3282–3291 (1999), Sharma et. al. *Oncogene* 18, 5349–5355 (1999), Isaacs, J. T. *Urol. Oncol.* 2, 115–116 (1996), Bentei et. al. *In Vitro Cell Dev. Biol.* 35, 655–662 (1999), Suzuki et. al. *J. Steroid Biochem. Mol. Biol.* 37, 559–567 (1990), Peehl, D. M. *Urol. Oncol.* 2, 100–102 (1996), Wytske et. al. *Urol. Oncol.* 2, 122–125 (1996), Leland, C. W. K. *Urol. Oncol.* 2, 126–128 (1996), Buhler et. al. *The Prostate* 43, 63–70 (2000), Navone et. al. *Clin. Cancer Res.* 6, 1190–1197 (2000), Etreby et. al. *The Prostate* 42, 99–106 (2000), Jongsma et. al. *Cancer Res.* 60, 741–748 (2000), Jongsma et. al. *Amer. J. Path.* 154, 543–551 (1999), Ye et. al. *Clin. Cancer Res.* 5, 2171–2177 (1999), Navone et. al. *Clin. Cancer Res.* 3, 2493–2500 (1997), Klein et. al. *Nature Medicine* 3, 402–408 (1997), Chen et. al. *Cancer Res.* 58, 2777–2783 (1998), and Craft et. al. *Cancer Res.* 59, 5030–5036 (1999).

In this embodiment, the agonist or antagonist activity of a potential SARM is also measured in a normal, nontumor cell line. Examples of normal, nontumor cells lines useful in this method include, but are not limited to, primary rat prostate epithelial and stromal cells, murine muscle cell line C2C12, primary guinea pig smooth muscle cells, primary smooth-muscle cells from immature (I-PSMC) or adult (A-PSMC) rat penis, primary rabbit smooth muscle cell line, prostatic smooth muscle cell line PS-1, prostatic smooth muscle cell line PSMC1, mouse bone cell cultures and osteoblasts cells and primary rat seminal vesicle lines SVC-1 and SCV-2. Such cell lines are described in the following exemplary references and the references contained therein: Nemeth et. al. *J. Andrology* 19, 718–724 (1998), Zhuang et. al. *J. Steroid Biochem. Mol. Biol.* 41, 693–696 (1992), Zhang et. al. *Prostate* 30, 117–129 (1997), Ricciardelli et. al. *J. Endocrinol.* 140, 373–383 (1994), Gonzalez-Cadavid et. al. *Mol. Cell. Endocrinol.* 90, 219–229 (1993), Sadeghi-Nejad et. al. *Int. J. Impotence Res.* 10, 165–169 (1998), Gerdes et. al. *Endocrinology* 139, 3569–3577 (1998), Sarah et. al. *J. Cell. Physiol.* 185, 416–424 (2000), Chen et. al., *FEBS Letters* 491, 91–93 (2001) and Tajana et. al. *EMBO J.* 3, 637–644 (1984).

Alternatively, the agonist and antagonist effects of SARMs are measured in nontumor tissues via a series of in vivo rat models in which surrogate endpoints are measured in tissues including, but not limited to, the prostate, seminal vesicle, and levitor ani muscle, as well as the hypothalmic axis via measurement of plasma luteinizing hormone (LH) levels. Several surrogate endpoint in vivo assays can also be utilized to examine the effects of agents on the AR pathway. These assays involve measuring the effects of agents on normal androgen dependent tissues and functions, such as, but not limited to, prostate, seminal vesicle, levator ani muscle, bone, libido, fertility and hypothalamus (measurement of blood LH levels). These assays are widely recognized as having a direct correlation to the effects of the agents on the AR pathways in humans. Some examples of such surrogate endpoint in vivo assays can be found in, but are not limited to, the following references and the references contained therein: Ashby et. al. *J. Appl. Tox.* 20, 35–47 (2000), Yamada et. al. *Tox. Sciences* 53, 289–296 (2000), Hamann et. al. *J. Med. Chem.* 41, 623–639 (1998), Furr et. al. *Eur. Urol* 29, 83–95 (1996), Broulik et. al. *Bone* 20, 473–475 (1997), Wang et. al. *Poster # P3-126, Endocrine Society 80th Annual Meeting* (1998), Hamann et. al. *Presentation # S39-2, Endocrine Society 80th Annual Meeting* (1998), Maucher et. al. *J. Cancer Res. Clin. Oncol.* 119, 669–674(1993),and Risek et al. Presentation #P1-497, Endocrine Society 83rd Annual Meeting (2001).

Animal models bearing a hormone-dependent tumor can also be used to assess the antagonist activity of a potential SARM against the tumor and the agonist or antagonist activity against AR containing normal nontumor tissues in the animal. For example, the above surrogate endpoint in vivo assays can be run using a rat bearing an androgen-dependent rat prostate tumor, such as the Dunning R-3327. In this manner, effects of a SARM on a rat androgen-dependent prostate tumor can be determined while simultaneously examining the effects of the SARM agent on AR containing normal nontumor tissues such as, but not limited to, prostate, seminal vesicle, and levitor ani muscle as well as effects on the hypothalmic axis via measurements of plasma LH levels. In a similar fashion, immune compromised nude rats bearing human androgen-dependent prostate tumors can be employed. In this manner, effects of a SARM on a human androgen-dependent prostate tumor can be determined while simultaneously examining the effects of the SARM agent on normal tissues such as, but not limited to, prostate, seminal vesicle, and levitor ani muscle as well as effects on the hypothalmic axis via measurements of plasma LH levels. In addition, in vivo rat assays can be employed to determine the effect of SARMs on libido and reproduction.

SARMs having antagonist activity in hormone-induced tumors and no activity, or more preferably agonist activity, in other nontumor tissues can also be designed using information about the AR crystal structure and the estrogen receptor (ER) crystal structure with estradiol, tamoxifen or raloxifen. The crystal structure of the androgen receptor ligand binding domain (AR-LBD) has been determined to 2.0 Å resolution and is described in U.S. patent application Ser. No. 09/687,609, filed Oct. 13, 2000 and corresponding PCT/US00/28495, Matias et al., *J. Biol. Chem.* 275, 26164–26171 (2000) and Sack et. al., *Proc. Natl. Acad. Sci. USA* 98, 4904–4909 (2001), herein incorporated by reference. The crystal structure of ER is disclosed, for example, in WO 99/50658, herein incorporated by reference. Using these crystal structures, structure-based or rational drug design techniques can be used to design, select, and synthesize chemical entities, including the inhibitory and stimulatory SARMs of the present invention.

One particularly useful drug design technique enabled by this invention is iterative drug design. Iterative drug design is a method for optimizing associations between a protein and a compound by determining and evaluating the three-dimensional structures of successive sets of protein/ligand complexes. Those of skill in the art will understand upon this disclosure that association of natural ligands or substrates with the binding pockets of their corresponding receptors or enzymes is the basis of many biological mechanisms of action. The term "binding pocket" as used herein, refers to a region of a molecule or molecular complex, that, as a result of its shape, favorably associates with another chemical entity or compound, i.e. ligand. Similarly, many drugs exert their biological effects through association with the binding pockets of receptors and enzymes. Such associations may occur with all or any parts of the binding pockets. An understanding of such associations will help lead to the design of drugs having more favorable associations with their target receptor or enzyme, and thus, improved biological effects. Therefore, this information is valuable in designing potential SARMs of this invention.

The term "associating with" refers to a condition of proximity between chemical entities or compounds, or portions thereof, i.e. ligands. The association may be non-covalent, wherein the juxtaposition is energetically favored by hydrogen bonding or van der Waals or electrostatic interactions, or it may be covalent.

In iterative drug design, crystals of a series of protein/ligand complexes are obtained. The three-dimensional structures of each complex are then solved. Such an approach provides insight into the association between the proteins and ligands of each complex. This is accomplished by selecting compounds with inhibitory activity, obtaining crystals of this new protein/ligand complex, solving the three dimensional structure of the complex, and comparing the associations between the new protein/ligand complex and previously solved protein/ligand complexes. By observing how changes in the compound effect the protein/ligand associations, these associations may be optimized.

In some cases, iterative drug design is carried out by forming successive protein/ligand complexes and then crystallizing each new complex. Alternatively, a pre-formed protein crystal is soaked in the presence of an inhibitor, thereby forming a protein/ligand complex and obviating the need to crystallize each individual protein/ligand complex.

As used herein, the term "soaked" refers to a process in which the crystal is transferred to a solution containing the compound of interest.

The present invention also provides for computational methods using three-dimensional models of the androgen and/or estrogen receptors that are based on crystals of AR-LBD/AR-LBD ligand complex and/or the ER-LBD/ER-LBD ligand complex. Generally, the computational method of designing receptor ligands determines which amino acid or amino acids of the receptor ligand binding domain interact with at least one chemical moiety of the ligand. A ligand is then docked into the binding site of the receptor LBD using the three dimensional model of a crystallized protein comprising the AR-LBD or ER-LBD. The orientation of the ligand in the binding site is then optimized (vide infra) and is then used to design at least one chemical modification of a chemical moiety of the ligand that produces a second chemical moiety of the ligand structure that either decreases or increases an interaction between the interacting amino acid(s) from the receptor LDB and the second chemical moiety compared to the interaction between the interacting amino acid and the corresponding chemical moiety on the natural hormones.

The computational methods of the present invention are for designing SARMs using such crystal and three-dimensional structural information to generate synthetic ligands that modulate the conformational changes of the androgen receptor's LBD and/or the estrogen receptor's LBD. These computational methods are particularly useful in designing SARMs to the androgen receptor, wherein the SARM has an extended moiety that prevents any one of a number of ligand-induced molecular events that alter the receptor's influence on the regulation of gene expression, such as preventing the normal coordination of the activation domain observed for a naturally occurring ligand or other ligands that mimic the naturally occurring ligand, such as an agonist. Based upon the structures of the ER-LBD complexed with agonist or antagonist (Shiau, et al. Cell 1998 95:927–937; Pike et al. EMBO J. 1999 18(17): 4608–4618) and the structures of AR-LDB coupled with DHT or other ligands (described in U.S. patent application Ser. No. 09/687,609, filed Oct. 13, 2000 and corresponding PCT/US00/28495, incorporated herein in their entirety and Table A as provided herein) it can be determined how to modify chemical compounds so that they specifically interact with AR-LBD amino acids in the binding site. In particular, the above extended moiety can be directed towards helix-12 of the AR structure in such a fashion as to influence the position of this helix as was seen in the structure of ER complexed with tamoxifen or raloxifen and differing from the position of helix-12 seen in the crystal structure of AR bound with DHT or R1881, a synthetic analog of DHT that is a more potent agonist (Matias, et al., *J. Biol. Chem.* 275, 26164–26171 (2000)), and the crystal structure of ER bound with estradiol. Residues on helix-12 that may be affected or in contact with a ligand in the AR-LBD binding site include M894, M895, A896, E897, I898, I899, S900, V901, Q902, V903, P904, K905, I906 and L907. The present invention also relates to the three-dimensional crystal structure as defined by the structure coordinates listed in Table A. The crystal structure of the invention preferably contains at least 25%, more preferably at least 50%, more preferably at least 75%, more preferably at least 90%, more preferably at least 95%, more preferably at least 99%, and most preferably all of the coordinates listed in Table A. More preferably, molecule or molecular complexes are provided comprising all or any part of the ligand binding site defined by structure coordinates of AR-LBD amino acids V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, M894, M895, A896, E897, I898, I899, S900, V901, Q902, V903, P904, K905, I906 and L907 according to Table A as provided herein, or a mutant or homologue of said molecule or molecular complex. Most preferred are molecules or molecular complexes comprising all or any part of the ligand binding site defined by structure coordinates of AR-LBD amino acids N705, W741, Q711, R752, F764, T877, M895 and I898, according to Table A, or a mutant or homologue of said molecule or molecular complex.

The term "complex" or "molecular complex" as used herein means AR-LBD or a mutant or homologue of AR-LBD in a covalent or non-covalent association with a chemical entity or ligand.

For purposes of the present invention, by "at least a portion of" it is meant all or any part of the ligand binding site defined by these structure coordinates.

By "mutant or homologue" as used herein it is meant a molecule or molecular complex having a similar structure and/or sequences to AR-LBD. By "similar structure" it is meant a mutant or homologue having a binding pocket that has a root mean square deviation from the backbone atoms of said AR-LBD amino acids of not more than 1.5 Angstroms. By "similar sequence" it is meant a mutant or homologue having 30%, or more preferably 75%, identity with AR-LBD.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein or protein complex from the relevant portion of the backbone of the AR portion of the complex as defined by the structure coordinates described herein.

Once the structure coordinates of a protein crystal have been determined they are useful in solving the structures of other crystals.

Thus, in accordance with the present invention, the structure coordinates of an androgen receptor/ligand complex, and portions thereof is stored in a machine-readable storage medium. Such data may be used for a variety of purposes, such as drug discovery and x-ray crystallographic analysis or protein crystal.

Accordingly, in one embodiment of this invention is provided a machine-readable data storage medium comprising a data storage material encoded with the structure coordinates set forth in Table A. One embodiment utilizes System 10 as disclosed in WO 98/11134, the disclosure of which is incorporated herein by reference in its entirety.

The structure coordinates set forth in Table A can also be used to aid in obtaining structural information about another crystallized molecule or molecular complex. This may be achieved by any of a number of well-known techniques, including molecular replacement.

The structure coordinates set forth in Table A can also be used for determining at least a portion of the three-dimensional structure of molecules or molecular complexes which contain at least some structurally similar features to AR. In particular, structural information about another crystallized molecule or molecular complex may be obtained. This may be achieved by any of a number of well-known techniques, including molecular replacement.

Therefore, in another embodiment this invention provides a method of utilizing molecular replacement to obtain structural information about a crystallized molecule or molecular complex whose structure is unknown comprising the steps of:
a) generating an X-ray diffraction pattern from said crystallized molecule or molecular complex;
b) applying at least a portion of the structure coordinates set forth in Table A to the X-ray diffraction pattern to generate a three-dimensional electron density map of the molecule or molecular complex whose structure is unknown; and
c) using all or a portion of the structure coordinates set forth in Table A to generate homology models of AR-LBD or any other nuclear hormone receptor ligand binding domain.

Preferably, the crystallized molecule or molecular complex is obtained by soaking a crystal of this invention in a solution.

By using molecular replacement, all or part of the structure coordinates of the AR-LBD/AR-LBD ligand complex provided by this invention or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the AR-LBD/AR-LBD ligand complex according to Table A within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55–77 (1985); M. G. Rossmann, ed., "The Molecular Replacement Method", Int. Sci. Rev. Set., No. 13, Gordon & Breach, New York (1972)].

The structure of any portion of any crystallized molecule or molecular complex, or mutant, homologue or orphan receptor that is sufficiently homologous to any portion of the AR-LBD/AR-LBD ligand complex can be solved by this method. Along with the aforementioned AR, there also exist a number of receptors for which the activating or deactivating ligands may not be characterized. These proteins are classified as nuclear hormone receptors due to strong sequence homology to AR, and are known as orphan receptors.

The structure coordinates are also particularly useful to solve the structure of crystals of AR-LBD/AR-LBD ligand co-complexed with a variety of chemical entities. This approach enables the determination of the optimal sites for interaction between chemical entities, including interaction of candidate AR inhibitors with the complex. For example, high resolution X-ray diffraction data collected from crystals exposed to different types of solvent allows the determination of where each type of solvent molecule resides. Small molecules that bind tightly to these sites can then be designed and synthesized and tested for their AR inhibition activity.

All of the complexes referred to above may be studied using well-known X-ray diffraction techniques and may be refined versus 1.5–3 Å resolution X-ray data to an R value of about 0.20 or less using computer software, such as X-PLOR [Yale University, 1992, distributed by Molecular Simulations, Inc.; see, e.g., Blundell & Johnson, supra; Meth. Enzymol., vol. 114 & 115, H. W. Wyckoff et al., eds., Academic Press (1985)]. This information may thus be used to optimize known AR agonists, partial agonists, antagonists, partial antagonists and SARMS, and more importantly, to design new AR agonists/antagonists.

Accordingly, the present invention is also directed to a binding site in AR-LBD for an AR-LBD ligand in which a portion of AR-LBD ligand is in van der Walls contact or hydrogen bonding contact with at least one of the following residues: V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904, K905, I906, or L907 of AR-LBD according to Table A. For purposes of this invention, by AR-LBD binding site it is also meant to include mutants or homologues thereof In a preferred embodiment, the mutants or homologues have at least 25% identity, more preferably 50% identity, more preferably 75% identity, and most preferably 95% identity to residues V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904, K905, I906, or L907 of AR-LBD binding sites according to Table A.

The present invention is also directed to a machine-readable data storage medium, comprising a data storage material encoded with machine readable data, wherein the data is defined by the structure coordinates of an AR-LBD/AR-LBD ligand according to Table A or a homologue of said complex, wherein said homologue comprises backbone atoms that have a root mean square deviation from the backbone atoms of the complex of not more than 3.0 Å. Preferably, the machine-readable data storage medium, according to the invention, is wherein said molecule or molecular complex is defined by the set of structure coordinates for AR-LBD/AR-LBD ligand according to Table A, or a homologue of said molecule or molecular complex, said homologue having a root mean square deviation from the backbone atoms of said amino acids of not more than 2.0 Å. In a preferred embodiment the machine-readable data storage medium comprises a data storage material encoded with a first set of machine readable data comprising a Fourier transform of at least a portion of the structural coordinates for an AR-LBD/AR-LBD ligand according to Table A; which, when combined with a second set of machine readable data comprising an X-ray diffraction pattern of a molecule or molecular complex of unknown structure, using a machine programmed with instructions for using said first set of data and said second set of data, can determine at least a portion of the structure coordinates corresponding to the second set of machine readable data, said first set of data and said second set of data.

The present invention also provides for computational methods using three dimensional models of the androgen receptor that are based on crystals of AR-LBD/AR-LBD ligand complex. Generally, the computational method of designing an androgen receptor ligand determines which amino acid or amino acids of the AR-LBD interact with a chemical moiety (at least one) of the ligand using a three dimensional model of a crystallized protein comprising the AR-LBD with a bound ligand, and selecting a chemical modification (at least one) of the chemical moiety to produce a second chemical moiety with a structure that either decreases or increases an interaction between the interacting amino acid and the second chemical moiety compared to the interaction between the interacting amino acid and the corresponding chemical moiety on the natural hormone. In a preferred embodiments, the method for identifying a compound that modulates androgen receptor activity comprises any combination of the following steps:

a. modeling test compounds that fit spatially into the AR-LBD as defined by structure coordinates according to Table A, or using a three-dimensional structural model of AR-LBD, mutant AR-LBD or AR-LBD homologue or portion thereof;

b. using the AR-LBD structure coordinates or ligand binding site as set forth herein to identify structural and chemical features;

c. employing identified structural or chemical features to design or select compounds as potential SARMs;

d. employing the three-dimensional structural model or the ligand binding site to design or select compounds as potential SARMs;

e. synthesizing the potential SARMs;

f. screening the potential SARMs in an assay characterized by binding of a test compound to the AR-LBD; and g. modifying or replacing one or more amino acids from AR-LBD selected from the group consisting of V685, L700, L701, S702, S703, L704, N705, E706, L707, G708, E709, Q711, A735, I737, Q738, Y739, S740, W741, M742, G743, L744, M745, V746, F747, A748, M749, G750, R752, Y763, F764, A765, L768, F770, M780, M787, I869, L873, H874, F876, T877, F878, L880, L881, V889, F891, P892, E893, M894, M895, A896, E897, I898, I899, S900, V901, Q902, V903, P904, K905, I906 or L907 of AR-LBD according to Table A.

The computational methods of the present invention are for designing androgen receptor synthetic ligands using such crystal and three dimensional structural information to generate synthetic ligands that modulate the conformational changes of the androgen receptor's LBD. These computational methods are particularly useful in designing an agonist, partial agonist, antagonist or partial antagonist or SARM to the androgen receptor, wherein the agonist, partial agonist, antagonist or partial antagonist or SARM has an extended moiety that prevents any one of a number of ligand-induced molecular events that alter the receptor's influence on the regulation of gene expression, such as preventing the normal coordination of the activation domain observed for a naturally occurring ligand or other ligands that mimic the naturally occurring ligand, such as an agonist. As described herein, synthetic ligands of the androgen receptor will be useful in modulating androgen receptor activity in a variety of medical conditions.

It is also possible to design an extended chemical moiety that is directed towards helix-3 or helix-11 that stabilize or disrupt critical ligand-receptor interactions (Humm et al. Arch. Pharm. (Weinheim) 1990 323:83–87; Poujol, et al. J. Biol. Chem. 2000 275(31):24022–24031). The structure of AR-LBD complexed with DHT shows that the 17α-hydroxyl group of androgens (DHT) forms critical hydrogen bonds with Thr-877 and Asn-705 of the AR-LBD (Sack et al. Proc. Natl Acad. Sci. (USA) 98(9):4904–4909 (2001)). Experiments show that when Asn-705 is mutated to alanine (N705A), that nonsteroidal antiandrogens have low antagonistic properties compared to wild type AR. Asn-705 thus plays a crucial role in the anchoring of nonsteroidal antiandrogens and design of chemical moieties directed at Ans-705 and Thr-877 can also be used for development of a SARM. As described herein, synthetic ligands of the androgen receptor will be useful in inhibiting androgen receptor activity in hormone-induced tumors and activating androgen receptors in other androgen receptor containing nontumor tissues.

The location of the secondary structure (SS) elements for three dimensional structures of ER-LDB and AR-LBD are depicted below. The amino acid sequence alignment shown is based upon a structural superposition of the AR-LBD and the ER-LDB. Sequence numbering is for the AR-LBD. H (or G) indicates that a particular amino acid is in a helix, E (or B) indicates a particular amino acid is in a beta strand. The AR-LDB amino acids extend from Ile-672 through His-917 (SEQ ID NO:1) and the ER-LBD amino acids extend from Ser-305 through Arg-548 (SEQ ID NO:2). Helix numbering is indicated below sequence and structure definitions.

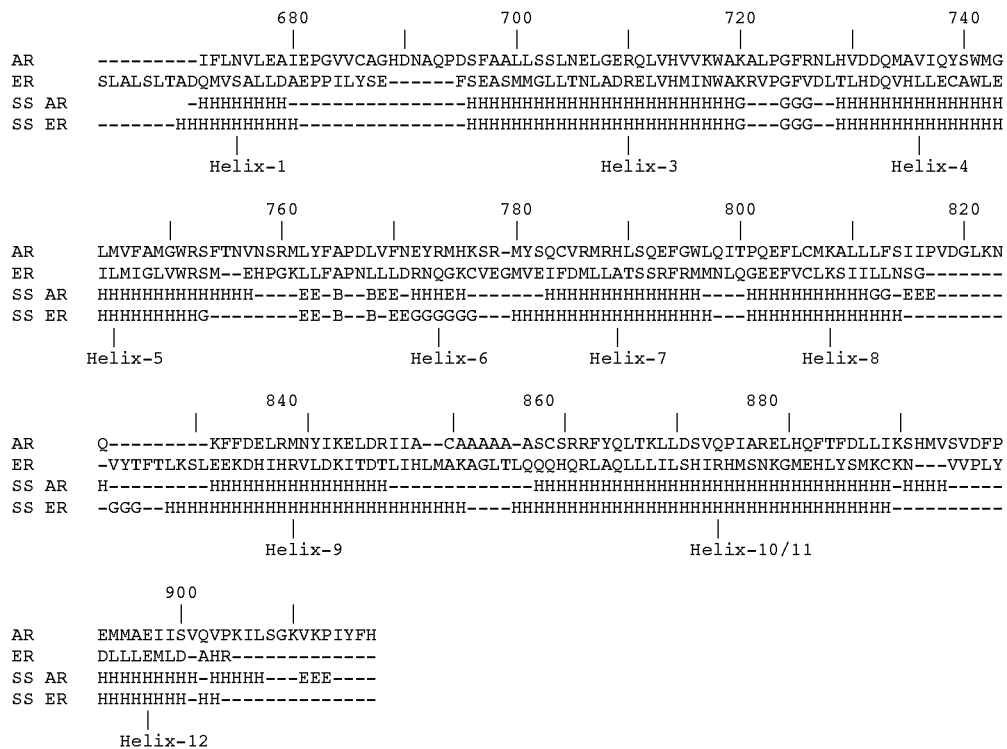

Various computer programs are available that use crystallography data such as available for AR and ER and enable the rational design of SARMs of the present invention. Software programs such as ICM (version 2.7 or higher; Molsoft LLC, La Jolla, Calif.) or SYBYL® (Tripos Inc. St Louis, Mo.) can be used with the atomic coordinates from AR and ER crystals to generate three-dimensional models and/or determine the structures involved in ligand binding. Other molecular visualization programs such as INSIGHT II® (Pharmacopeia/Molecular Simulations, Inc., San Diego, Calif.) and GRASP (Columbia University, New York, N.Y.) allow for further manipulation and the ability to introduce new structures. In addition, a number computer modeling systems are available in which the sequence of the AR-LBD and the AR-LBD structure can be entered. The computer system then generates the structural details of the site in which a potential AR modulator binds so that complementary structural details of the potential modulators can be determined. Design in these modeling systems is generally based upon the compound being capable of physically and structurally associating with AR-LBD. In addition, the compound must be able to assume a conformation that allows it to associate with AR-LBD. Some modeling systems estimate the potential inhibitory or binding effect of a potential AR modulator prior to actual synthesis and testing.

Methods for screening chemical entities or fragments for their ability to associate with AR and ER are also well known. Often these methods begin by visual inspection of the active site on the computer screen. Selected fragments or chemical entities are then positioned with the AR-LBD or ER-LBD. Docking is accomplished using software, followed by optimization of the ligand in the receptor binding site by global optimization procedures or molecular dynamics and minimization protocols with standard molecular mechanic forcefields such as CHARMM and AMBER. Examples of computer programs which assist in molecular docking and the selection of chemical fragments or chemical entities useful in the present invention include, but are not limited to, GRID (Goodford, P. J. J. Med. Chem. 1985 28:849–857), AUTODOCK (Goodsell, D. S. and Olsen, A. J. Proteins, Structure, Functions, and Genetics 1990 8:195–202), and DOCK (Kunts et al. J. Mol. Biol. 1982 161:269–288) and ICM (Molsoft LLC, La Jolla Calif., ICM 2.7 Program manual, Abagan et al. 1994 J. Mol. Biol. 235:983–1002, Totrov et al. 1997 Proteins Suppl. 1:215–220).

Upon selection of preferred chemical entities or fragments, their relationship to each other and AR or ER can be visualized and the entities or fragments can be assembled into a single potential modulator. Programs useful in assembling the individual chemical entities include, but are not limited to CAVEAT (Bartlett et al. Molecular Recognition in Chemical and Biological Problems Special Publication, Royal Chem. Soc. 78, 182–196 (1989)) and 3D Database systems (Martin, Y. C. J. Med. Chem. 1992 35:2145–2154).

Alternatively, compounds can be designed de novo using either an empty active site or optionally including some portion of a known inhibitor. Methods of this type of design include, but are not limited to LUDI (Bohm H-J, J. Comp. Aid. Molec. Design 1992 6:61–78) and LeapFrog™(Tripos Associates, St. Louis. Mo.).

Numerous protocols have been developed to score the designed and docked chemical entities in the receptor binding sites. Programs useful in scoring the chemical entities in protein binding sites include, but are not limited to DOCK (Kunts et al. J. Mol. Biol. 1982 161:269–288, ICM (Molsoft LLC, La Jolla Calif., Totrov et al. 1997 Proteins Suppl. 1:215–220, Schapira et al. 2000 Proc. Natl. Acad. Sci USA 97(3):1008–1013) and SYBYL® (Tripos Inc. St Louis, Mo.

Once a computationally designed ligand (CDL) is synthesized, it can be tested using assays such as those described herein to establish its activity as an antagonist in hormone-dependent tumors and to assess its activity in other nonmalignant AR containing tissues. A CDL, which acts as an antagonist in hormone-dependent tumors and exhibits no activity, or more preferably partial agonist or agonist activity, in other nontumor AR containing tissues is a SARM in accordance with this invention. After such testing, the CDLs can be further refined by generating LBD crystals with a CDL bound to the LBD. The structure of the CDL can then be further refined using established chemical modification methods for three-dimensional models to improve the activity or affinity of the CDL and make second generation CDLs with improved properties, such as that of a "super SARM", meaning a compound having superior agonist activity while maintaining antagonist activity in selected tissues.

In a particularly preferred embodiment of the present invention, SARMs having the following activity levels are contemplated. Such SARMs are preferred in the methods and compositions of the present invention, and exhibit antagonist activity levels described in the following section (i) and/or (ii), and no activity, or more preferably agonist activity levels described in the following sections (iii) and/or (iv):

(i) an $IC_{50}$ of about 1 $\mu$M or less, more preferably 0.5 $\mu$M or less, most preferable 0.1 $\mu$M or less relative, to the maximal signal induction obtained for DHT, for the inhibition of at least one hormone-dependent tumor cell line, preferably a prostate tumor cell line or another hormone-dependent tumor cell line predictive of activity in a prostate tumor cell line, such as those described above in connection with screening for SARMs of the present invention and in Examples 3, 4, and 6 below; and/or (ii) inhibition of hormone dependent tumor growth in vivo in a model such as described above and in Examples 10, 11, 12 or 13 below; and preferably;

(iii) at least 30% activation at 1 $\mu$M as compared to DHT, more preferably an $EC_{50}$ of about 0.5 $\mu$M or less, most preferably an $EC_{50}$ of about 0.1 $\mu$M or less, in normal AR-responsive tissue;

(iv) and/or more than 20%, preferably more than 40%, more preferably more than 70%, more preferably more than 90% of an activation effect, in vivo as compared to control animals on the weights of the ventral prostate, seminal vesicles, levator ani and/or luteinizing hormone serum levels as described above and in Example 8. Preferred SARMs of the present invention also act to maintain average normal bone density, average normal muscle mass, average normal reproductive function, and average normal libido seen in ugonadal warm-blooded male mammals, preferably human males. In a preferred embodiment, SARMs of the present invention exhibit antagonist activity against hormone-dependent tumors, while exhibiting no activity or agonist activity against at the same amount or range of amounts. When administered to a patient, this amount or range of amounts is the preferred therapeutically useful range. As will be understood by those of skill in the art upon reading this disclosure, SARMs of the present invention, when used in amounts outside the preferred therapeutically useful range, may exhibit the same antagonist activity against hormone-dependent tumors and no activity or agonist activity against nontumor containing tissues or may no longer exhibit the same specificity or selectivity. For example, SARMs of the present invention, when used in amounts exceeding the preferred therapeutically useful range may exhibit some antagonist activity in nontumor containing tissues.

The present invention is also directed to a selective androgen receptor modulator (SARM), which includes any compound that is an antagonist in hormone-induced tumors and inactive, or more preferably an agonist, in other AR containing nontumor tissues. In a preferred embodiment, the SARM is identified via screening assays as set forth herein or designed in accordance with the computational processes described herein. Compounds, which are small molecules, especially compounds other than peptides or steroids, are preferred. Without limitation to a particular chemotype, compounds selected from the following formulae Ia or Ib are preferred as SARMs of the present invention, especially particular compounds of these formulae set forth in the Examples herein. Compounds of the formula Ia are described further (as compounds of the "formula I") in U.S. Provisional Patent Application Ser. No. 60/214,392, filed Jun. 28, 2000, U.S. Provisional Patent Application Ser. No. 60/284,617, filed Apr. 18, 2001, and U.S. patent application Ser. No. 09/885,798, entitled "Fused Cyclic Modulators of Nuclear Hormone Receptor Function", by Salvati et al., filed Jun. 20, 2001; compounds of the formula Ib are described further (as compounds of the "formula I") in U.S. Provisional Patent Application Ser. No. 60/233,519, filed Sep. 19, 2000, U.S. Provisional Patent Application Ser. No. 60/284, 730, filed Apr. 18, 2001, and U.S. patent application Ser. No. 09/885,381, entitled "Fused Heterocyclic Succinimide Compounds and Analogs Thereof, Modulators of Nuclear Hormone receptor Function", by Salvati et al., filed Jun. 20, 2001, all of which applications are incorporated herein by reference in their entirety. Formula Ia is as follows:

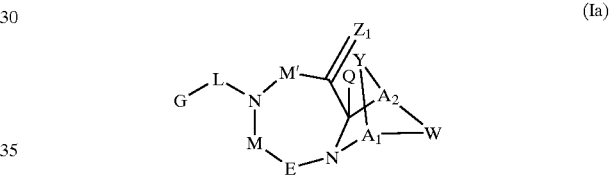

(Ia)

where the symbols have the following meanings unless otherwise indicated, and are, for each occurrence, independently selected:

G is an aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1OC=O$, $R^1C=O$, $R^1C=S$, $R^1HNC=O$, $R^1R^2NC=O$, $HOCR^3R^{3'}$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1'}$, $(R^1O)(R^{1'}O)P=O$, $(R^1)(R^{1'})P=O$, or $(R^{1'})(NHR^1)P=O$;

E is $C=Z_2$, $CR^7R^{7'}$(e.g. $CHR^7$), $SO_2$, $P=OR^2$, or $P=OOR^2$;

$Z_1$ is O, S, NH, or $NR^6$;

$Z_2$ is O, S, NH, or $NR^6$;

$A_1$ is $CR^7$ or N;

$A_2$ is $CR^7$ or N;

Y is J-J'-J" where J is $(CR^7R^{7'})n$ and n=0–3, J' is a bond or O, S, S=O, $SO_2$, NH, $NR^6$, C=O, OC=O, $NR^1C=O$, $CR^7R^{7'}$, $C=CR^8R^{8'}$, $R^2P=O$, $OPOOR^2$, $OPO_2$, $OSO_2$, C=N, NHNH, $NHNR^6$, $NR^6NH$, N=N, cycloalkyl or substituted cycloalkyl, cycloalkenyl or substituted cycloalkenyl, heterocyclo or substituted heterocyclo or aryl or substituted aryl, and J" is $(CR^7R^{7'})n$ and n=0–3, where Y is not a bond;

W is CR⁷R⁷'—CR⁷R⁷', CR⁸=CR⁸', CR⁷R⁷'—C=O, NR⁹—CR⁷R⁷', N=CR⁸, N=N, NR⁹—NR⁹', cycloalkyl or substituted cycloalkyl, cycloalkenyl or substituted cycloalkenyl, heterocyclo or substituted heterocyclo, or aryl or substituted aryl;

Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, R¹OC=O, R⁴C=O, R⁵R⁶NC=O, HOCR⁷R⁷', nitro, R¹OCH₂, R¹O, NH₂, C=OSR¹, SO₂R¹ or NR⁴R⁵;

M is a bond, O, CR⁷R⁷' or NR¹⁰, and M' is a bond or NR¹⁰, with the proviso that at least one of M or M' must be a bond;

L is a bond, (CR⁷R⁷')n, NH, NR⁵ or N(CR⁷R⁷')n, where n=0–3;

R¹ and R¹' are each independently H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl;

R² is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

R³ and R³' are each independently H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, hydroxylamine, hydroxamide, alkoxy or substituted alkoxy, amino, NR¹R², thiol, alkylthio or substituted alkylthio;

R⁴ is H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, R¹C=O, R¹NHC=O, SO₂OR¹, or SO₂NR¹R¹';

R⁵ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, R¹C=O, R¹NHC=O, SO₂R¹, SO₂OR¹, or SO₂NR¹R¹';

R⁶ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, OR¹, R¹C=O, R¹NHC=O, SO₂R¹, SO₂OR¹, or SO₂NR¹R¹';

R⁷ and R⁷' are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, OR¹, nitro, hydroxylamine, hydroxylamide, amino, NHR⁴, NR²R⁵, NOR¹, thiol, alkylthio or substituted alkylthio, R¹C=O, R¹OC=O, R¹NHC=O, SO₂R¹, SOR¹, PO₃R¹R¹', R¹R¹'NC=O, C=OSR¹, SO₂R¹, SO₂OR¹, or SO₂NR¹R¹';

R⁸ and R⁸' are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, OR¹, amino, NHR⁴, NR²R⁵, NOR¹, alkylthio or substituted alkylthio, C=OSR¹, R¹OC=O, R¹C=O, R¹NHC=O, R¹R¹'NC=O, SO₂OR¹, S=OR¹, SO₂R¹, PO₃R¹R¹', or SO₂NR¹R¹';

R⁹ and R⁹' are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, OR¹, R¹C=O, R¹OC=O, R¹NHC=O, SO₂R¹, SO₂OR¹, or SO₂NR¹R¹'; and R¹⁰ is H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, OR¹, R¹C=O, R¹OC=O, R¹R¹'NC=O, SO₂R¹, SO₂OR¹, or SO₂NR¹R¹'.

Formula Ib is as follows:

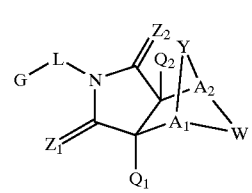

(Ib)

where the symbols have the following meanings unless otherwise indicated, and are, for each occurrence, independently selected:

G is an aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, R¹OC=O, R¹C=O, R¹C=S, R¹HNC=O, R¹R²NC=O, HOCR³R³', nitro, R¹OCH₂, R¹O, NH₂, NR$^4$R$^5$, SR$^1$, S=OR$^1$, SO$_2$R$^1$, SO$_2$OR$^1$, SO$_2$NR$^1$R$^{1'}$, (R$^1$O)(R$^1$O)P=O, oxo, (R$^1$)(R$^{1'}$)P=O, or (R$^1$)(NHR$^1$)P=O;

Z, is O, S, NH, or NR$^6$;

Z$_2$ is O, S, NH, or NR$^6$;

A$_1$ is CR$^7$ or N;

A$_2$ is CR$^7$ or N;

Y is J-J'-J" where J is (CR$^7$R$^{7'}$)n and n=0–3, J' is a bond or O, S, S=O, SO$_2$, NH, NR$^7$, C=O, OC=O, NR$^1$C=O, CR$^7$R$^{7'}$, C=CR$^8$R$^{8'}$, R$^2$P=O, R$^2$P=S, R$^2$OP=O, R$^2$NHP=O, OP=OOR$^2$, OP=ONHR$^2$, OP=OR$^2$, OSO$_2$, C=NR$^7$, NHNH, NHNR$^6$, NR$^6$NH, N=N, cycloalkyl or substituted cycloalkyl, cycloalkenyl or substituted cycloalkenyl, heterocyclo or substituted heterocyclo or aryl or substituted aryl, and J" is (CR$^7$R$^{7'}$)n and n=0–3, where Y is not a bond;

W is CR$^7$R$^{7'}$—CR$^7$R$^{7'}$, CR$^8$=CR$^{8'}$, CR$^7$R$^{7'}$—C=O, NR$^9$—CR$^7$R$^{7'}$, N=CR$^8$, N=N, NR$^9$—NR$^{9'}$, S—CR$^7$R$^{7'}$, SO—CR$^7$R$^{7'}$, SO$_2$—CR$^7$R$^{7'}$, cycloalkyl or substituted cycloalkyl, cycloalkenyl or substituted cycloalkenyl, heterocyclo or substituted heterocyclo, or aryl or substituted aryl, wherein when W is not NR$^9$—CR$^7$R$^{7'}$, N=CR$^8$, N=N, NR$^9$—NR$^{9'}$, S—CR$^7$R$^{7'}$, SO—CR$^7$R$^{7'}$, SO$_2$—CR$^7$R$^{7'}$, or heterocyclo or substituted heterocyclo, then J' must be O, S, S=O, SO$_2$, NH, NR$^7$, OC=O, NR$^1$C=O, OP=OOR$^2$, OP=ONHR$^2$, OSO$_2$, NHNH, NHNR$^6$, NR$^6$NH, or N=N;

Q$_1$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, R$^1$OC=O, R$^4$C=O, R$^5$R$^6$NC=O, HOCR$^7$R$^{7'}$, nitro, R$^1$OCH$_2$, R$^1$O, NH$_2$, C=OSR$^1$, SO$_2$R$^1$ or NR$^4$R$^5$;

Q$_2$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, R$^1$OC=O, R$^4$C=O, R$^5$R$^6$NC=O, HOCR$^7$R$^{7'}$, nitro, R$^1$OCH$_2$, R$^1$O, NH$_2$, C=OSR$^1$, SO$_2$R$^1$ or NR$^4$R$^5$;

L is a bond, (CR$^7$R$^{7'}$)n, NH, NR$^5$, NH (CR$^7$R$^{7'}$)n, or NR$^5$ (CR$^7$R$^{7'}$)n, where n=0–3;

R$^1$ and R$^{1'}$ are each independently H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl;

R$^2$ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

R$^3$ and R$^{3'}$ are each independently H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, hydroxylamine, hydroxamide, alkoxy or substituted alkoxy, amnino, NR$^1$R$^2$, thiol, alkylthio or substituted alkylthio;

R$^4$ is H, alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, R$^1$C=O, R$^1$NHC=O, SO$_2$OR$^1$, or SO$_2$NR$^1$R$^{1'}$;

R$^5$ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, R$^1$C=O, R$^1$NHC=O, SO$_2$R$^1$, SO$_2$OR$^1$, or SO$_2$NR$^1$R$^{1'}$;

R$^6$ is alkyl or substituted alkyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, OR$^1$, R$^1$C=O, R$^1$NHC=O, SO$_2$R$^1$, SO$_2$OR$^1$, or SO$_2$NR$^1$R$^{1'}$;

R$^7$ and R$^{7'}$ are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, OR$^1$, nitro, hydroxylamine, hydroxylamide, amino, NHR$^4$, NR$^2$R$^5$, NOR$^1$, thiol, alkylthio or substituted alkylthio, R$^1$C=O, R$^1$OC=O, R$^1$NHC=O, SO$_2$R$^1$, SOR$^1$, PO$_3$R$^1$R$^{1'}$, R$^1$R$^{1'}$NC=O, C=OSR$^1$, SO$_2$R$^1$, SO$_2$OR$^1$, or SO$_2$NR$^1$R$^{1'}$, or wherein A$_1$ or A$_2$ contains a group R$^7$ and W contains a group R$^7$, said R7 groups of A$_1$ or A$_2$ and W together form a heterocyclic ring;

R$^8$ and R$^{8'}$ are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, OR$^1$, amino, NHR$^4$, NR$^2$R$^5$, NOR$^1$, alkylthio or substituted alkylthio, C=OSR$^1$, R$^1$OC=O, R$^1$C=O, R$^1$NHC=O, R$^1$R$^{1'}$NC=O, SO$_2$OR$^1$, S=OR$^1$, SO$_2$R$^1$, PO$_3$R$^1$R$^{1'}$, or SO$_2$NR$^1$R$^{1'}$; and R$^9$ and R$^{9'}$ are each independently H, alkyl or substituted alkyl, alkenyl or substituted alkenyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, OR$^1$, R$^1$C=O, R$^1$OC=O, R$^1$NHC=O, SO$_2$R$^1$, SO$_2$OR$^1$, or SO$_2$NR$^1$R$^{1'}$.

The present invention is further directed to methods of using SARMs to inhibit the growth of hormone-induced tumors. Hormone-induced tumors can be treated by administering to a patient an effective amount of a SARM with antagonist activity in hormone-induced tumors and no activity, or more preferably agonist activity, in other nontumor AR containing tissues. By "effective amount" it is meant an amount or concentration of SARM that inhibits the growth of hormone-induced tumor cells in the patient. In a preferred embodiment, "effective amount" also refers to an amount or concentration, which induces agonist activity in nontumor AR containing tissues. Such amounts or concentrations can be determined routinely by those of ordinary skill in the art, for example, based upon cell based assays such as described herein or through other art-recognized means.

SARMs of the present invention can be administered alone or simultaneously or sequentially with radiation and/or one or more active agents, such as chemotherapeutic agents. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A–F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 30 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The combinations of the present invention can also be formulated or co-administered with other therapeutic agents that are selected for their particular usefulness in administering therapies associated with the aforementioned conditions. For example, the compounds of the invention may be formulated with agents to prevent nausea, hypersensitivity and gastric irritation, such as antiemetics, and $H_1$ and $H_2$ antihistaminics.

SARMs of the present invention, for example, compounds identified as SARMs by the methods disclosed herein, which are active when given orally can be formulated as liquids, for example, syrups, suspensions or emulsions, tablets, capsules and lozenges. A liquid composition will generally comprise a suspension or solution of the compound in a suitable liquid carrier(s), for example, ethanol, glycerin, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener. A composition in the form of a tablet can be prepared using any suitable pharmaceutical carrier(s), such as those routinely used for preparing solid compositions. Examples of such carriers include magnesium stearate, starch, lactose, sucrose, microcrystalline cellulose, and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix. A composition in the form of a capsule can be prepared, for example, using routine encapsulation procedures, such as by incorporation of active compound and excipients into a hard gelatin capsule. Other examples of capsule preparation include, for example, filling a hard gelatin capsule with a semi-solid matrix of active compound and high molecular weight polyethylene glycol; or filling a soft gelatin capsule with a solution of active compound in polyethylene glycol or a suspension in edible oil, for example liquid paraffin or fractionated coconut oil.

SARMs of the present invention, for example, compounds identified by the methods disclosed herein, which are active when given parenterally, can be formulated, for example, for any suitable mode of parenteral administration, such as for intramuscular or intravenous administration. A typical composition for intra-muscular administration will comprise a suspension or solution of active ingredient in an oil, for example arachis oil or sesame oil. A typical composition for intravenous administration will comprise a sterile isotonic aqueous solution containing, for example, active ingredient, dextrose, sodium chloride, a co-solvent, for example polyethylene glycol and, optionally, a chelating agent, for example ethylenediaminetetracetic acid and an anti-oxidant, for example, sodium metabisulphite. Alternatively, the solution can be freeze dried and then reconstituted with a suitable solvent just prior to administration.

SARMs of the present invention, for example, compounds identified as SARMs by the methods disclosed herein, which are active on rectal administration, can be formulated as suppositories. A typical suppository formulation will generally comprise active ingredient with a binding and/or lubricating agent such as a gelatin or cocoa butter or other low melting vegetable or synthetic wax or fat.

SARMs of the present invention, for example, compounds identified as SARMs by the methods disclosed herein, which are active on topical administration, can be formulated, for example, as transdermal compositions. Such compositions include, for example, a backing, active compound reservoir, a control membrane, liner and contact adhesive.

The typical daily dose of SARM varies according to the activity of the SARM, the individual needs, the condition to be treated and the route of administration. Exemplary suitable doses are in the general range of from 0.001 to 10 mg/kg bodyweight of the recipient per day.

The following nonlimiting examples are provided to further illustrate the present invention.

EXAMPLES

Example 1

Exemplary SARMs of the Present Invention

Exemplary SARMS of the present invention are depicted in Table 1. The absolute configuration for the following compounds was not determined. For simplicity in nomenclature, compound [3aR-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile is designated herein as having an "R" configuration and compound [3aS-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile is designated herein as having an "S" configuration. Enantiomerically pure products derived from [3aR-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile are designated herein as having an "R" configuration and enantiomerically pure products derived from compound [3aS-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile are designated herein as having an "S" configuration. For simplicity in nomenclature, compound [3aS-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile is designated herein as having an "S" configuration and compound [3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile is designated herein as having an "R" configuration. Enantiomerically pure products derived from [3aS-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile are designated herein as having an "S" configuration and enantiomerically pure products derived from [3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile are designated herein as having an "R" configuration. Enantiomerically pure products derived from [3aR-(3aα,4β,5β,7β,7aα)]-4-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-2-(trifluoromethyl)-benzonitrile are designated herein as having a "R" configuration and enantiomerically pure products derived from [3aS-(3aα,4β,5β,7β,7aα)]-4-[7-[2-[[(1,1-Dimethyl-ethyl)dimethylsilyl]oxy]ethyl]octahydro-5-hydroxy-4-methyl-1,3-dioxo-4,7-epoxy-2H-isoindol-2-yl]-2-(trifluoromethyl)benzonitrile are designated herein as having an "S" configuration.

The chromatography techniques used to determine the compound retention times of Table 1 are as follows: LCMS= YMC S5 ODS column, 4.6×50 mm eluting with 10–90% MeOH/H2O over 4 minutes containing 0.1% TFA; 4 mL/min, monitoring at 220 nm; LC=YMC S5 ODS column, 4.6×50 mm eluting with 10–90% MeOH/H2O over 4 minutes containing 0.2% phosphoric acid; 4 mL/min, monitoring at 220 nm. The molecular mass of the compounds listed in Table 1, where provided, were determined by MS(ES) by the formula m/z.

TABLE 1

| Cmp # | Structure | Compound Name | Retention Time Min./Molecular Mass | Proc. of Ex. |
|---|---|---|---|---|
| 1 | 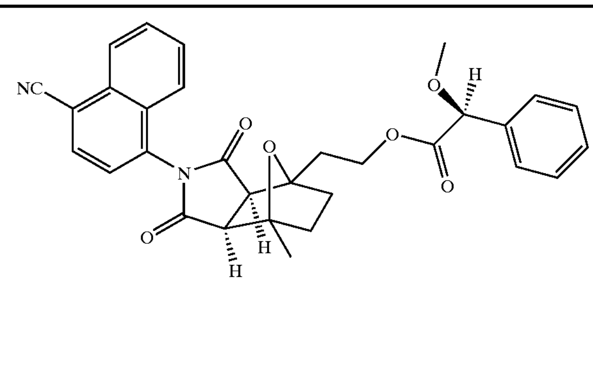 | (αR)-α-Methoxybenzeneacetic acid, 2-[(3aα,4β,7β,7aα)-2-(4-cyano-1-naphthalenyl)octahydro-7-methyl-1,3-dioxo-4,7-epoxy-4H-isoindol-4-yl]ethyl ester. | 3.28 & 3.74 LC Atrop Isomers 547.26 [M + Na]+ | 2f, 2j |

TABLE 1-continued

| Cmp # | Structure | Compound Name | Retention Time Min./Molecular Mass | Proc. of Ex. |
|---|---|---|---|---|
| 2 | 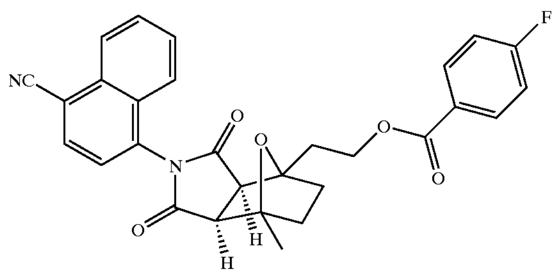 | 4-Fluorobenzoic acid, 2-[(3aα,4β,7β,7aα)-2-(4-cyano-1-naphthalenyl)octahydro-7-methyl-1,3-dioxo-4,7-epoxy-4H-isoindol-4-yl]ethyl ester. | 3.64 & 3.77 LC Atrop Isomers 499.8 [M + Na]$^+$ | 2f, 2j |
| 3 | 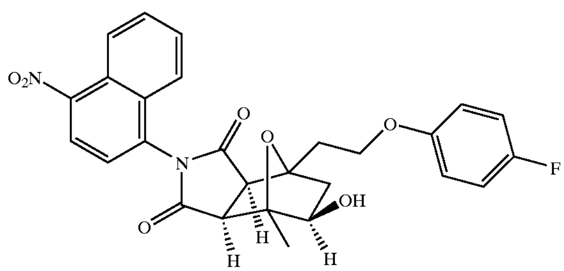 | (3aα,4β,7β,7aα)-7-[2-(4-Fluorophenoxy)ethyl]-hexahydro-5-hydroxy-4-methyl-2-(4-nitro-1-naphthalenyl)-4,7-epoxy-1H-isoindole-1,3(2H)-dione. | 3.53 LC 505.2 [M − H]$^-$ | 2k |
| 4 | 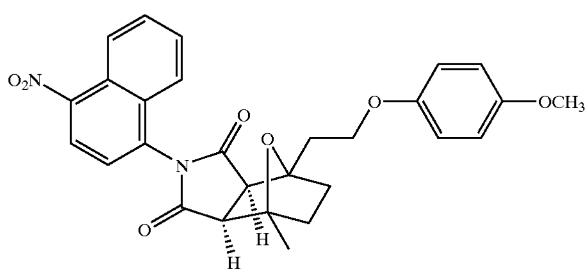 | (3aα,4β,7β,7aα)-Hexahydro-4-[2-(4-methoxyphenoxy)ethyl]-7-methyl-2-(4-nitro-1-naphthalenyl)-4,7-epoxy-1H-isoindole-1,3(2H)-dione. | 3.42 & 3.55 LC Atrop Isomers 503.21 [M + Na]$^+$ | 2f, 2j |
| 5 | 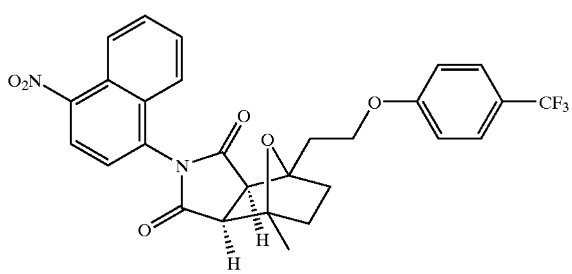 | (3aα,4β,7β,7aα)-Hexahydro-4-methyl-2-(4-nitro-1-naphthalenyl)-7-[2-[4-(trifluoromethyl)phenoxy]ethyl]-4,7-epoxy-1H-isoindole-1,3(2H)-dione. | 3.81 & 3.93 LC Atrop Isomers 563.12 [M + Na]$^+$ | 2f, 2j |
| 6 | 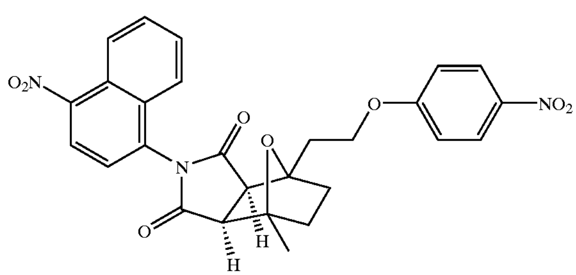 | (3aα,4β,7β,7aα)-Hexahydro-4-methyl-2-(4-nitro-1-naphthalenyl)-7-[2-(4-nitrophenoxy)ethyl]-4,7-epoxy-1H-isoindole-1,3(2H)-dione. | 3.48 & 3.61 LC Atrop Isomers 540.17 [M + Na]$^+$ | 2f, 2j |

TABLE 1-continued

| Cmp # | Structure | Compound Name | Retention Time Min./Molecular Mass | Proc. of Ex. |
|---|---|---|---|---|
| 7 | 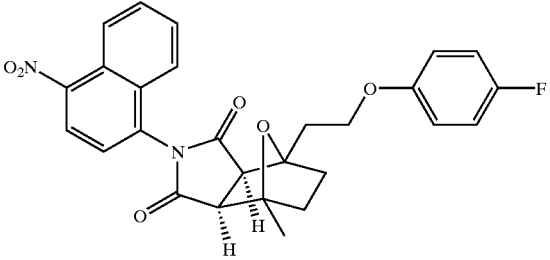 | (3aα,4β,7β,7aα)-4-[2-(4-Fluorophenoxy)ethyl]-hexahydro-7-methyl-2-(4-nitro-1-naphthalenyl)-4,7-epoxy-1H-isoindole-1,3(2H)-dione. | 3.48 & 3.61 LC Atrop Isomers 491.46 [M + H]$^+$ | 2f, 2j |
| 8 | 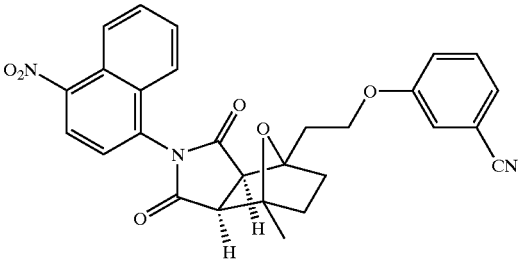 | (3aα,4β,7β,7aα)-4-[Octahydro-7-methyl-2-(4-nitro-1-naphthalenyl)-1,3-dioxo-4,7-epoxy-4H-isoindol-4-yl]ethoxy]benzonitrile. | 3.63 LC 498.12 [M + H]$^+$ | 2f, 2j |
| 9 | 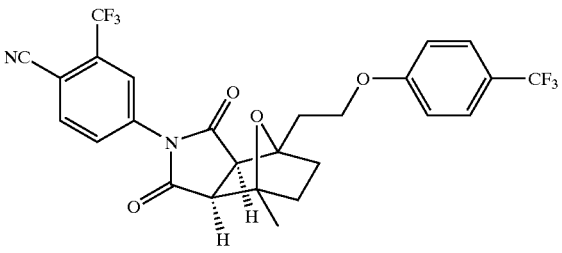 | (3aα,4β,7β,7aα)-4-[Octahydro-4-methyl-1,3-dioxo-7-[2-[4-(trifluoromethyl)phenoxy]ethyl]-4,7-epoxy-2H-isoindol-2-yl]-2-(trifluoromethyl)benzonitrile. | 3.93 LC | 2f, 2j |
| 10 | 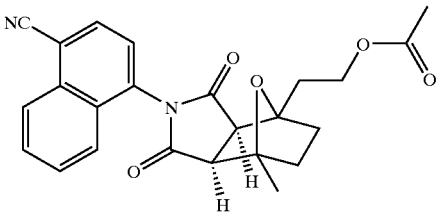 | (3aα,4β,7β,7aα)-4-[2-(Acetyloxy)ethyl]-2-(4-cyano-1-naphthalenyl)hexahydro-7-methyl-4,7-epoxy-1H-isoindole-1,3(2H)-dione. | 2.84 & 3.03 LC Atrop Isomers | 2f, 2j |
| 11 | 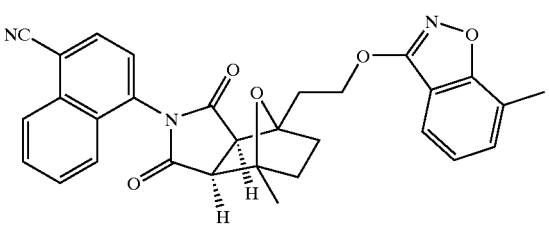 | (3aα,4β,7β,7aα)-4-[Octahydro-4-methyl-7-[2-[(7-methyl-1,2-benzisoxazol-3-yl)oxy]ethyl]-1,3-dioxo-4,7-epoxy-2H-isoindol-2-yl]-1-naphthalenecarbonitrile. | 3.79 & 3.92 LC Atrop Isomers | 2r |
| 12 | 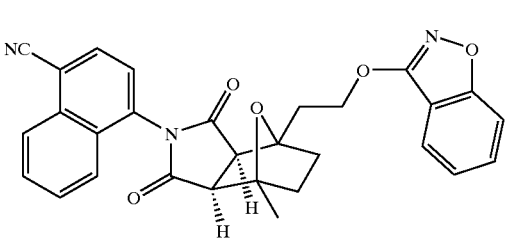 | (3aα,4β,7β,7aα)-4-[4-[2-(1,2-Benzisoxazol-3-yloxy)ethyl]octahydro-7-methyl-1,3-dioxo-4,7-epoxy-2H-isoindol-2-yl]-1-naphthalenecarbonitrile. | 3.55 & 3.70 LC Atrop Isomers | 2r |

TABLE 1-continued

| Cmp # | Structure | Compound Name | Retention Time Min./Molecular Mass | Proc. of Ex. |
|---|---|---|---|---|
| 13 | 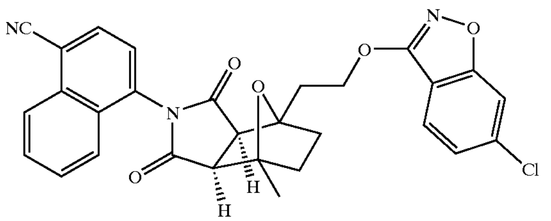 | (3aα,4β,7β,7aα)-4-[4-[2-[(6-Chloro-1,2-benzisoxazol-3-yl)oxy]ethyl]octahydro-7-methyl-1,3-dioxo-4,7-epoxy-2H-isoindol-2-yl]-1-naphthalenecarbonitrile. | 3.89 & 4.02 LC Atrop Isomers 528.0 [M + H]$^+$ | 2r |
| 14 | 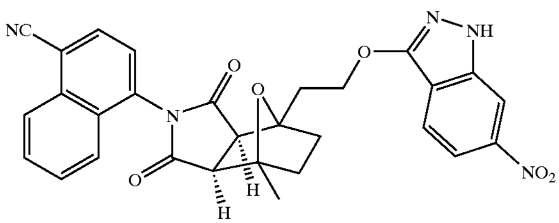 | (3aα,4β,7β,7aα)-4-[Octahydro-4-methyl-7-[2-[(6-nitro-1H-indazol-3-yl)oxy]ethyl]-1,3-dioxo-4,7-epoxy-2H-isoindol-2-yl]-1-naphthalenecarbonitrile. | 3.60 & 3.74 LC Atrop Isomers 536.0 [M − H]$^-$ | 2s |
| 15 | 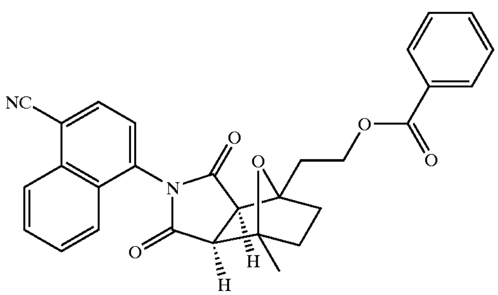 | (3aα,4β,7β,7aα)-4-[2-(Benzoyloxy)ethyl]-2-(4-cyano-1-naphthalenyl)hexahydro-7-methyl-4,7-epoxy-1H-isoindole-1,3(2H)-dione. | 3.51 & 3.66 LC Atrop Isomers | 2f, 2j |
| 16 | 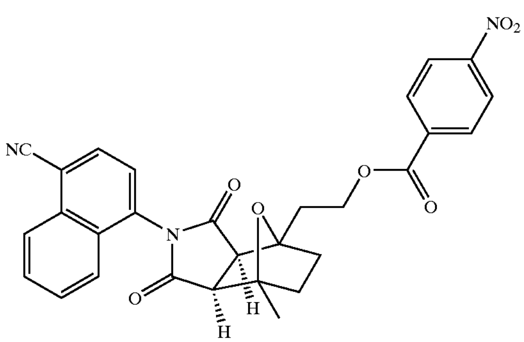 | (3aα,4β,7β,7aα)-2-(4-Cyano-1-naphthalenyl)-4-[2-[(4-nitrobenzoyl)oxy]ethyl]hexahydro-7-methyl-4,7-epoxy-1H-isoindole-1,3(2H)-dione. | 3.52 & 3.67 LC Atrop Isomers | 2f, 2j |
| 17 | 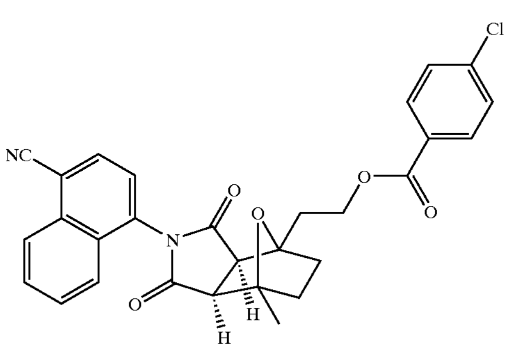 | 4-Chlorobenzoic acid, 2-[(3aα,4β,7β,7aα)-2-(4-cyano-1-naphthalenyl)octahydro-7-methyl-1,3-dioxo-4,7-epoxy-4H-isoindol-4-yl]ethyl ester. | 3.79 & 3.83 LC Atrop Isomers | 2f, 2j |

TABLE 1-continued

| Cmp # | Structure | Compound Name | Retention Time Min./Molecular Mass | Proc. of Ex. |
|---|---|---|---|---|
| 18 | 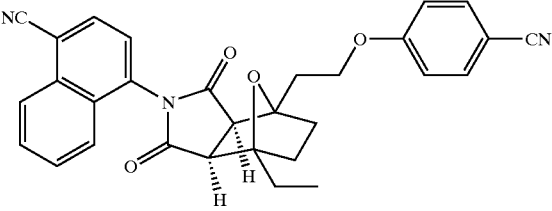 | (3aα,4β,7β,7aα)-4-[4-[2-(4-Cyanophenoxy)ethyl]-7-ethyloctahydro-1,3-dioxo-4,7-epoxy-2H-isoindol-2-yl]-1-naphthalenecarbonitrile. | 3.65 LC 492.16 [M + H]+ | 2v |
| 19 | 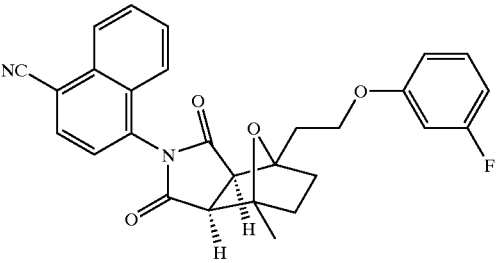 | [3aR-(3aα,4β,7β,7aα)]-4-[4-[2-(3-Fluorophenoxy)ethyl]-octahydro-7-methyl-1,3-dioxo-4,7-epoxy-2H-isoindol-2-yl]-1-naphthalenecarbonitrile. | 3.80 LC 471.65 [M + H]+ | 2n, 2o |
| 20 | 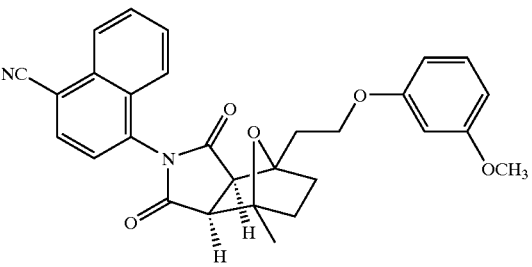 | [3aR-(3aα,4β,7β,7aα)]-4-[Octahydro-4-[2-(3-methoxyphenoxy)ethyl]-7-methyl-1,3-dioxo-4,7-epoxy-2H-isoindol-2-yl]-1-naphthalenecarbonitrile. | 3.73 LC 483.65 [M + H]+ | 2n, 2o |
| 21 | 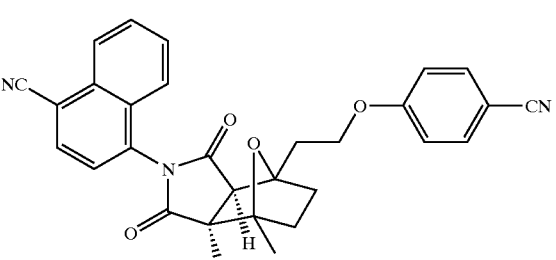 | [3aR-(3aα,4β,7β,7aα)]-4-[4-[2-(4-Cyanophenoxy)ethyl]-octahydro-7-methyl-1,3-dioxo-4,7-epoxy-2H-isoindol-2-yl]-1-naphthalenecarbonitrile. | 3.80 LC | 2n, 2o |
| 22 | 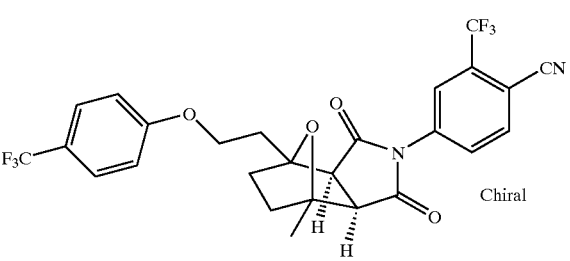 | [3aR-(3aα,4β,7β,7aα)]-4-[Octahydro-4-methyl-1,3-dioxo-7-[2-[4-(trifluoromethyl)phenoxy]ethyl]-4,7-epoxy-2H-isoindol-2-yl]-2-(trifluoromethyl)benzonitrile, faster eluting antipode. | 3.93 LC | 2i |

TABLE 1-continued

| Cmp # | Structure | Compound Name | Retention Time Min./Molecular Mass | Proc. of Ex. |
|---|---|---|---|---|
| 23 | 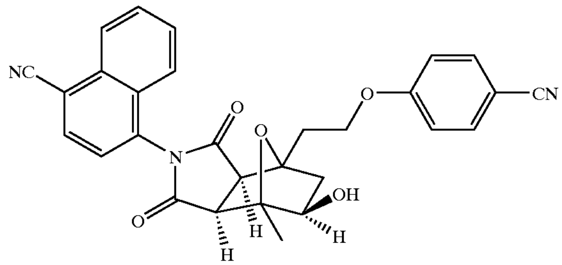 | [3aR-(3aα,4β,5β,7β,7aα]-4-[7-[2-(4-Cyanophenoxy)ethyl]-octahydro-5-hydroxy-4-methyl-1,3-dioxo-4,7-epoxy-2H-isoindol-2-yl]-1-naphthalenecarbonitrile. | 3.07 LC 494.09 [M + H]$^+$ | 2p, 2q |
| 24 | 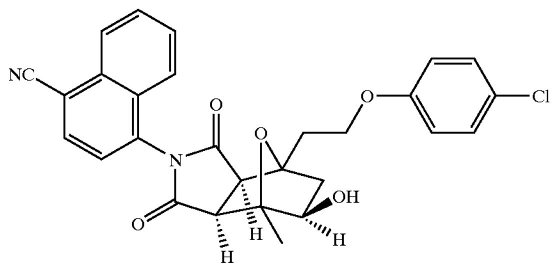 | [3aR-(3aα,4β,5β,7β,7aα]-4-[7-[2-(4-Chlorophenoxy)ethyl]-octahydro-5-hydroxy-4-methyl-1,3-dioxo-4,7-epoxy-2H-isoindol-2-yl]-1-naphthalenecarbonitrile. | 3.51 LC 503.08 [M + H]$^+$ | 2p, 2q |
| 25 | 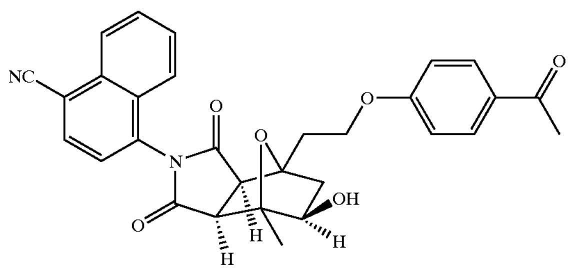 | [3aR-(3aα,4β,5β,7β,7aα]-4-[7-[2-(4-Acetylphenoxy)ethyl]-octahydro-5-hydroxy-4-methyl-1,3-dioxo-4,7-epoxy-2H-isoindol-2-yl]-1-naphthalenecarbonitrile. | 3.05 LC 511.13 [M + H]$^+$ | 2p, 2q |
| 26 | 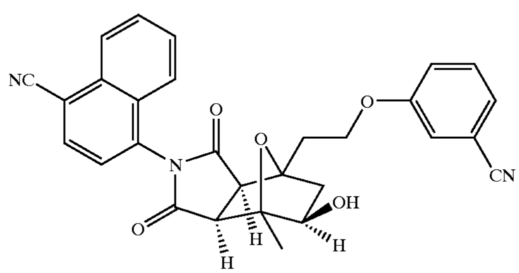 | [3aR-(3aα,4β,5β,7β,7aα]-4-[7-[2-(3-Cyanophenoxy)ethyl]-octahydro-5-hydroxy-4-methyl-1,3-dioxo-4,7-epoxy-2H-isoindol-2-yl]-1-naphthalenecarbonitrile. | 3.85 LC 494.13 [M + H]$^+$ | 2p, 2q |
| 27 | 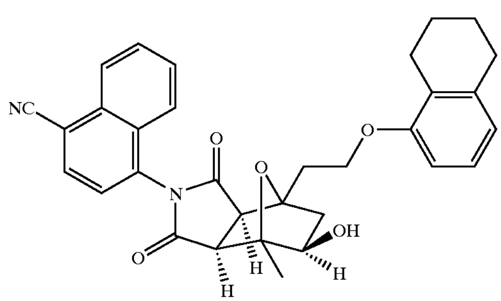 | [3aR-(3aα,4β,5β,7β,7aα]-4-[Octahydro-5-hydroxy-4-methyl-1,3-dioxo-7-[2-[(5,6,7,8-tetrahydro-1-naphthalenyl)oxy]ethyl]-4,7-epoxy-2H-isoindol-2-yl]-1-naphthalenecarbonitrile. | 3.85 LC 523.17 [M + H]$^+$ | 2p, 2q |

TABLE 1-continued

| Cmp # | Structure | Compound Name | Retention Time Min./Molecular Mass | Proc. of Ex. |
|---|---|---|---|---|
| 28 | 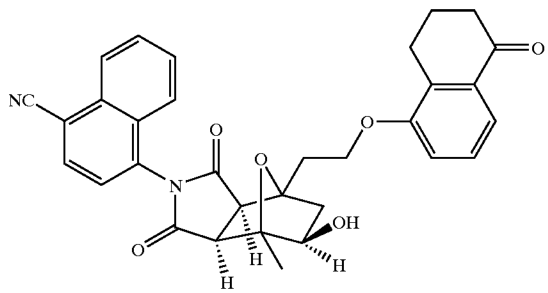 | [3aR-(3aα,4β,5β,7β,7aα]-4-[Octahydro-5-hydroxy-4-methyl-1,3-dioxo-7-[2-[(5,6,7,8-tetrahydro-5-oxo-1-naphthalenyl)oxy]ethyl]-4,7-epoxy-2H-isoindol-2-yl]-1-naphthalenecarbonitrile. | 3.29 LC 537.13 [M + H]+ | 2p, 2q |
| 29 | 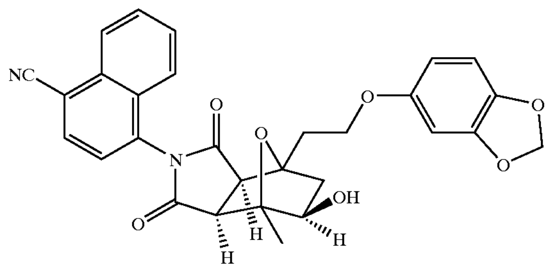 | [3aR-(3aα,4β,5β,7β,7aα]-4-[7-[2-(1,3-Benzodioxol-5-yloxy)ethyl]oxtahydro-5-hydroxy-4-methyl-1,3-dioxo-4,7-epoxy-2H-isoindol-2-yl]-1-naphthalenecarbonitrile. | 3.22 LC 571.2 [M − H + OAc]− | 2p, 2q |
| 30 | 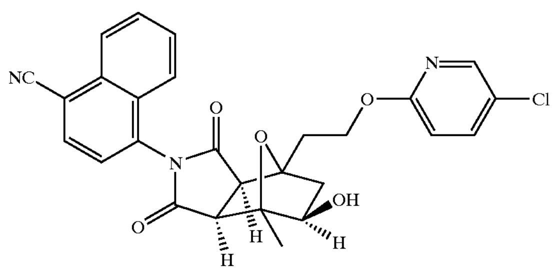 | [3aR-(3aα,4β,5β,7β,7aα]-4-[7-[2-[(5-Chloro-2-pyridinyl)oxy]ethyl]-octahydro-5-hydroxy-4-methyl-1,3-dioxo-4,7-epoxy-2H-isoindol-2-yl]-1-naphthalenecarbonitrile. | 3.37 LC 504.0 [M + H]+ | 2p, 2q |
| 31 | 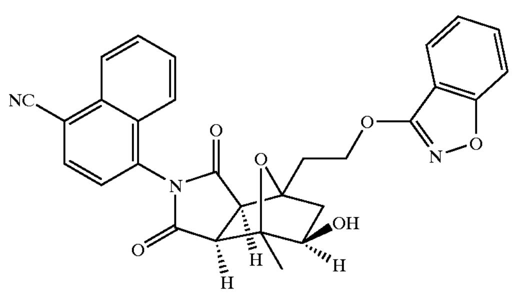 | [3aR-(3aα,4β,5β,7β,7aα]-4-[7-[2-(1,2-Benzisoxazol-3-yloxy)ethyl]octahydro-5-hydroxy-4-methyl-1,3-dioxo-4,7-epoxy-2H-isoindol-2-yl]-1-naphthalenecarbonitrile | 3.29 LC 510.4 [M + H]+ | 2p, 2q |
| 32 | 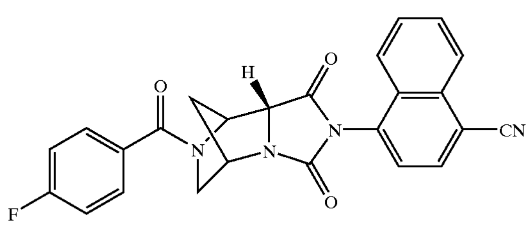 | [5S-(5α,8α,8aα)]-2-(4-Cyano-1-naphthalenyl)-7-(4-fluorobenzoyl)tetrahydro-5,8-methanoimidazo[1,5-a]pyrazine-1,3(2H,5H)-dione. | 2.76 LC 441.09 [M + H]+ | 2d |

TABLE 1-continued

| Cmp # | Structure | Compound Name | Retention Time Min./Molecular Mass | Proc. of Ex. |
|---|---|---|---|---|
| 33 | 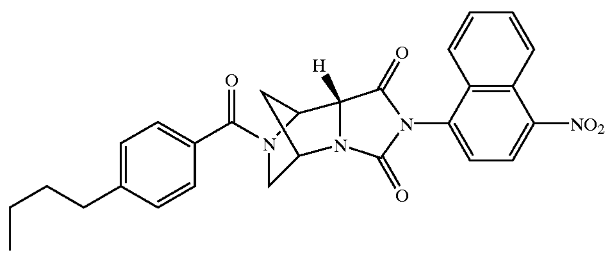 | [5S-(5α,8α,8aα)]-7-(4-Butylbenzoyl)tetrahydro-2-(4-nitro-1-naphthalenyl)-5,8-methanoimidazo[1,5-a]pyrazine-1,3(2H,5H)-dione. | 3.69 LC 499.45 [M + H]+ | 2d |
| 34 | 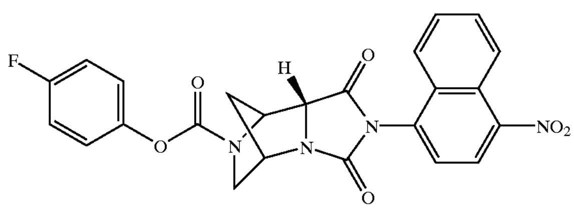 | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-fluorophenyl ester. | 3.21 LC 477.38 [M + H]+ | 2d |
| 35 | 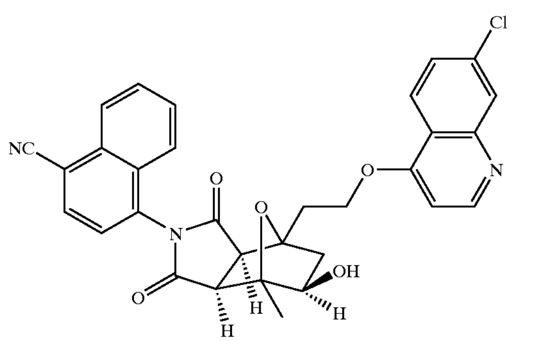 | [3aR-(3aα,4β,7β,7aα)]-4-[7-[2-[(7-Chloro-4-quinolinyl)oxy]ethyl]-octahydro-5-hydroxy-4-methyl-1,3-dioxo-4,7-epoxy-2H-isoindol-2-yl]-1-naphthalenecarbonitrile, trifluoroacetate (1:1). | 2.53 LC 554.27 [M + H]+ | 2p, 2q |
| 36 | 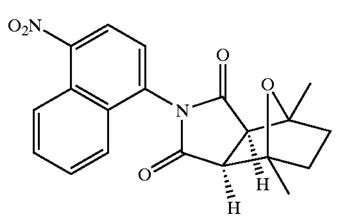 | (3aα,4β,7β,7aα)-Hexahydro-4,7-dimethyl-2-(4-nitro-1-naphthalenyl)-4,7-epoxy-1H-isoindole-1,3(2H)-dione. | 3.04 LCMS | 2e |
| 37 | 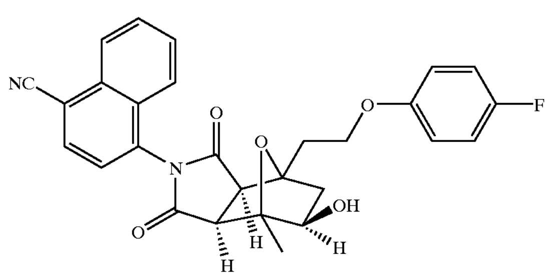 | [3aR-(3aα,4β,7β,7aα)]-4-[7-[2-(4-Fluorophenoxy)ethyl]-octahydro-5-hydroxy-4-methyl-1,3-dioxo-4,7-epoxy-2H-isoindol-2-yl]-1-naphthalenecarbonitrile. | 3.27 LC 487.11 [M + H]+ | 2p, 2q |

TABLE 1-continued

| Cmp # | Structure | Compound Name | Retention Time Min./Molecular Mass | Proc. of Ex. |
|---|---|---|---|---|
| 38 | 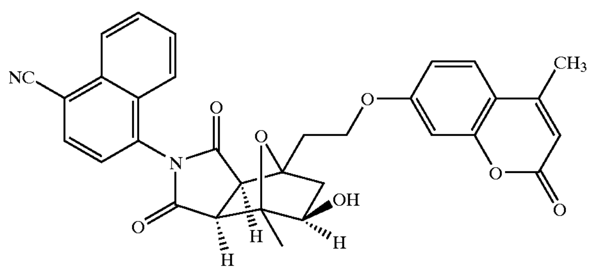 | [3aR-(3aα,4β,7β,7aα)]-4-[Octahydro-5-hydroxy-4-methyl-7-[2-[(4-methyl-2-oxo-2H-1-benzopyran-7-yl)oxy]ethyl]-1,3-dioxo-4,7-epoxy-2H-isoindol-2-yl]-1-naphthalenecarbonitrile. | 3.15 LC 551.15 [M + H]$^+$ | 2p, 2q |
| 39 | 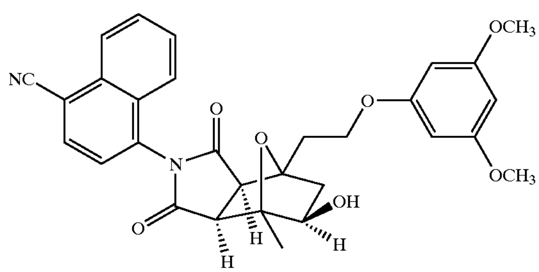 | [3aR-(3aα,4β,7β,7aα)]-4-[7-[2-(3,5-Dimethoxyphenoxy)-ethyl]octahydro-5-hydroxy-4-methyl-1,3-dioxo-4,7-epoxy-2H-isoindol-2-yl]-1-naphthalenecarbonitrile. | 3.26 LC 529.12 [M + H]$^+$ | 2p, 2q |
| 40 | 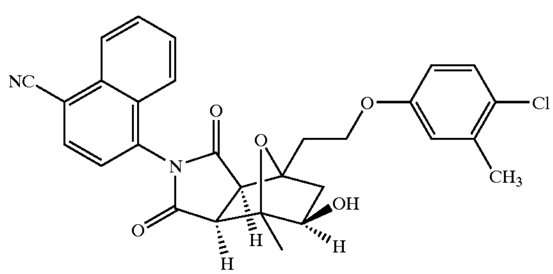 | [3aR-(3aα,4β,7β,7aα)]-]-4-[7-[2-(4-Chloro-3-methylphenoxy)ethyl]-octahydro-5-hydroxy-4-methyl-1,3-dioxo-4,7-epoxy-2H-isoindol-2-yl]-1-naphthalenecarbonitrile | 3.68 LC 517.33 [M + H]$^+$ | 2p, 2q |
| 41 | 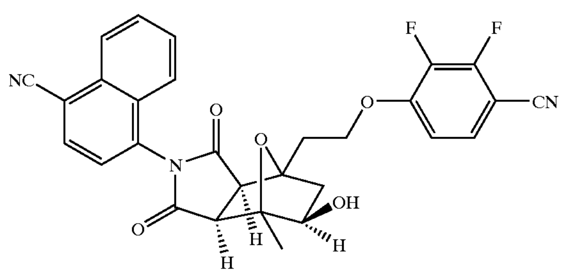 | [3aR-(3aα,4β,7β,7aα)]-4-[7-[2-(4-Cyano-2,3-difluorophenoxy)ethyl]octahydro-5-hydroxy-4-methyl-1,3-dioxo-4,7-epoxy-2H-isoindol-2-yl]-1-naphthalenecarbonitrile. | 3.23 LC 530.13 [M + H]$^+$ | 2p, 2q |
| 42 | 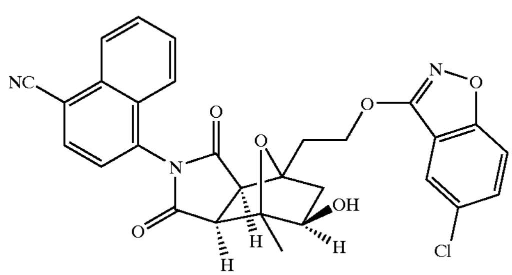 | [3aR-(3aα,4β,7β,7aα)]-4-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-1-naphthalenecarbonitrile. | 3.57 LC 602.0 [M − H + OAc]$^-$ | 2p, 2q |

TABLE 1-continued

| Cmp # | Structure | Compound Name | Retention Time Min./Molecular Mass | Proc. of Ex. |
|---|---|---|---|---|
| 43 | 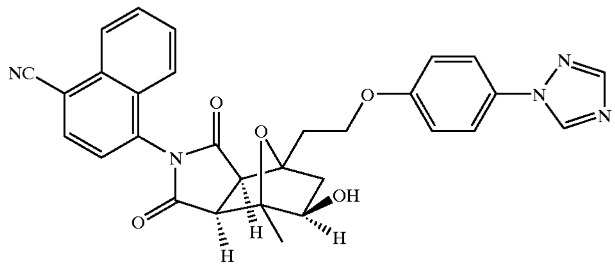 | [3aR-(3aα,4β,7β,7aα)]-4-[Octahydro-5-hydroxy-4-methyl-1,3-dioxo-7-[2-[4-(1H-1,2,4-triazol-1-yl)phenoxy]ethyl]-4,7-epoxy-2H-isoindol-2-yl]-1-naphthalenecarbonitrile. | 2.93 LC 536.30 [M + H]$^+$ | 2p, 2q |
| 44 | 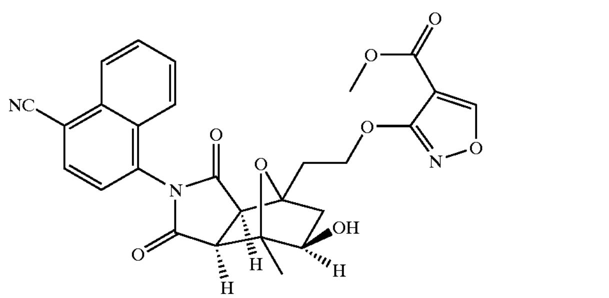 | [3aR-(3aα,4β,7β,7aα)]-3-[2-[2-(4-Cyano-1-naphthalenyl)octahydro-6-hydroxy-7-methyl-1,3-dioxo-4,7-epoxy-4H-isoindol-4-yl]ethoxy]-5-isoxazolecarboxylic acid, methyl ester. | 2.90 LC 518.27 [M + H]$^+$ | 2p, 2q |
| 46 | 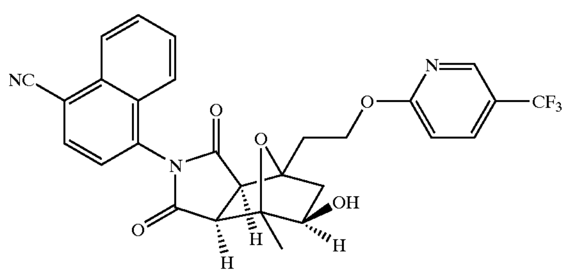 | [3aR-(3α,4β,5β,7β,7aα)]-4-[Octahydro-5-hydroxy-4-methyl-1,3-dioxo-7-[2-[[5-(trifluoromethyl)-2-pyridinyl]oxy]ethyl]-4,7-epoxy-2H-isoindol-2-yl]-1-naphthalenecarbonitrile | 3.45 LC 538.23 [M + H]$^+$ | 2p, 2q |
| 47 | 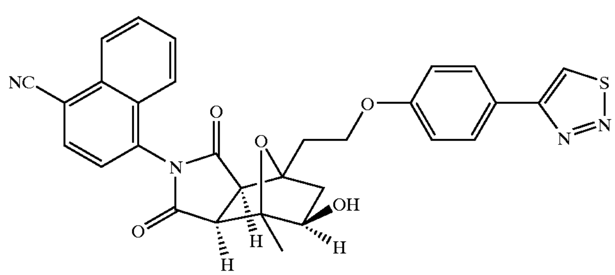 | [3aR-(3α,4β,5β,7β,7aα)]-4-[Octahydro-5-hydroxy-4-methyl-7-[2-[4-(1,2,3-thiadiazol-5-yl)phenoxy]ethyl]-1,3-dioxo-4,7-epoxy-2H-isoindol-2-yl]-1-naphthalenecarbonitrile | 3.20 LC 553.25 [M + H]$^+$ | 2p, 2q |
| 48 | 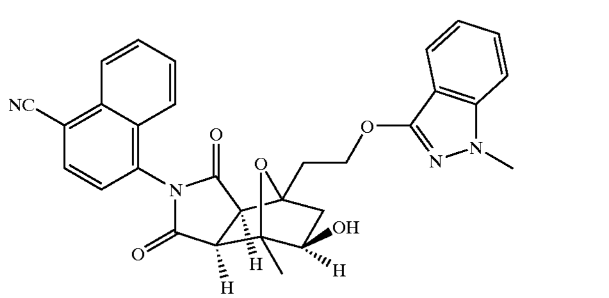 | [3aR-(3α,4β,5β,7β,7aα)[-4-[Octahydro-5-hydroxy-4-methyl-7-[2-[(1-methyl-1H-indazol-3-yl)oxy]ethyl]-1,3-dioxo-4,7-epoxy-2H-isoindol-2-yl]-1-naphthalenecarbonitrile | 3.33 LC | 2p, 2q |

TABLE 1-continued

| Cmp # | Structure | Compound Name | Retention Time Min./Molecular Mass | Proc. of Ex. |
|---|---|---|---|---|
| 49 | 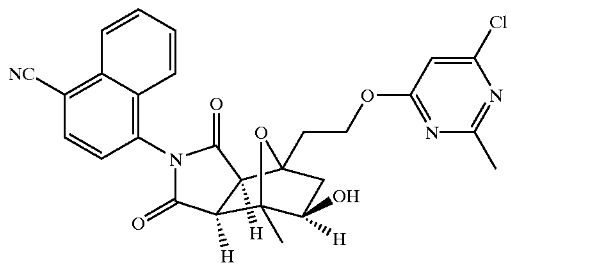 | [3aR-(3aα,4β,5β,7β,7aα)]-4-[7-[2-[(6-Chloro-2-methyl-4-pyrimidinyl)oxy]ethyl]octahydro-5-hydroxy-4-methyl-1,3-dioxo-4,7-epoxy-2H-isoindol-2-yl]-1-naphthalenecarbonitrile | 3.02 LC | 2p, 2q |
| 50 | 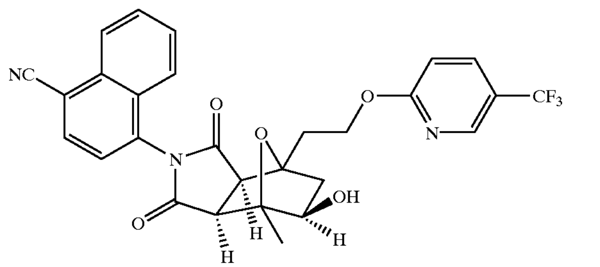 | [3aR-(3aα,4β,5β,7β,7aα)]-4-[Octahydro-5-hydroxy-4-methyl-1,3-dioxo-7-[2-[[5-(trifluoromethyl)-2-pyridinyl]oxy]ethyl]-4,7-epoxy-2H-isoindol-2-yl]-1-naphthalenecarbonitrile | 3.46 LC 538.24 [M + H]$^+$ | 2p, 2q |
| 60 | 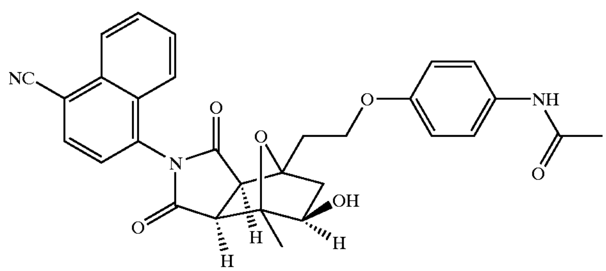 | [3aR-(3aα,4β,5β,7β,7aα)]-N[4-[2-[2-(4-Cyano-1-naphthalenyl)octahydro-5-hydroxy-4-methyl-1,3-dioxo-4,7-epoxy-7H-isoindol-7-yl]ethoxy]phenyl]acetamide | 2.747 LC 526.28 [M + H]$^+$ | 2p, 2q |
| 61 | 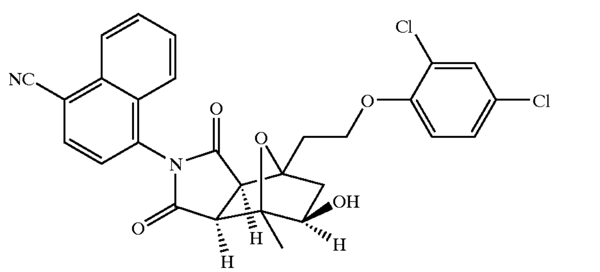 | [3aR-(3aα,4β,5β,7β,7aα)]-4-[7-[2-(2,4-Dichlorophenoxy)ethyl]octahydro-5-hydroxy-4-methyl-1,3-dioxo-4,7-epoxy-2H-isoindol-2-yl]-1-naphthalenecarbonitrile | 3.71 LC 537.17 [M + H]$^+$ | 2p, 2q |
| 62 | 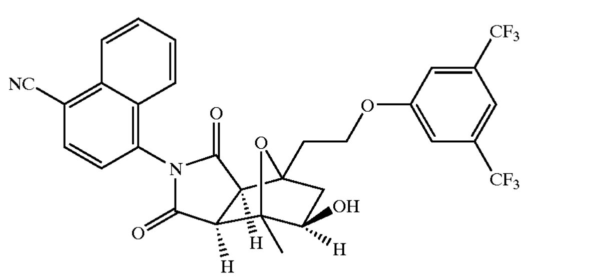 | [3aR-(3aα,4β,5β,7β,7aα)]-4-[7-[2-[3,5-Bis(trifluoromethyl)phenoxy]ethyl]octahydro-5-hydroxy-4-methyl-1,3-dioxo-4,7-epoxy-2H-isoindol-2-yl]-1-naphthalenecarbonitrile | 3.89 LC 605.25 [M + H]$^+$ | 2p, 2q |

TABLE 1-continued

| Cmp # | Structure | Compound Name | Retention Time Min./Molecular Mass | Proc. of Ex. |
|---|---|---|---|---|
| 63 | 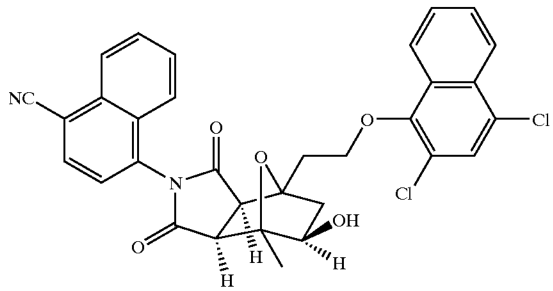 | [3aR-(3aα,4β,5β,7β,7aα)]-4-[7-[2-[(5,7-Dichloro-8-quinolinyl)oxy]ethyl]-octahydro-5-hydroxy-4-methyl-1,3-dioxo-4,7-epoxy-2H-isoindol-2-yl]-1-naphthalene carbonitrile, trifluoroacetate (1:1) | 3.70 LC 588.26 [M + H]$^+$ | 2p, 2q |
| 64 | 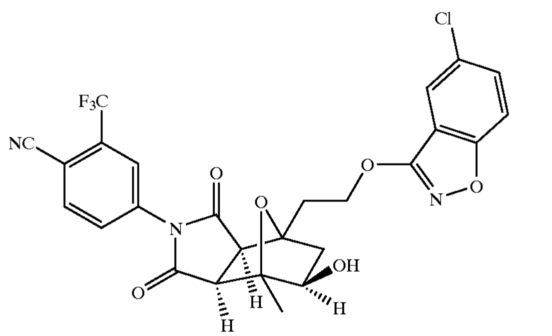 | [3aS-(3aα,4β,5β,7β,7aα)]-4-7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-2-(trifluoromethyl) benzonitrile | 3.563 LC 562.08 [M + H]$^+$ | 2a(i) |
| 65 | 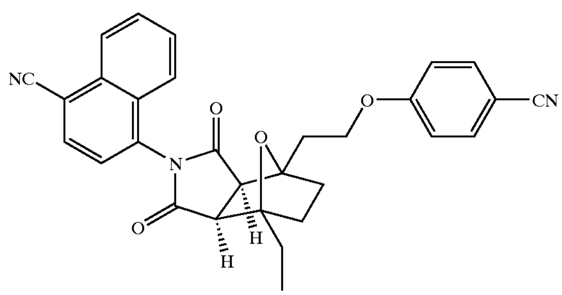 | (3aα,4β,7β,7aα)-4-[2-(4-Cyanophenoxy)ethyl]-7-ethyloctahydro-1,3-dioxo-4,7-epoxy-2H-isoindol-2-yl]-1-naphthalenecarbonitrile | 3.65 LC 562.08 [M + H]$^+$ | 2v |
| 66 | 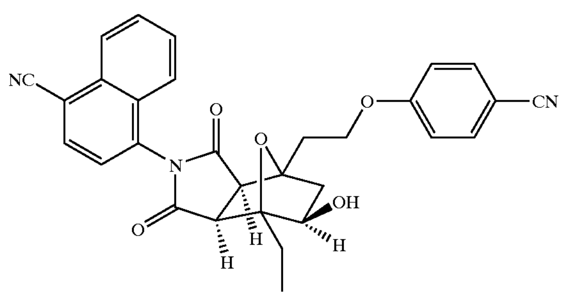 | (3aα,4β,5β,7β,7aα)-4-[7-[2-(4-Cyanophenoxy)ethyl]-4-ethyloctahydro-5-hydroxy-1,3-dioxo-4,7-epoxy-2H-isoindol-2-yl]-1-naphthalenecarbonitrile | 3.15 LC 508.14 [M + H]$^+$ | 2c(i) |
| 67 | 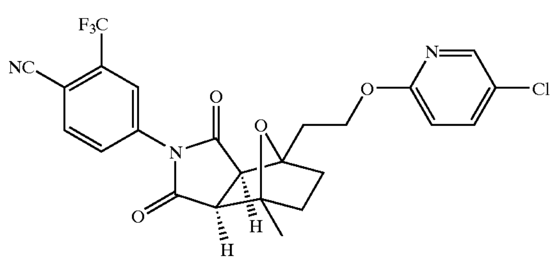 | [3aR-(3aα,4β,5β,7β,7aα)]-4-[7-[2-[(5-Chloro-2-pyridinyl)oxy]ethyl]-octahydro-5-hydroxy-4-methyl-1,3-dioxo-4,7-epoxy-2H-isoindol-2-yl]-2-(trifluoromethyl)benzonitrile | 3.37 LC 522.08 [M + H]$^+$ | 2a(i) |

The in vitro activity of these exemplary SARMs was examined in the MDA MB-453 breast tumor line reporter assay, the Shionogi mouse breast tumor line proliferation assay and C2C12 muscle cell reporter assay. Both the $IC_{50}$ (antagonist mode, in the presence of DHT) and the $EC_{50}$ (agonist mode, in the absence of DHT) relative to the maximal signal obtained by DHT were determined. In addition, for the reporter assays, % activation (absence of DHT) and % inhibition (presence of DHT) at a set drug concentration relative to DHT were determined. For the Shionogi proliferation assay, the % proliferation (absence of DHT) and % inhibition (presence of DHT) of proliferation at a set drug concentration relative to DHT were also determined. Unless indicated in the above Table, compounds were presented as a racemic mixture. While differing in some degree in their level of activity, all the exemplary compounds in the above Table demonstrated a SARM profile in accordance with the present invention.

Specifically, all exemplary SARMs tested exhibited an $IC_{50}$ of less than 0.8 $\mu M$ and an $EC_{50}$ of greater than 5 $\mu M$ in the MDA MB-453 breast tumor line reporter assay. Similar results were observed in the Shionogi mouse breast tumor line proliferation assay for a number of the SARMs tested. Specifically, several of the compounds exhibited an $IC_{50}$ of less than 0.8 $\mu M$ and an $EC_{50}$ of greater than 5 $\mu M$. In contrast, in the C2C12 muscle cell reporter assay a number of the compounds tested exhibited an $IC_{50}$ of 3 $\mu M$ or greater and a particularly preferred subset of the compounds tested exhibited an $EC_{50}$ of less than 0.8 $\mu M$ or an agonist activity of greater than 25%. Preferred exemplary SARMs of Table 1, which were tested, include Compounds, 3, 7, 11, 13, 19, 23, 24, 25, 30, 31 and 67.

In addition, the effects of SARMS of Table 1 were compared with full AR antagonists in a Mature Rat Prostate Weight Assay (MRPW, Example 9). To compare the effect of AR full antagonists with SARM Compounds 7, 9, and 36 on ventral prostate (VP), seminal vesicles (SV), levator ani (LA), and Leutinizing hormone (LH) serum levels, mature male rats (n=5) were dosed orally for fourteen consecutive days followed by analysis of organ weights and serum. Compared with the full AR antagonists, in particular, the Compound 2e (prepared in Example 2 below) and Casodex (a known AR antagonist) which showed significant inhibitory effects, SARM Compounds 9 and 36 showed only a modest inhibitory effect on VP, SV, and LA weights at the highest dose (100 mg/kg or "mpk"). Compound 7, also exhibiting only modest inhibition fuirther showed (in contrast with Compounds 9 and 36) a reverse dose response, being even less potent as an inhibitor of VP, SV and LA weights at 100 mpk. The serum LH levels were very similar to the intact controls suggesting very weak, if any, activity of these SARMs at the hypothalamus-pituitary axis.

In vivo agonist activities of the SARM Compounds 7 and 9 of the present invention were also examined in the Rat Levator Ani Muscle Model (Example 8) using a preventative schedule of drug administration. In this animal model, sexually mature (6–8 weeks old) male Sprague-Dawley rats were used. The rats were castrated and broken up into treatment groups and treated with test materials beginning three days following surgery. Potential SARM effects of Compounds 7 and 9 were compared to testosterone via a dose-response study comparing testosterone proprionate (0.3 mg/kg–3 mg/kg) to these SARMs. Both SARMs were tested at 90 mg/kg via oral delivery. Compound 7 increased the levator ani wet weight by 27% compared to the vehicle-treated castrated control while having no effect on the prostate wet weight. Compound 9 was ineffective on both the levator ani muscle and prostate.

Compounds 7 and 9 (which are racemic) were also compared with Casodex in the CWR-22 prostate carcinoma model in nude mice (n=8). All three compounds were administered orally for 14 consecutive days. Both Compounds 7 and 9 exhibited inhibition similar to Casodex (150 mg/kg) when dosed at 75 rnpk. The two antipodes of Compound 9 were then separated into Compound 22 (shown in Table 1) and its mirror image Compound 22' (not shown in Table 1). Both compounds were tested in vivo in the immature wet prostate weight assay. Compound 22 showed little activity in the normal tissues while the full antagonist enantiomer Compound 22' showed clear activity and a dose response. This is unexpected given the stronger binding affinity and antagonist activity (in MID-453) of Compound 5 22. Testing of both compounds in the CWR22 human prostate xenograft model showed the opposite activity profile: Compound 22 was as potent as Casodex (150 mg/kg) at a 19 mg/kg dose while Compound 22' showed no significant activity at the maximum dose tested (75 mpk).

The in vivo data obtained mirrored the in vitro data, showing that the compounds were antagonists to the two AR dependent tumor cell lines while being agonists towards the normal muscle cell line.

Example 2

Chemical Synthesis of SARMs

Exemplary chemical syntheses of SARMs of the present invention are included in the following Examples 2a–2d(i). As will be understood by those of skill in the art upon reading this disclosure, other methods than those set forth herein can also be used in the synthesis of these exemplary SARMs.

The following abbreviations are used herein:
DBU=1,8-diazabicyclo[5.4.0]undec-7-ene
4-DMAP=4-dimethylaminopyridine
ee=enantiomeric excess
DMF=dimethylformamide
EtOAc=ethyl acetate
Me=methyl
RT=retention time
TFA=trifluoroacetic acid
THF=tetrahydrofuran
TLC=thin layer chromatography
pTSA=para-toluenesulfonic acid
t-Bu=tert-butyl
Ph=phenyl
Pd/C=palladium on activated charcoal
Ts=tosyl
TBS=tert-butyldimethylsilane
TEA=triethylamine
n-Bu=n-butyl
rt=room temperature
LC=liquid chromatography
Et=ethyl
MS=molecular sieves
MS(ES)=Electro-Spray Mass Spectrometry
DEAD=diethyl azodicarboxylate
WSDCC=water soluble dicarbonyldiimide 1-(3-dimethylaminopropyl-3-ethylcarbodiimide hydrochloride
TBAF-tetrabutylammonium floride
DBAD-Di-tert-butylazodicarboxylate
ADDP-1,1-[azodicarbonyl]dipiperdine

Example 2a

Production of [5S-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester (2a)

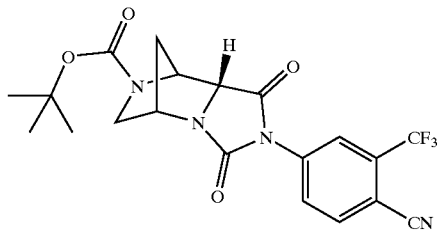

To a solution of 4-isocyanato-2-(trifluoromethyl)-benzonitrile (1.0 mmol) in toluene (4 mL) with activated 4 Å MS (0.300 g) was added (1S-exo)-2,5-diazabicyclo[2.2.1]heptane-2,6-dicarboxylic acid, 2-(1,1-dimethylethyl) 6-methyl ester (2a(1)) (0.220 g, 0.856 mmol) in toluene (6 mL). After 10 h at 25° C., DBU (0.166 mL, 1.11 mmol) was added and the reaction was heated at 81° C. for 2 h. The reaction was then cooled to 25° C. and poured into 1 N HCl (50 mL). The solution was then extracted with methylene chloride (3×30 mL) and the combined organics were dried over anhydrous sodium sulfate. The resulting crude material was purified by flash chromatography on SiO$_2$ eluting with acetone/chloroform (0–2–4–8% acetone) to give 2a (0.155 g, 42%) MS (ES): m/z 437.09 [M+H]$^+$. HPLC RT=3.280 min (100%) (YMC S5 ODS column, 4.6×50 mm; 10–90% MeOH/H$_2$O gradient, +0.1% TFA; 4 mL/min, 220 nM detection). HPLC RT=3.133 min (100%) (YMC S5 ODS column, 4.6×50 mm; 10–90% MeOH/H$_2$O gradient, +0.1% TFA; 4 mL/min, 220 nM detection); as white foam.

The starting compound, 2a(1), was made by the following procedure:

N-(tert-butoxycarbonyl)-L-4-hydroxyproline (10.0 g, 43.3 mmol) was dissolved in THF and cooled to 0° C. Borane/THF (1.0 M solution, 86.6 mL) was then added over a 15 min period. The reaction was then warmed to 25° C. followed by heating to reflux for 16 h. The reaction flask was then removed from the heat source and anhydrous methanol (35 mL) was added slowly. After cooling to 25° C., the solvent was removed in vacuo and the resulting crude diol intermediate was taken on directly. The crude diol (1.81 g, 8.34 mmol) was dissolved in methylene chloride (50 mL), 2,6-lutidine (1.46 mL, 12.51 mmol) was added and the mixture was cooled to −78° C. tert-Butyl dimethylsilyltrifluoro-methansulfonate (1.92 mL, 8.34 mmol) was then added. After 2 h, the mixture was poured into 1 N HCl (100 mL), extracted with methylene chloride (2×100 mL) and the organics were dried over anhydrous sodium sulfate. The resulting crude alcohol was purified by flash chromatography on SiO$_2$ eluting with acetone in chloroform (0–5–10% acetone) to give 1.011 g (37% for 2-steps) of (2S-trans)-4-hydroxy-2-[[[(1,1-dimethylethyl)dimethylsilyl]oxy]methyl]-1-pyrrolidinecarboxylic acid, 1,1-dimethylethyl ester (2a(2)) as a clear oil:

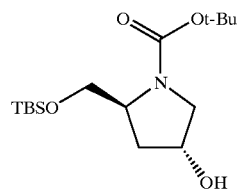

2a(2) (3.41 g, 10.3 mmol) was dissolved in anhydrous pyridine (30.0 mL) and cooled to 0° C. p-Toluenesulfonylchloride (5.89 g, 30.9 mmol) was then added in portions over a 10 minute period. The flask was then placed in a refrigerator at 4° C. for 48 h. The resulting solution was poured into 1 N HCl (300 mL), extracted with methylene chloride (3×200 mL) and the organics were dried over anhydrous sodium sulfate. The crude tosylate intermediate was dissolved in THF (50 mL), to which was added H$_2$O (0.5 mL) followed by pTSA-H$_2$O (1.03 mmol). Once the reaction was complete as determined by TLC, the mixture was poured into saturated aqueous NaHCO$_3$ (150 mL) and extracted with methylene chloride (3×50 mL). The combined organics were dried over sodium sulfate. The crude alcohol was purified by flash chromatography on SiO$_2$ eluting with acetone/chloroform (0–5–10% acetone) to give 2.71 g (71% for 2-steps) of (2S-trans)-2-hydroxymethyl-4-[[(4-methylphenyl)sulfonyl]oxy]-1-pyrrolidinecarboxylic acid, 1,1-dimethylethyl ester (2a(3)) as a clear oil:

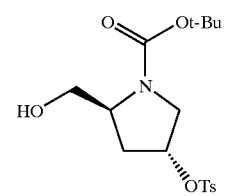

To a solution of oxalyl chloride (2.0 M soln in CH$_2$Cl$_2$, 2.82 mL) in CH$_2$Cl$_2$ (40 mL) at −78° C. was added anhydrous dimethylsulfoxide (0.462 mL, 6.51 mmol). The mixture was allowed to stand for 15 min, after which a solution of 2a(3) (1.61 g, 4.34 mmol) in CH$_2$Cl$_2$ (10 mL) was slowly added. After an additional 30 min, triethylamine (1.81 mL, 13.02 mmol) was added and the reaction was slowly warmed to 0° C. The reaction was then quenched with H$_2$O (25 mL) and diluted with CH$_2$Cl$_2$ (100 mL). The mixture was then washed sequentially with 1 N HCl (1×100 mL), saturated aqueous NaHCO$_3$ (50 mL), and water (2×50 mL). The organics were dried over anhydrous sodium sulfate and the volatile organics removed in vacuo. The crude aldehyde intermediate (1.60 g, 4.34 mmol) was dissolved in THF (25 mL) and diethyl cyanophosphonate (90%, 0.95 mL, 5.64 mmol) was added followed by benzyl amine (1.23 mL, 11.3 mmol). After 2 h, the reaction was complete, as observed by TLC and the volatile organics were removed in vacuo. The crude reaction mixture was purified by flash chromatography on SiO$_2$ eluting with acetone/chloroform (0–2–3% acetone) to give 1.48 g (70%) of (2S-trans)-2-[cyano[(phenylmethyl)amino]methyl]-4-[[(4-methylphenyl)-sulfonyl]oxy]-1-pyrrolidinecarboxylic acid, 1,1-dimethylethyl ester (2a(4))as a white solid. 2a(4) (structure below) was determined to be a ~1:1 mixture of diastereomers by NMR spectroscopy.

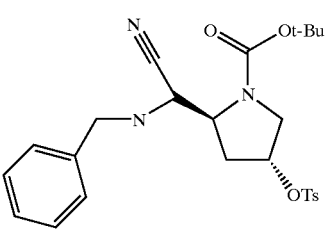

2a(4) (1.48 g, 3.05 mmol) was dissolved in dichloroethane (25 mL) and diisopropyl ethylamine (1.45 mL) was added. The mixture was heated to 100° C. in a sealed tube for 18 h. The volatiles were then removed in vacuo and the resulting crude material was purified by flash chromatography on SiO$_2$ eluting with acetone/chloroform (0–2–3% acetone), to yield a mixture of (1S-endo)-6-cyano-5-(phenylmethyl)-2,5-diazabicyclo[2.2.1]heptane-2-carboxylic acid, 1,1-dimethylethyl ester (2a(5A)) (0.591 g, 62%) and (1S-exo)-6-cyano-5-(phenylmethyl)-2,5-diazabicyclo[2.2.1]heptane-2-carboxylic acid, 1,1-dimethylethyl ester (2a(5B)) (0.370 g, 38%) as clear oils. Structural assignments for these compounds were made after NOE, COESY and DEPT NMR experiments:

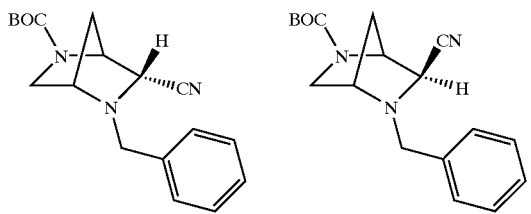

(2a(5A) (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2h at 0° C. the reaction was poured into saturated aqueous NaHCO$_3$ (50 mL). The mixture was extracted with CH$_2$Cl$_2$ (3×50 mL) and the combined organics were dried over anhydrous sodium sulfate. The crude ester was purified by flash chromatography on SiO$_2$ eluting with chloroform/acetone (0–2–4% acetone) to give 0.320 g (0.92 mmol, 72%) of (1-S-endo)-5-(phenylmethyl)-2,5-diazabicyclo[2.2.1]heptane-2,6-dicarboxylic acid, 2-(1,1-dimethylethyl) 6-methyl ester (2a(6A)) as a clear oil:

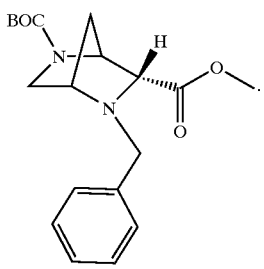

2a(5B) (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous NaHCO$_3$ (50 mL). The mixture was extracted with CH$_2$Cl$_2$ (3×50 mL) and the combined organics were dried over anhydrous sodium sulfate. The crude ester was purified by flash chromatography on SiO$_2$ eluting with chloroform/acetone (0–2–4% acetone) to give 0.290 g (0.85 mmol, 66%) of (1S-exo)-5-phenylmethyl)-2,5-diazabicyclo[2.2.1]heptane-2,6-dicarboxylic acid, 2-(1,1-dimethylethyl) 6-methyl ester (2a(6B)) as a clear oil:

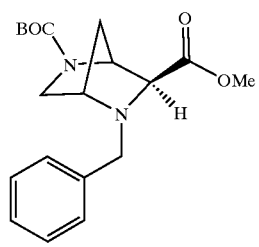

2a(6A) (0.280 g, 0.81 mmol) was dissolved in absolute EtOH (10.0 mL) and Pd/C (10% Pd, 0.080 g) was added. An atmosphere of H$_2$ was introduced via a balloon and the reaction was stirred at 25° C. for 20 h. The Pd was removed by filtration through celite followed by rinsing with EtOAc. The volatiles were removed in vacuo to give 2a(1) (0.205 g, 99%) as viscous yellow oil. This compound was taken on directly without purification. MS(ES)=m/z 257.18 [M+H]$^+$. HPLC RT=1.223 min (95%) (YMC S5 ODS column, 4.6×50 mm; 10–90% MeOH/H$_2$O gradient, +0.1% TFA; 4 mL/min, 220 nM detection):

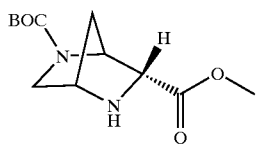

Example 2b

Production of 5S-(5α,8α,8aα)-4-(Hexahydro-1,3-dioxo-5,8-methanoimidazo[1,5-a]pyrazin-2(3H)-yl)-2-(trifluoromethyl)benzonitrile (2b)

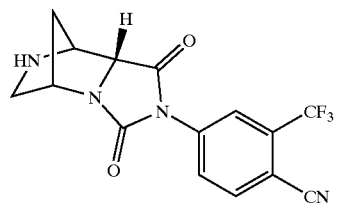

2a (0.115 g, 0.264 mmol) was dissolved in anhydrous methylene chloride (3 mL) and anhydrous TFA (1.0 mL) was added at 25° C. After 1 h, the reaction was concentrated in vacuo and the resulting residue was dissolved in methylene chloride and poured into saturated aq NaHCO$_3$. This solution was then extracted with methylene chloride (3×10 mL) and the combined organics dried over anhydrous sodium sulfate. This gave 0.089 g (97%) of free 2b as a yellow solid. MS (ES): m/z 359.09 [M+Na]$^+$. HPLC RT=1.477 min (100%) (YMC S5 ODS column, 4.6×50 mm; 10–90% MeOH/H$_2$O gradient, +0.1% TFA; 4 mL/min, 220 nM detection).

Example 2c

Production of [5S-(5α,8α,8aα)]-7-(4-Fluorobenzoyl)tetrahydro-2-(4-nitro-1-naphthalenyl)-5,8-methanoimidazo[1,5-a]pyrazine-1,3(2H,5H)-dione (2c)

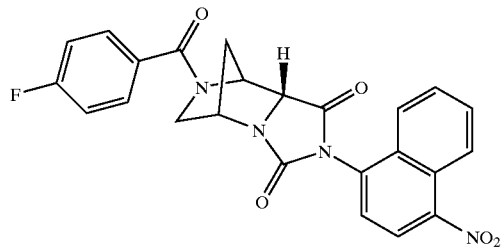

[5S-(5α,8α,8aα)]-Tetrahydro-2-(4-nitro-1-naphthalenyl)-5,8 methanoimidazo[1,5-a]pyrazine-1,3(2H,5H)-dione (2c (1)) (0.077 g, 0.228 mmol) was dissolved in methylene chloride (2.0 mL) and TEA (0.127 mL, 0.912 mmol) and 4-DMAP (0.001 g) were added. The reaction was cooled to 0° C. and 4-fluorobenzoylchloride (0.040 mL, 0.342 mmol) was added. The reaction was then slowly warmed to 25° C. After 3 h, the reaction was diluted with methylene chloride (50 mL) and then washed successively with 1N HCl and sat aq NaHCO$_3$ then and dried over anhydrous sodium sulfate. The crude material was purified by preparative TLC on silica eluting with 5% acetone in chloroform to give 0.022 g of 2c as a yellow solid. HPLC: 100% at 2.960 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 461.07 [M+H]$^+$. The starting material was made as described following.

[5S-(5α,8α,8aα)]-Tetrahydro-2-(4-nitro-1-naphthalenyl)-5,8 methanoimidazo[1,5-a]pyrazine-1,3(2H,5H)-dione (2c(1))

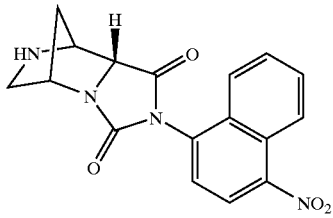

[5S-(5α,8α,8aα)]Hexahydro-2-(4-nitro-1-naphthalenyl)-1,3-dioxo-5,8-methanoimidazo[1,5-a]pyrazine-7(8H)-carboxylic acid, 1,1-dimethylethyl ester (2c(2)) (0.160 g, 0.37 mmol) was dissolved in methylene chloride (5.0 mL) and TFA (1.5 mL) was added at 25° C. After 1.5 h, the reaction was concentrated in vacuo and redissolved in methylene chloride. This solution was washed with sat aq NaHCO$_3$. The aqueous layer was extracted with methylene chloride (3×25 mL). The combined organics were then dried over anhydrous sodium sulfate. Concentration in vacuo gave 0.115 g of 2c(1) as a yellow solid. HPLC: 93% at 1.747 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 369.07 [M+MeOH]$^+$.

[5S-(5(5α,8α,8aα)]Hexahydro-2-(4-nitro-1-naphthalenyl)-1,3-dioxo-5,8-methanoimidazo[1,5-a]pyrazine-7(8H)-carboxylic acid, 1,1-dimethylethyl ester (2c(2))

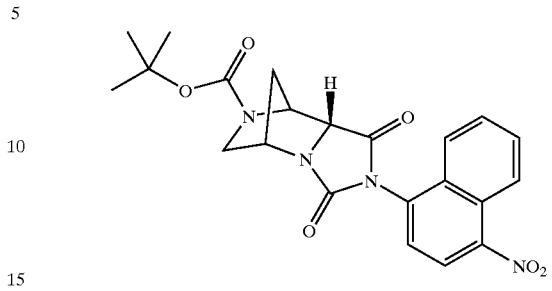

2a(1) (0.220 g, 0.856 mmol) was added to a suspension of freshly activated 4 Å molecular sieves (0.300 g) in dry toluene (10.0 mL). To this mixture was added 4-nitronaphthal-1-isocyanate (0.214 g, 1.0 mmol). After stirring at 25° C. for 14 h, DBU (0.166 mL, 1.11 mmol) was added and the reaction was heated at 80° C. for 2 h. After 2 h, the reaction was cooled to 25° C. and then poured into 1 N HCl (50 mL). This solution was extracted with methylene chloride (3×30 mL) and the combined organics were dried over anhydrous sodium sulfate. The crude material was purified by flash chromatography on silica eluting with 0–2–6% acetone in chloroform to give 0.211 g of 2c(2) as a yellow foam. HPLC: 95% at 3.130 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 439.19 [M+H]$^+$.

Example 2d

Production of [5S-(5α,8α,8aα)]-2-(4-Cyano-1-naphthalenyl)tetrahydro-7-(5-isoxazolylcarbonyl)-5,8-methanoimidazo[1,5-a]pyrazine-1,3(2H,5H)-dione (2dLibSyn1), [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, 4-fluorophenyl ester (2dLibSyn2), [5S-(5α,8α,8aα)]-2-(4-Cyano-1-naphthalenyl)tetrahydro-7-[(1-methyl-1H-imidazol-4-yl)sulfonyl]-5,8-methanoimidazo[1,5-a]pyrazine-1,3(2H,5H)-dione (2dLibSyn3) & [5S-(5α,8α,8aα)]-2-(4-Cyano-1-naphthalenyl)-N-(4-fluorophenyl)hexahydro-1,3-dioxo-5,8-methanoimidazo[1,5-a]pyrazine-7(8H)-carboxamide (2dLibSyn4)

Solution Phase Library Synthesis

The below procedure is a general approach to the synthesis of SARMs of the present invention in a solution phase library format. A more detailed description of individual compounds made via this combinatorial approach follows. A series of free amine starting materials analogous to 2c(1) (0.05 mmol, prepared as described above) were dissolved in dichloromethane (1.5 mL) in a polystyrene tube with a coarse frit. N,N-(Diisopropyl)aminomethyl polystyrene (3.49 mmol/g, 60 mg) was then added to each reaction vessel followed by addition of the desired acid chloride, isocyanate, chloroformate or sulfonyl chloride (0.10 mmol) in 0.5 mL dichloroethane by automated synthesizer. The reaction vessels were shaken at 25° C. for 24 h and then Tris-(2-Aminoethyl)amine Polystyrene HL (200–400 mesh, 3.3 mmol/g, 75 mg) was added to each reaction vessel and the vessels shaken again for 18 h at 25° C. The liquid from each tube was drained into pretared 2.5 ml STR tubes and the resin was rinsed with dichloromethane (3×0.25 mL). The pretared tubes were then concentrated and analyzed by analytical HPLC and LC-MS. HPLC: (Phenomenex Prime 5μ C-18 column 4.6×50 mm eluting with 10–90% aqueous methanol over 4 minutes containing 0.1% TFA, 4 mL/min, monitoring at 220 n).

[5S-(5α,8α,8aα)]-2-(4-Cyano-1-naphthalenyl) tetrahydro-7-(5-isoxazolylcarbonyl)-5,8-methanoimidazo[1,5-a]pyrazine-1,3(2H,5H)-dione (2dLibSyn1)

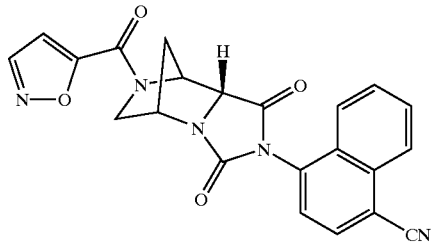

[5S-(5α,8α,8aα)]-4-(Hexahydro-1,3-dioxo-5,8-methanoimidazo[1,5-a]pyrazin-2(3H)-yl)-1-naphthalenecarbonitrile (2d(1)) (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of isoxazolacid chloride (0.025 g, 0.19 mmol) The tube was shaken at 25° C. for 24 h and then Tris-(2-Aminoethyl)amine Polystyrene HL (200–400 mesh, 3.3 mmol/g, 75 mg) was added to the reaction vessel and it was shaken again for 18 h at 25° C. The liquid was drained into pretared 2.5 ml STR tube and the resin was rinsed with dichloromethane (3×0.25 mL). Concentration in vacuo gave the crude 2dLibSyn1 (0.058 g) was a yellow solid. No purification was necessary. HPLC: 100% at 2.237 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 414.11 [M+H]+.

[5S-(5α,8α,8aα)]-2-(4-Cyano-1-naphthalenyl) hexahydro-1,3-dioxo-5,8-methanoimidazo[1,5-a] pyrazine-7(8H)-carboxylic acid, 4-fluorophenyl ester (2dLibSyn2)

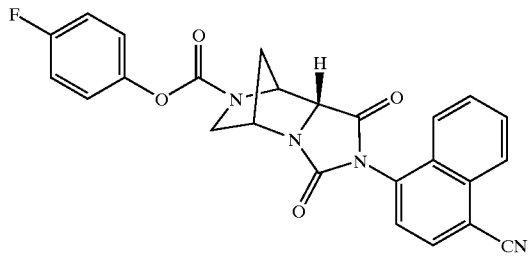

2d(1) (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of 4-fluorophenylchloroformate (0.033 g, 0.19 mmol) The tube was shaken at 25° C. for 24 h and then Tris-(2-aminoethyl)amine Polystyrene HL (200–400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave crude 2dLibSyn2 (0.053 g) as a yellow solid. No purification was necessary. HPLC: 93% at 2.987 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 457.07 [M+H]+.

[5S-(5α,8α,8aα)]-2-(4-Cyano-1-naphthalenyl) tetrahydro-7-[(1-methyl-1H-imidazol-4-yl)sulfonyl]-5,8-methanoimidazo[1,5-a]pyrazine-1,3(2H,5H)-dione (2dLibSyn3)

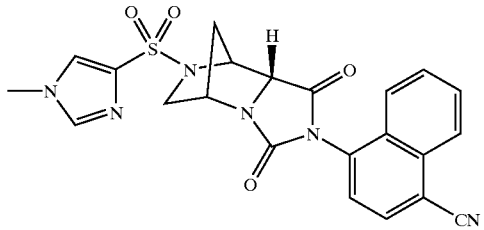

2d(1) (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of imidazolesulfonylchloride (0.034 g, 0.19 mmol). The tube was shaken at 25° C. for 24 h and then Tris-(2-aminoethyl)amine Polystyrene HL (200–400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave the crude 2dLibSyn3 (0.043 g) as a yellow solid. No purification was necessary. HPLC: 70% at 1.603 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 463.07 [M+H]+.

[5S-(5α,8α,8aα)]-2-(4-Cyano-1-naphthalenyl)-N-(4-fluorophenyl)hexahydro-1,3-dioxo-5,8-methanoimidazo[1,5-a]pyrazine-7(8H)-carboxamide (2dLibSyn4)

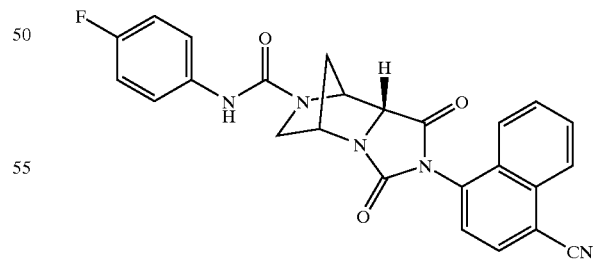

2d(1) (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of 4-fluorophenylisocyanate (0.026 g, 0.19 mmol). The tube was shaken at 25° C. for 24 h and then Tris-(2-aminoethyl)amine Polystyrene HL (200–400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave the crude 2dLibSyn4 (0.058 g) as a yellow solid. No purification was necessary. HPLC: 100% at 2.890 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 456.4 [M+H]+.

Example 2e

Production of (3aα,4β,7β,7aα)-4-(Octahydro-4,7-dimethyl-1,3-dioxo-4,7-epoxy-2H-isoindol-2-yl)-2-(trifluoromethyl)benzonitrile (2e)

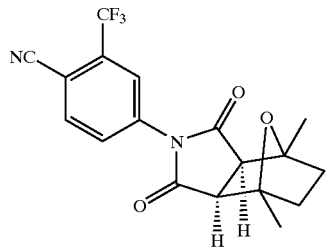

(3aα,4β,7β,7aα)-Hexahydro-4,7-epoxyisobenzofuran-1,3-dione (2e(1))

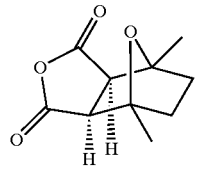

Freshly distilled dimethyl furan (1.60 mL, 15.3 mmol) was dissolved in CH$_2$Cl$_2$ (2.0 mL) and maleic anhydride (1.0 g, 10.2 mmol) was added. The reaction was stirred at 25° C. for 16 h and was then concentrated in vacuo to give a yellow solid. This solid was dissolved in ethyl acetate (30 mL) and Pd/C (10% Pd, 0.200 g) was added. Hydrogen was then introduced by a balloon and the reaction stirred for 24 h. The Pd was removed by filtration through celite rinsing with EtOAc followed by concentration in vacuo to give 2e(1) (1.69 g) as a white solid. 2-Dimensional NOE experiments confirmed the structural assignment to be that of 2e(1).

(3aα,4β,7β,7aα)-4-(Octahydro-4,7-dimethyl-1,3-dioxo-4,7-epoxy-2H-isoindol-2-yl)-2-(trifluoromethyl)benzonitrile (2e)

A solution of 2e(1) (640 mg, 3.44 mmol, 1.07 eq) and TsOH (10 mg, cat amount) in toluene (5 mL) was heated in a sealed tube for 2 days. The reaction mixture was cooled to room temperature and then concentrated under reduced pressure. Purification by flash chromatography on silica gel eluting with 50% EtOAc/hexanes gave 400 mg (1.10 mmol, 34%) of 2e as a white solid. HPLC: 99% at 3.04 min (retention time) (YMC S5 ODS column 4.6×50 mm, 10–90% aqueous methanol over 4 minutes containing 0.2% phosphoric acid, 4 mL/min, monitoring at 220 nm), MS (ESI): m/z 382.2 [M+NH$_4$]+.

Example 2f

Production of (3aα,4β,7β,7aα)-4-[4-[2-(4-Fluorophenoxy)ethyl]octahydro-7-methyl-1,3-dioxo-4,7-epoxy-2H-isoindol-2-yl]-2-(trifluoromethyl)benzonitrile (2f)

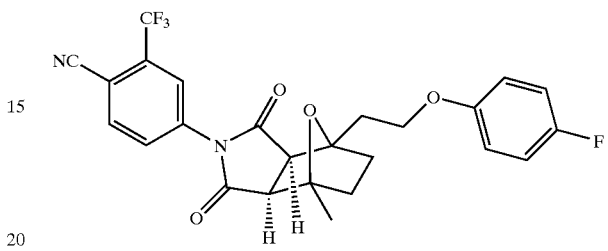

DEAD (0.06 mL, 0.380 mmol, 1.5 eq) was added to a solution of triphenylphosphine (100 mg, 0.380 mmol, 1.5 eq) in THF (1.3 mL) at room temperature under an inert atmosphere. After stirring for 10 mins, 4-fluorophenol (43 mg, 0.380 mmol, 1.5 eq) was added in one portion. The reaction mixture was stirred for 5 mins, (3aα,4β,7β,7aα)-4-[octahydro-4-(2-hydroxyethyl)-7-methyl-1,3-dioxo-4,7-epoxy-2H-isoindol-2-yl]-2-(trifluoromethyl)benzonitrile (2f(1)) (100 mg, 0.254 mmol, 1 eq) was added and stirring was continued for 3.5 h. Purification by flash chromatography on silica gel eluting with 50% EtOAc/Hexanes followed by preparative chromatography [HPLC: 11.93 min (retention time) (YMC S5 ODS column 20×100 mm, 0–100% aqueous methanol over 10 minutes containing 0.1% TFA, 20 mL/min, monitoring at 220 nm)] gave 72 mg (58%) of 2f as a solid. HPLC: 99% at 3.74 min (retention time) (YMC S5 ODS column 4.6×50 mm, 10–90% aqueous methanol over 4 minutes containing 0.2% phosphoric acid, 4 mL/min, monitoring at 220 nm), MS (ESI): m/z 487.1 [M−H]−.

The starting compound, 2f(1), was made by the following procedure:

A solution of n-BuLi (83 mL, 133.0 mmol, 1.2 eq, 1.6 M in hexanes) was added to a stirred solution of 2-methylfuran (10 mL, 110.8 mmol, 1 eq) in THF (85 mL) at 0° C. under inert atmosphere. The reaction mixture was stirred for 4 h at room temperature then cooled to 0° C. Ethylene oxide (8.3 mL, 166.3 mmol, 1.5 eq) was added dropwise and the reaction mixture was allowed to warm to room temperature overnight. After quenching with saturated aqueous NH$_4$Cl, the resulting layers were separated and the aqueous layer was extracted with Et$_2$O (2×). The combined organic layers were dried over Na$_2$SO$_4$ and concentrated under reduced pressure. Distillation at atmospheric pressure (170–185° C.) gave 10.13 g (80.3 mmol, 72%) of 5-methyl-2-furanethanol (2f(2)) as a light yellow oil:

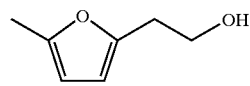

A solution of 2f(2) (252 mg, 2 mmol, 1 eq) and 4-(2,5-dihydro-2,5-dioxo-1H-pyrrol-1-yl)-3-trifluoromethylbenzonitrile (798 mg, 3 mmol, 1.5 eq) in CH$_2$Cl$_2$ (10 mL) was stirred at room temperature for 2 days. The reaction mixture was concentrated under reduced pressure. Purification by flash chromatography on silica gel eluting with 65% EtOAc/hexanes gave 217 mg of pure (3aα,4β,7β,7aα)-4-[1,3,3a,4,7,7a-hexahydro-4-(2-hydroxyethyl)-7-methyl-1,3-dioxo-4,7-epoxy-2H-isoindol-2-yl]-2-(trifluoromethyl)benzonitrile (2f(3A)), 73 mg of pure (3aα,4α,7α,7aα)-4-[1,3,3a,4,7,7a-hexahydro-4-(2-hydroxyethyl)-7-methyl-1,3-dioxo-4,7-epoxy-2H-isoindol-2-yl]-2-(trifluoromethyl)benzonitrile (2f(3B)) and 310 mg of a mixture of both 2f(3A) and 2f(3B). All three fractions were isolated as white solids with a total isolated yield of 600 mg (1.53 mmol, 76.5%). 2f(3A): HPLC 90% at 2.56 min (retention time) (YMC S5 ODS column 4.6×50 mm, 10–90% aqueous methanol over 4 minutes containing 0.2% phosphoric acid, 4 mL/min, monitoring at 220 nm). 2f(3B): HPLC 90% at 2.56 min (retention time) (YMC S5 ODS column 4.6×50 mm, 10–90% aqueous methanol over 4 minutes containing 0.2% phosphoric acid, 4 mL/min, monitoring at 220 nm).

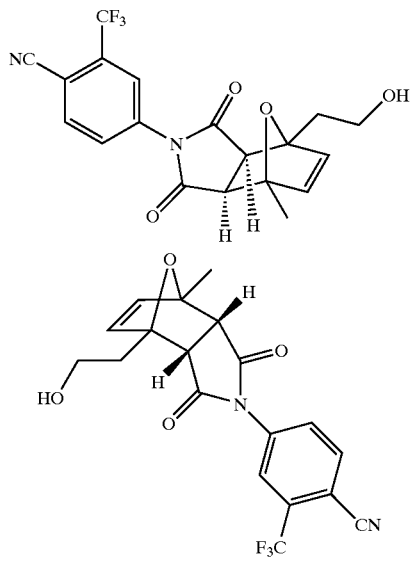

A solution of 2f(3A) (0.2 g, 0.51 mmol, 1 eq) and 10% Pd/C (43 mg, cat.) in EtOH (12 mL) was stirred under a hydrogen atmosphere at room temperature for 2 h. The reaction mixture was filtered through celite and concentrated under reduced pressure to give 0.2 g (0.51 mmol, 100%) of 2f(1)as a white solid. HPLC: 95% at 2.59 min (retention time) (YMC S5 ODS column 4.6×50 mm eluting with 10–90% aqueous methanol over 4 minutes containing 0.1% TFA, 4 mL/min, monitoring at 220 nm), MS (ESI): m/z 394.97 [M+H]$^+$:

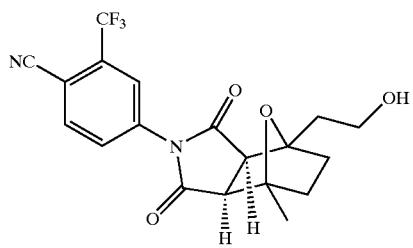

Example 2g

Production of (3aα,4β,7β,7aα)-4-[4-(2-Bromoethyl] octahydro-7-methyl-1,3-dioxo-4,7-epoxy-2H-isoindol-2-yl]-2-(trifluoromethyl)benzonitrile (2g)

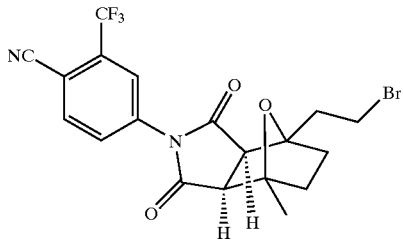

A solution of 2f(1)(495 mg, 1.26 mmol, 1 eq) and pyridine (0.1 ml, 1.26 mmol, 1 eq) in CH$_2$Cl$_2$ (2 ml) was added to a solution of Ph$_3$PBr$_2$ (636 mg, 1.51 mmol, 1.2 eq) in CH$_2$Cl$_2$ (2 ml) at 0° C. The reaction mixture was stirred at room temperature for 3 hr, then the solvent was removed under reduced pressure. The resulting residue was washed 2× with 10 ml portions of EtOAc-hexane (6:4) and the combined washings were purified by flash chromatography on silica gel eluting with 60% EtOAc/hexane to give 390 mg (0.85 mmol, 67.7%) of 2 g as a white solid. HPLC: 99% at 3.51 min (retention time) (YMC S5 ODS column 4.6×50 mm, 10–90% aqueous methanol over 4 minutes containing 0.2% phosphoric acid, 4 mL/min, monitoring at 220 nm). MS (ESI): m/z 456.7 [M–H]$^-$.

Example 2h

Production of (3aα,4β,7β,7aα)-4-[Octahydro-4-(2-hydroxyethyl)-7-methyl-1,3-dioxo-4,7-epoxy-2H-isoindol-2-yl]-2-(trifluoromethyl)benzonitrue (2h)

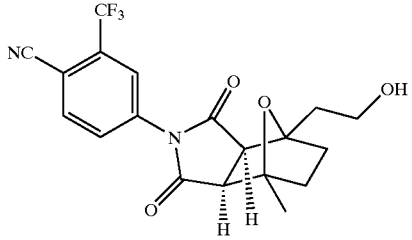

(3aα,4β,7β,7aα)-4-[4-[2-[[(1,1-Dimethylethyl) dimethylsilyl]oxy]ethyl]octahydro-7-methyl-1,3-dioxo-4,7-epoxy-2H-isoindol-2-yl]-2-(trifluoromethyl)benzonitrile (2h(1)) (0.031 g, 0.061 mmol) was dissolved in THF (0.5 mL) and transferred to a polypropylene container followed by cooling to 0° C. HF.pyridine (~47% HF, 0.1 mL) was then added. After 15 min, the reaction was complete as determined by LC and was poured into cold sat aqueous NaHCO$_3$. The mixture was extracted with CH$_2$Cl$_2$ (3×10 mL). The combined organic layers were washed with 1 N HCl (1×20 mL) and dried over anhydrous Na$_2$SO$_4$. 2h was isolated as a yellow oil. No purification was necessary HPLC: 95% at 2.59 min (retention time) (YMC S5 ODS column 4.6×50 mm eluting with 10–90% aqueous methanol over 4 minutes containing 0.1% TFA, 4 mL/min, monitoring at 220 nm). MS (ESI): m/z 394.97 [M+H]$^+$.

The starting material, 2h(1), was made by the following procedure.

To a solution of 5-methyl-2-furanethanol 2f(2) (2.00 g, 15.9 mmol) in DMF (50 mL) was added imidazole (1.62 g, 23.9 mmol), followed by tert-butyldimethylsilyl chloride (2.63 g, 17.5 mmol). After 2 h at 25° C., the reaction was poured into diethyl ether (300 mL) and washed with water (1×100 mL), 1N HCl (1×100 mL), water (1×100 mL), brine (1×50 mL) and dried over anhydrous MgSO$_4$. Crude 2-[2-[[(1,1-dimethylethyl)dimethylsilyl]oxy]ethyl]-5-methylfuran (2h(2)) was analyzed by LCMS and NMR and determined to be pure enough to be carried on directly to the next step. HPLC: 100% at 4.347 min (retention time) (YMC S5 ODS column 4.6×50 mm eluting with 10–90% aqueous methanol over 4 minutes containing 0.1% TFA, 4 mL/min, monitoring at 220 nm):

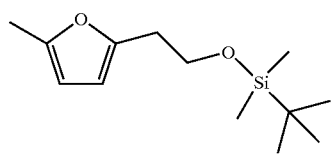

2h(2) (4.0 g, 18.9 mmol) and maleic anhydride (1.42 g, 14.51 mmol) were dissolved in dichloroethane (10 mL) and stirred at 25° C. for 60 hours. The volatiles were then removed in vacuo and the resulting orange oil was dissolved in absolute ethanol (50 mL) and Pd/C (10% Pd, 1.00 g) was added. Hydrogen was then introduced via a balloon. After 3 h, the reaction was filtered through celite rinsing with EtOAc and concentrated in vacuo. The crude anhydride was purified by rapid flash chromatography in SiO$_2$ eluting with acetone/chloroform (0–2–4% acetone) to give 1.30 g of (3aα,4β,7β,7aα)-4-[2-[[(1,1-dimethylethyl)dimethylsilyl]-oxy]ethyl] hexahydro-7-methyl-4,7-epoxy-1H-isobenzofuran-1,3(2H)-dione (2h(3)) as a clear oil, in addition to 3.00 g of the starting 2-[2-[[(1,1-dimethylethyl)dimethylsilyl]oxy]ethyl]-5-methylfuran. Characterization by proton NMR spectroscopy showed only the exo isomer. 1H NMR, 400 MHz, CDCl3, 3.83 (2 H, t, J=6.0 Hz), 3.22 (1 H, d, J=8.2 Hz), 3.06 (1 H, d, J=8.2 Hz), 1.70–2.25 (6 H, m), 1.55 (3 H, s), 0.82 (9 H, s), 0.00 (6 H, s):

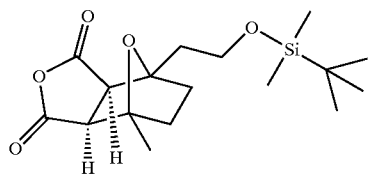

2h(3) (0.250 g, 0.8 mmol) and 4-amino-2-trifluoromethylbenzonitrile (0.124 g, 0.668 mmol) were suspended in dry toluene (2.0 mL) in a sealed tube. MgSO$_4$ (0.200 g) and triethylamine (0.5 mL) were then added and the tube was sealed and placed in a oil bath at 125° C. After 40 h, the reaction was cooled to 25° C., filtered and concentrated in vacuo. The crude material was purified by flash chromatography on SiO$_2$ eluting with CH$_2$Cl$_2$ to give 0.111 g of 2h(1) as a yellow solid. HPLC: 92% at 4.203 min (retention time) (YMC S5 ODS column 4.6×50 mm eluting with 10–90% aqueous methanol over 4 minutes containing 0.1% TFA, 4 mL/min, monitoring at 220 nm). MS (ESI): m/z 531.1 [M+Na]$^+$:

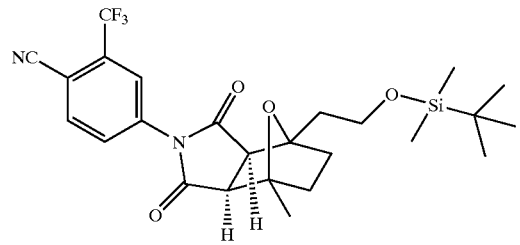

Example 2i

Production of [3aR-(3aα,4β,7β,7aα)]-4-[Octahydro-4-methyl-1,3-dioxo-7-[2-[4-(trifluoromethyl) phenoxy]ethyl]-4,7-epoxy-2H-isoindol-2-yl]-2-(trifluoromethyl)benzonitrile (2iA), faster eluting antipode and [3aS-(3aα, 4β,7β,7aα)]-4-[Octahydro-4-methyl-1,3-dioxo-7-[2-[4-(trifluoromethyl) phenoxy]ethyl]-4,7-epoxy-2H-isoindol-2-yl]-2-(trifluoromethyl)benzonitrile (2iB), slower eluting enantiomer

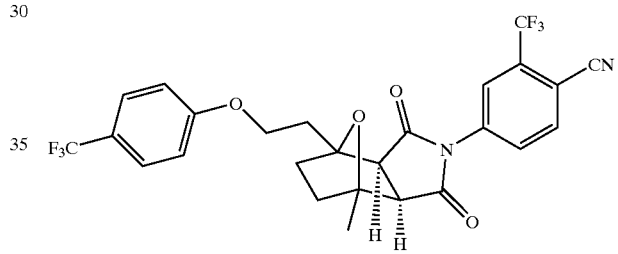

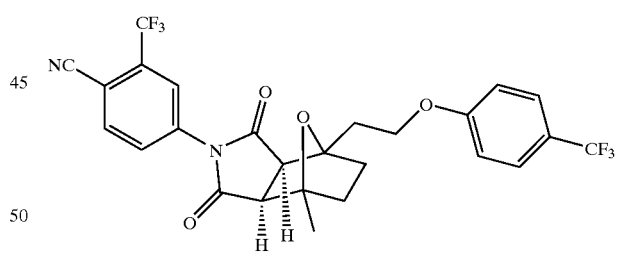

The racemic compound, synthesized as described for 2f, was separated into the individual antipodes by chiral normal phase liquid chromatography. A Chiralpak AD column (50× 500 mm) was used eluting with 85% hexanes/7.5% methanol/7.5% ethanol, @ 50 mL/min. UV detection at 220 nm was used. The faster eluting isomer isomer 2iA (retention time=55.86 min) was found to have 95.8% ee ($[\alpha]_D^{25}$=−53.02°, C=3.134 mg/cc in CH$_2$Cl$_2$) and the slower eluting isomer 2iB (retention time=62.86 min) was 86% ee ($[\alpha]_D^{25}$=+48.74°, C=2.242 mg/cc in CH$_2$Cl$_2$) by analytical chiral normal phase chromatography.

Example 2j

Production of (αR)-α-Methoxybenzeneacetic acid, 2-[(3aα,4β,7β,7aα)-2-(4-cyano-1-naphthalenyl) octahydro-7-methyl-1,3-dioxo-4,7-epoxy-4H-isoindol-4-y]ethyl ester (2j)

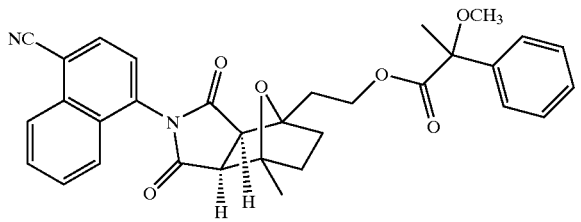

(3aα,4β,7β,7aα)-4-[4-[2-[[(1,1-Dimethylethyl) dimethylsilyl]oxy]ethyl]octahydro-7-methyl-1,3-dioxo-4,7-epoxy-2H-isoindol-2-yl]-1-naphthalenecarbonitrile (2j(1))

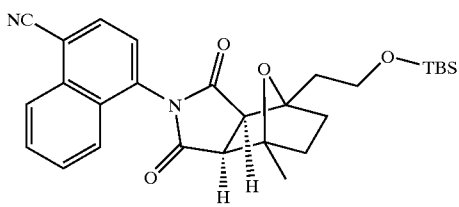

A solution of 4-amino-1-naphthalenecarbonitrile (19.2 g, 114 mmol) and maleic anhydride (14.0 g, 113 mmol) in AcOH (230 mL) was heated at 115° C. for 12 h. After cooling to rt, the reaction mixture was concentrated under reduced pressure then diluted with CH$_2$Cl$_2$ (2.5 L). The organic layer was washed 3× with H$_2$O (3 L), 1× with sat. aq Na$_2$CO$_3$ (1 L) and 1× with brine (1 L), dried over MgSO$_4$ and concentrated to ~200 mL under reduced pressure. Purification by flash chromatography on cation exchange resin (60 g, CUBX13M6 from United Chemical Technologies) eluting with CH$_2$Cl$_2$ gave 25.0 g (88%) of 4-(2,5-Dihydro-2,5-dioxo-1H-1-yl)-1-naphthalenecarbonitrile as a yellow solid. HPLC 96% at 2.48 min (Phenomenex-prime S5-C18 column 4.6×50 mm, 10–90% aqueous methanol over 4 minutes containing 0.2% phosphoric acid, 4 mL/min, monitoring at 220 nm), MS (ES): m/z 249.25 [M+H]$^+$.

4-(2,5-Dihydro-2,5-dioxo-1H-1-yl)-1-naphthalenecarbonitrile (1.00 g, 4.03 mmol) was suspended in benzene (6.0 mL) in a sealed tube and 2h(2) (1.11 g, 5.24 mmol) was added. The reaction was heated at 60° C. for 16 h and then cooled to 25° C. The benzene was removed in vacuo to give a yellow solid. The solid was dissolved in ethyl acetate (40 mL) and Pd/C (10% Pd, 0.300 g) was added. Hydrogen was then introduced via a balloon. After 4 h, the reaction was filtered through celite rinsing with ethyl acetate. Concentration in vacuo gave a pale yellow solid. Which was purified by flash chromatography on silica gel eluting with acetone/chloroform (0%–1.5%–3% acetone) to give 2j(1) (1.53 g) as a yellow foam. HPLC: 86% at 4.173 min (retention time) (YMC S5 ODS column 4.6×50 mm eluting with 10–90% aqueous methanol over 4 minutes containing 0.2% phosphoric acid, 4 mL/min, monitoring at 220 nm).

(3aα,4β,7β,7aα)-4-[Octahydro-4-(2-hydroxyethyl)-7-methyl-1,3-dioxo-4,7-epoxy-2H-isoindol-2-yl]-1-naphthalenecarbonitrile (2j (2))

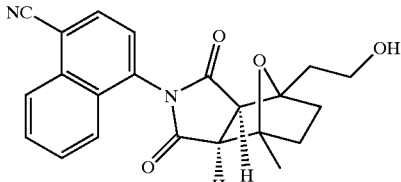

2j(1) (1.37 g, 2.97 mmol) was dissolved in THF (8.0 mL) and transferred to a polypropylene bottle and cooled to 0° C. HF.Pyridine (2.0 mL) was then added. After 20 min, the reaction was carefully poured into cold sat. aq sodium bicarbonate and extracted with methylene chloride (3×30 mL). The organics were then washed with 1 N HCl and dried over anhydrous sodium sulfate. Concentration in vacuo gave the 2j(2) (0.99 g) as a yellow foam which was not purified further. HPLC: 96% at 2.443 and 2.597 (atropisomers) min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 399.02 [M+Na]$^+$.

(αR)-α-Methoxybenzeneacetic acid, 2-[(3aα,4β,7β, 7aα-2-(4-cyano-1-naphthalenyl)octahydro-7-methyl-1,3-dioxo-4,7-epoxy-4H-isoindol-4-y]ethyl ester (2j)

2j(2) (0.200 g, 0.575 mmol) was added to a solution of WSDCC (0.138 g, 0.719 mmol) and (R)-mandelic acid (0.096 g, 0.575 mmol) in dichloromethane (6.0 mL). 4-DMAP (0.005 g) was then added and the reaction stirred at 25° C. for 4 h. The mixture was then diluted with dichloromethane and washed with 1 N HCl (2×10 mL), once with sodium bicarbonate (10 mL) and dried over anhydrous sodium sulfate. Concentration in vacuo gave 2j (0.220 g) as a yellow solid which was not purified further. HPLC: 100% at 3.283 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 547.26 [M+Na]$^+$.

Example 2k

Production of (3aα,4β,7β,7aα)-7-[2-[[(1,1-Dimethylethyl)dimethylsilyl]oxy]ethyl]hexahydro-5-hydroxy4-methyl-2-(4-nitro-1-naphthalenyl)-4,7-epoxy-1H-isoindole-1,3(2H)-dione (2k)

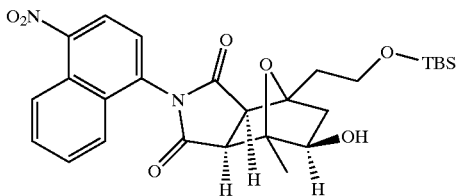

(3aα,4β,7β,7aα)-4-[2-[[(1,1-Dimethylethyl) dimethylsilyl]oxy]ethyl]-3a, 4,7,7a-tetrahydro-7-methyl-2-(4-nitro-1-naphthalenyl)-4,7-epoxy-1H-isoindole-1,3(2H)-dione (2k(1))

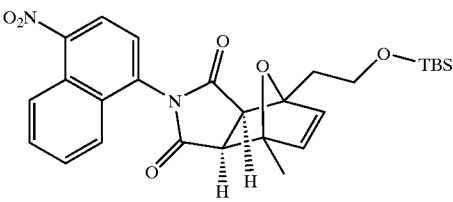

A solution of 2h(2) (455 mg, 1.894 mmol) and 1-[4-nitronaphthalene]-1H-pyrrole-2,5-dione (254 mg, 0.947 mmol) in benzene (2 mL) was heated at 60° C. overnight. 1-[4-nitronaphthalene]-1H-pyrrole-2,5-dione was made as described in 2j(1). The reaction mixture was concentrated under reduced pressure to give crude 2h(2) as a brown solid, which was used directly in the next step without further purification.

(3aα,4β,5β,7β,7aα)-7-[2-[[(1,1-Dimethylethyl) dimethylsilyl]oxy]ethyl]hexahydro-5-hydroxy-4-methyl-2-(4-nitro-1-naphthalenyl)-4,7-epoxy-1-isoindole-1,3(2H)-dione (2k)

BH$_3$.THF (0.95 mL, 0.95 mmol, 1M solution in THF) was added to a solution of crude 2k(1) (0.95 mmol) in THF (2 mL) at 0° C. After 2k(1) was consumed, the reaction mixture was concentrated under reduced pressure. The resulting residue was then dissolved in toluene (2 mL), Me$_3$NO (71 mg, 2.84 mmol) was added and the mixture was heated to reflux overnight. The reaction mixture was then cooled to rt, added to H$_2$O and extracted with EtOAc (3×). The combined organic layers were dried over MgSO$_4$ and concentrated under reduced pressure. Purification by flash chromatography on SiO$_2$ eluting with a mixture of 75% EtOAc/30% hexanes, gave 130.2 mg (26%) of 2k as a brown solid. HPLC: 94% at 3.92 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 527.5 [M+H]$^+$.

Example 2l

Production of (3aα,4β,5β,7β,7aα)-Hexahydro-5-hydroxy-7-(2-hydroxyethyl)-4-methyl-2-(4-nitro-1-naphthalenyl)-4,7-epoxy-1H-isoindole-1,3(2H)-dione (2l)

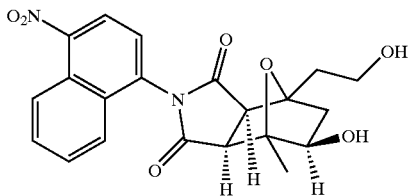

A mixture of TBAF (0.3 mL, 0.296 mmol, 1 M solution in THF) and HF (0.3 mL, 50% in H$_2$O) in CH$_3$CN (6 mL) was added to a solution of 2k (104 mg, 0.197 mmol) in THF (2 mL) at 0° C. The reaction mixture was stirred overnight at rt. After the starting material was consumed, as was evident by TLC, H$_2$O and EtOAc were added and the layers were separated. The aqueous layer was extracted with EtOAc (1×) and the combined organic layers were washed with H$_2$O (1×) and brine (1×), dried over Na$_2$SO$_4$ and concentrated under reduced pressure. Purification by flash chromatography on SiO$_2$ eluting with 5% MeOH/CH$_2$Cl$_2$ gave 61.2 mg (75%) of 2l as a yellow solid. HPLC: 99% at 2.47 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 411.2 [M–H]$^-$.

Example 2m

Production of (3aα,4β,5β,7β,7aα)-7-[2-(4-Fluorophenoxy)ethyl]hexahydro-5-hydroxy-4-methyl-2-(4-nitro-1-naphthalenyl)-4,7-epoxy-1H-isoindole-1,3(2H)-dione (2m)

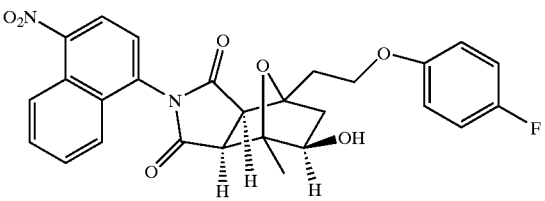

DBAD (37.7 mg, 0.164 mmol, 1.5 eq) was added to a solution of PPh$_3$ (43 mg, 0.164 mmol, 1.5 eq) in THF (1 mL). After stirring for 10 mins, 4-fluorophenol (18.3 mg, 0.164 mmol, 1.5 eq) was added and the reaction mixture was stirred for a further 5 mins. A solution of 2l (45 mg, 0.109 mmol, 1 eq) in THF (1 mL) was added and the mixture was stirred at rt overnight. HPLC showed the crude reaction mixture to contain mostly starting diol (2l), so this mixture was added to a preformed mixture as before of PPh$_3$ (86 mg, 3 eq), DBAD (75.4 mg, 3 eq) and phenol (36.6 mg, 3 eq) in THF (4 mL) at rt. Stirring was continued until all of 2l was consumed as was evident by HPLC. The reaction was concentrated under reduced pressure. Purification by preparative chromatography [HPLC at 15.2 min (retention time) (YMC S5 ODS A column 20×100 mm, 10–90% aqueous methanol over 15 minutes containing 0.1% TFA, 20 mL/min, monitoring at 220 nm)] gave 25.0 mg (45%) of 2m as a light yellow solid. HPLC: 99% at 3.53 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 505.2 [M–H]$^-$.

DBAD (37.7 mg, 0.164 mmol) was added to a solution of PPh$_3$ (43 mg, 0.164 mmol) in THF (1 mL). After stirring for 10 mins, 4-fluorophenol (18.3 mg, 0.164 mmol) was added and the reaction mixture was stirred for a further 5 min. A solution of compound 2l (45 mg, 0.109 mmol) in THF (1 mL) was added and the mixture was stirred at rt overnight. HPLC showed the crude reaction mixture to contain mostly starting diol (compound 2l), so this mixture was added to a preformed mixture as before of PPh$_3$ (86 mg), DBAD (75.4 mg) and phenol (36.6 mg) in THF (4 mL) at rt. Stirring was continued until all of 2l was consumed. The reaction was then concentrated under reduced pressure. Purification by preparative chromatography [HPLC at 15.2 min (retention time) (YMC S5 ODS A column 20×100 mm, 10–90% aqueous methanol over 15 minutes containing 0.1% TFA, 20 mL/min, monitoring at 220 nm)] gave 25.0 mg (45%) of 2m as a light yellow solid. HPLC: 99% at 3.53 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 505.2 [M–H]−.

Example 2n

Production of [3aR-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile (2nA) & [3aS-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile (2nB)

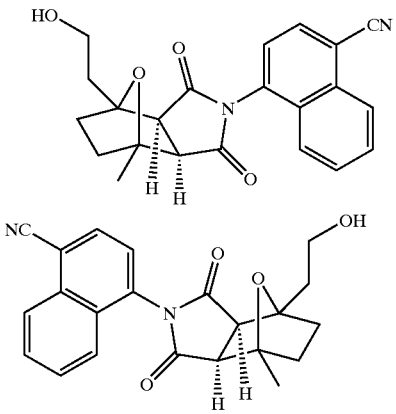

Racemic 2j(2) was separated into its enantiomers by preparative chiral HPLC (CHIRALPAK AD 5×50 cm column; eluting with 20% MeOH/EtOH (1:1) in heptane (isocratic) at 50 mL/min, @ 220 nm) to give the faster eluting compound 2nA (Chiral HPLC: 13.54 min; CHIRALPAK AD 4.6×250 mm column; eluting with 20% MeOH/EtOH (1:1) in heptane at 1 mL/min) and the slower eluting compound 2nB (Chiral HPLC: 14.99 min; CHIRALPAK AD 4.6×250 mm column; eluting with 20% MeOH/EtOH (1:1) in heptane at 1 mL/min). The absolute conformation for compounds 2nA and 2nB have not been established. For simplicity in nomenclature, we have designated compound 2nA as having an "R" configuration and compound 2nB as having a "S" configuration. Enantiomerically pure products derived from 2nA will be designated as having a "R" configuration and enantiomerically pure products derived from 2nB will be designated as having a "S" configuration.

Example 2o

Production of [3aR-(3aα,4β,7β,7aα)]-4-[4-[2-(3-Fluorophenoxy)ethyl]octahydro-7-methyl-1,3-dioxo-4,7-epoxy-2H-isoindol-2-yl]-1-naphthalenecarbonitrile (2oA) & [3aS-(-(3aα,4β,7β,7aα)]-4-[4-[2-(3-Fluorophenoxy)ethyl]octahydro-7-methyl-1,3-dioxo-4,7-epoxy-2H-isoindol-2-yl]-1-naphthalenecarbonitrile (2oB)

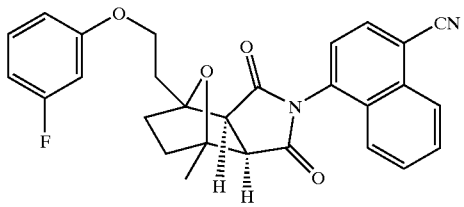

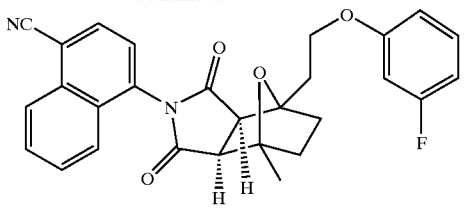

To a solution of triphenylphosphine (0.0524 g, 0.20 mmol) in THF (2.0 mL) was added DBAD (0.046 g, 0.2 mmol). After 10 min, 3-fluorophenol (0.018 mL, 0.2 mmol) was added. After 10 additional minutes, enantiomerically pure 2nA (0.050 g, 0.133 mmol) was added. After 3 h at 25° C., the reaction was concentrated in vacuo and purified by preparative HPLC (YMC S5 ODS 20×100 mm, 10–90% aqueous methanol over 15 minutes containing 0.2% TFA, 20 mL/min, monitoring at 220 nm) to give 0.031 g of compound 2oA as a white solid. This process was repeated with enantiomerically pure compound 2nB to yield 2oB. 2oA: HPLC: 100% at 3.80 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 471.65 [M+H]+, $[\alpha]_D^{25}$=−47.371 (c=4.412 mg/cc, $CH_2Cl_2$). 2oB: HPLC: 100% at 3.80 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 471.65 [M+H]+, $[\alpha]_D^{25}$=+24.3 (c=4.165 mg/cc, $CH_2Cl_2$).

Example 2p

Production of [3aS-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile (2pA) & [3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile (2pB)

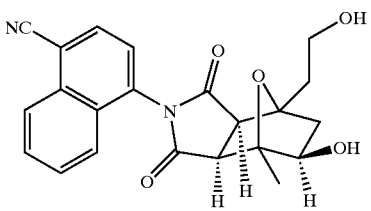

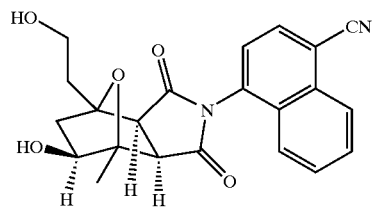

(3aα,4β,7β,7aα)-4-[4-[2-[[(1,1-Dimethylethyl)
dimethylsilyl]oxy]ethyl]-1,3,4,7,7a-hexahydro-1,3-
dioxo4,7-epoxy-2H-isoindol-2-yl]-1-
naphthalenecarbonitrile (2p(1))

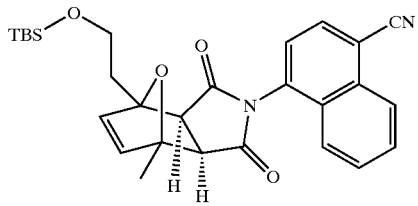

4-(2,5-Dihydro-2,5-dioxo-1H-1-yl)-1-naphthalenecarbonitrile (18.3 g, 68.7 mmol) was added to a solution of 2h(2) (26.6 g, 110.6 mmol) in benzene (75 mL) and heated to 60° C. overnight. After cooling to rt, the reaction mixture was concentrated under reduced pressure. The residue was treated with MeOH (250 mL) with stirring at 0° C. for 10 min. The resulting solid was filtered, washed with cold MeOH (2×10 mL) and dried to give 26.7 g (79.5%) of 2p(1) as a yellow solid. HPLC analysis of the above solid revealed it to be 95% pure (HPLC conditions: 95% at 2.48 min (Phenomenex-prime S5-C18 column, 4.6× 50 mm, 10%–90% aqueous methanol over 4 minute gradient with 0.2% $H_3PO_4$, detecting at 220 nm)). The filtrate was then concentrated under reduced pressure and the resulting solid was chromatographed, eluting with 3% acetone/ $CHCl_3$, to give an additional 4.36 g of 2p(1) (13%), giving a total final yield of 92.5%.

(3aα,4β,5β,7β,7aα)-4-[7-[2-[[(1,1-Dimethylethyl)
dimethylsilyl]oxy]ethyl]octahydro-5-hydroxy-4-
methyl-1,3-dioxo-4,7-epoxy-2H-isoindol-2-yl]-1-
naphthalenecarbonitrile (2p(2))

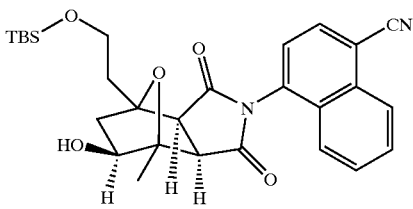

A mixture of 2p(1) (10 g, 20.46 mmol) and RhCl(PPh$_3$)$_3$ (0.947 mg, 1.02 mmol) was evacuated and filled with argon (3×). THF (200 mL) was added and once all particulates had dissolved, catecholborane (4.4 mL, 40.93 mmol) was slowly added dropwise. When the formation of product ceased, as was determined by HPLC, the reaction mixture was cooled to 0° C. and quenched with phosphate buffer (330 mL, pH 7.2) then EtOH (130 mL) and $H_2O_2$ (300 mL, 30% aq sol) were added. Once boronate was consumed, the mixture was extracted with $CH_2Cl_2$ (3×) and the combined organic layers were washed with 1N NaOH, 10% aq NaHSO$_3$ (1:1, 1×) and brine (1×). The combined washes was extracted with $CH_2Cl_2$ (1×) and the combined organic layers were dried over $Na_2SO_4$. Purification by flash chromatography on silica gel eluting with 10% to 30% acetone/CHCl$_3$ gradient over 25 min gave 7.1 g (68%) of 2p(2) as a light yellow solid. HPLC conditions: 98% at 3.82 min (Phenomenex-prime S5-C18 column 4.6×50 mm, 10%–90% aqueous methanol over 4 minute gradient with 0.2% $H_3PO_4$, detecting at 220 nm).

[3aS-(3aα,4β,5β,7β,7aα)]4-[7-[2-[[(1,1-
Dimethylethyl)dimethylsilyl]oxy]ethyl]octahydro-5-
hydroxy-4-methyl-1,3-dioxo-4,7-epoxy-2H-isoindol-
2-yl]-1-naphthalenecarbonitrile (2p(3A)) and [3aR-
(3aα,4β,5β,7β,7aα)]-4-[7-[2-[[(1,1Dimethylethyl)
dimethylsilyl]oxy]ethyl]octahydro-5-hydroxy-4-
methyl-1,3-dioxo-4,7-epoxy-2H-isoindol-2-yl]-1-
naphthalenecarbonitrile (2p(3B))

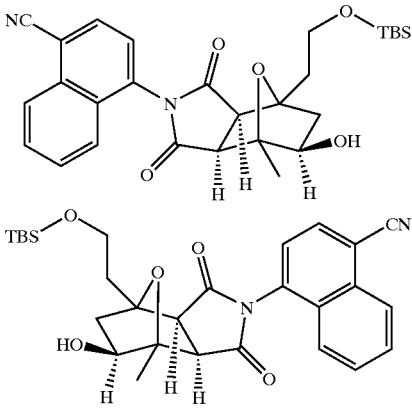

The racemic compound 2p(2) was separated into the individual enantiomers by chiral normal phase liquid chromatography. A Chiralpak OD column (50×500 mm) was used, eluting with 13% EtOH/hexanes over 99 min at 50 mL/min detecting at 220 mn. The faster eluting isomer 2p(3A) had a retention time=45 min and the slower eluting isomer 2p(3B) had a retention time=66 min.

[3aS-(3aα,4β,5β,7β,7aα)]-4-[Octahydro-5-hydroxy-
7-(2-hydroxyethyl)-4-methyl-1,3-dioxo-4,7-epoxy-
2H-isoindol-2-yl]-1-naphthalenecarbonitrile (2pA)
and [3aR-(3aα,4β,5β,7β,7aα)]-4-[Octahydro-5-
hydroxy-7-(2-hydroxyethyl)-4-methyl-1,3-dioxo-4,
7-epoxy-2H-isoindol-2-yl]-1-
naphthalenecarbonitrile, (2pB)

2p(3A) (0.84 g, 2.14 mmol) was dissolved in 2% 12 N HCl/EtOH (20 mL), stirred for 5 minutes and concentrated under reduced pressure. Purification by flash chromatography on silica gel eluting with 5–10% MeOH/CH$_2$Cl$_2$ gave 0.57 g (88%) of 2pA. 2pA which came from the faster eluting isomer (2p(3A)) was found to be 99.7% ee by analytical chiral normal phase chromatography. HPLC conditions: 99.7% at 2.17 min (Chiralcel OJ 44.6×250 mm, 10 micron, 40° C., isocratic 80% Heptane/20% EtOH/MeOH (1:1), 1.0 mL/min., detection at 288 nm).

2p(3B) (0.86 g, 2.19 mmol) was dissolved in 2% 12N HCl/EtOH (20 mL), stirred for 5 minutes and concentrated under reduced pressure. Purification by flash chromatography on silica gel eluting with 5–10% MeOH/CH$_2$Cl$_2$ gave 0.60 g (90%) of 2pB. 2pB which came from the slower eluting isomer (2p(3B)) was found to have 87.1% ee by analytical chiral normal phase chromatography. HPLC conditions: 87.1% at 18.4 min (Chiralcel OJ 44.6×250 mm, 10 micron, 40° C., isocratic 80% heptane/20% EtOH/MeOH (1:1), 1.0 mL/min., detection at 288 nm).

The absolute conformation for compounds 2pA and 2pB has not been determined. For simplicity in nomenclature, we have designated compound 2pA as having an "S" configuration and compound 2pB as having a "R" configuration. Enantiomerically pure products derived from compound 2pA will be designated as having a "S" configuration and enantiomerically pure products derived from compound 2pB will be designated as having a "R" configuration

Example 2q

Production of [3aS-(3aα,4β,5β,7β,7aα)]-4-[7-[2-(4-Cyanophenoxy)ethyl]octahydro-5-hydroxy-4-methyl-1,3-dioxo-4,7-epoxy-2H-isoindol-2-yl]-1-naphthalenecarbonitrile (2qA) and [3aR-(3aα,4β,5β,7β,7aα)]-4-[7-[2-(4-Cyanophenoxy)ethyl]octahydro-5-hydroxy-4-methyl-1,3-dioxo-4,7-epoxy-2H-isoindol-2-yl]-1-naphthalenecarbonitrile, (2qB)

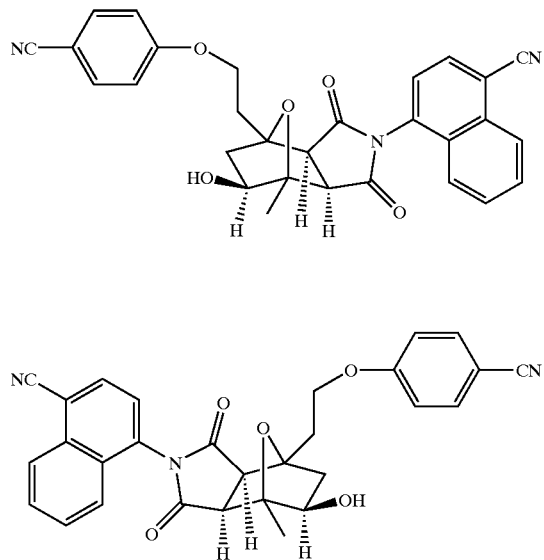

DBAD (26 mg, 0.115 mmol) was added to a solution of PPh$_3$ (30 mg, 0.115 mmol) in THF (0.65 mL). After stirring for 10 min, 4-cyanophenol (13.6 mg, 0.115 mmol) was added and the reaction mixture was stirred for a further 5 min. Compound 2pA (30 mg, 0.076 mmol) was added and the mixture was stirred at rt for 1 h. The reaction was concentrated under reduced pressure. Purification by flash chromatography on silica gel eluting with 30% acetone/70% CHCl$_3$ gave 23.1 mg (0.047 mmol, 61.7%) of compound 2qA. HPLC conditions: 95% at 3.06 min (YMC S5 ODS 4.6×50 mm, 10%–90% aqueous methanol over 4 minute gradient with 0.2% H$_3$PO$_4$, detecting at 220 nm). MS (ES): m/z 494.09 [M+H]$^+$. [α]$_D$=53.30°, C=4.5 mg/cc in THF, (589 nm)

DBAD (26 mg, 0.115 mmol) was added to a solution of PPh$_3$ (30 mg, 0.115 mmol) in THF (0.65 mL). After stirring for 10 min, 4-cyanophenol (13.6 mg, 0.115 mmol) was added and the reaction mixture was stirred for a further 5 min. Compound 2pB (30 mg, 0.076 mmol) was added and the mixture was stirred at rt for 1 h. The reaction was concentrated under reduced pressure. Purification by flash chromatography on silica gel eluting with 30% acetone/70% CHCl$_3$ gave 20.3 mg (0.041 mmol, 54.2%) of compound 2qB. HPLC conditions: 90% at 3.07 min (YMC S5 ODS 4.6×50 mm, 10%–90% aqueous methanol over 4 minute gradient with 0.2% H$_3$PO$_4$, detecting at 220 nm). MS (ES): m/z 494.09 [M+H]$^+$. [α]$_D$=−42.87°, C=6.6 mg/cc in THF, @ 589 nm)

Example 2r

Production of (3aα,4β,7β,7aα)-4-[4-[2-[(6-Chloro-1,2-benzisoxazol-3-yl)oxy]ethyl]octahydro-7-methyl-1,3-dioxo-4,7-epoxy-2H-isoindol-2-yl]-1-naphthalenecarbonitrile (2r)

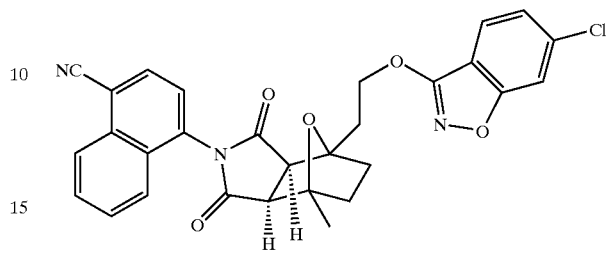

To a solution of PPh$_3$ (52 mg, 0.20 mmol) in 0.5 mL THF was added DBAD (46 mg, 0.20 mmol) as one solid portion. The resulting mixture was stirred for 10 min before 6-chloro-3-hydroxy-1,2-benzisoxazole (34 mg, 0.20 mmol) was added. Stirring was continued for 10 min before a solution of 2j(2) (50 mg, 0.13 mmol) in 0.5 mL THF was introduced via canula. The resulting mixture was stirred at ambient temperature for 24 h, concentrated and purified by preparative reverse phase HPLC (YMC S5 ODS 20×100 mm column; eluting with 30–100% aqueous MeOH containing 0.1% TFA over 10 min at 20 mL/min) to yield a white solid. The obtained solids were dissolved in CH$_2$Cl$_2$, washed with sat. NaHCO$_3$ solution, dried over Na$_2$SO$_4$ and concentrated to yield 50 mg (71%) of 2r as a colorless oil. HPLC: 26% at 3.89 min and 74% at 4.02 min (mixture of atropisomers, retention time) (YMC S5 ODS column 4.6×50 mm Ballistic, 10–90% aqueous methanol over 4 minutes containing 0.2% H$_3$PO$_4$, 4 mL/min, monitoring at 220 nm), MS (ES): m/z 528.4 [M+H]$^+$.

Example 2s

Production of (3aα,4β,7β,7aα)-4-[Octahydro-4-methyl-7-[2-[(6-nitro-1H-indazol-3-yl)oxy]ethyl]-1,3-dioxo-4,7-epoxy-2H-isoindol-2-yl]-1-naphthalenecarbonitrile (2s)

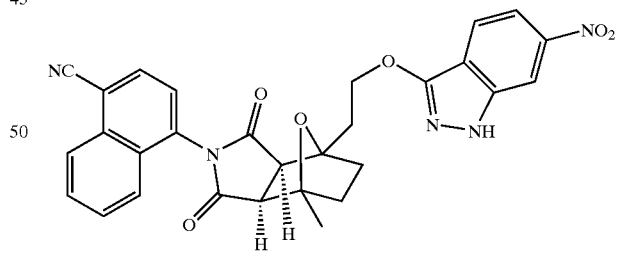

To a solution of 2j(2) (50 mg, 0.13 mmol) in toluene (1 mL) was added ADDP (50 mg, 0.20 mmol), 6-nitro-3-indazolinone (36 mg, 0.20 mmol) and n-Bu$_3$P (50 μL, 0.2 mmol). The resulting mixture was heated to 80° C. for 24 h, concentrated and purified by a combination of preparative reverse phase HPLC (YMC S5 ODS 20×100 mm column; eluting with 30–100% aqueous MeOH containing 0.1% TFA over 10 min at 20 mL/min) and flash chromatography (silica gel, 25% acetone in CHCl$_3$) to give 17 mg (25%) of 2s as a yellow solid. HPLC: 24% at 3.60 min and 76% at 3.74 min (mixture of atropisomers, retention time) (YMC S5 ODS column 4.6×50 mm Ballistic, 10–90% aqueous methanol over 4 minutes containing 0.2% $H_3PO_4$, 4 mL/min, monitoring at 220 nm), MS (ES): m/z 537.6 $[M+H]^+$.

Example 2t

Production of [3aS-(3aα,4β,5β,7β,7aα)]-4-[7-[2-(1,2-Benzisoxazol-3-yloxy)ethyl]octahydro-5-hydroxy-4-methyl-1,3-dioxo-4,7-epoxy-2H-isoindol-2-yl]-1-naphthalenecarbonitrile (2t)

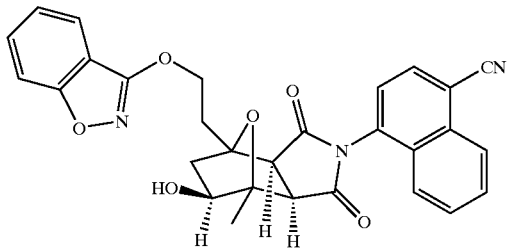

$PPh_3$ (47 mg, 0.18 mmol), DBAD (41 mg, 0.18 mmol), 3-hydroxy-1,2-benzisoxazole (24 mg, 0.18 mmol) and compound 2pA (35 mg, 0.09 mmol) were reacted according to the procedure given for 2r. Purification was achieved by reverse phase HPLC (YMC S5 ODS 20×100 mm column; eluting with 30–100% aqueous MeOH containing 0.1% TFA over 10 min at 20 mL/min) to yield a white solid. The obtained solids were dissolved in $CH_2Cl_2$, washed with sat. $NaHCO_3$ solution, dried over $Na_2SO_4$ and concentrated furnishing 29 mg (64%) of 2t as a colorless oil. HPLC: 96% at 3.29 min (mixture of atropisomers, retention time) (YMC S5 ODS column 4.6×50 mm Ballistic, 0–100% aqueous methanol over 4 minutes containing 0.2% $H_3PO_4$, 4 mL/min, monitoring at 220 nm), MS (ES): m/z 510.2 $[M+H]^+$.

Example 2u

Production of [3aR-(3aα,4β,5β,7β,7aα)]-4-[7-[2-(1,2-Benzisoxazol-3-yloxy)ethyl]octahydro-5-hydroxy-4-methyl-1,3-dioxo-4,7-epoxy-2H-isoindol-2-yl]-1-naphthalenecarbonitrile (2u)

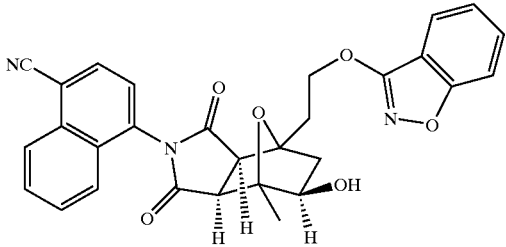

$PPh_3$ (47 mg, 0.18 mmol), DBAD (41 mg, 0.18 mmol), 3-hydroxy-1,2-benzisoxazole (24 mg, 0.18 mmol) and 2pB (35 mg, 0.09 mmol) were reacted according to the procedure given for 2r. Purification was achieved by reverse phase HPLC (YMC S5 ODS 20×100 mm column; eluting with 30–100% aqueous MeOH containing 0.1% TFA over 10 min at 20 mL/min) to yield a white solid. The obtained solids were dissolved in $CH_2Cl_2$, washed with sat. $NaHCO_3$ solution, dried over $Na_2SO_4$ and concentrated furnishing 23 mg (51%) of 2u as a colorless oil. HPLC: 95% at 3.29 min (mixture of atropisomers, retention time) (YMC S5 ODS column 4.6×50 mm Ballistic, 0–100% aqueous methanol over 4 minutes containing 0.2% $H_3PO_4$, 4 mL/min, monitoring at 220 nm), MS (ES): m/z 510.4 $[M+H]^+$.

Example 2v

Production of (3aα,4β,7β,7aα)-4-[4-[2-(4-Cyanophenoxy)ethyl]-7-ethyloctahydro-1,3-dioxo-4,7-epoxy-2H-isoindol-2-yl]-1-naphthalenecarbonitrile, (2v)

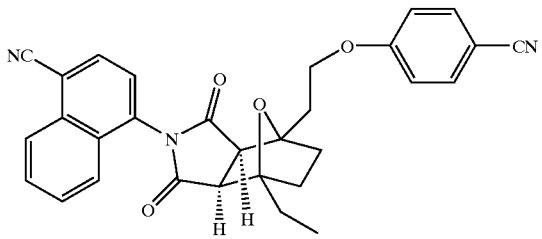

2-Ethyl-5-(2-hydroxyethyl)furan (2v(1))

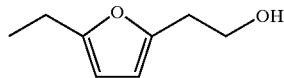

n-BuLi (2.5 M in hexane, 4.4 mL, 11 mmol) was added to a solution of 2-ethylfuran (1.05 mL, 10 mmol) in THF (10 mL) at −25° C. The solution was warmed to rt and stirred for 3 h. Ethylene oxide (0.75 mL) was added at −78° C. The reaction was stirred for 0.5 h at −15° C. and overnight at rt. Aqueous sat. $NH_4Cl$ was added and the mixture was extracted with ether (3×). The combined extracts were washed with water (1×) and brine (1×) and dried over $Na_2SO_4$. Purification by flash chromatography on silica gel eluting with 30% EtOAc/70% hexane gave 1.12 g (8.02 mmol, 80.2%) of 2v(1) as a yellow oil.

(3aα,4β,7β,7aα)-4-[4-Ethyl-1,3,3a,4,7,7a-hexahydro-7-(2-hydroxyethyl)-1,3-dioxo-4,7-epoxy-2H-isoindol-2-yl]-1-naphthalenecarbonitrile (2v(2))

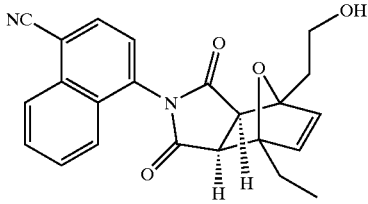

A solution of 2v(1) (280 mg, 2.00 mmol) and the 4-(2,5-dihydro-2,5-dioxo-1H-1-yl)-1-naphthalenecarbonitrile (496 mg, 2.00 mmol) in benzene (2 mL) was stirred at 60° C. for 2 h. The reaction mixture was concentrated under reduced pressure. The yellow solid, 2v(2), was used directly in the next step.

(3aα,4β,7β,7aα)-4-[4-Ethyloctahydro-7-(2-hydroxyethyl)-1,3-dioxo-4,7-epoxy-2H-isoindol-2-yl]-1-naphthalenecarbonitrile (2v(3))

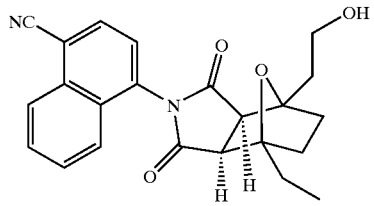

A mixture of 2v(2) (764 mg, 1.97 mmol) and 10% Pd/C (115 mg, cat.) in EtOAc (36 mL) was stirred under a hydrogen atmosphere at rt for 2 h. The reaction mixture was filtered through celite and concentrated under reduced pressure to give 779 mg of crude 2v(3). Purification of this crude product by flash chromatography on silica gel eluting with 70% EtOAc/30% hexane gave 235 mg (0.6 mmol, 30.1%) of 2v(3). HPLC conditions: 99% at 2.84 min (YMC S5 ODS 4.6×50 mm, 10%–90% aqueous methanol over 4 minute gradient with 0.2% $H_3PO_4$, detecting at 220 nm). MS (ES): m/z 391.12 $[M+H]^+$.

(3aα,4β,7β,7aα)-4-[4-[2-(4-Cyanophenoxy)ethyl]-7-ethyloctahydro-1,3-dioxo-4,7-epoxy-2H-isoindol-2-yl]-1-naphthalenecarbonitrile (2v)

DBAD (44.2 mg, 0.192 mmol) was added to a solution of $PPh_3$ (50.4 mg, 0.192 mmol) in THF (1 mL). After stirring for 10 mins, 4-cyanophenol (23 mg, 0.192 mmol) was added and the reaction mixture was stirred for an additional 5 mins. 2v(3) (50 mg, 0.128 mmol) was added and the mixture was stirred at rt for 2 h. The reaction was concentrated under reduced pressure. Purification by flash chromatography on silica gel eluting with 40% EtOAc/60% hexane gave 43 mg (0.087 mmol, 68.4%) of compound 2v as a white solid. HPLC conditions: 99% at 3.65 min (YMC S5 ODS 4.6×50 mm, 10%–90% aqueous methanol over 4 minute gradient with 0.2% $H_3PO_4$, detecting at 220 nm). MS (ES): m/z 492.16 $[M+H]^+$.

Example 2w

Production of [3aS-(3aα,4β,5β,7β,7aα)]-4-[7-[2-(Acetyloxy)ethyl]octahydro-5-hydroxy-4-methyl-1,3-dioxo-4,7-epoxy-2H-isoindol-2-yl]-1-naphthalenecarbonitrile (2wA) and [3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile(2wB)

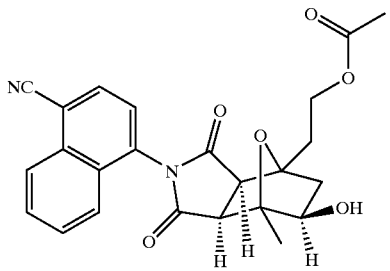

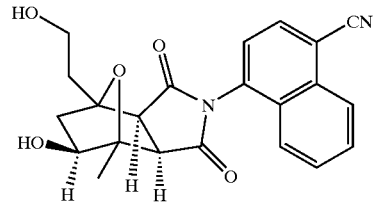

A racemic mixture of compounds 2pA and 2pB (1.90 gram) were dissolved in 100 mL of anhydrous THF in a 2 L flask. Anhydrous tert-butyl-methyl ether (900 mL) and vinyl acetate (40 mL) were transferred into the flask with stirring and lipase (20 g, type II, crude, from porcine pancreas; Sigma, Cat# L3126) was added. The reaction mixture was stirred for 21 hr at rt at which point an additional 5 grams of the lipase and 20 mL of vinyl acetate were added. The reaction was stirred at rt for an additional 19 h, stored at 4° C. without stirring for 36 h and then stirred at rt for another 22 h (until the desired % ee was apparent by chiral HPLC). To monitor the reaction, 200 uL of the mixture was withdrawn and centrifuged. The supernatant (100 uL) was dried under nitrogen and the resulting residue was dissolved in 100 uL of EtOH and subjected to HPLC analysis:

1) Reverse phase HPLC: Column, YMC-ODS AQ 150× 4.6; flow rate, 1.2 mL/min; sample size, 10 uL solvent $A_1$: 1 mM HCl in water; solvent B, MeCN; monitored at 300 nm Gradient: Time(min) 0 8 8.5 9.5 10 12 B% 30 60 85 85 30 30

2) Chiral-HPLC: Column, CHIRALCEL OJ 4.6×250 mm mobile phase, Hexane/MeOH/EtOH (8:1:1) flow rate, 1 mL/min; sample size, 20 uL monitored at both 220 and 300 nm performed at 25° C. & 40° C. (for ee % determination of reaction mixture)

The enzyme was removed by filtration and filtrate was concentrated under vacuum. The resulting mixture was dissolved in $CHCl_3$ and adsorbed onto silica gel (63–200 microns). These solids were applied to a VLC funnel (3 cm I.D., VLC is vacuum liquid chromatography using glass funnels having 24/40 joints at the bottom) containing a 5 cm bed height of silica gel (25–40 microns) and a step gradient was carried out. The gradient was 100% $CHCl_3$ in the first 3 fractions, followed by $CHCl_3$-1% MeOH (3 fractions), $CHCl_3$-2% MeOH (3 fractions), $CHCl_3$-3% MeOH (3 fractions), $CHCl_3$-4% MeOH (3 fractions), and finally with $CHCl_3$-5% MeOH (3 fractions). The volume of the fractions was 100 mL until reaching $CHCl_3$-3% MeOH and from that point on it was 200 mL. 2wA elutes in the last two fractions of 100% $CHCl_3$ and until the first fraction of $CHCl_3$-2% MeOH. 2wB elutes starting with the second fraction of $CHCl_3$-2% MeOH, and continues to the first fraction of $CHCl_3$-5% MeOH. The crude compound 2wB contained a small amount of a colored impurity which was removed by a Sephadex column [LH-20 swollen in $CHCl_3$-MeOH (2:1), column (2.5 cm I.D. & 90 cm long) to yield 632 mg of compound 2wB. Compound 2wA: HPLC conditions: 98% at 7.2 min (method 1), chiral HPLC conditions: 29.0 min @ 25° C. (method 2). Compound 2wB: HPLC conditions: 98% at 4.6 min (method 1), chiral HPLC conditions: 96% ee at 25.7 min @ 25° C) & 19.8 min @ 40° C.) (method 2).

Example 2x

Production of (3aα,4β,7β,7aα)-4-[4-[2-[[(1,1-Dimethylethyl)dimethylsilyl]oxy]ethyl]-1,3,3a,4,7,7a-hexahydro-7-methyl-1,3-dioxo-4,7-epoxy-2H-isoindol-2-yl]-2-(trifluoromethyl)benzonitrile & (3aα,4α,7α,7aα)-4-[4-[2-[[(1,1-Dimethylethyl)dimethylsilyl]oxy]ethyl]-1,3,3a,4,7,7a-hexahydro-7-methyl-1,3-dioxo-4,7-epoxy-2H-isoindol-2-yl]-2-(trifluoromethyl)benzonitrile (2xA & 2xB)

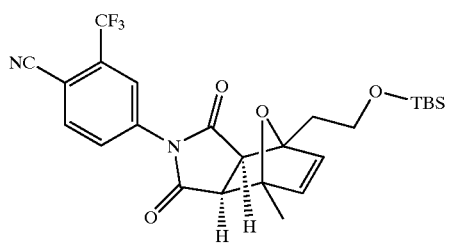

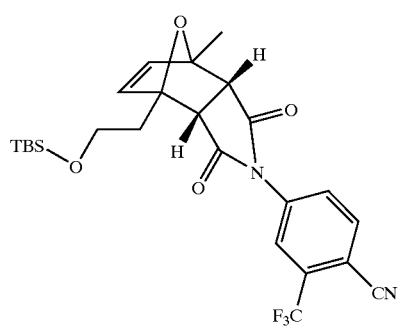

Compound 2h(2) (2.00 g, 8.50 mmol) and 4-(2,5-Dihydro-2,5-dioxo-1H-pyrrol-1-yl)-2-trifluoromethyl-benzonitrile (1.50 g, 5.60 mmol) were mixed in benzene (5.0 mL) and heated at 60° C. for 14 h, then cooled to 25° C. The solvent was removed at 40° C. under vacuum for 1 h to give the crude material which was purified by flash chromatography on SiO₂ eluting with 0.5% EtOAc/CH₂Cl₂ to give 2.0 g of compound 2xA and 1.3 g of compound 2xB, both as light brown solids. Compound 2xA: HPLC: 95% at 4.200 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 507.1 [M+H]⁺. Compound 2xB: HPLC: 95% at 4.20 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 507.1 [M+H]⁺.

Example 2y

Production of [3aR-(3aα,4β,5β,7β,7aα)]-4-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-2-(trifluoromethyl)benzonitrile & [3aS-(3aα,4β,5β,7β,7aα)]-4-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-2-(trifluoromethyl)benzonitrile (2yA & 2yB)

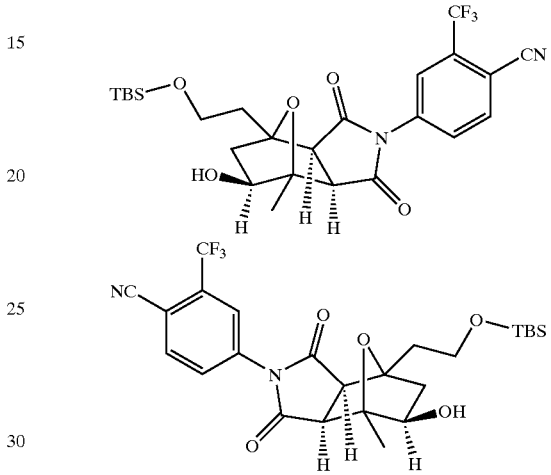

Compound 2xA (1.40 g, 2.77 mmol) and RhCl(PPh₃)₃ (0.128 g, 0.14 mmol) were mixed in a flask. The flask was then evacuated and filled with argon three times, followed by the syringe addition of THF (3.0 mL). Once all particulates were dissolved, catecholborane (0.59 mL, 5.54 mmol) was added dropwise. The reaction mixture was stirred at 25° C. under argon for 30 min, then cooled to 0° C. Phosphate buffer (pH=7, 20 mL) was added, followed by EtOH (10 mL), 30% H₂O₂/H₂O (2 mL). The reaction mixture was stirred at 0° C. for 3 h, then extracted with dichloromethane (3×25 mL). The combined organic layers were washed with 1 N NaOH (25 mL), 10% Na₂SO₃ (25 mL) and brine (25 mL). The crude material was then concentrated and purified by flash chromatography on SiO₂ eluting with 2% EtOAc/CH₂Cl₂ to 10% EtOAc/CH₂Cl₂ to give 0.63 g of a racemic mixture of compounds 2yA & 2yB as a light yellow solid. HPLC: 99% at 3.867 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 525.1 [M+H]

The racemic mixture of compounds 2yA & 2yB was separated by normal phase preparative chiral HPLC using a Chiracel OD column (5 cm×50 cm), eluting with 13% solvent B (EtOH) in solvent A (Hexane), flow rate: 50 mL/min. Compound 2yA eluted from 34 min to 38 min and compound 2yB eluted from 44 min to 49 min. Enantiomeric excess was determined by chiral HPLC. Compound 2yA: >99% ee (12.576 min (retention time) (Chiralcel OJ column 4.6×250 mm eluting with isocratic 85% heptane/15%

MeOH/ethanol (1:1), 1 mL/min, monitoring at 220 nm, 40° C.). Compound 2yB: 99% ee (18.133 min (retention time) (Chiralcel OJ column 4.6×250 mm eluting with isocratic 85% heptane/15% MeOH/ethanol (1:1), 1 mL/min, monitoring at 220 nm, 40° C.).

The absolute configuration for compounds 2yA & 2yB were not established. For simplicity in nomenclature, compound 2yA is designated herein as having an "R" configuration and compound 2yB as having an "S" configuration. Enantiomerically pure products derived from compound 2yA are designated herein as having a "R" configuration and enantiomerically pure products derived from compound 2yB are designated herein as having an "S" configuration.

Example 2z

Production of [3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-2-(trifluoromethyl)benzonitrile & [3aS-(3aα,4β,5β,7β,7aα)]-4-[Octahydro-5-hydroxy-7-(2-hydroxyethyl)4-methyl-1,3-dioxo-4,7-epoxy-2H-isoindol-2-yl]-2-(trifluoromethyl)benzonitrile (2zA & 2zB)

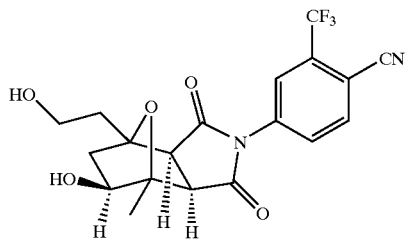

Compound 2yA (180 mg, 0.34 mmol) was dissolved in 2% HCl/EtOH (5.0 mL). After 30 min, saturated NaHCO₃ was added and the aqueous layer was extracted with dichloromethane (20 mL×3), washed with brine and dried over Na₂SO₄ to give 135 mg of compound 2zA as a white solid. HPLC: 99% at 2.257 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): mn/z 411.1 [M+H]⁺.

The above procedure was repeated with compound 2yB to yield the desired diol compound 2zB in similar yield.

Example 2a(i)

Production of [3aR-(3aα,4β,5β,7β,7aα)]-4-[7-[2-[(5-Chloro-2-pyridinyl)oxy]ethyl]octahydro-5-hydroxy-4-methyl-1,3-dioxo-4,7-epoxy-2H-isoindol-2-yl]-2-(trifluoromethyl)benzonitrile (2a(i))

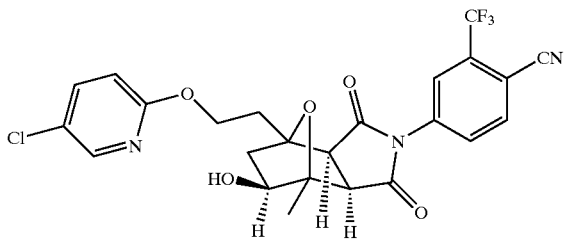

Triphenylphosphine (0.026 g, 0.098 mmol) and DBAD (0.023 g, 0.098 mmol) were mixed in THF (0.5 mL). After allowing the previous mixture to react for 15 min, 2-hydroxy-6-chloropyrimidine (0.016 g, 0.100 mmol) was added, the mixture was allowed to stir for 10 min and compound 2zA (0.020 g, 0.049 mmol) was added. The reaction mixture was stirred at 25° C. for 2 h and then the crude material was purified by preparative TLC, eluting with 10% acetone/CHCl₃, to give 0.014 g of compound 2a(i) as a light brown solid. HPLC: 100% at 3.370 min (retention time) (YMC S5 ODS column 4.6×50 mm eluting with 10–90% aqueous methanol over 4 minutes containing 0.1% TFA, 4 mL/min, monitoring at 220 mn), MS (ES): m/z 522.08 [M+H]⁺.

Example 2b(i)

Production of (3aα,4β,5β,7β,7aα)-4-[4-Ethyloctahydro-5-hydroxy-7-(2-hydroxyethyl)-1,3-dioxo4,7-epoxy-2H-isoindol-2-yl]-1-naphthalenecarbonitrile (2b(i)C)

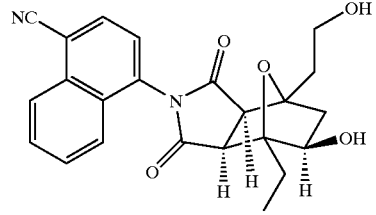

tert-Butyl-[2-(5-ethyl-furan-2-yl)-ethoxy]-dimethyl-silane (2b(i)A)

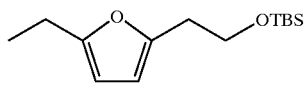

Imidazole (255 mg, 3.75 mmol) and TBSCl (414 mg, 2.75 mmol) were added to the solution of (2v(1)) (350 mg, 2.5 mmol) in DMF (4 mL). The mixture was stirred at rt for 15 hr and then 100 mg (0.66 mmol) of additional TBSCl was added to drive the reaction to completion. After stirring for an additional hour, the reaction mixture was diluted with diethylether (100 mL) and washed with water (20 mL), 1 N HCl (20 mL), water (20 mL) and brine (20 mL). The organic layer was dried over Na₂SO₄ and concentrated under reduced pressure to give 509 mg of compound 2b(i)A (80.3%) as a yellow oil.

(3aα,4β,7β,7aα)-4-[4-[2-[[(1,1-Dimethylethyl) dimethylsilyl]oxy]ethyl]-4-ethyl-1,3,3a,4,7,7a-hexahydro-1,3-dioxo-4,7-epoxy-2H-isoindol-2-yl]-1-naphthalenecarbonitrile (2b(i)B)

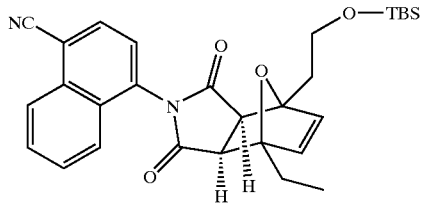

A solution of compound 2b(i)A (509 mg, 2.00 mmol) and 4-(2,5-dihydro-2,5-dioxo-1H-1-yl)-1-naphthalenecarbonitrile (498 mg, 2.00 mmol) in benzene (2 mL) was heated at 60° C. for 18 h. The reaction mixture was concentrated under reduced pressure to give 992 mg (99%) of crude compound 2b(i)B, which was used directly in the next step without further purification.

(3aα,4β,5β,7β,7aα)-4-[4-Ethyloctahydro-5-hydroxy-7-(2-hydroxyethyl)-1,3-dioxo-4,7-epoxy-2H-isoindol-2-yl]-1-naphthalenecarbonitrile (2b(i)C)

A mixture of compound 2b(i)B (992 mg, 1.98 mmol) and RhCl₂(PPh₃)₃ (183 mg, 0.198 mmol) was evacuated and filled with argon (3x). THF (20 mL) was added and once all particulates had dissolved, catecholborane (0.42 mL, 3.96 mmol) was slowly added dropwise. When the formation of product ceased, as was determined by HPLC, the reaction mixture was cooled to 0° C. and quenched with phosphate buffer (34 mL, pH 7.2) followed by the addition of EtOH (19 mL) and H₂O₂ (2.9 mL, 30% aq sol). After 2 h, additional phosphate buffer (6.8 mL, pH 7.2), EtOH (3.8 mL) and H₂O₂ (0.6 mL) were added. The reaction mixture was stirred at rt for 3 h. Once the boronate intermediate was consumed, the mixture was extracted with CH₂Cl₂ (300 mL) and the combined organic layers were washed with 1N NaOH, 10% aq NaHSO₃ and brine. The combined organic layers were dried over Na₂SO₄. Purification by flash chromatography on silica gel eluting with 10% MeOH/CH₂Cl₂ gave 75 mg (9.3%) of compound 2b(i)C as a gray solid. HPLC conditions: 97% at 2.43 min (Phenomenex-prime S5-C18 column 4.6x50 mm, 10%–90% aqueous methanol over 4 minute gradient with 0.2% H₃PO₄, detecting at 220 nm). MS (ES): m/z 407.18 [M+H]⁺.

Example 2c(i)

Production of (3aα,4β,5β,7β,7aα)-4-[7-[2-(4-Cyanophenoxy)ethyl]-4-ethyloctahydro-5-hydroxy-1,3-dioxo-4,7-epoxy-2H-isoindol-2-yl]-1-naphthalenecarbonitrile (2c(i))

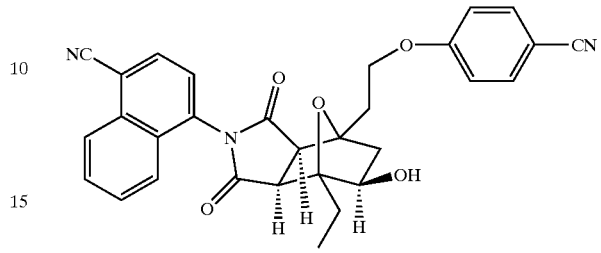

DBAD (39.6 mg, 0.172 mmol) was added to a solution of PPh₃ (45.1 mg, 0.172 mmol) in THF (0.8 mL). After stirring for 10 min, 4-cyanophenol (20.5 mg, 0.172 mmol) was added and the reaction mixture was stirred for an additional 5 min Compound 2b(i)C (25.0 mg, 0.062 mmol) was added and the mixture was stirred at rt for 2 h. The reaction was concentrated under reduced pressure. Purification by Prep TLC eluting with 10% acetone/CHCl₃ gave 18.1 mg (0.036 mmol, 57.6%) of compound 2c(i). HPLC conditions: 96% at 3.15 min (YMC S5 ODS 4.6x50 mm, 10%–90% aqueous methanol over 4 minute gradient with 0.2% H₃PO₄, detecting at 220 nm). MS (ES): m/z 508.14 [M+H]⁺.

Example 2d(i)

Production of (3aα,4β,5β,7β,7aα)-4-[Octahydro-5-hydroxy-7-(2-hydroxyethyl)-4-methyl-1,3-dioxo-4,7-epoxy-2H-isoindol-2-yl]-1-naphthalenecarbonitrile (2d(i))

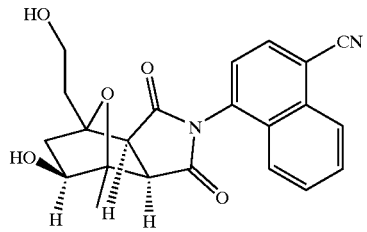

Compounds (2j(1)) and (2j(2)) were converted to compound 2d(i) by biotransformation.
Microbial Hydroxylation of Compound 2j(1)
Step 1: Reaction
One frozen vial (approximately 2 ml) of *Streptomyces griseus* ATCC 10137 was added to a 500 ml flask containing 100 ml of transformation medium. The transformation medium was prepared as follows: to a 2 liter plastic beaker, 20 g of dextrose, 5.0 g of yeast extract, 5.0 g of soybean meal, 5.0 g of sodium chloride, 5.0 g of potassium phosphate, diabasic and one liter of deionized water were added and the mixture was stirred at room temperature for 3 to 30 min. The pH of the mixture was then adjusted to 7.0 with 1 N HCl or 1 N NaOH. The resulting mixture was dispensed into 500 ml flask (100 ml per flask). The flasks were covered with Bio/Wrap and autoclaved at 121° C. for 15 min. and cooled down to room temperature before use.

The culture was incubated at 28° C. and 250 rpm for 3 days. One ml of the resulting culture was added to a 500 ml flask containing 100 ml of the transformation medium and the flask was incubated at 28° C. and 250 rpm for 24 hours. Ten ml of the resulting culture was transferred to a 50 ml flask, to which 1 mg of compound 2j(1) in 0.2 ml ethanol was added. The flask was incubated at 28° C. and 250 rpm for 23 hours and the reaction culture was extracted with EtOAc (10 ml). The EtOAc extract was dried under $N_2$ and the residue was dissolved in 1 ml of MeOH (reaction extract). HPLC analysis showed that peak area ratio of compound 2d(i) to compound 2j(1) in the reaction culture was about 1.1/1.

Step 2: Product Analysis

HPLC

10 μl of the reaction extract was injected into HPLC column (YMC ODS-AQ C-18 column, 150×6.0 mm i.d.). The column was eluted with 1 mM HCl in water/$CH_3CN$ at 1.2 ml/min flow rate: 30 to 60% $CH_3CN$ over 8 min, 60 to 85% $CH_3CN$ over 0.5 min, 85% $CH_3CN$ for 1 min, 85 to 30% $CH_3CN$ over 0.5 min. The eluents were monitored at 300 nm. Two major peaks with about 1 to 1 area ratio were observed, which had same UV spectra as those of compounds 2d(i) and (2j(1)), and had retention times of 4.55 min and 7.23 min, respectively, matching the retention times of authentic samples of compound 2d(i)(4.53 min) and compound (2j(1)) (7.2 min).

LC/MS

The reaction extract: two major UV peaks. Peak 1, Tr 4.68 min: 391 [M+H]$^+$, 343, 319, 303, 289 Peak 2, Tr 5.35 min: 375 [M+H]$^+$, 345

Authentic Samples

Compound 2d(i), Tr 4.82 min: 391 [M+H]$^+$, 343, 319, 289
Compound (2j(1)), Tr 5.48 min: 375 [M+H]$^+$, 345

As will be understood by those of skill in the art upon reading this disclosure, additional SARMs for use in the present invention can also be identified in accordance with the methods described herein. For example, a test compound suspected of having selective androgen receptor modulating activity can be screened for antagonist activity in a hormone-dependent tumor cell line such as a human or mouse breast tumor cell line and screened for agonist activity in another nontumor androgen receptor containing cell line such as a muscle, prostate or seminal vesicle cell line as described in the assays below. These screening assays can be performed routinely in accordance with the teachings provided herein.

Example 3

AR Binding Assay

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals), respectively, were incubated at 37° C. to remove any endogenous ligand that might be complexed with the receptor in the cells. After 48 hours, either a saturation analysis to determine the Kd for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM –0.2% CA-FBS) containing [$^3$H]-DHT (in concentrations ranging from 0.1 nM to 16 nM) in the absence (total binding) or presence (non-specific binding) of a 500-fold molar excess of unlabeled DHT were added to the cells. After 4 hours at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45–99, (1981), the disclosure of which is herein incorporated by reference.

For the competition studies, media containing 1 nM [$^3$H]-DHT and a test compound in concentrations ranging from 10$^{-10}$ to 10$^{-5}$ M were added to the cells. Two replicates were used for each sample. After 4 hours at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified (IC$_{50}$) after log-logit transformation. The $K_I$ values were determined by application of the Cheng-Prusoff equation to the IC$_{50}$ values, where:

$$K_I = \frac{IC_{50}}{\left(1 + \left(^3H\text{-}DHT\right)/K_d \text{ for } ^3H\text{-}DHT\right)}.$$

After correcting for non-specific binding, IC$_{50}$ values were determined. The IC$_{50}$ is defined as the concentration of competing ligand needed to reduce specific binding by 50%. The $K_d$s for [$^3$H]-DHT for MDA 453 and LNCaP were 0.7 and 0.2 nM respectively.

Example 4

Human Prostate Cell Proliferation Assay

The effects of test compound on proliferation of human prostate cancer cell lines was also examined. For that, MDA PCa2b cells, a cell line derived from the metastasis of a patient that failed castration (Navone et al., Clin. Cancer Res., 3, 2493–500 (1997)), were incubated with or without the test compounds for 72 hours and the amount of [$^3$H]-thymidine incorporated into DNA was quantified as a way to assess number of cells and therefore proliferation. The MDA PCa2b cell line was maintained in BRFF-HPCl media (Biological Research Faculty & Facility Inc., MD.) supplemented with 10% FBS. For the assay, cells were plated in Biocoated 96-well microplates and incubated at 37° C. in 10% FBS (charcoal-stripped)/BRFF-BMZERO (without androgens). After 24 hours, the cells were treated in the absence (blank) or presence of 1 nM DHT (control) or with test compounds (sample) in concentrations ranging from 10$^{-10}$ to 10$^{-5}$M. Duplicates were used for each sample. The compound dilutions were performed on a Biomek 2000 laboratory work station. Seventy two hours later 0.44 uCi. of [$^3$H]-Thymidine (Amersham) was added per well and incubated for another 24 h followed by trypsinization, harvesting of the cells onto GF/B filters. Micro-scint PS were added to the filters before counting them on a Beckman TopCount.

The % Inhibition was calculated as:

% Inhibition=100×(1−[average$_{control}$−average$_{blank}$/average$_{sample}$−average$_{blank}$])

Data was plotted and the concentration of compound that inhibited 50% of the [$^3$H]-Thymidine incorporation was quantified (IC$_{50}$).

Example 5

C2C12 Mouse Myoblast Transactivation Assay

Two functional transactivation assays were developed to assess the efficacy of androgen agonists in a muscle cell background using a luciferase reporter. The first assay (ARTA Stable 1) uses a cell line, Stable 1 (clone #72), which stably expresses the full length rat androgen receptor but requires the transient transfection of an enhancer/reporter. This cell line was derived from C2C12 mouse myoblast cells. The second assay (ARTA Stable 2) uses a cell line, Stable 2 (clone #133), derived from Stable 1, which stably expresses both rAR and the enhancer/luciferase reporter. These assays and cell lines The enhancer/reporter construct used in this system is pGL3/2XDR-1/luciferase. 2XDR-1 was reported to be an AR specific response element in CV-1 cells, Brown et. al. The Journal of Biological Chemistry 272, 8227–8235, (1997). It was developed by random mutagenesis of an AR/GR consensus enhancer sequence.

For the ARTA Stable 1 assay, Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5×Antibiotic-Antimycotic, and 800 ug/ml Geneticin (Gibco BRL, Cat. No.: 10131-035). Forty-eight hours later, cells are transfected with pGL3/2XDR-1/luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 µl/well Opti-MEM media (Gibco BRL, Cat. No.: 31985-070). To this, 0.5 µl/well Plus reagent is added. This mixture is incubated for 15 minutes at room temperature. In a separate vessel, 0.385 ul/well LipofectAMINE reagent is diluted with 5 µl well Opti-MEM. The DNA mixture is then combined with the LipofectAMINE mixture and incubated for an additional 15 minutes at room temperature. During this time, the media from the cells is removed and replaced with 60 µl/well of Opti-MEM. To this is added 10 µl/well of the DNA/LipofectAMINE transfection mixture. The cells are incubated for 4 hours. Following the incubation, the transfection mixture is removed from the cells and replaced with 90 ul of high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, and 800 µg/ml Geneticin (Gibco BRL, Cat. No.: 10131-035). Test compounds, 10 µl/well at an appropriate drug dilution, are then placed in each well. Twenty-four hours later, the Steady-Glo™ Luciferase Assay System is used to detect activity according to the manufacturer's instructions (Promega, Cat. No.: E2520).

For the ARTA stable 2 assay, Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, 800 µg/ml Geneticin (Gibco BRL, Cat. No.: 10131-035) and 800 µg/ml Hygromycin β (Gibco BRL, Cat. No.: 10687-010). Forty-eight hours later, the media on the cells is removed and replaced with 90 µl fresh. Test compounds, 10 µl/well at an appropriate drug dilution, are then placed in each well. Twenty-four hours later, the Steady-Glo™ Luciferase Assay System is used to detect activity according to the manufacturer's instructions (Promega, Cat. No.: E2520). See U.S. patent application Ser. No. 09/885,831 (unassigned), entitled "Cell Lines and Cell-Based Assays for Identification of Androgen Receptor Modulators", filed Jun. 20, 2001, by Jacek Ostrowski et al., which patent application is incorporated herein by reference by its entirety.

Example 6

Murine Breast Cell Proliferation Assay

The ability of test compounds to modulate the function of the AR was determined by testing said compounds in a proliferation assay using the androgen responsive murine breast cell line derived form the Shionogi tumor (Hiraoka et al., Cancer Res., 47, 6560–6564 (1987)). Stable AR dependent clones of the parental Shionogi line were established by passing tumor fragments under the general procedures originally described in Tetuo, et. al. (Cancer Research 25, 1168–1175 (1965)). From the above procedure, one stable line, SC114, was isolated, characterized and utilized for the testing of example compounds. SC114 cells were incubated with or without the test compounds for 72 hours and the amount of [3H]-thymidine incorporated into DNA was quantified as a surrogate endpoint to assess the number of cells and therefore the proliferation rate as described in Suzuki et. al. (J. Steroid Biochem. Mol. Biol. 37, 559–567 (1990)). The SC114 cell line was maintained in MEM containing 10$^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1;1, v/v) containing 0.1% BSA] with (antagonist mode) or without (agonist mode) 10$^{-8}$ M testosterone and the test compounds of the present invention in concentrations ranging from 10$^{-10}$ to 10$^{-5}$ M. Duplicates were used for each sample. The compound dilutions were performed on a Biomek 2000 laboratory work station. Seventy two hours later 0.44 uCi. of [3H]-Thymidine (Amersham) was added per well and incubated for another 2 hr followed by trypsinization, and harvesting of the cells onto GF/B filters. Micro-scint PS were added to the filters before counting them on a Beckman TopCount.

For the antagonist mode, the % Inhibition was calculated as:

% Inhibition=100×(1−[average$_{sample}$−average$_{blank}$/average$_{control}$−average$_{blank}$])

Data was plotted and the concentration of compound that inhibited 50% of the [$^3$H]-Thymidine incorporation was quantified (IC$_{50}$).

For the agonist mode, % Control was referred as the effect of the tested compound compared to the maximal effect observed with the natural hormone, in this case DHT, and was calculated as:

% Control=100×(average$_{sample}$−average$_{blank}$)/(average$_{control}$−average$_{blank}$)

Data was plotted and the concentration of compound that inhibited 50% of the [$^3$H]-Thymidine incorporation was quantified (EC$_{50}$).

Example 7

Wet Prostate Weight Assay AR Antagonist Assay

The activity of test compounds as AR antagonists was investigated in an immature male rat model, a standard, recognized test of antiandrogen activity of a given compound (Hershberger et al. Proc. Soc. Expt. Biol. Med., 83, 175 (1953); Walsh. P. C. and Gittes, R. F., Endocrinology, 86, 624 (1970); and Furr et al., J. Endocrinol., 113, R7–9 (1987)). The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men (Labrie et al. Clin. Invest. Med., 16, 475–492 (1993)). However, this is not a major pathway, since in both animals and humans castration leads to almost complete involution of the prostate and seminal vesicles without concomitant adrenalectomy. Therefore, under normal conditions, the adrenals do not support significant growth of prostate tissues (Luke, M. C. and Coffey, D. S. "The Physiology of Reproduction" ed. By E. Knobil and J. D. Neill, 1, 1435–1487 (1994)). Since the male sex organs are the tissues most responsive to modulation of the androgen activity, this model is used to determine the androgen dependent growth of the sex accessory organs in immature castrated rats.

Male immature rats (19–20 days old Sprague-Dawley, Harlan Sprague-Dawley) were castrated under metofane anesthesia. Five days after surgery these castrated rats (60–70 g, 23–25 day-old) were dosed for 3 days. Animals were dosed sub-cutaneously (s.c.) 1 mg/kg with Testosterone Proprionate (TP) in arachis oil vehicle and test compounds (compounds of the present invention) were administered orally by gavage (p.o.) in dissolved/suspensions of 80% PEG 400 and 20% Tween 80 (PEGTW). Animals were dosed (v/w) at 0.5 ml of vehicle /100 g body weight. Experimental groups were as follows:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To assess antagonist activity, a test compound was administered (p.o. in PEGTW, QD) with TP (s.c. as administered in group 2) in a range of doses.
5. To assess agonist activity, a test compound was administered alone (p.o. in PEGTW, QD) in a range of doses.

At the end of the 3-day treatment, the animals were sacrificed, and the ventral prostate weighed. To compare data from different experiments, weights of the sexual organs were first standardized as mg per 100 g of body weight, and the increase in organ weight induced by TP was considered as the maximum increase (100%). ANOVA followed by one-tailed Student or Fischer's exact test was used for statistical analysis.

The gain and loss of sexual organ weight reflect the changes of the cell number (DNA content) and cell mass (protein content), depending upon the serum androgen concentration (Okuda et al., J. Urol., 145, 188–191 (1991)). Therefore, measurement of organ wet weight is sufficient to indicate the bioactivity of androgens and androgen antagonists. In immature castrated rats, replacement of exogenous androgens increases seminal vesicles (SV) and the ventral prostate (VP) in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

In this immature castrated rat model, a known AR antagonist (Casodex) was also administered simultaneously with 0.1 mg of TP ($ED_{80}$), inhibiting the testosterone-mediated increase in the weights of the VP and SV in a dose dependent manner. The antagonist effects were similar when dosing orally or subcutaneously. SARMs of the invention also exhibited AR antagonist activity by suppressing the testosterone-mediated increase in the weights of VP and SV.

Example 8

Levator Ani & Wet Prostate Weight Assay AR Agonist Assay

The activity of test compounds as AR agonists was investigated in an immature male rat model, a recognized test of anabolic effects in muscle and sustaining effects in sex organs for a given compound (Hershberger et al., *Proc. Soc. Expt. Biol. Med.*, 83, 175 (1953); Beyler et al., *J. Amer. Med. Women's Ass.*, 23, 708 (1968); Fukuda et al., *Nago Dai. Yak. Ken. Nem.* 14, 84 (1966)). The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized (Masuoka et al., *Am. J. Anat.* 119, 263 (1966); Gori et al., *Boll.—Soc. Ital. Biol. Sper.* 42, 1596 (1966); Gori et al., *Boll.—Soc. Ital. Biol. Sper.* 42, 1600 (1966); Boris et al., *Steroids* 15, 61 (1970)). As described in Example 6, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats.

Sexually mature rats (200–250 g, 6–8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)

3. TP plus Casodex (administered p.o. in PEGTW, QD), a recognized antiandrogen, as a reference compound.
4. To assess antagonist activity, a test compound was administered (p.o. in PEGTW, QD) with TP (s.c. as administered in group 2) in a range of doses.
5. To assess agonist activity, a test compound was administered alone (p.o. in PEGTW, QD) in a range of doses.

At the end of the 7–14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Superanova (one factor) was used for statistical analysis.

The gain and loss of sexual organ weight reflect the changes of the cell number (DNA content) and cell mass (protein content), depending upon the serum androgen concentration (Okuda et al., *J. Urol.*, 145, 188–191 (1991)). Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4- to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

Example 9

Mature Rat Prostate Weight Assay

The activity of test compounds was also investigated in a mature male rat model, which is a variation of the Levator ani and wet prostate weight assay described in Example 7. The in vivo assays of Examples 6 and 7 are recognized assays for determining the anabolic effects in muscle and sustaining effects in sex organs for a given compound (Hershberger et al., *Proc. Soc. Expt. Biol. Med.*, 83, 175 (1953); Beyler et al., *J. Amer. Med. Women's Ass.* 23, 708 (1968); Fukuda et al., *Nago Dai. Yak. Ken. Nem.* 14, 84 (1966)). The basis of this assay lies in the well-defined action of androgenic agents on the maintenance and growth of muscle tissues and sexual accessory organs in animals and man.

The male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men (Labrie et. al. *Clin. Invest. Med.*, 45, 475–492 (1993)). However, this is not a major pathway, since in both animals and humans, castration leads to almost complete involution of the prostate and seminal vesicles without concomitant adrenalectomy. Therefore, under normal conditions, the adrenals do not support significant growth of prostate tissues (Luke, M. C. and Coffey, D. S. "The Physiology of Reproduction" ed. By E. Knobil and J. D. Neill, 1, 1435–1487 (1994)). Since the male sex organs and the levator ani are the tissues most responsive to modulation of the androgen activity, this model is used to determine the activity of compounds that modulate the androgen receptor pathway in mature rats.

Along with its mitogenic activity on tissues such as prostate, seminal vesicle and muscle, testosterone also serves as a negative regulator for its own biosynthesis. Testosterone production in the Leydig cells of the testis is controlled by the level of circulating LH released from the pituitary gland. LH levels are themselves controlled by the level of LHRH produced in the hypothalmic region. Testosterone levels in the blood serve to inhibit the secretion of LHRH and subsequently reduce levels of LH and ultimately the levels of circulating testosterone levels. By measuring blood levels of LH as they are effected by test compounds, it is possible to determine the level of agonist or antagonist activity of said compounds at the hypothalamic axis of this endocrine cycle.

Matched sets of Harlan Sprague-Dawley rats (40–42 days old, 180–220 g), were dosed orally by gavage (p.o.) with the test compounds in dissolved/suspensions of 80% PEG 400 and 20% Tween 20 (PEGTW] for 14 days. Two control groups, one intact and one castrated were dosed orally only with the PEGTW vehicle. Animals were dosed (v/w) at 0.5 ml of vehicle /100 g body weight. Experimental groups were as follows:

1. Intact vehicle (p.o., PEGTW, QD)
2. Control vehicle (p.o., PEGTW, QD)
3. Biacalutamide (Casodex, a recognized antiandrogen, as a reference compound) or a test compound, p.o. in PEGTW QD. (in a range of doses). At the end of the 14-day treatment, the animals were sacrificed, and the ventral prostate, the seminal vesicles, and the levator ani were removed surgically and weighed. To compare data from different experiments, the organs weights were first standardized as mg per 100 g of body weight, and expressed as a percentage of the value of the respective organ in the intact group.

Rat luteinizing hormone (rLH) is quantitatively determined with the Biotrak [$^{125}$I] kit (Amersham Pharmacia Biotek), following the manufacturer directions. The assay is based on the competition by the LH present in the serum of the binding of [$^{125}$I] rLH to an Amerlex-M bead/antibody suspension. The radioactivity that remains after incubation with the serum and subsequent washes is extrapolated into a standard curve to obtain a reading in ng/ml.

The gain and loss of sexual organ and levator ani weight reflect the changes of the cell number (DNA content) and cell mass (protein content), depending upon the serum androgen concentration (Okuda et al.,*J. Urol.*, 145, 188–191 (1991)). Therefore, measurement of organ wet weight is sufficient to indicate the bioactivity of androgens and androgen antagonist. In the mature rats assay, active agonist agents will have no effect or will increase the weight of one or more of the androgen responsive organs (levator ani, prostate, seminal vesicle) and will have no effect or a suppressive effect on LH secretion. Compounds with antagonist activity will decrease the weight of one or more of the androgen responsive organs (levator ani, prostate, seminal vesicle) and will have no effect or a reduced suppressive effect on LH secretion.

Example 10

MDA PCa2b Human Prostate Zenograft Assay

For in vivo antitumor testing, MDA-PCa-2b human prostate tumors were maintained in Balb/c nu/nu nude mice. Tumors were propagated as subcutaneous transplants in adult male nude mice (4–6 weeks old) using tumor fragments obtained from donor mice. Tumor passage occurred every 5–6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approximately 100–200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula:

Tumor weight=(length×width2)÷2

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

TVDT=Median time (days) for control tumors to reach target size−Median time (days) for control tumors to reach half the target size $s$ and, Log cell kill was then calculated with the formula Log cell kill=$(T-C) \div (3.32 \times TVDT)$ Statistical evaluations of data were performed using Gehan's generalized Wilcoxon test.

Example 11

CWR22 Human Prostate Zenograft Assay

In vivo antitumor testing was also performed with CWR22 human prostate tumors maintained in Balb/c nu/nu nude mice. Tumors were propagated as subcutaneous transplants in adult male nude mice (4–6 weeks old) using tumor fragments obtained from donor mice. Tumor passage occurred every 5–6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approximately 100–200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight= (length×width2)÷2

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

TVDT=Median time (days) for control tumors to reach target size−Median time (days) for control tumors to reach half the target size $s$ Log cell kill was calculated with the formula:

Log cell kill=$(T-C) \div (3.32 \times TVDT)$

Statistical evaluations of data were performed using Gehan's generalized Wilcoxon test.

Example 12

Dunning R3327H Rat Prostate Tumor Assay

Dunning R3327H prostate tumor is a spontaneously derived, well differentiated androgen responsive adenocarcinoma of the prostate (Smolev et al. *Cancer Treat Rep.* 61, 273–287 (1977)). The growth of the R3327H subline has been selected for its highly androgen-dependent and reproducible growth in intact male rats. Therefore, this model and other sublines of this tumor have been widely used to evaluate in vivo antitumor activities of antiandrogens such as flutamide and bacilutamide/Casodex (Maucher A., and von Angerer, *J. Cancer Res. Clin,. Oncol.* 119, 669–674 (1993), Furr B. J. A. *Euro. URL.* 18(suppl. 3), 2–9 (1990), Shain S. A. and Huot R I. *J. Steriod Biochem.* 31, 711–718 (1988)). For this assay, Dunning tumor pieces (about 4×4 mm) are transplanted subcutaneously to the flank of mature male Copenhagen rats (6–7 weeks old, Harlan-Sprague Dawley, Indianapolis, Md.). About 6 weeks after the implantation, the animals with tumors of measurable size (about 80–120 mm$^2$) are randomized into treatment groups (8–10 rats/group) and the treatments are initiated. One group of the rats are castrated to serve as the negative control of tumor growth. Animals are treated daily with test compounds, standard antiandrogens such as bacilutamide or vehicle (control) for an average of 10 to 14 weeks. Test compounds are dissolved in a vehicle of (2.5 ml/kg of body weight) 10% polyethylene glycol and 0.05% Tween-80 in 1% carboxymethyl cellulose, PEG/CMC, (Sigma, St. Louis, Mo.). Typical experiments include three groups of three escalating doses for each standard or test compound (in a range of 300–3 mg/kg).

Tumors in the vehicle group the control group tumors reach a size of 1500 to 2500 mm$^3$. In contrast, the castrated animal group typically shows tumor stasis over the 14 weeks of observation. Animals treated orally with 20 mg/kg of bicalutamide or flutamide are expected to show 40% reduction in tumor volumes compared to controls after 14 weeks of treatment. The size of tumors are measured weekly by vernier caliper (Froboz, Switzerland), taking perpendicular measurements of length and width. Tumor volumes are measured in mm³ using the formula: Length×Width× Height=Volume. Statistical differences between treatment groups and control are evaluated using multiple ANOVA analysis followed by one tail non-parametric Student t test.

Example 13

Dunning R3327H Rat Prostate Tumor and Wet Prostate Weight Assay

Dunning tumor pieces (about 4×4 mm), as described in Example 11, are transplanted subcutaneously to the flank of mature male Copenhagen rats (6–7 weeks old, Harlan-Sprague Dawley, Indianapolis, Md.). About 6 weeks after the implantation, the animals with tumors of measurable size (about 80–120 mm²) are randomized into treatment groups (8–10 rats/group) and the treatments are initiated. One group of the rats are castrated to serve as the negative control of tumor growth. Animals are treated daily with test compounds, standard antiandrogens such as bacilutamide or vehicle (control) for an average of 10 to 14 weeks. Test compounds are dissolved in a vehicle of (2.5 ml/kg of body weight) 10% polyethylene glycol and 0.05% Tween-80 in 1% carboxymethyl cellulose, PEG/CMC, (Sigma, St Louis, Mo.). Typical therapeutic experiments would include three groups of three escalating doses for each standard or test compound (in a range of 300–3 mg/kg).

Tumors in the vehicle group the control group tumors reach a size of 1500 to 2500 mm³. In contrast, the castrated animal group typically shows tumor stasis over the 14 weeks of observation. Animals treated orally with 20 mg/kg of bicalutamide or flutamide are expected to show 40% reduction in tumor volumes compared to control after 14 weeks of treatment. The size of tumors are measured weekly by vernier caliper (Froboz, Switzerland), taking perpendicular measurements of length and width. Tumor volumes are measured in mm³ using the formula: Length×Width× Height=Volume. Statistical differences between treatment groups and control are evaluated using multiple ANOVA analysis followed by one tail non-parametric Student t test.

At the end of the treatment, the animals were sacrificed, and the ventral prostate, the seminal vesicles, and the levator ani were removed surgically and weighed. To compare data from different experiments, the organs weights were first standardized as mg per 100 g of body weight, and expressed as a percentage of the value of the respective organ in the intact group.

Rat luteinizing hormone (rLH) can be quantitatively determined in these animals with the Biotrak [$^{125}$I] kit (Amersham Pharmacia Biotek), following the manufacturer directions. The assay is based on the competition by the LH present in the serum of the binding of [$^{125}$I] rLH to an Amerlex-M bead/antibody suspension. The radioactivity that remains after incubation with the serum and subsequent washes is extrapolated into a standard curve to obtain a reading in ng/ml.

The gain and loss of sexual organ and levator ani weight reflect the changes of the cell number (DNA content) and cell mass (protein content), depending upon the serum androgen concentration (Okuda et al., J. Urol., 145, 188–191 (1991)). Therefore, measurement of organ wet weight is sufficient to indicate the bioactivity of androgens and androgen antagonist. In this rat assay, active agonist agents will have no effect or will increase the weight of one or more of the androgen responsive organs (levator ani, prostate, seminal vesicle) and will have no effect or a suppressive effect on LH secretion. Compounds with antagonist activity will decrease the weight of one or more of the androgen responsive organs (levator ani, prostate, seminal vesicle) and will have no effect or a reduced suppressive effect on LH secretion.

TABLE A

| ATOM | 1 | CB | ILE | 672 | 15.585 | 25.993 | 23.410 | 1.00 | 31.24 |
|---|---|---|---|---|---|---|---|---|---|
| ATOM | 2 | CG2 | ILE | 672 | 14.852 | 27.128 | 24.154 | 1.00 | 30.88 |
| ATOM | 3 | CG1 | ILE | 672 | 16.008 | 24.898 | 24.385 | 1.00 | 31.15 |
| ATOM | 4 | CD1 | ILE | 672 | 16.804 | 25.398 | 25.547 | 1.00 | 31.82 |
| ATOM | 5 | C | ILE | 672 | 15.338 | 24.127 | 21.758 | 1.00 | 30.41 |
| ATOM | 6 | O | ILE | 672 | 16.366 | 24.192 | 21.075 | 1.00 | 30.37 |
| ATOM | 7 | N | ILE | 672 | 13.327 | 25.032 | 22.857 | 1.00 | 31.02 |
| ATOM | 8 | CA | ILE | 672 | 14.670 | 25.387 | 22.310 | 1.00 | 30.84 |
| ATOM | 9 | N | PHE | 673 | 14.730 | 22.987 | 22.058 | 1.00 | 29.49 |
| ATOM | 10 | CA | PHE | 673 | 15.233 | 21.694 | 21.628 | 1.00 | 28.89 |
| ATOM | 11 | CB | PHE | 673 | 14.309 | 20.587 | 22.143 | 1.00 | 28.59 |
| ATOM | 12 | CG | PHE | 673 | 14.827 | 19.211 | 21.890 | 1.00 | 28.37 |
| ATOM | 13 | CD1 | PHE | 673 | 15.903 | 18.721 | 22.616 | 1.00 | 28.33 |
| ATOM | 14 | CD2 | PHE | 673 | 14.259 | 18.412 | 20.900 | 1.00 | 27.95 |
| ATOM | 15 | CE1 | PHE | 673 | 16.411 | 17.447 | 22.358 | 1.00 | 28.35 |
| ATOM | 16 | CE2 | PHE | 673 | 14.753 | 17.151 | 20.634 | 1.00 | 27.76 |
| ATOM | 17 | CZ | PHE | 673 | 15.831 | 16.665 | 21.361 | 1.00 | 28.28 |
| ATOM | 18 | C | PHE | 673 | 15.368 | 21.591 | 20.108 | 1.00 | 28.44 |
| ATOM | 19 | O | PHE | 673 | 16.387 | 21.137 | 19.594 | 1.00 | 28.30 |
| ATOM | 20 | N | LEU | 674 | 14.334 | 22.000 | 19.387 | 1.00 | 28.13 |
| ATOM | 21 | CA | LEU | 674 | 14.393 | 21.950 | 17.940 | 1.00 | 27.74 |
| ATOM | 22 | CB | LEU | 674 | 13.033 | 22.315 | 17.337 | 1.00 | 28.50 |
| ATOM | 23 | CG | LEU | 674 | 12.094 | 21.110 | 17.212 | 1.00 | 29.52 |
| ATOM | 24 | CD1 | LEU | 674 | 12.732 | 20.084 | 16.273 | 1.00 | 29.84 |
| ATOM | 25 | CD2 | LEU | 674 | 11.846 | 20.487 | 18.590 | 1.00 | 29.46 |
| ATOM | 26 | C | LEU | 674 | 15.472 | 22.876 | 17.402 | 1.00 | 27.02 |
| ATOM | 27 | O | LEU | 674 | 16.174 | 22.529 | 16.452 | 1.00 | 26.73 |
| ATOM | 28 | N | ASN | 675 | 15.605 | 24.048 | 18.017 | 1.00 | 26.63 |
| ATOM | 29 | CA | ASN | 675 | 16.595 | 25.031 | 17.592 | 1.00 | 26.23 |
| ATOM | 30 | CB | ASN | 675 | 16.584 | 26.238 | 18.547 | 1.00 | 26.53 |
| ATOM | 31 | CG | ASN | 675 | 15.229 | 26.955 | 18.575 | 1.00 | 26.69 |
| ATOM | 32 | OD1 | ASN | 675 | 14.771 | 27.475 | 17.568 | 1.00 | 25.27 |
| ATOM | 33 | ND2 | ASN | 675 | 14.587 | 26.973 | 19.740 | 1.00 | 28.17 |

TABLE A-continued

| | | | | | | | | |
|---|---|---|---|---|---|---|---|---|
| ATOM | 34 | C | ASN | 675 | 17.971 | 24.371 | 17.578 | 1.00 | 25.92 |
| ATOM | 35 | O | ASN | 675 | 18.716 | 24.475 | 16.599 | 1.00 | 25.60 |
| ATOM | 36 | N | VAL | 676 | 18.284 | 23.666 | 18.663 | 1.00 | 25.22 |
| ATOM | 37 | CA | VAL | 676 | 19.561 | 22.979 | 18.800 | 1.00 | 24.86 |
| ATOM | 38 | CB | VAL | 676 | 19.667 | 22.306 | 20.180 | 1.00 | 24.40 |
| ATOM | 39 | CG1 | VAL | 676 | 20.987 | 21.567 | 20.300 | 1.00 | 23.97 |
| ATOM | 40 | CG2 | VAL | 676 | 19.525 | 23.354 | 21.271 | 1.00 | 24.34 |
| ATOM | 41 | C | VAL | 676 | 19.777 | 21.920 | 17.715 | 1.00 | 24.78 |
| ATOM | 42 | O | VAL | 676 | 20.857 | 21.835 | 17.123 | 1.00 | 23.74 |
| ATOM | 43 | N | LEU | 677 | 18.742 | 21.115 | 17.471 | 1.00 | 24.81 |
| ATOM | 44 | CA | LEU | 677 | 18.804 | 20.055 | 16.471 | 1.00 | 25.01 |
| ATOM | 45 | CB | LEU | 677 | 17.540 | 19.181 | 16.561 | 1.00 | 24.69 |
| ATOM | 46 | CG | LEU | 677 | 17.645 | 17.937 | 17.468 | 1.00 | 25.09 |
| ATOM | 47 | CD1 | LEU | 677 | 18.155 | 18.298 | 18.847 | 1.00 | 24.53 |
| ATOM | 48 | CD2 | LEU | 677 | 16.287 | 17.270 | 17.570 | 1.00 | 24.88 |
| ATOM | 49 | C | LEU | 677 | 19.018 | 20.560 | 15.037 | 1.00 | 24.85 |
| ATOM | 50 | O | LEU | 677 | 19.770 | 19.967 | 14.274 | 1.00 | 24.74 |
| ATOM | 51 | N | GLU | 678 | 18.362 | 21.655 | 14.675 | 1.00 | 25.51 |
| ATOM | 52 | CA | GLU | 678 | 18.504 | 22.232 | 13.334 | 1.00 | 25.67 |
| ATOM | 53 | CB | GLU | 678 | 17.413 | 23.284 | 13.103 | 1.00 | 27.59 |
| ATOM | 54 | CG | GLU | 678 | 17.732 | 24.340 | 12.046 | 1.00 | 30.04 |
| ATOM | 55 | CD | GLU | 678 | 16.621 | 25.379 | 11.918 | 1.00 | 32.44 |
| ATOM | 56 | OE1 | GLU | 678 | 16.830 | 26.423 | 11.237 | 1.00 | 33.09 |
| ATOM | 57 | OE2 | GLU | 678 | 15.534 | 25.140 | 12.505 | 1.00 | 33.23 |
| ATOM | 58 | C | GLU | 678 | 19.874 | 22.873 | 13.187 | 1.00 | 24.83 |
| ATOM | 59 | O | GLU | 678 | 20.541 | 22.715 | 12.171 | 1.00 | 24.31 |
| ATOM | 60 | N | ALA | 679 | 20.286 | 23.591 | 14.224 | 1.00 | 24.77 |
| ATOM | 61 | CA | ALA | 679 | 21.571 | 24.273 | 14.244 | 1.00 | 24.70 |
| ATOM | 62 | CB | ALA | 679 | 21.703 | 25.072 | 15.515 | 1.00 | 24.21 |
| ATOM | 63 | C | ALA | 679 | 22.744 | 23.315 | 14.125 | 1.00 | 25.17 |
| ATOM | 64 | O | ALA | 679 | 23.752 | 23.637 | 13.499 | 1.00 | 25.65 |
| ATOM | 65 | N | ILE | 680 | 22.623 | 22.137 | 14.722 | 1.00 | 25.38 |
| ATOM | 66 | CA | ILE | 680 | 23.716 | 21.172 | 14.676 | 1.00 | 25.89 |
| ATOM | 67 | CB | ILE | 680 | 23.829 | 20.417 | 15.999 | 1.00 | 25.44 |
| ATOM | 68 | CG2 | ILE | 680 | 23.886 | 21.427 | 17.143 | 1.00 | 24.98 |
| ATOM | 69 | CG1 | ILE | 680 | 22.649 | 19.439 | 16.135 | 1.00 | 24.49 |
| ATOM | 70 | CD1 | ILE | 680 | 22.583 | 18.702 | 17.442 | 1.00 | 24.31 |
| ATOM | 71 | C | ILE | 680 | 23.620 | 20.140 | 13.563 | 1.00 | 26.38 |
| ATOM | 72 | O | ILE | 680 | 24.482 | 19.270 | 13.472 | 1.00 | 26.49 |
| ATOM | 73 | N | GLU | 681 | 22.586 | 20.227 | 12.728 | 1.00 | 26.84 |
| ATOM | 74 | CA | GLU | 681 | 22.414 | 19.262 | 11.641 | 1.00 | 28.06 |
| ATOM | 75 | CB | GLU | 681 | 21.074 | 19.473 | 10.946 | 1.00 | 28.71 |
| ATOM | 76 | CG | GLU | 681 | 20.790 | 18.472 | 9.850 | 1.00 | 29.82 |
| ATOM | 77 | CD | GLU | 681 | 20.527 | 17.083 | 10.393 | 1.00 | 31.25 |
| ATOM | 78 | OE1 | GLU | 681 | 20.168 | 16.187 | 9.588 | 1.00 | 32.01 |
| ATOM | 79 | OE2 | GLU | 681 | 20.677 | 16.887 | 11.623 | 1.00 | 31.32 |
| ATOM | 80 | C | GLU | 681 | 23.533 | 19.348 | 10.605 | 1.00 | 28.62 |
| ATOM | 81 | O | GLU | 681 | 23.755 | 20.398 | 9.993 | 1.00 | 29.09 |
| ATOM | 82 | N | PRO | 682 | 24.247 | 18.235 | 10.384 | 1.00 | 28.78 |
| ATOM | 83 | CD | PRO | 682 | 24.071 | 16.919 | 11.017 | 1.00 | 28.67 |
| ATOM | 84 | CA | PRO | 682 | 25.348 | 18.198 | 9.420 | 1.00 | 28.68 |
| ATOM | 85 | CB | PRO | 682 | 25.864 | 16.764 | 9.533 | 1.00 | 28.60 |
| ATOM | 86 | CG | PRO | 682 | 25.440 | 16.337 | 10.882 | 1.00 | 28.67 |
| ATOM | 87 | C | PRO | 682 | 24.886 | 18.505 | 8.004 | 1.00 | 28.93 |
| ATOM | 88 | O | PRO | 682 | 23.765 | 18.165 | 7.620 | 1.00 | 29.17 |
| ATOM | 89 | N | GLY | 683 | 25.760 | 19.141 | 7.233 | 1.00 | 28.83 |
| ATOM | 90 | CA | GLY | 683 | 25.438 | 19.454 | 5.855 | 1.00 | 28.82 |
| ATOM | 91 | C | GLY | 683 | 25.843 | 18.296 | 4.951 | 1.00 | 29.01 |
| ATOM | 92 | O | GLY | 683 | 26.077 | 17.187 | 5.421 | 1.00 | 28.29 |
| ATOM | 93 | N | VAL | 684 | 25.935 | 18.569 | 3.652 | 1.00 | 29.33 |
| ATOM | 94 | CA | VAL | 684 | 26.293 | 17.569 | 2.648 | 1.00 | 29.92 |
| ATOM | 95 | CB | VAL | 684 | 26.276 | 18.182 | 1.223 | 1.00 | 30.47 |
| ATOM | 96 | CG1 | VAL | 684 | 26.393 | 17.069 | 0.166 | 1.00 | 30.24 |
| ATOM | 97 | CG2 | VAL | 684 | 25.004 | 19.006 | 1.025 | 1.00 | 29.99 |
| ATOM | 98 | C | VAL | 684 | 27.666 | 16.933 | 2.855 | 1.00 | 29.77 |
| ATOM | 99 | O | VAL | 684 | 28.602 | 17.578 | 3.308 | 1.00 | 29.87 |
| ATOM | 100 | N | VAL | 685 | 27.768 | 15.657 | 2.512 | 1.00 | 29.69 |
| ATOM | 101 | CA | VAL | 685 | 29.014 | 14.922 | 2.631 | 1.00 | 29.84 |
| ATOM | 102 | CB | VAL | 685 | 28.973 | 13.936 | 3.834 | 1.00 | 29.89 |
| ATOM | 103 | CG1 | VAL | 685 | 30.357 | 13.368 | 4.084 | 1.00 | 29.18 |
| ATOM | 104 | CG2 | VAL | 685 | 28.441 | 14.642 | 5.088 | 1.00 | 29.80 |
| ATOM | 105 | C | VAL | 685 | 29.207 | 14.130 | 1.333 | 1.00 | 30.42 |
| ATOM | 106 | O | VAL | 685 | 28.378 | 13.291 | 0.975 | 1.00 | 30.40 |
| ATOM | 107 | N | CYS | 686 | 30.287 | 14.408 | 0.615 | 1.00 | 30.75 |
| ATOM | 108 | CA | CYS | 686 | 30.551 | 13.698 | −0.624 | 1.00 | 31.29 |
| ATOM | 109 | CB | CYS | 686 | 31.219 | 14.636 | −1.630 | 1.00 | 31.47 |
| ATOM | 110 | SG | CYS | 686 | 30.172 | 16.063 | −2.105 | 1.00 | 33.49 |
| ATOM | 111 | C | CYS | 686 | 31.415 | 12.459 | −0.366 | 1.00 | 31.56 |
| ATOM | 112 | O | CYS | 686 | 32.266 | 12.458 | 0.523 | 1.00 | 31.13 |

TABLE A-continued

| | | | | | | | | |
|---|---|---|---|---|---|---|---|---|
| ATOM | 113 | N | ALA | 687 | 31.180 | 11.405 | -1.147 | 1.00 | 31.88 |
| ATOM | 114 | CA | ALA | 687 | 31.905 | 10.157 | -0.987 | 1.00 | 32.66 |
| ATOM | 115 | CB | ALA | 687 | 31.072 | 8.989 | -1.531 | 1.00 | 32.89 |
| ATOM | 116 | C | ALA | 687 | 33.275 | 10.160 | -1.636 | 1.00 | 33.22 |
| ATOM | 117 | O | ALA | 687 | 34.138 | 9.365 | -1.259 | 1.00 | 33.23 |
| ATOM | 118 | N | GLY | 688 | 33.476 | 11.051 | -2.602 | 1.00 | 33.83 |
| ATOM | 119 | CA | GLY | 688 | 34.752 | 11.123 | -3.287 | 1.00 | 34.36 |
| ATOM | 120 | C | GLY | 688 | 34.838 | 10.039 | -4.345 | 1.00 | 35.22 |
| ATOM | 121 | O | GLY | 688 | 35.925 | 9.648 | -4.776 | 1.00 | 35.29 |
| ATOM | 122 | N | HIS | 689 | 33.681 | 9.540 | -4.762 | 1.00 | 35.46 |
| ATOM | 123 | CA | HIS | 689 | 33.639 | 8.497 | -5.773 | 1.00 | 36.39 |
| ATOM | 124 | CB | HIS | 689 | 32.328 | 7.713 | -5.650 | 1.00 | 36.01 |
| ATOM | 125 | CG | HIS | 689 | 32.136 | 6.683 | -6.716 | 1.00 | 35.72 |
| ATOM | 126 | CD2 | HIS | 689 | 32.433 | 5.361 | -6.742 | 1.00 | 35.47 |
| ATOM | 127 | ND1 | HIS | 689 | 31.590 | 6.977 | -7.946 | 1.00 | 35.68 |
| ATOM | 128 | CE1 | HIS | 689 | 31.557 | 5.882 | -8.684 | 1.00 | 35.61 |
| ATOM | 129 | NE2 | HIS | 689 | 32.063 | 4.887 | -7.976 | 1.00 | 35.45 |
| ATOM | 130 | C | HIS | 689 | 33.776 | 9.088 | -7.176 | 1.00 | 37.25 |
| ATOM | 131 | O | HIS | 689 | 33.125 | 10.078 | -7.512 | 1.00 | 36.54 |
| ATOM | 132 | N | ASP | 690 | 34.643 | 8.492 | -7.988 | 1.00 | 38.49 |
| ATOM | 133 | CA | ASP | 690 | 34.832 | 8.967 | -9.353 | 1.00 | 40.16 |
| ATOM | 134 | CB | ASP | 690 | 36.285 | 8.755 | -9.803 | 1.00 | 40.96 |
| ATOM | 135 | CG | ASP | 690 | 36.766 | 7.342 | -9.580 | 1.00 | 42.31 |
| ATOM | 136 | OD1 | ASP | 690 | 37.918 | 7.030 | -9.977 | 1.00 | 42.84 |
| ATOM | 137 | OD2 | ASP | 690 | 35.994 | 6.541 | -9.004 | 1.00 | 43.23 |
| ATOM | 138 | C | ASP | 690 | 33.870 | 8.242 | -10.293 | 1.00 | 40.81 |
| ATOM | 139 | O | ASP | 690 | 33.928 | 7.020 | -10.434 | 1.00 | 41.00 |
| ATOM | 140 | N | ASN | 691 | 32.972 | 8.997 | -10.919 | 1.00 | 41.55 |
| ATOM | 141 | CA | ASN | 691 | 31.992 | 8.419 | -11.838 | 1.00 | 42.66 |
| ATOM | 142 | CB | ASN | 691 | 30.917 | 9.450 | -12.195 | 1.00 | 42.57 |
| ATOM | 143 | CG | ASN | 691 | 30.002 | 9.782 | -11.031 | 1.00 | 42.88 |
| ATOM | 144 | OD1 | ASN | 691 | 29.206 | 10.721 | -11.115 | 1.00 | 43.45 |
| ATOM | 145 | ND2 | ASN | 691 | 30.096 | 9.014 | -9.946 | 1.00 | 42.16 |
| ATOM | 146 | C | ASN | 691 | 32.620 | 7.894 | -13.132 | 1.00 | 43.34 |
| ATOM | 147 | O | ASN | 691 | 31.931 | 7.304 | -13.962 | 1.00 | 43.67 |
| ATOM | 148 | N | ASN | 692 | 33.918 | 8.120 | -13.307 | 1.00 | 43.99 |
| ATOM | 149 | CA | ASN | 692 | 34.626 | 7.661 | -14.499 | 1.00 | 44.50 |
| ATOM | 150 | CB | ASN | 692 | 36.045 | 8.233 | -14.521 | 1.00 | 44.96 |
| ATOM | 151 | CG | ASN | 692 | 36.163 | 9.552 | -13.757 | 1.00 | 45.75 |
| ATOM | 152 | OD1 | ASN | 692 | 35.869 | 9.625 | -12.558 | 1.00 | 45.86 |
| ATOM | 153 | ND2 | ASN | 692 | 36.604 | 10.598 | -14.449 | 1.00 | 45.86 |
| ATOM | 154 | C | ASN | 692 | 34.703 | 6.138 | -14.431 | 1.00 | 44.51 |
| ATOM | 155 | O | ASN | 692 | 35.016 | 5.467 | -15.415 | 1.00 | 44.65 |
| ATOM | 156 | N | GLN | 693 | 34.401 | 5.620 | -13.247 | 1.00 | 44.30 |
| ATOM | 157 | CA | GLN | 693 | 34.432 | 4.195 | -12.933 | 1.00 | 44.20 |
| ATOM | 158 | CB | GLN | 693 | 34.091 | 4.004 | -11.452 | 1.00 | 44.34 |
| ATOM | 159 | CG | GLN | 693 | 34.453 | 2.664 | -10.864 | 1.00 | 44.63 |
| ATOM | 160 | CD | GLN | 693 | 35.935 | 2.552 | -10.548 | 1.00 | 44.93 |
| ATOM | 161 | OE1 | GLN | 693 | 36.544 | 3.501 | -10.055 | 1.00 | 44.97 |
| ATOM | 162 | NE2 | GLN | 693 | 36.518 | 1.383 | -10.813 | 1.00 | 44.61 |
| ATOM | 163 | C | GLN | 693 | 33.469 | 3.362 | -13.765 | 1.00 | 43.84 |
| ATOM | 164 | O | GLN | 693 | 32.271 | 3.634 | -13.802 | 1.00 | 44.50 |
| ATOM | 165 | N | PRO | 694 | 33.976 | 2.324 | -14.439 | 1.00 | 43.36 |
| ATOM | 166 | CD | PRO | 694 | 35.372 | 1.893 | -14.620 | 1.00 | 43.36 |
| ATOM | 167 | CA | PRO | 694 | 33.069 | 1.503 | -15.238 | 1.00 | 43.02 |
| ATOM | 168 | CB | PRO | 694 | 34.021 | 0.607 | -16.027 | 1.00 | 43.07 |
| ATOM | 169 | CG | PRO | 694 | 35.200 | 0.484 | -15.122 | 1.00 | 43.30 |
| ATOM | 170 | C | PRO | 694 | 32.111 | 0.717 | -14.338 | 1.00 | 42.75 |
| ATOM | 171 | O | PRO | 694 | 31.333 | -0.121 | -14.816 | 1.00 | 43.47 |
| ATOM | 172 | N | ASP | 695 | 32.174 | 0.993 | -13.036 | 1.00 | 41.47 |
| ATOM | 173 | CA | ASP | 695 | 31.309 | 0.342 | -12.056 | 1.00 | 40.30 |
| ATOM | 174 | CB | ASP | 695 | 29.858 | 0.406 | -12.521 | 1.00 | 40.36 |
| ATOM | 175 | CG | ASP | 695 | 28.998 | 1.238 | -11.610 | 1.00 | 40.64 |
| ATOM | 176 | OD1 | ASP | 695 | 27.988 | 1.793 | -12.085 | 1.00 | 40.36 |
| ATOM | 177 | OD2 | ASP | 695 | 29.329 | 1.329 | -10.411 | 1.00 | 41.36 |
| ATOM | 178 | C | ASP | 695 | 31.701 | -1.103 | -11.772 | 1.00 | 39.59 |
| ATOM | 179 | O | ASP | 695 | 32.158 | -1.829 | -12.661 | 1.00 | 39.66 |
| ATOM | 180 | N | SER | 696 | 31.519 | -1.511 | -10.523 | 1.00 | 37.97 |
| ATOM | 181 | CA | SER | 696 | 31.870 | -2.854 | -10.093 | 1.00 | 36.83 |
| ATOM | 182 | CB | SER | 696 | 33.334 | -3.141 | -10.409 | 1.00 | 36.85 |
| ATOM | 183 | OG | SER | 696 | 34.170 | -2.172 | -9.803 | 1.00 | 36.78 |
| ATOM | 184 | C | SER | 696 | 31.658 | -2.985 | -8.595 | 1.00 | 35.83 |
| ATOM | 185 | O | SER | 696 | 31.175 | -2.063 | -7.938 | 1.00 | 35.84 |
| ATOM | 186 | N | PHE | 697 | 32.034 | -4.135 | -8.058 | 1.00 | 34.43 |
| ATOM | 187 | CA | PHE | 697 | 31.886 | -4.376 | -6.639 | 1.00 | 33.31 |
| ATOM | 188 | CB | PHE | 697 | 31.970 | -5.872 | -6.353 | 1.00 | 32.81 |
| ATOM | 189 | CG | PHE | 697 | 31.755 | -6.225 | -4.910 | 1.00 | 32.02 |
| ATOM | 190 | CD1 | PHE | 697 | 30.601 | -5.839 | -4.253 | 1.00 | 31.59 |
| ATOM | 191 | CD2 | PHE | 697 | 32.712 | -6.939 | -4.207 | 1.00 | 31.69 |

TABLE A-continued

| | | | | | | | | |
|---|---|---|---|---|---|---|---|---|
| ATOM | 192 | CE1 | PHE | 697 | 30.411 | −6.162 | −2.913 | 1.00 | 31.45 |
| ATOM | 193 | CE2 | PHE | 697 | 32.522 | −7.264 | −2.871 | 1.00 | 31.30 |
| ATOM | 194 | CZ | PHE | 697 | 31.375 | −6.875 | −2.227 | 1.00 | 30.74 |
| ATOM | 195 | C | PHE | 697 | 32.959 | −3.634 | −5.849 | 1.00 | 32.77 |
| ATOM | 196 | O | PHE | 697 | 32.663 | −2.997 | −4.846 | 1.00 | 32.24 |
| ATOM | 197 | N | ALA | 698 | 34.199 | −3.701 | −6.326 | 1.00 | 32.43 |
| ATOM | 198 | CA | ALA | 698 | 35.333 | −3.059 | −5.659 | 1.00 | 32.06 |
| ATOM | 199 | CB | ALA | 698 | 36.628 | −3.462 | −6.351 | 1.00 | 32.14 |
| ATOM | 200 | C | ALA | 698 | 35.252 | −1.533 | −5.562 | 1.00 | 31.78 |
| ATOM | 201 | O | ALA | 698 | 35.503 | −0.958 | −4.506 | 1.00 | 31.59 |
| ATOM | 202 | N | ALA | 699 | 34.903 | −0.883 | −6.663 | 1.00 | 31.20 |
| ATOM | 203 | CA | ALA | 699 | 34.799 | 0.569 | −6.692 | 1.00 | 30.50 |
| ATOM | 204 | CB | ALA | 699 | 34.627 | 1.035 | −8.125 | 1.00 | 30.71 |
| ATOM | 205 | C | ALA | 699 | 33.658 | 1.117 | −5.837 | 1.00 | 30.14 |
| ATOM | 206 | O | ALA | 699 | 33.793 | 2.161 | −5.192 | 1.00 | 29.89 |
| ATOM | 207 | N | LEU | 700 | 32.525 | 0.425 | −5.856 | 1.00 | 29.56 |
| ATOM | 208 | CA | LEU | 700 | 31.353 | 0.846 | −5.092 | 1.00 | 29.08 |
| ATOM | 209 | CB | LEU | 700 | 30.166 | −0.054 | −5.431 | 1.00 | 29.19 |
| ATOM | 210 | CG | LEU | 700 | 29.075 | 0.521 | −6.332 | 1.00 | 30.19 |
| ATOM | 211 | CD1 | LEU | 700 | 29.649 | 1.531 | −7.321 | 1.00 | 29.81 |
| ATOM | 212 | CD2 | LEU | 700 | 28.377 | −0.636 | −7.053 | 1.00 | 30.55 |
| ATOM | 213 | C | LEU | 700 | 31.600 | 0.817 | −3.587 | 1.00 | 28.70 |
| ATOM | 214 | O | LEU | 700 | 31.687 | 1.858 | −2.939 | 1.00 | 28.63 |
| ATOM | 215 | N | LEU | 701 | 31.718 | −0.387 | −3.045 | 1.00 | 28.11 |
| ATOM | 216 | CA | LEU | 701 | 31.944 | −0.580 | −1.624 | 1.00 | 28.02 |
| ATOM | 217 | CB | LEU | 701 | 32.126 | −2.068 | −1.325 | 1.00 | 26.80 |
| ATOM | 218 | CG | LEU | 701 | 30.785 | −2.788 | −1.243 | 1.00 | 26.52 |
| ATOM | 219 | CD1 | LEU | 701 | 29.977 | −2.199 | −0.085 | 1.00 | 25.48 |
| ATOM | 220 | CD2 | LEU | 701 | 30.028 | −2.659 | −2.562 | 1.00 | 25.47 |
| ATOM | 221 | C | LEU | 701 | 33.126 | 0.200 | −1.079 | 1.00 | 28.03 |
| ATOM | 222 | O | LEU | 701 | 33.065 | 0.744 | 0.023 | 1.00 | 27.83 |
| ATOM | 223 | N | SER | 702 | 34.200 | 0.250 | −1.857 | 1.00 | 28.39 |
| ATOM | 224 | CA | SER | 702 | 35.397 | 0.965 | −1.446 | 1.00 | 28.48 |
| ATOM | 225 | CB | SER | 702 | 36.508 | 0.793 | −2.478 | 1.00 | 28.93 |
| ATOM | 226 | OG | SER | 702 | 37.745 | 1.184 | −1.922 | 1.00 | 30.72 |
| ATOM | 227 | C | SER | 702 | 35.078 | 2.440 | −1.266 | 1.00 | 27.81 |
| ATOM | 228 | O | SER | 702 | 35.585 | 3.072 | −0.345 | 1.00 | 28.06 |
| ATOM | 229 | N | SER | 703 | 34.233 | 2.984 | −2.140 | 1.00 | 27.29 |
| ATOM | 230 | CA | SER | 703 | 33.850 | 4.388 | −2.040 | 1.00 | 26.12 |
| ATOM | 231 | CB | SER | 703 | 33.349 | 4.916 | −3.385 | 1.00 | 26.33 |
| ATOM | 232 | OG | SER | 703 | 31.941 | 5.056 | −3.376 | 1.00 | 28.04 |
| ATOM | 233 | C | SER | 703 | 32.762 | 4.510 | −0.981 | 1.00 | 25.38 |
| ATOM | 234 | O | SER | 703 | 32.637 | 5.543 | −0.333 | 1.00 | 25.43 |
| ATOM | 235 | N | LEU | 704 | 31.975 | 3.453 | −0.791 | 1.00 | 24.62 |
| ATOM | 236 | CA | LEU | 704 | 30.945 | 3.492 | 0.247 | 1.00 | 23.83 |
| ATOM | 237 | CB | LEU | 704 | 29.987 | 2.306 | 0.122 | 1.00 | 23.34 |
| ATOM | 238 | CG | LEU | 704 | 28.843 | 2.445 | −0.888 | 1.00 | 22.81 |
| ATOM | 239 | CD1 | LEU | 704 | 27.962 | 1.199 | −0.844 | 1.00 | 22.05 |
| ATOM | 240 | CD2 | LEU | 704 | 28.010 | 3.673 | −0.530 | 1.00 | 22.63 |
| ATOM | 241 | C | LEU | 704 | 31.629 | 3.473 | 1.614 | 1.00 | 23.67 |
| ATOM | 242 | O | LEU | 704 | 31.212 | 4.171 | 2.537 | 1.00 | 23.27 |
| ATOM | 243 | N | ASN | 705 | 32.681 | 2.663 | 1.728 | 1.00 | 23.68 |
| ATOM | 244 | CA | ASN | 705 | 33.454 | 2.556 | 2.959 | 1.00 | 23.54 |
| ATOM | 245 | CB | ASN | 705 | 34.597 | 1.546 | 2.808 | 1.00 | 22.57 |
| ATOM | 246 | CG | ASN | 705 | 34.135 | 0.107 | 2.920 | 1.00 | 22.79 |
| ATOM | 247 | OD1 | ASN | 705 | 34.865 | −0.826 | 2.553 | 1.00 | 22.63 |
| ATOM | 248 | ND2 | ASN | 705 | 32.932 | −0.089 | 3.447 | 1.00 | 21.75 |
| ATOM | 249 | C | ASN | 705 | 34.051 | 3.920 | 3.248 | 1.00 | 23.95 |
| ATOM | 250 | O | ASN | 705 | 34.095 | 4.355 | 4.395 | 1.00 | 24.17 |
| ATOM | 251 | N | GLU | 706 | 34.513 | 4.599 | 2.204 | 1.00 | 24.44 |
| ATOM | 252 | CA | GLU | 706 | 35.110 | 5.907 | 2.402 | 1.00 | 25.29 |
| ATOM | 253 | CB | GLU | 706 | 35.729 | 6.452 | 1.118 | 1.00 | 26.16 |
| ATOM | 254 | CG | GLU | 706 | 36.404 | 7.788 | 1.340 | 1.00 | 27.89 |
| ATOM | 255 | CD | GLU | 706 | 37.478 | 7.726 | 2.428 | 1.00 | 29.25 |
| ATOM | 256 | OE1 | GLU | 706 | 37.936 | 8.799 | 2.881 | 1.00 | 29.77 |
| ATOM | 257 | OE2 | GLU | 706 | 37.868 | 6.604 | 2.831 | 1.00 | 30.55 |
| ATOM | 258 | C | GLU | 706 | 34.063 | 6.874 | 2.884 | 1.00 | 25.01 |
| ATOM | 259 | O | GLU | 706 | 34.352 | 7.747 | 3.694 | 1.00 | 25.76 |
| ATOM | 260 | N | LEU | 707 | 32.842 | 6.714 | 2.385 | 1.00 | 24.51 |
| ATOM | 261 | CA | LEU | 707 | 31.749 | 7.585 | 2.778 | 1.00 | 24.01 |
| ATOM | 262 | CB | LEU | 707 | 30.511 | 7.333 | 1.912 | 1.00 | 23.04 |
| ATOM | 263 | CG | LEU | 707 | 29.345 | 8.281 | 2.195 | 1.00 | 22.39 |
| ATOM | 264 | CD1 | LEU | 707 | 29.746 | 9.740 | 1.906 | 1.00 | 21.36 |
| ATOM | 265 | CD2 | LEU | 707 | 28.168 | 7.883 | 1.343 | 1.00 | 22.62 |
| ATOM | 266 | C | LEU | 707 | 31.382 | 7.379 | 4.230 | 1.00 | 24.28 |
| ATOM | 267 | O | LEU | 707 | 31.075 | 8.333 | 4.941 | 1.00 | 24.68 |
| ATOM | 268 | N | GLY | 708 | 31.414 | 6.126 | 4.666 | 1.00 | 24.48 |
| ATOM | 269 | CA | GLY | 708 | 31.052 | 5.818 | 6.033 | 1.00 | 24.27 |
| ATOM | 270 | C | GLY | 708 | 31.987 | 6.483 | 7.013 | 1.00 | 24.28 |

TABLE A-continued

| | | | | | | | | |
|---|---|---|---|---|---|---|---|---|
| ATOM | 271 | O | GLY | 708 | 31.557 | 6.976 | 8.043 | 1.00 | 24.53 |
| ATOM | 272 | N | GLU | 709 | 33.271 | 6.488 | 6.688 | 1.00 | 24.50 |
| ATOM | 273 | CA | GLU | 709 | 34.278 | 7.094 | 7.548 | 1.00 | 25.04 |
| ATOM | 274 | CB | GLU | 709 | 35.676 | 6.727 | 7.037 | 1.00 | 26.02 |
| ATOM | 275 | CG | GLU | 709 | 36.846 | 7.291 | 7.830 | 1.00 | 28.27 |
| ATOM | 276 | CD | GLU | 709 | 36.963 | 6.712 | 9.238 | 1.00 | 30.06 |
| ATOM | 277 | OE1 | GLU | 709 | 36.142 | 7.085 | 10.116 | 1.00 | 30.97 |
| ATOM | 278 | OE2 | GLU | 709 | 37.882 | 5.884 | 9.466 | 1.00 | 30.27 |
| ATOM | 279 | C | GLU | 709 | 34.083 | 8.613 | 7.571 | 1.00 | 24.49 |
| ATOM | 280 | O | GLU | 709 | 34.176 | 9.240 | 8.624 | 1.00 | 24.26 |
| ATOM | 281 | N | ARG | 710 | 33.792 | 9.198 | 6.414 | 1.00 | 23.72 |
| ATOM | 282 | CA | ARG | 710 | 33.581 | 10.639 | 6.342 | 1.00 | 23.54 |
| ATOM | 283 | CB | ARG | 710 | 33.426 | 11.097 | 4.885 | 1.00 | 23.22 |
| ATOM | 284 | CG | ARG | 710 | 34.715 | 10.999 | 4.073 | 1.00 | 23.82 |
| ATOM | 285 | CD | ARG | 710 | 34.524 | 11.398 | 2.626 | 1.00 | 24.53 |
| ATOM | 286 | NE | ARG | 710 | 35.807 | 11.550 | 1.952 | 1.00 | 25.26 |
| ATOM | 287 | CZ | ARG | 710 | 35.967 | 12.064 | 0.737 | 1.00 | 25.57 |
| ATOM | 288 | NH1 | ARG | 710 | 34.920 | 12.481 | 0.036 | 1.00 | 25.76 |
| ATOM | 289 | NH2 | ARG | 710 | 37.183 | 12.180 | 0.226 | 1.00 | 26.08 |
| ATOM | 290 | C | ARG | 710 | 32.365 | 11.065 | 7.152 | 1.00 | 23.53 |
| ATOM | 291 | O | ARG | 710 | 32.404 | 12.074 | 7.867 | 1.00 | 23.75 |
| ATOM | 292 | N | GLN | 711 | 31.286 | 10.294 | 7.052 | 1.00 | 23.34 |
| ATOM | 293 | CA | GLN | 711 | 30.081 | 10.627 | 7.786 | 1.00 | 23.12 |
| ATOM | 294 | CB | GLN | 711 | 28.893 | 9.819 | 7.274 | 1.00 | 22.95 |
| ATOM | 295 | CG | GLN | 711 | 28.250 | 10.414 | 6.037 | 1.00 | 22.79 |
| ATOM | 296 | CD | GLN | 711 | 26.952 | 9.724 | 5.655 | 1.00 | 23.04 |
| ATOM | 297 | OE1 | GLN | 711 | 26.165 | 9.329 | 6.519 | 1.00 | 23.05 |
| ATOM | 298 | NE2 | GLN | 711 | 26.715 | 9.587 | 4.356 | 1.00 | 22.64 |
| ATOM | 299 | C | GLN | 711 | 30.285 | 10.400 | 9.273 | 1.00 | 23.07 |
| ATOM | 300 | O | GLN | 711 | 29.672 | 11.072 | 10.092 | 1.00 | 22.74 |
| ATOM | 301 | N | LEU | 712 | 31.159 | 9.458 | 9.617 | 1.00 | 23.12 |
| ATOM | 302 | CA | LEU | 712 | 31.459 | 9.179 | 11.018 | 1.00 | 22.87 |
| ATOM | 303 | CB | LEU | 712 | 32.475 | 8.046 | 11.131 | 1.00 | 22.35 |
| ATOM | 304 | CG | LEU | 712 | 33.072 | 7.933 | 12.536 | 1.00 | 22.63 |
| ATOM | 305 | CD1 | LEU | 712 | 31.940 | 7.890 | 13.580 | 1.00 | 22.01 |
| ATOM | 306 | CD2 | LEU | 712 | 33.969 | 6.701 | 12.615 | 1.00 | 22.12 |
| ATOM | 307 | C | LEU | 712 | 32.029 | 10.452 | 11.651 | 1.00 | 23.01 |
| ATOM | 308 | O | LEU | 712 | 31.681 | 10.822 | 12.784 | 1.00 | 22.93 |
| ATOM | 309 | N | VAL | 713 | 32.907 | 11.119 | 10.907 | 1.00 | 22.87 |
| ATOM | 310 | CA | VAL | 713 | 33.498 | 12.362 | 11.374 | 1.00 | 22.95 |
| ATOM | 311 | CB | VAL | 713 | 34.344 | 13.042 | 10.255 | 1.00 | 23.84 |
| ATOM | 312 | CG1 | VAL | 713 | 34.691 | 14.487 | 10.648 | 1.00 | 22.62 |
| ATOM | 313 | CG2 | VAL | 713 | 35.613 | 12.226 | 9.988 | 1.00 | 23.07 |
| ATOM | 314 | C | VAL | 713 | 32.384 | 13.319 | 11.796 | 1.00 | 22.67 |
| ATOM | 315 | O | VAL | 713 | 32.475 | 13.957 | 12.847 | 1.00 | 22.99 |
| ATOM | 316 | N | HIS | 714 | 31.333 | 13.404 | 10.981 | 1.00 | 22.28 |
| ATOM | 317 | CA | HIS | 714 | 30.211 | 14.302 | 11.266 | 1.00 | 22.20 |
| ATOM | 318 | CB | HIS | 714 | 29.444 | 14.647 | 9.980 | 1.00 | 22.70 |
| ATOM | 319 | CG | HIS | 714 | 30.235 | 15.456 | 9.001 | 1.00 | 22.67 |
| ATOM | 320 | CD2 | HIS | 714 | 30.626 | 16.751 | 9.026 | 1.00 | 22.73 |
| ATOM | 321 | ND1 | HIS | 714 | 30.735 | 14.928 | 7.830 | 1.00 | 23.24 |
| ATOM | 322 | CE1 | HIS | 714 | 31.401 | 15.863 | 7.175 | 1.00 | 22.99 |
| ATOM | 323 | NE2 | HIS | 714 | 31.350 | 16.979 | 7.880 | 1.00 | 23.40 |
| ATOM | 324 | C | HIS | 714 | 29.215 | 13.816 | 12.310 | 1.00 | 21.81 |
| ATOM | 325 | O | HIS | 714 | 28.598 | 14.627 | 12.994 | 1.00 | 22.68 |
| ATOM | 326 | N | VAL | 715 | 29.031 | 12.509 | 12.429 | 1.00 | 21.29 |
| ATOM | 327 | CA | VAL | 715 | 28.099 | 11.992 | 13.423 | 1.00 | 20.49 |
| ATOM | 328 | CB | VAL | 715 | 27.785 | 10.476 | 13.188 | 1.00 | 20.64 |
| ATOM | 329 | CG1 | VAL | 715 | 27.000 | 9.897 | 14.361 | 1.00 | 20.52 |
| ATOM | 330 | CG2 | VAL | 715 | 26.960 | 10.318 | 11.921 | 1.00 | 19.86 |
| ATOM | 331 | C | VAL | 715 | 28.697 | 12.211 | 14.808 | 1.00 | 20.28 |
| ATOM | 332 | O | VAL | 715 | 27.975 | 12.476 | 15.759 | 1.00 | 20.31 |
| ATOM | 333 | N | VAL | 716 | 30.020 | 12.119 | 14.917 | 1.00 | 19.96 |
| ATOM | 334 | CA | VAL | 716 | 30.680 | 12.331 | 16.203 | 1.00 | 19.21 |
| ATOM | 335 | CB | VAL | 716 | 32.214 | 12.047 | 16.125 | 1.00 | 18.74 |
| ATOM | 336 | CG1 | VAL | 716 | 32.889 | 12.440 | 17.427 | 1.00 | 17.72 |
| ATOM | 337 | CG2 | VAL | 716 | 32.457 | 10.566 | 15.849 | 1.00 | 18.72 |
| ATOM | 338 | C | VAL | 716 | 30.463 | 13.766 | 16.693 | 1.00 | 19.14 |
| ATOM | 339 | O | VAL | 716 | 30.008 | 13.976 | 17.806 | 1.00 | 19.96 |
| ATOM | 340 | N | LYS | 717 | 30.788 | 14.748 | 15.865 | 1.00 | 18.52 |
| ATOM | 341 | CA | LYS | 717 | 30.620 | 16.139 | 16.256 | 1.00 | 18.43 |
| ATOM | 342 | CB | LYS | 717 | 31.233 | 17.074 | 15.181 | 1.00 | 19.20 |
| ATOM | 343 | CG | LYS | 717 | 32.760 | 17.074 | 15.191 | 1.00 | 20.49 |
| ATOM | 344 | CD | LYS | 717 | 33.397 | 17.385 | 13.835 | 1.00 | 22.01 |
| ATOM | 345 | CE | LYS | 717 | 33.242 | 18.841 | 13.423 | 1.00 | 23.42 |
| ATOM | 346 | NZ | LYS | 717 | 34.179 | 19.195 | 12.301 | 1.00 | 23.88 |
| ATOM | 347 | C | LYS | 717 | 29.149 | 16.462 | 16.484 | 1.00 | 17.83 |
| ATOM | 348 | O | LYS | 717 | 28.809 | 17.280 | 17.330 | 1.00 | 18.37 |
| ATOM | 349 | N | TRP | 718 | 28.276 | 15.806 | 15.733 | 1.00 | 17.26 |

TABLE A-continued

| | | | | | | | | | |
|---|---|---|---|---|---|---|---|---|---|
| ATOM | 350 | CA | TRP | 718 | 26.844 | 16.032 | 15.863 | 1.00 | 16.62 |
| ATOM | 351 | CB | TRP | 718 | 26.096 | 15.283 | 14.747 | 1.00 | 15.39 |
| ATOM | 352 | CG | TRP | 718 | 24.636 | 15.139 | 14.991 | 1.00 | 13.87 |
| ATOM | 353 | CD2 | TRP | 718 | 23.955 | 13.949 | 15.416 | 1.00 | 13.60 |
| ATOM | 354 | CE2 | TRP | 718 | 22.583 | 14.272 | 15.530 | 1.00 | 13.27 |
| ATOM | 355 | CE3 | TRP | 718 | 24.373 | 12.639 | 15.710 | 1.00 | 12.87 |
| ATOM | 356 | CD1 | TRP | 718 | 23.683 | 16.105 | 14.871 | 1.00 | 13.87 |
| ATOM | 357 | NE1 | TRP | 718 | 22.444 | 15.594 | 15.191 | 1.00 | 13.38 |
| ATOM | 358 | CZ2 | TRP | 718 | 21.622 | 13.334 | 15.929 | 1.00 | 12.65 |
| ATOM | 359 | CZ3 | TRP | 718 | 23.417 | 11.705 | 16.106 | 1.00 | 12.99 |
| ATOM | 360 | CH2 | TRP | 718 | 22.054 | 12.060 | 16.212 | 1.00 | 12.90 |
| ATOM | 361 | C | TRP | 718 | 26.378 | 15.565 | 17.243 | 1.00 | 16.98 |
| ATOM | 362 | O | TRP | 718 | 25.760 | 16.319 | 18.012 | 1.00 | 15.96 |
| ATOM | 363 | N | ALA | 719 | 26.692 | 14.312 | 17.549 | 1.00 | 17.83 |
| ATOM | 364 | CA | ALA | 719 | 26.326 | 13.721 | 18.819 | 1.00 | 18.17 |
| ATOM | 365 | CB | ALA | 719 | 26.835 | 12.287 | 18.887 | 1.00 | 18.35 |
| ATOM | 366 | C | ALA | 719 | 26.891 | 14.534 | 19.978 | 1.00 | 18.72 |
| ATOM | 367 | O | ALA | 719 | 26.148 | 14.907 | 20.886 | 1.00 | 18.90 |
| ATOM | 368 | N | LYS | 720 | 28.195 | 14.822 | 19.933 | 1.00 | 19.47 |
| ATOM | 369 | CA | LYS | 720 | 28.870 | 15.570 | 21.003 | 1.00 | 20.52 |
| ATOM | 370 | CB | LYS | 720 | 30.358 | 15.793 | 20.663 | 1.00 | 21.24 |
| ATOM | 371 | CG | LYS | 720 | 31.257 | 14.541 | 20.709 | 1.00 | 21.82 |
| ATOM | 372 | CD | LYS | 720 | 31.657 | 14.170 | 22.135 | 1.00 | 22.50 |
| ATOM | 373 | CE | LYS | 720 | 32.458 | 12.850 | 22.217 | 1.00 | 23.14 |
| ATOM | 374 | NZ | LYS | 720 | 33.777 | 12.847 | 21.507 | 1.00 | 22.87 |
| ATOM | 375 | C | LYS | 720 | 28.215 | 16.912 | 21.316 | 1.00 | 20.70 |
| ATOM | 376 | O | LYS | 720 | 28.338 | 17.418 | 22.429 | 1.00 | 21.08 |
| ATOM | 377 | N | ALA | 721 | 27.520 | 17.487 | 20.338 | 1.00 | 20.77 |
| ATOM | 378 | CA | ALA | 721 | 26.844 | 18.760 | 20.549 | 1.00 | 20.21 |
| ATOM | 379 | CB | ALA | 721 | 26.944 | 19.614 | 19.300 | 1.00 | 20.14 |
| ATOM | 380 | C | ALA | 721 | 25.378 | 18.592 | 20.944 | 1.00 | 20.23 |
| ATOM | 381 | O | ALA | 721 | 24.664 | 19.582 | 21.088 | 1.00 | 20.39 |
| ATOM | 382 | N | LEU | 722 | 24.925 | 17.352 | 21.116 | 1.00 | 20.40 |
| ATOM | 383 | CA | LEU | 722 | 23.536 | 17.103 | 21.497 | 1.00 | 21.36 |
| ATOM | 384 | CB | LEU | 722 | 23.166 | 15.627 | 21.282 | 1.00 | 21.25 |
| ATOM | 385 | CG | LEU | 722 | 22.682 | 15.273 | 19.866 | 1.00 | 21.90 |
| ATOM | 386 | CD1 | LEU | 722 | 22.656 | 13.756 | 19.658 | 1.00 | 20.78 |
| ATOM | 387 | CD2 | LEU | 722 | 21.312 | 15.893 | 19.632 | 1.00 | 21.16 |
| ATOM | 388 | C | LEU | 722 | 23.228 | 17.497 | 22.944 | 1.00 | 22.09 |
| ATOM | 389 | O | LEU | 722 | 24.085 | 17.429 | 23.826 | 1.00 | 22.42 |
| ATOM | 390 | N | PRO | 723 | 21.996 | 17.941 | 23.202 | 1.00 | 22.76 |
| ATOM | 391 | CD | PRO | 723 | 20.936 | 18.384 | 22.273 | 1.00 | 22.83 |
| ATOM | 392 | CA | PRO | 723 | 21.688 | 18.318 | 24.586 | 1.00 | 23.30 |
| ATOM | 393 | CB | PRO | 723 | 20.256 | 18.860 | 24.490 | 1.00 | 23.27 |
| ATOM | 394 | CG | PRO | 723 | 20.207 | 19.447 | 23.086 | 1.00 | 22.63 |
| ATOM | 395 | C | PRO | 723 | 21.787 | 17.131 | 25.539 | 1.00 | 23.84 |
| ATOM | 396 | O | PRO | 723 | 21.100 | 16.132 | 25.360 | 1.00 | 23.75 |
| ATOM | 397 | N | GLY | 724 | 22.658 | 17.236 | 26.537 | 1.00 | 24.31 |
| ATOM | 398 | CA | GLY | 724 | 22.788 | 16.172 | 27.524 | 1.00 | 24.68 |
| ATOM | 399 | C | GLY | 724 | 23.653 | 14.966 | 27.180 | 1.00 | 25.55 |
| ATOM | 400 | O | GLY | 724 | 23.896 | 14.114 | 28.040 | 1.00 | 25.10 |
| ATOM | 401 | N | PHE | 725 | 24.113 | 14.876 | 25.935 | 1.00 | 25.87 |
| ATOM | 402 | CA | PHE | 725 | 24.950 | 13.757 | 25.535 | 1.00 | 26.37 |
| ATOM | 403 | CB | PHE | 725 | 25.373 | 13.898 | 24.077 | 1.00 | 25.67 |
| ATOM | 404 | CG | PHE | 725 | 26.116 | 12.706 | 23.560 | 1.00 | 25.20 |
| ATOM | 405 | CD1 | PHE | 725 | 25.428 | 11.572 | 23.140 | 1.00 | 24.92 |
| ATOM | 406 | CD2 | PHE | 725 | 27.505 | 12.689 | 23.546 | 1.00 | 24.47 |
| ATOM | 407 | CE1 | PHE | 725 | 26.117 | 10.429 | 22.712 | 1.00 | 24.76 |
| ATOM | 408 | CE2 | PHE | 725 | 28.198 | 11.554 | 23.121 | 1.00 | 24.71 |
| ATOM | 409 | CZ | PHE | 725 | 27.498 | 10.422 | 22.704 | 1.00 | 24.40 |
| ATOM | 410 | C | PHE | 725 | 26.202 | 13.693 | 26.412 | 1.00 | 27.46 |
| ATOM | 411 | O | PHE | 725 | 26.593 | 12.622 | 26.880 | 1.00 | 27.31 |
| ATOM | 412 | N | ARG | 726 | 26.830 | 14.851 | 26.618 | 1.00 | 28.62 |
| ATOM | 413 | CA | ARG | 726 | 28.039 | 14.951 | 27.430 | 1.00 | 29.72 |
| ATOM | 414 | CB | ARG | 726 | 28.557 | 16.389 | 27.416 | 1.00 | 30.89 |
| ATOM | 415 | CG | ARG | 726 | 29.272 | 16.781 | 26.134 | 1.00 | 32.52 |
| ATOM | 416 | CD | ARG | 726 | 30.536 | 15.963 | 25.976 | 1.00 | 34.40 |
| ATOM | 417 | NE | ARG | 726 | 31.176 | 15.731 | 27.271 | 1.00 | 35.49 |
| ATOM | 418 | CZ | ARG | 726 | 32.382 | 15.196 | 27.428 | 1.00 | 36.20 |
| ATOM | 419 | NH1 | ARG | 726 | 32.878 | 15.024 | 28.649 | 1.00 | 36.46 |
| ATOM | 420 | NH2 | ARG | 726 | 33.098 | 14.846 | 26.365 | 1.00 | 36.56 |
| ATOM | 421 | C | ARG | 726 | 27.855 | 14.480 | 28.879 | 1.00 | 29.93 |
| ATOM | 422 | O | ARG | 726 | 28.825 | 14.378 | 29.636 | 1.00 | 29.51 |
| ATOM | 423 | N | ASN | 727 | 26.613 | 14.212 | 29.274 | 1.00 | 29.89 |
| ATOM | 424 | CA | ASN | 727 | 26.374 | 13.717 | 30.616 | 1.00 | 30.24 |
| ATOM | 425 | CB | ASN | 727 | 24.891 | 13.782 | 30.968 | 1.00 | 30.69 |
| ATOM | 426 | CG | ASN | 727 | 24.511 | 15.087 | 31.645 | 1.00 | 31.99 |
| ATOM | 427 | OD1 | ASN | 727 | 23.357 | 15.539 | 31.562 | 1.00 | 32.19 |
| ATOM | 428 | ND2 | ASN | 727 | 25.479 | 15.699 | 32.339 | 1.00 | 32.26 |

TABLE A-continued

| ATOM | 429 | C | ASN | 727 | 26.856 | 12.279 | 30.644 | 1.00 | 30.26 |
|---|---|---|---|---|---|---|---|---|---|
| ATOM | 430 | O | ASN | 727 | 27.412 | 11.835 | 31.632 | 1.00 | 30.96 |
| ATOM | 431 | N | LEU | 728 | 26.659 | 11.562 | 29.541 | 1.00 | 30.22 |
| ATOM | 432 | CA | LEU | 728 | 27.080 | 10.167 | 29.444 | 1.00 | 30.16 |
| ATOM | 433 | CB | LEU | 728 | 26.884 | 9.629 | 28.020 | 1.00 | 29.53 |
| ATOM | 434 | CG | LEU | 728 | 25.469 | 9.476 | 27.448 | 1.00 | 29.44 |
| ATOM | 435 | CD1 | LEU | 728 | 25.558 | 9.204 | 25.960 | 1.00 | 29.24 |
| ATOM | 436 | CD2 | LEU | 728 | 24.738 | 8.351 | 28.144 | 1.00 | 29.16 |
| ATOM | 437 | C | LEU | 728 | 28.545 | 10.049 | 29.800 | 1.00 | 30.48 |
| ATOM | 438 | O | LEU | 728 | 29.315 | 10.995 | 29.624 | 1.00 | 30.21 |
| ATOM | 439 | N | HIS | 729 | 28.925 | 8.884 | 30.302 | 1.00 | 30.85 |
| ATOM | 440 | CA | HIS | 729 | 30.310 | 8.638 | 30.643 | 1.00 | 31.47 |
| ATOM | 441 | CB | HIS | 729 | 30.453 | 7.268 | 31.327 | 1.00 | 31.98 |
| ATOM | 442 | CG | HIS | 729 | 31.872 | 6.884 | 31.611 | 1.00 | 32.66 |
| ATOM | 443 | CD2 | HIS | 729 | 32.844 | 6.406 | 30.796 | 1.00 | 32.89 |
| ATOM | 444 | ND1 | HIS | 729 | 32.461 | 7.060 | 32.845 | 1.00 | 33.17 |
| ATOM | 445 | CE1 | HIS | 729 | 33.735 | 6.713 | 32.777 | 1.00 | 33.16 |
| ATOM | 446 | NE2 | HIS | 729 | 33.994 | 6.314 | 31.545 | 1.00 | 33.32 |
| ATOM | 447 | C | HIS | 729 | 31.105 | 8.650 | 29.326 | 1.00 | 31.63 |
| ATOM | 448 | O | HIS | 729 | 30.583 | 8.279 | 28.273 | 1.00 | 31.40 |
| ATOM | 449 | N | VAL | 730 | 32.359 | 9.078 | 29.400 | 1.00 | 31.76 |
| ATOM | 450 | CA | VAL | 730 | 33.250 | 9.133 | 28.250 | 1.00 | 32.24 |
| ATOM | 451 | CB | VAL | 730 | 34.731 | 9.282 | 28.713 | 1.00 | 32.50 |
| ATOM | 452 | CG1 | VAL | 730 | 35.658 | 9.405 | 27.508 | 1.00 | 32.05 |
| ATOM | 453 | CG2 | VAL | 730 | 34.872 | 10.489 | 29.632 | 1.00 | 32.57 |
| ATOM | 454 | C | VAL | 730 | 33.161 | 7.860 | 27.408 | 1.00 | 33.08 |
| ATOM | 455 | O | VAL | 730 | 33.019 | 7.919 | 26.181 | 1.00 | 33.09 |
| ATOM | 456 | N | ASP | 731 | 33.268 | 6.715 | 28.085 | 1.00 | 33.39 |
| ATOM | 457 | CA | ASP | 731 | 33.246 | 5.400 | 27.449 | 1.00 | 33.76 |
| ATOM | 458 | CB | ASP | 731 | 33.558 | 4.322 | 28.491 | 1.00 | 34.69 |
| ATOM | 459 | CG | ASP | 731 | 34.969 | 4.433 | 29.033 | 1.00 | 36.10 |
| ATOM | 460 | OD1 | ASP | 731 | 35.190 | 4.055 | 30.214 | 1.00 | 36.28 |
| ATOM | 461 | OD2 | ASP | 731 | 35.856 | 4.892 | 28.270 | 1.00 | 36.30 |
| ATOM | 462 | C | ASP | 731 | 31.946 | 5.054 | 26.738 | 1.00 | 33.23 |
| ATOM | 463 | O | ASP | 731 | 31.971 | 4.444 | 25.674 | 1.00 | 33.20 |
| ATOM | 464 | N | ASP | 732 | 30.822 | 5.428 | 27.344 | 1.00 | 32.63 |
| ATOM | 465 | CA | ASP | 732 | 29.502 | 5.172 | 26.784 | 1.00 | 31.98 |
| ATOM | 466 | CB | ASP | 732 | 28.418 | 5.345 | 27.861 | 1.00 | 32.27 |
| ATOM | 467 | CG | ASP | 732 | 28.566 | 4.358 | 29.018 | 1.00 | 32.72 |
| ATOM | 468 | OD1 | ASP | 732 | 29.043 | 3.223 | 28.783 | 1.00 | 33.04 |
| ATOM | 469 | OD2 | ASP | 732 | 28.185 | 4.711 | 30.159 | 1.00 | 32.04 |
| ATOM | 470 | C | ASP | 732 | 29.203 | 6.107 | 25.606 | 1.00 | 31.68 |
| ATOM | 471 | O | ASP | 732 | 28.410 | 5.768 | 24.722 | 1.00 | 31.75 |
| ATOM | 472 | N | GLN | 733 | 29.826 | 7.285 | 25.604 | 1.00 | 30.91 |
| ATOM | 473 | CA | GLN | 733 | 29.631 | 8.249 | 24.526 | 1.00 | 30.18 |
| ATOM | 474 | CB | GLN | 733 | 30.481 | 9.514 | 24.740 | 1.00 | 30.21 |
| ATOM | 475 | CG | GLN | 733 | 30.198 | 10.316 | 25.996 | 1.00 | 31.08 |
| ATOM | 476 | CD | GLN | 733 | 31.070 | 11.577 | 26.086 | 1.00 | 32.11 |
| ATOM | 477 | OE1 | GLN | 733 | 32.282 | 11.528 | 25.855 | 1.00 | 33.33 |
| ATOM | 478 | NE2 | GLN | 733 | 30.458 | 12.699 | 26.429 | 1.00 | 31.97 |
| ATOM | 479 | C | GLN | 733 | 30.049 | 7.610 | 23.202 | 1.00 | 29.54 |
| ATOM | 480 | O | GLN | 733 | 29.263 | 7.553 | 22.258 | 1.00 | 28.86 |
| ATOM | 481 | N | MET | 734 | 31.287 | 7.124 | 23.146 | 1.00 | 29.26 |
| ATOM | 482 | CA | MET | 734 | 31.818 | 6.505 | 21.929 | 1.00 | 29.62 |
| ATOM | 483 | CB | MET | 734 | 33.347 | 6.432 | 21.993 | 1.00 | 31.24 |
| ATOM | 484 | CG | MET | 734 | 34.044 | 7.704 | 21.512 | 1.00 | 34.06 |
| ATOM | 485 | SD | MET | 734 | 33.906 | 8.000 | 19.707 | 1.00 | 37.92 |
| ATOM | 486 | CE | MET | 734 | 35.327 | 7.026 | 19.055 | 1.00 | 36.58 |
| ATOM | 487 | C | MET | 734 | 31.253 | 5.124 | 21.588 | 1.00 | 28.35 |
| ATOM | 488 | O | MET | 734 | 31.280 | 4.722 | 20.428 | 1.00 | 28.45 |
| ATOM | 489 | N | ALA | 735 | 30.765 | 4.398 | 22.589 | 1.00 | 26.73 |
| ATOM | 490 | CA | ALA | 735 | 30.181 | 3.081 | 22.347 | 1.00 | 26.10 |
| ATOM | 491 | CB | ALA | 735 | 30.003 | 2.310 | 23.669 | 1.00 | 26.35 |
| ATOM | 492 | C | ALA | 735 | 28.825 | 3.298 | 21.676 | 1.00 | 24.76 |
| ATOM | 493 | O | ALA | 735 | 28.531 | 2.705 | 20.653 | 1.00 | 24.32 |
| ATOM | 494 | N | VAL | 736 | 28.012 | 4.160 | 22.272 | 1.00 | 24.18 |
| ATOM | 495 | CA | VAL | 736 | 26.704 | 4.487 | 21.734 | 1.00 | 23.42 |
| ATOM | 496 | CB | VAL | 736 | 26.022 | 5.579 | 22.592 | 1.00 | 23.57 |
| ATOM | 497 | CG1 | VAL | 736 | 25.268 | 6.570 | 21.713 | 1.00 | 23.51 |
| ATOM | 498 | CG2 | VAL | 736 | 25.071 | 4.932 | 23.573 | 1.00 | 23.24 |
| ATOM | 499 | C | VAL | 736 | 26.895 | 4.985 | 20.301 | 1.00 | 23.21 |
| ATOM | 500 | O | VAL | 736 | 26.228 | 4.516 | 19.375 | 1.00 | 23.40 |
| ATOM | 501 | N | ILE | 737 | 27.827 | 5.917 | 20.129 | 1.00 | 22.03 |
| ATOM | 502 | CA | ILE | 737 | 28.117 | 6.479 | 18.816 | 1.00 | 21.62 |
| ATOM | 503 | CB | ILE | 737 | 29.228 | 7.550 | 18.883 | 1.00 | 20.18 |
| ATOM | 504 | CG2 | ILE | 737 | 29.787 | 7.795 | 17.510 | 1.00 | 20.01 |
| ATOM | 505 | CG1 | ILE | 737 | 28.685 | 8.855 | 19.468 | 1.00 | 19.45 |
| ATOM | 506 | CD1 | ILE | 737 | 29.770 | 9.894 | 19.681 | 1.00 | 18.31 |
| ATOM | 507 | C | ILE | 737 | 28.550 | 5.428 | 17.795 | 1.00 | 22.21 |

TABLE A-continued

| | | | | | | | | |
|---|---|---|---|---|---|---|---|---|
| ATOM | 508 | O | ILE | 737 | 28.040 | 5.403 | 16.678 | 1.00 | 22.12 |
| ATOM | 509 | N | GLN | 738 | 29.502 | 4.576 | 18.161 | 1.00 | 22.07 |
| ATOM | 510 | CA | GLN | 738 | 29.949 | 3.572 | 17.225 | 1.00 | 22.29 |
| ATOM | 511 | CB | GLN | 738 | 31.255 | 2.943 | 17.701 | 1.00 | 23.58 |
| ATOM | 512 | CG | GLN | 738 | 32.411 | 3.940 | 17.806 | 1.00 | 23.70 |
| ATOM | 513 | CD | GLN | 738 | 33.698 | 3.287 | 18.280 | 1.00 | 23.85 |
| ATOM | 514 | OE1 | GLN | 738 | 33.682 | 2.436 | 19.165 | 1.00 | 24.48 |
| ATOM | 515 | NE2 | GLN | 738 | 34.819 | 3.695 | 17.702 | 1.00 | 23.64 |
| ATOM | 516 | C | GLN | 738 | 28.891 | 2.499 | 16.970 | 1.00 | 21.96 |
| ATOM | 517 | O | GLN | 738 | 28.771 | 2.037 | 15.838 | 1.00 | 22.01 |
| ATOM | 518 | N | TYR | 739 | 28.112 | 2.125 | 17.990 | 1.00 | 20.77 |
| ATOM | 519 | CA | TYR | 739 | 27.073 | 1.115 | 17.800 | 1.00 | 19.98 |
| ATOM | 520 | CB | TYR | 739 | 26.468 | 0.627 | 19.120 | 1.00 | 20.07 |
| ATOM | 521 | CG | TYR | 739 | 27.407 | 0.014 | 20.133 | 1.00 | 20.08 |
| ATOM | 522 | CD1 | TYR | 739 | 28.400 | −0.886 | 19.754 | 1.00 | 20.37 |
| ATOM | 523 | CE1 | TYR | 739 | 29.221 | −1.484 | 20.703 | 1.00 | 21.09 |
| ATOM | 524 | CD2 | TYR | 739 | 27.254 | 0.295 | 21.485 | 1.00 | 19.66 |
| ATOM | 525 | CE2 | TYR | 739 | 28.065 | −0.301 | 22.444 | 1.00 | 20.66 |
| ATOM | 526 | CZ | TYR | 739 | 29.050 | −1.182 | 22.049 | 1.00 | 20.98 |
| ATOM | 527 | OH | TYR | 739 | 29.902 | −1.706 | 22.998 | 1.00 | 22.42 |
| ATOM | 528 | C | TYR | 739 | 25.897 | 1.621 | 16.964 | 1.00 | 19.75 |
| ATOM | 529 | O | TYR | 739 | 25.249 | 0.845 | 16.250 | 1.00 | 19.75 |
| ATOM | 530 | N | SER | 740 | 25.592 | 2.910 | 17.063 | 1.00 | 18.92 |
| ATOM | 531 | CA | SER | 740 | 24.450 | 3.432 | 16.316 | 1.00 | 18.02 |
| ATOM | 532 | CB | SER | 740 | 23.648 | 4.420 | 17.181 | 1.00 | 18.07 |
| ATOM | 533 | OG | SER | 740 | 24.292 | 5.666 | 17.302 | 1.00 | 18.74 |
| ATOM | 534 | C | SER | 740 | 24.831 | 4.069 | 14.984 | 1.00 | 16.97 |
| ATOM | 535 | O | SER | 740 | 23.969 | 4.442 | 14.198 | 1.00 | 16.64 |
| ATOM | 536 | N | TRP | 741 | 26.129 | 4.150 | 14.741 | 1.00 | 16.05 |
| ATOM | 537 | CA | TRP | 741 | 26.689 | 4.725 | 13.529 | 1.00 | 16.05 |
| ATOM | 538 | CB | TRP | 741 | 28.189 | 4.350 | 13.492 | 1.00 | 17.09 |
| ATOM | 539 | CG | TRP | 741 | 29.006 | 4.764 | 12.306 | 1.00 | 19.02 |
| ATOM | 540 | CD2 | TRP | 741 | 30.294 | 4.238 | 11.932 | 1.00 | 20.22 |
| ATOM | 541 | CE2 | TRP | 741 | 30.662 | 4.848 | 10.713 | 1.00 | 20.50 |
| ATOM | 542 | CE3 | TRP | 741 | 31.170 | 3.302 | 12.512 | 1.00 | 20.91 |
| ATOM | 543 | CD1 | TRP | 741 | 28.667 | 5.657 | 11.335 | 1.00 | 19.78 |
| ATOM | 544 | NE1 | TRP | 741 | 29.657 | 5.711 | 10.368 | 1.00 | 20.54 |
| ATOM | 545 | CZ2 | TRP | 741 | 31.864 | 4.554 | 10.057 | 1.00 | 22.12 |
| ATOM | 546 | CZ3 | TRP | 741 | 32.363 | 3.006 | 11.865 | 1.00 | 21.59 |
| ATOM | 547 | CH2 | TRP | 741 | 32.702 | 3.632 | 10.643 | 1.00 | 22.46 |
| ATOM | 548 | C | TRP | 741 | 25.911 | 4.300 | 12.257 | 1.00 | 15.45 |
| ATOM | 549 | O | TRP | 741 | 25.401 | 5.150 | 11.526 | 1.00 | 14.12 |
| ATOM | 550 | N | MET | 742 | 25.791 | 2.998 | 12.020 | 1.00 | 15.44 |
| ATOM | 551 | CA | MET | 742 | 25.090 | 2.466 | 10.845 | 1.00 | 15.95 |
| ATOM | 552 | CB | MET | 742 | 25.100 | 0.932 | 10.863 | 1.00 | 16.16 |
| ATOM | 553 | CG | MET | 742 | 24.447 | 0.326 | 9.646 | 1.00 | 16.45 |
| ATOM | 554 | SD | MET | 742 | 25.477 | 0.591 | 8.187 | 1.00 | 17.11 |
| ATOM | 555 | CE | MET | 742 | 26.513 | −0.885 | 8.352 | 1.00 | 16.44 |
| ATOM | 556 | C | MET | 742 | 23.635 | 2.924 | 10.665 | 1.00 | 16.26 |
| ATOM | 557 | O | MET | 742 | 23.259 | 3.451 | 9.597 | 1.00 | 16.31 |
| ATOM | 558 | N | GLY | 743 | 22.826 | 2.683 | 11.698 | 1.00 | 16.23 |
| ATOM | 559 | CA | GLY | 743 | 21.422 | 3.049 | 11.682 | 1.00 | 15.96 |
| ATOM | 560 | C | GLY | 743 | 21.210 | 4.531 | 11.437 | 1.00 | 16.26 |
| ATOM | 561 | O | GLY | 743 | 20.346 | 4.935 | 10.645 | 1.00 | 16.71 |
| ATOM | 562 | N | LEU | 744 | 21.990 | 5.351 | 12.123 | 1.00 | 15.86 |
| ATOM | 563 | CA | LEU | 744 | 21.888 | 6.791 | 11.952 | 1.00 | 15.37 |
| ATOM | 564 | CB | LEU | 744 | 22.935 | 7.512 | 12.805 | 1.00 | 14.98 |
| ATOM | 565 | CG | LEU | 744 | 22.689 | 7.629 | 14.308 | 1.00 | 15.65 |
| ATOM | 566 | CD1 | LEU | 744 | 23.916 | 8.274 | 14.960 | 1.00 | 16.45 |
| ATOM | 567 | CD2 | LEU | 744 | 21.447 | 8.482 | 14.581 | 1.00 | 14.77 |
| ATOM | 568 | C | LEU | 744 | 22.100 | 7.146 | 10.483 | 1.00 | 15.33 |
| ATOM | 569 | O | LEU | 744 | 21.350 | 7.939 | 9.918 | 1.00 | 14.53 |
| ATOM | 570 | N | MET | 745 | 23.121 | 6.551 | 9.874 | 1.00 | 15.35 |
| ATOM | 571 | CA | MET | 745 | 23.420 | 6.819 | 8.474 | 1.00 | 16.27 |
| ATOM | 572 | CB | MET | 745 | 24.723 | 6.138 | 8.046 | 1.00 | 17.33 |
| ATOM | 573 | CG | MET | 745 | 25.987 | 6.659 | 8.711 | 1.00 | 19.23 |
| ATOM | 574 | SD | MET | 745 | 27.427 | 6.326 | 7.658 | 1.00 | 22.31 |
| ATOM | 575 | CE | MET | 745 | 27.320 | 4.566 | 7.432 | 1.00 | 20.16 |
| ATOM | 576 | C | MET | 745 | 22.297 | 6.350 | 7.540 | 1.00 | 16.24 |
| ATOM | 577 | O | MET | 745 | 21.939 | 7.060 | 6.596 | 1.00 | 16.31 |
| ATOM | 578 | N | VAL | 746 | 21.755 | 5.156 | 7.804 | 1.00 | 15.42 |
| ATOM | 579 | CA | VAL | 746 | 20.685 | 4.615 | 6.981 | 1.00 | 14.36 |
| ATOM | 580 | CB | VAL | 746 | 20.250 | 3.215 | 7.462 | 1.00 | 13.88 |
| ATOM | 581 | CG1 | VAL | 746 | 18.936 | 2.830 | 6.808 | 1.00 | 13.61 |
| ATOM | 582 | CG2 | VAL | 746 | 21.310 | 2.198 | 7.121 | 1.00 | 13.23 |
| ATOM | 583 | C | VAL | 746 | 19.474 | 5.532 | 7.025 | 1.00 | 14.30 |
| ATOM | 584 | O | VAL | 746 | 18.894 | 5.835 | 5.998 | 1.00 | 14.06 |
| ATOM | 585 | N | PHE | 747 | 19.102 | 5.959 | 8.229 | 1.00 | 14.31 |
| ATOM | 586 | CA | PHE | 747 | 17.953 | 6.831 | 8.433 | 1.00 | 14.49 |

TABLE A-continued

| | | | | | | | | |
|---|---|---|---|---|---|---|---|---|
| ATOM | 587 | CB | PHE | 747 | 17.748 | 7.074 | 9.923 | 1.00 | 13.20 |
| ATOM | 588 | CG | PHE | 747 | 16.425 | 7.677 | 10.263 | 1.00 | 12.24 |
| ATOM | 589 | CD1 | PHE | 747 | 15.247 | 6.951 | 10.089 | 1.00 | 11.83 |
| ATOM | 590 | CD2 | PHE | 747 | 16.348 | 8.954 | 10.802 | 1.00 | 12.05 |
| ATOM | 591 | CE1 | PHE | 747 | 14.017 | 7.491 | 10.450 | 1.00 | 11.38 |
| ATOM | 592 | CE2 | PHE | 747 | 15.120 | 9.498 | 11.168 | 1.00 | 11.97 |
| ATOM | 593 | CZ | PHE | 747 | 13.951 | 8.765 | 10.991 | 1.00 | 10.82 |
| ATOM | 594 | C | PHE | 747 | 18.094 | 8.180 | 7.715 | 1.00 | 15.24 |
| ATOM | 595 | O | PHE | 747 | 17.192 | 8.590 | 6.994 | 1.00 | 15.13 |
| ATOM | 596 | N | ALA | 748 | 19.211 | 8.870 | 7.930 | 1.00 | 15.97 |
| ATOM | 597 | CA | ALA | 748 | 19.445 | 10.154 | 7.274 | 1.00 | 17.37 |
| ATOM | 598 | CB | ALA | 748 | 20.765 | 10.746 | 7.728 | 1.00 | 15.48 |
| ATOM | 599 | C | ALA | 748 | 19.460 | 9.940 | 5.758 | 1.00 | 18.41 |
| ATOM | 600 | O | ALA | 748 | 18.875 | 10.702 | 4.998 | 1.00 | 19.17 |
| ATOM | 601 | N | MET | 749 | 20.120 | 8.882 | 5.323 | 1.00 | 19.85 |
| ATOM | 602 | CA | MET | 749 | 20.190 | 8.612 | 3.909 | 1.00 | 21.36 |
| ATOM | 603 | CB | MET | 749 | 21.056 | 7.388 | 3.661 | 1.00 | 20.95 |
| ATOM | 604 | CG | MET | 749 | 21.368 | 7.151 | 2.206 | 1.00 | 23.14 |
| ATOM | 605 | SD | MET | 749 | 20.021 | 6.300 | 1.350 | 1.00 | 24.54 |
| ATOM | 606 | CE | MET | 749 | 20.381 | 4.591 | 1.837 | 1.00 | 23.82 |
| ATOM | 607 | C | MET | 749 | 18.762 | 8.415 | 3.395 | 1.00 | 22.45 |
| ATOM | 608 | O | MET | 749 | 18.405 | 8.880 | 2.305 | 1.00 | 21.89 |
| ATOM | 609 | N | GLY | 750 | 17.938 | 7.740 | 4.193 | 1.00 | 23.36 |
| ATOM | 610 | CA | GLY | 750 | 16.562 | 7.522 | 3.787 | 1.00 | 23.69 |
| ATOM | 611 | C | GLY | 750 | 15.934 | 8.874 | 3.507 | 1.00 | 24.41 |
| ATOM | 612 | O | GLY | 750 | 15.329 | 9.091 | 2.451 | 1.00 | 23.64 |
| ATOM | 613 | N | TRP | 751 | 16.097 | 9.793 | 4.461 | 1.00 | 25.13 |
| ATOM | 614 | CA | TRP | 751 | 15.559 | 11.144 | 4.342 | 1.00 | 25.53 |
| ATOM | 615 | CB | TRP | 751 | 15.937 | 11.957 | 5.570 | 1.00 | 25.52 |
| ATOM | 616 | CG | TRP | 751 | 15.490 | 13.393 | 5.533 | 1.00 | 24.81 |
| ATOM | 617 | CD2 | TRP | 751 | 14.156 | 13.886 | 5.715 | 1.00 | 24.48 |
| ATOM | 618 | CE2 | TRP | 751 | 14.223 | 15.295 | 5.669 | 1.00 | 24.36 |
| ATOM | 619 | CE3 | TRP | 751 | 12.911 | 13.273 | 5.913 | 1.00 | 24.15 |
| ATOM | 620 | CD1 | TRP | 751 | 16.283 | 14.488 | 5.380 | 1.00 | 24.77 |
| ATOM | 621 | NE1 | TRP | 751 | 15.532 | 15.635 | 5.464 | 1.00 | 24.45 |
| ATOM | 622 | CZ2 | TRP | 751 | 13.096 | 16.104 | 5.816 | 1.00 | 24.20 |
| ATOM | 623 | CZ3 | TRP | 751 | 11.794 | 14.072 | 6.058 | 1.00 | 24.68 |
| ATOM | 624 | CH2 | TRP | 751 | 11.893 | 15.481 | 6.009 | 1.00 | 24.71 |
| ATOM | 625 | C | TRP | 751 | 16.068 | 11.846 | 3.085 | 1.00 | 26.37 |
| ATOM | 626 | O | TRP | 751 | 15.279 | 12.381 | 2.308 | 1.00 | 26.71 |
| ATOM | 627 | N | ARG | 752 | 17.384 | 11.850 | 2.890 | 1.00 | 27.04 |
| ATOM | 628 | CA | ARG | 752 | 17.963 | 12.478 | 1.713 | 1.00 | 27.72 |
| ATOM | 629 | CB | ARG | 752 | 19.476 | 12.286 | 1.672 | 1.00 | 26.90 |
| ATOM | 630 | CG | ARG | 752 | 20.229 | 13.200 | 2.598 | 1.00 | 25.98 |
| ATOM | 631 | CD | ARG | 752 | 21.661 | 13.368 | 2.123 | 1.00 | 25.78 |
| ATOM | 632 | NE | ARG | 752 | 22.336 | 12.086 | 1.971 | 1.00 | 24.53 |
| ATOM | 633 | CZ | ARG | 752 | 22.620 | 11.278 | 2.986 | 1.00 | 24.29 |
| ATOM | 634 | NH1 | ARG | 752 | 22.286 | 11.628 | 4.222 | 1.00 | 23.93 |
| ATOM | 635 | NH2 | ARG | 752 | 23.237 | 10.127 | 2.764 | 1.00 | 23.51 |
| ATOM | 636 | C | ARG | 752 | 17.373 | 11.933 | 0.427 | 1.00 | 28.66 |
| ATOM | 637 | O | ARG | 752 | 17.107 | 12.694 | −0.508 | 1.00 | 29.23 |
| ATOM | 638 | N | SER | 753 | 17.169 | 10.620 | 0.367 | 1.00 | 29.64 |
| ATOM | 639 | CA | SER | 753 | 16.612 | 10.015 | −0.836 | 1.00 | 30.86 |
| ATOM | 640 | CB | SER | 753 | 16.626 | 8.485 | −0.739 | 1.00 | 30.75 |
| ATOM | 641 | OG | SER | 753 | 17.950 | 7.982 | −0.831 | 1.00 | 30.65 |
| ATOM | 642 | C | SER | 753 | 15.196 | 10.508 | −1.049 | 1.00 | 31.73 |
| ATOM | 643 | O | SER | 753 | 14.681 | 10.498 | −2.162 | 1.00 | 31.89 |
| ATOM | 644 | N | PHE | 754 | 14.578 | 10.951 | 0.034 | 1.00 | 33.09 |
| ATOM | 645 | CA | PHE | 754 | 13.220 | 11.457 | −0.006 | 1.00 | 34.65 |
| ATOM | 646 | CB | PHE | 754 | 12.604 | 11.394 | 1.391 | 1.00 | 34.66 |
| ATOM | 647 | CG | PHE | 754 | 11.246 | 12.019 | 1.478 | 1.00 | 35.49 |
| ATOM | 648 | CD1 | PHE | 754 | 10.165 | 11.463 | 0.799 | 1.00 | 35.64 |
| ATOM | 649 | CD2 | PHE | 754 | 11.051 | 13.185 | 2.209 | 1.00 | 35.56 |
| ATOM | 650 | CE1 | PHE | 754 | 8.913 | 12.061 | 0.845 | 1.00 | 35.75 |
| ATOM | 651 | CE2 | PHE | 754 | 9.802 | 13.792 | 2.264 | 1.00 | 35.98 |
| ATOM | 652 | CZ | PHE | 754 | 8.732 | 13.232 | 1.581 | 1.00 | 36.01 |
| ATOM | 653 | C | PHE | 754 | 13.154 | 12.899 | −0.519 | 1.00 | 35.79 |
| ATOM | 654 | O | PHE | 754 | 12.448 | 13.193 | −1.481 | 1.00 | 35.70 |
| ATOM | 655 | N | THR | 755 | 13.896 | 13.789 | 0.133 | 1.00 | 37.07 |
| ATOM | 656 | CA | THR | 755 | 13.904 | 15.204 | −0.219 | 1.00 | 38.07 |
| ATOM | 657 | CB | THR | 755 | 14.561 | 16.051 | 0.890 | 1.00 | 37.76 |
| ATOM | 658 | OG1 | THR | 755 | 15.981 | 15.846 | 0.877 | 1.00 | 38.00 |
| ATOM | 659 | CG2 | THR | 755 | 14.019 | 15.656 | 2.243 | 1.00 | 37.83 |
| ATOM | 660 | C | THR | 755 | 14.626 | 15.516 | −1.521 | 1.00 | 38.94 |
| ATOM | 661 | O | THR | 755 | 14.855 | 16.684 | −1.834 | 1.00 | 39.37 |
| ATOM | 662 | N | ASN | 756 | 14.995 | 14.487 | −2.275 | 1.00 | 39.70 |
| ATOM | 663 | CA | ASN | 756 | 15.693 | 14.712 | −3.533 | 1.00 | 40.27 |
| ATOM | 664 | CB | ASN | 756 | 17.194 | 14.427 | −3.369 | 1.00 | 40.38 |
| ATOM | 665 | CG | ASN | 756 | 17.888 | 15.424 | −2.434 | 1.00 | 40.95 |

TABLE A-continued

| ATOM | 666 | OD1 | ASN | 756 | 17.610 | 15.469 | −1.237 | 1.00 | 41.37 |
| ATOM | 667 | ND2 | ASN | 756 | 18.792 | 16.229 | −2.986 | 1.00 | 41.31 |
| ATOM | 668 | C | ASN | 756 | 15.128 | 13.904 | −4.702 | 1.00 | 40.62 |
| ATOM | 669 | O | ASN | 756 | 14.494 | 14.460 | −5.599 | 1.00 | 40.90 |
| ATOM | 670 | N | VAL | 757 | 15.337 | 12.594 | −4.687 | 1.00 | 41.04 |
| ATOM | 671 | CA | VAL | 757 | 14.869 | 11.743 | −5.776 | 1.00 | 41.30 |
| ATOM | 672 | CB | VAL | 757 | 15.939 | 10.680 | −6.104 | 1.00 | 41.48 |
| ATOM | 673 | CG1 | VAL | 757 | 17.218 | 11.363 | −6.562 | 1.00 | 41.53 |
| ATOM | 674 | CG2 | VAL | 757 | 16.226 | 9.835 | −4.878 | 1.00 | 41.39 |
| ATOM | 675 | C | VAL | 757 | 13.529 | 11.051 | −5.518 | 1.00 | 41.34 |
| ATOM | 676 | O | VAL | 757 | 13.206 | 10.046 | −6.154 | 1.00 | 41.09 |
| ATOM | 677 | N | ASN | 758 | 12.747 | 11.597 | −4.593 | 1.00 | 41.49 |
| ATOM | 678 | CA | ASN | 758 | 11.455 | 11.012 | −4.246 | 1.00 | 41.40 |
| ATOM | 679 | CB | ASN | 758 | 10.433 | 11.290 | −5.346 | 1.00 | 41.86 |
| ATOM | 680 | CG | ASN | 758 | 9.848 | 12.682 | −5.251 | 1.00 | 42.34 |
| ATOM | 681 | OD1 | ASN | 758 | 9.032 | 12.968 | −4.370 | 1.00 | 42.45 |
| ATOM | 682 | ND2 | ASN | 758 | 10.269 | 13.561 | −6.153 | 1.00 | 42.55 |
| ATOM | 683 | C | ASN | 758 | 11.548 | 9.511 | −3.993 | 1.00 | 41.14 |
| ATOM | 684 | O | ASN | 758 | 10.546 | 8.794 | −4.062 | 1.00 | 41.19 |
| ATOM | 685 | N | SER | 759 | 12.760 | 9.043 | −3.716 | 1.00 | 40.61 |
| ATOM | 686 | CA | SER | 759 | 13.003 | 7.639 | −3.418 | 1.00 | 40.58 |
| ATOM | 687 | CB | SER | 759 | 11.925 | 7.113 | −2.462 | 1.00 | 40.93 |
| ATOM | 688 | OG | SER | 759 | 11.878 | 7.895 | −1.277 | 1.00 | 41.37 |
| ATOM | 689 | C | SER | 759 | 13.114 | 6.704 | −4.616 | 1.00 | 40.19 |
| ATOM | 690 | O | SER | 759 | 13.004 | 5.490 | −4.459 | 1.00 | 40.32 |
| ATOM | 691 | N | ARG | 760 | 13.320 | 7.255 | −5.809 | 1.00 | 39.83 |
| ATOM | 692 | CA | ARG | 760 | 13.482 | 6.412 | −6.996 | 1.00 | 39.13 |
| ATOM | 693 | CB | ARG | 760 | 13.278 | 7.220 | −8.289 | 1.00 | 40.09 |
| ATOM | 694 | CG | ARG | 760 | 13.929 | 6.590 | −9.533 | 1.00 | 41.59 |
| ATOM | 695 | CD | ARG | 760 | 13.150 | 6.877 | −10.827 | 1.00 | 42.76 |
| ATOM | 696 | NE | ARG | 760 | 13.856 | 6.452 | −12.047 | 1.00 | 44.10 |
| ATOM | 697 | CZ | ARG | 760 | 14.317 | 5.221 | −12.290 | 1.00 | 44.02 |
| ATOM | 698 | NH1 | ARG | 760 | 14.169 | 4.244 | −11.402 | 1.00 | 44.29 |
| ATOM | 699 | NH2 | ARG | 760 | 14.926 | 4.966 | −13.437 | 1.00 | 44.11 |
| ATOM | 700 | C | ARG | 760 | 14.897 | 5.843 | −6.951 | 1.00 | 37.86 |
| ATOM | 701 | O | ARG | 760 | 15.200 | 4.841 | −7.603 | 1.00 | 37.94 |
| ATOM | 702 | N | MET | 761 | 15.760 | 6.489 | −6.169 | 1.00 | 36.18 |
| ATOM | 703 | CA | MET | 761 | 17.144 | 6.040 | −6.030 | 1.00 | 34.54 |
| ATOM | 704 | CB | MET | 761 | 18.026 | 6.693 | −7.095 | 1.00 | 34.81 |
| ATOM | 705 | CG | MET | 761 | 17.649 | 6.378 | −8.531 | 1.00 | 35.67 |
| ATOM | 706 | SD | MET | 761 | 18.836 | 7.089 | −9.710 | 1.00 | 35.66 |
| ATOM | 707 | CE | MET | 761 | 18.291 | 8.796 | −9.734 | 1.00 | 35.50 |
| ATOM | 708 | C | MET | 761 | 17.727 | 6.352 | −4.652 | 1.00 | 32.75 |
| ATOM | 709 | O | MET | 761 | 17.347 | 7.329 | −4.009 | 1.00 | 32.64 |
| ATOM | 710 | N | LEU | 762 | 18.661 | 5.521 | −4.211 | 1.00 | 30.58 |
| ATOM | 711 | CA | LEU | 762 | 19.309 | 5.728 | −2.924 | 1.00 | 28.84 |
| ATOM | 712 | CB | LEU | 762 | 19.967 | 4.435 | −2.457 | 1.00 | 28.33 |
| ATOM | 713 | CG | LEU | 762 | 19.019 | 3.248 | −2.303 | 1.00 | 28.15 |
| ATOM | 714 | CD1 | LEU | 762 | 19.810 | 2.045 | −1.847 | 1.00 | 28.12 |
| ATOM | 715 | CD2 | LEU | 762 | 17.924 | 3.575 | −1.308 | 1.00 | 27.94 |
| ATOM | 716 | C | LEU | 762 | 20.356 | 6.838 | −3.040 | 1.00 | 27.76 |
| ATOM | 717 | O | LEU | 762 | 21.341 | 6.713 | −3.779 | 1.00 | 27.12 |
| ATOM | 718 | N | TYR | 763 | 20.135 | 7.921 | −2.302 | 1.00 | 26.72 |
| ATOM | 719 | CA | TYR | 763 | 21.041 | 9.071 | −2.318 | 1.00 | 26.03 |
| ATOM | 720 | CB | TYR | 763 | 20.224 | 10.355 | −2.181 | 1.00 | 26.73 |
| ATOM | 721 | CG | TYR | 763 | 20.832 | 11.570 | −2.836 | 1.00 | 28.00 |
| ATOM | 722 | CD1 | TYR | 763 | 20.532 | 11.894 | −4.159 | 1.00 | 28.78 |
| ATOM | 723 | CE1 | TYR | 763 | 21.064 | 13.037 | −4.764 | 1.00 | 29.17 |
| ATOM | 724 | CD2 | TYR | 763 | 21.686 | 12.414 | −2.131 | 1.00 | 28.81 |
| ATOM | 725 | CE2 | TYR | 763 | 22.226 | 13.561 | −2.729 | 1.00 | 29.70 |
| ATOM | 726 | CZ | TYR | 763 | 21.907 | 13.865 | −4.045 | 1.00 | 29.56 |
| ATOM | 727 | OH | TYR | 763 | 22.410 | 15.005 | −4.629 | 1.00 | 30.24 |
| ATOM | 728 | C | TYR | 763 | 22.074 | 9.000 | −1.180 | 1.00 | 25.05 |
| ATOM | 729 | O | TYR | 763 | 21.886 | 9.607 | −0.130 | 1.00 | 24.70 |
| ATOM | 730 | N | PHE | 764 | 23.154 | 8.253 | −1.386 | 1.00 | 23.85 |
| ATOM | 731 | CA | PHE | 764 | 24.176 | 8.138 | −0.363 | 1.00 | 23.36 |
| ATOM | 732 | CB | PHE | 764 | 25.167 | 7.026 | −0.687 | 1.00 | 22.20 |
| ATOM | 733 | CG | PHE | 764 | 24.592 | 5.665 | −0.577 | 1.00 | 20.93 |
| ATOM | 734 | CD1 | PHE | 764 | 24.141 | 4.997 | −1.703 | 1.00 | 21.03 |
| ATOM | 735 | CD2 | PHE | 764 | 24.484 | 5.049 | 0.654 | 1.00 | 20.64 |
| ATOM | 736 | CE1 | PHE | 764 | 23.590 | 3.728 | −1.600 | 1.00 | 21.11 |
| ATOM | 737 | CE2 | PHE | 764 | 23.936 | 3.785 | 0.765 | 1.00 | 20.71 |
| ATOM | 738 | CZ | PHE | 764 | 23.489 | 3.123 | −0.360 | 1.00 | 20.65 |
| ATOM | 739 | C | PHE | 764 | 24.921 | 9.442 | −0.246 | 1.00 | 23.54 |
| ATOM | 740 | O | PHE | 764 | 25.270 | 9.866 | 0.848 | 1.00 | 23.77 |
| ATOM | 741 | N | ALA | 765 | 25.154 | 10.067 | −1.394 | 1.00 | 23.97 |
| ATOM | 742 | CA | ALA | 765 | 25.854 | 11.346 | −1.488 | 1.00 | 24.26 |
| ATOM | 743 | CB | ALA | 765 | 27.346 | 11.142 | −1.219 | 1.00 | 24.01 |
| ATOM | 744 | C | ALA | 765 | 25.627 | 11.880 | −2.909 | 1.00 | 24.66 |

TABLE A-continued

| | | | | | | | | |
|---|---|---|---|---|---|---|---|---|
| ATOM | 745 | O | ALA | 765 | 25.211 | 11.130 | −3.789 | 1.00 | 24.88 |
| ATOM | 746 | N | PRO | 766 | 25.888 | 13.178 | −3.153 | 1.00 | 25.03 |
| ATOM | 747 | CD | PRO | 766 | 26.345 | 14.222 | −2.220 | 1.00 | 25.22 |
| ATOM | 748 | CA | PRO | 766 | 25.687 | 13.740 | −4.496 | 1.00 | 25.14 |
| ATOM | 749 | CB | PRO | 766 | 26.159 | 15.190 | −4.335 | 1.00 | 25.71 |
| ATOM | 750 | CG | PRO | 766 | 25.841 | 15.485 | −2.888 | 1.00 | 25.20 |
| ATOM | 751 | C | PRO | 766 | 26.485 | 12.980 | −5.554 | 1.00 | 25.17 |
| ATOM | 752 | O | PRO | 766 | 25.984 | 12.693 | −6.651 | 1.00 | 25.08 |
| ATOM | 753 | N | ASP | 767 | 27.721 | 12.634 | −5.208 | 1.00 | 25.17 |
| ATOM | 754 | CA | ASP | 767 | 28.600 | 11.898 | −6.117 | 1.00 | 25.59 |
| ATOM | 755 | CB | ASP | 767 | 30.058 | 12.292 | −5.858 | 1.00 | 25.95 |
| ATOM | 756 | CG | ASP | 767 | 30.531 | 11.898 | −4.470 | 1.00 | 27.34 |
| ATOM | 757 | OD1 | ASP | 767 | 29.780 | 12.093 | −3.487 | 1.00 | 26.89 |
| ATOM | 758 | OD2 | ASP | 767 | 31.668 | 11.400 | −4.355 | 1.00 | 29.03 |
| ATOM | 759 | C | ASP | 767 | 28.457 | 10.374 | −6.012 | 1.00 | 25.16 |
| ATOM | 760 | O | ASP | 767 | 29.215 | 9.644 | −6.636 | 1.00 | 25.56 |
| ATOM | 761 | N | LEU | 768 | 27.507 | 9.891 | −5.214 | 1.00 | 24.75 |
| ATOM | 762 | CA | LEU | 768 | 27.298 | 8.453 | −5.076 | 1.00 | 24.23 |
| ATOM | 763 | CB | LEU | 768 | 28.070 | 7.909 | −3.870 | 1.00 | 23.92 |
| ATOM | 764 | CG | LEU | 768 | 28.183 | 6.378 | −3.771 | 1.00 | 23.88 |
| ATOM | 765 | CD1 | LEU | 768 | 28.910 | 5.819 | −4.974 | 1.00 | 23.45 |
| ATOM | 766 | CD2 | LEU | 768 | 28.943 | 6.011 | −2.523 | 1.00 | 24.21 |
| ATOM | 767 | C | LEU | 768 | 25.808 | 8.129 | −4.944 | 1.00 | 24.57 |
| ATOM | 768 | O | LEU | 768 | 25.285 | 7.931 | −3.846 | 1.00 | 24.30 |
| ATOM | 769 | N | VAL | 769 | 25.133 | 8.081 | −6.088 | 1.00 | 24.78 |
| ATOM | 770 | CA | VAL | 769 | 23.702 | 7.802 | −6.149 | 1.00 | 24.65 |
| ATOM | 771 | CB | VAL | 769 | 22.998 | 8.807 | −7.089 | 1.00 | 24.73 |
| ATOM | 772 | CG1 | VAL | 769 | 21.480 | 8.621 | −7.031 | 1.00 | 24.37 |
| ATOM | 773 | CG2 | VAL | 769 | 23.398 | 10.245 | −6.700 | 1.00 | 24.01 |
| ATOM | 774 | C | VAL | 769 | 23.560 | 6.391 | −6.698 | 1.00 | 24.90 |
| ATOM | 775 | O | VAL | 769 | 24.156 | 6.061 | −7.717 | 1.00 | 25.44 |
| ATOM | 776 | N | PHE | 770 | 22.794 | 5.554 | −6.007 | 1.00 | 24.72 |
| ATOM | 777 | CA | PHE | 770 | 22.615 | 4.180 | −6.434 | 1.00 | 24.40 |
| ATOM | 778 | CB | PHE | 770 | 22.631 | 3.224 | −5.243 | 1.00 | 24.46 |
| ATOM | 779 | CG | PHE | 770 | 23.994 | 2.714 | −4.867 | 1.00 | 23.68 |
| ATOM | 780 | CD1 | PHE | 770 | 25.125 | 3.522 | −4.993 | 1.00 | 22.58 |
| ATOM | 781 | CD2 | PHE | 770 | 24.128 | 1.452 | −4.294 | 1.00 | 23.29 |
| ATOM | 782 | CE1 | PHE | 770 | 26.363 | 3.087 | −4.552 | 1.00 | 22.46 |
| ATOM | 783 | CE2 | PHE | 770 | 25.370 | 1.003 | −3.841 | 1.00 | 23.62 |
| ATOM | 784 | CZ | PHE | 770 | 26.497 | 1.833 | −3.974 | 1.00 | 23.15 |
| ATOM | 785 | C | PHE | 770 | 21.323 | 3.959 | −7.167 | 1.00 | 24.70 |
| ATOM | 786 | O | PHE | 770 | 20.237 | 4.104 | −6.593 | 1.00 | 24.80 |
| ATOM | 787 | N | ASN | 771 | 21.449 | 3.604 | −8.438 | 1.00 | 24.57 |
| ATOM | 788 | CA | ASN | 771 | 20.298 | 3.288 | −9.259 | 1.00 | 24.55 |
| ATOM | 789 | CB | ASN | 771 | 20.531 | 3.729 | −10.699 | 1.00 | 24.45 |
| ATOM | 790 | CG | ASN | 771 | 21.892 | 3.329 | −11.216 | 1.00 | 24.66 |
| ATOM | 791 | OD1 | ASN | 771 | 22.551 | 2.424 | −10.678 | 1.00 | 24.49 |
| ATOM | 792 | ND2 | ASN | 771 | 22.321 | 3.991 | −12.277 | 1.00 | 24.40 |
| ATOM | 793 | C | ASN | 771 | 20.195 | 1.770 | −9.175 | 1.00 | 24.68 |
| ATOM | 794 | O | ASN | 771 | 21.009 | 1.131 | −8.510 | 1.00 | 24.39 |
| ATOM | 795 | N | GLU | 772 | 19.211 | 1.185 | −9.842 | 1.00 | 25.37 |
| ATOM | 796 | CA | GLU | 772 | 19.052 | −0.263 | −9.790 | 1.00 | 25.97 |
| ATOM | 797 | CB | GLU | 772 | 17.885 | −0.698 | −10.673 | 1.00 | 26.94 |
| ATOM | 798 | CG | GLU | 772 | 16.519 | −0.461 | −10.013 | 1.00 | 28.24 |
| ATOM | 799 | CD | GLU | 772 | 15.988 | −1.704 | −9.306 | 1.00 | 29.05 |
| ATOM | 800 | OE1 | GLU | 772 | 15.347 | −1.562 | −8.235 | 1.00 | 29.60 |
| ATOM | 801 | OE2 | GLU | 772 | 16.203 | −2.819 | −9.835 | 1.00 | 29.05 |
| ATOM | 802 | C | GLU | 772 | 20.318 | −0.987 | −10.190 | 1.00 | 26.14 |
| ATOM | 803 | O | GLU | 772 | 20.737 | −1.934 | −9.518 | 1.00 | 26.09 |
| ATOM | 804 | N | TYR | 773 | 20.948 | −0.530 | −11.270 | 1.00 | 25.97 |
| ATOM | 805 | CA | TYR | 773 | 22.166 | −1.170 | −11.734 | 1.00 | 25.56 |
| ATOM | 806 | CB | TYR | 773 | 22.734 | −0.445 | −12.944 | 1.00 | 26.25 |
| ATOM | 807 | CG | TYR | 773 | 24.033 | −1.034 | −13.428 | 1.00 | 25.78 |
| ATOM | 808 | CD1 | TYR | 773 | 24.073 | −2.281 | −14.040 | 1.00 | 25.69 |
| ATOM | 809 | CE1 | TYR | 773 | 25.282 | −2.830 | −14.469 | 1.00 | 26.68 |
| ATOM | 810 | CD2 | TYR | 773 | 25.228 | −0.344 | −13.256 | 1.00 | 26.64 |
| ATOM | 811 | CE2 | TYR | 773 | 26.448 | −0.876 | −13.683 | 1.00 | 26.53 |
| ATOM | 812 | CZ | TYR | 773 | 26.469 | −2.113 | −14.286 | 1.00 | 26.86 |
| ATOM | 813 | OH | TYR | 773 | 27.676 | −2.624 | −14.705 | 1.00 | 26.83 |
| ATOM | 814 | C | TYR | 773 | 23.222 | −1.234 | −10.648 | 1.00 | 25.39 |
| ATOM | 815 | O | TYR | 773 | 23.823 | −2.286 | −10.420 | 1.00 | 25.85 |
| ATOM | 816 | N | ARG | 774 | 23.468 | −0.117 | −9.975 | 1.00 | 24.83 |
| ATOM | 817 | CA | ARG | 774 | 24.467 | −0.129 | −8.913 | 1.00 | 24.13 |
| ATOM | 818 | CB | ARG | 774 | 24.806 | 1.293 | −8.493 | 1.00 | 23.53 |
| ATOM | 819 | CG | ARG | 774 | 25.745 | 1.963 | −9.465 | 1.00 | 23.97 |
| ATOM | 820 | CD | ARG | 774 | 25.760 | 3.472 | −9.277 | 1.00 | 24.07 |
| ATOM | 821 | NE | ARG | 774 | 26.915 | 4.069 | −9.934 | 1.00 | 24.01 |
| ATOM | 822 | CZ | ARG | 774 | 27.280 | 5.332 | −9.778 | 1.00 | 23.94 |
| ATOM | 823 | NH1 | ARG | 774 | 26.576 | 6.124 | −8.989 | 1.00 | 24.20 |

TABLE A-continued

| | | | | | | | | |
|---|---|---|---|---|---|---|---|---|
| ATOM | 824 | NH2 | ARG | 774 | 28.350 | 5.797 | −10.405 | 1.00 | 24.95 |
| ATOM | 825 | C | ARG | 774 | 24.016 | −0.965 | −7.714 | 1.00 | 23.78 |
| ATOM | 826 | O | ARG | 774 | 24.836 | −1.553 | −7.027 | 1.00 | 23.53 |
| ATOM | 827 | N | MET | 775 | 22.714 | −1.019 | −7.470 | 1.00 | 23.55 |
| ATOM | 828 | CA | MET | 775 | 22.189 | −1.818 | −6.375 | 1.00 | 24.24 |
| ATOM | 829 | CB | MET | 775 | 20.680 | −1.654 | −6.298 | 1.00 | 23.35 |
| ATOM | 830 | CG | MET | 775 | 20.279 | −0.409 | −5.602 | 1.00 | 22.56 |
| ATOM | 831 | SD | MET | 775 | 18.562 | −0.102 | −5.803 | 1.00 | 23.81 |
| ATOM | 832 | CE | MET | 775 | 18.596 | 1.595 | −6.444 | 1.00 | 23.32 |
| ATOM | 833 | C | MET | 775 | 22.544 | −3.302 | −6.556 | 1.00 | 25.19 |
| ATOM | 834 | O | MET | 775 | 22.837 | −4.011 | −5.589 | 1.00 | 24.45 |
| ATOM | 835 | N | HIS | 776 | 22.530 | −3.757 | −7.806 | 1.00 | 26.18 |
| ATOM | 836 | CA | HIS | 776 | 22.845 | −5.141 | −8.119 | 1.00 | 26.92 |
| ATOM | 837 | CB | HIS | 776 | 22.313 | −5.505 | −9.510 | 1.00 | 27.27 |
| ATOM | 838 | CG | HIS | 776 | 22.615 | −6.914 | −9.913 | 1.00 | 28.49 |
| ATOM | 839 | CD2 | HIS | 776 | 21.882 | −8.049 | −9.798 | 1.00 | 28.49 |
| ATOM | 840 | ND1 | HIS | 776 | 23.841 | −7.299 | −10.415 | 1.00 | 28.47 |
| ATOM | 841 | CE1 | HIS | 776 | 23.851 | −8.611 | −10.586 | 1.00 | 28.94 |
| ATOM | 842 | NE2 | HIS | 776 | 22.675 | −9.089 | −10.219 | 1.00 | 29.04 |
| ATOM | 843 | C | HIS | 776 | 24.344 | −5.376 | −8.070 | 1.00 | 27.70 |
| ATOM | 844 | O | HIS | 776 | 24.818 | −6.350 | −7.481 | 1.00 | 28.14 |
| ATOM | 845 | N | LYS | 777 | 25.086 | −4.474 | −8.699 | 1.00 | 28.16 |
| ATOM | 846 | CA | LYS | 777 | 26.536 | −4.555 | −8.760 | 1.00 | 28.25 |
| ATOM | 847 | CB | LYS | 777 | 27.050 | −3.468 | −9.702 | 1.00 | 28.87 |
| ATOM | 848 | CG | LYS | 777 | 26.568 | −3.632 | −11.138 | 1.00 | 29.22 |
| ATOM | 849 | CD | LYS | 777 | 27.637 | −4.263 | −12.030 | 1.00 | 29.26 |
| ATOM | 850 | CE | LYS | 777 | 28.063 | −5.643 | −11.572 | 1.00 | 29.02 |
| ATOM | 851 | NZ | LYS | 777 | 29.216 | −6.132 | −12.387 | 1.00 | 29.65 |
| ATOM | 852 | C | LYS | 777 | 27.234 | −4.440 | −7.398 | 1.00 | 28.38 |
| ATOM | 853 | O | LYS | 777 | 28.306 | −5.006 | −7.196 | 1.00 | 28.33 |
| ATOM | 854 | N | SER | 778 | 26.638 | −3.701 | −6.468 | 1.00 | 28.47 |
| ATOM | 855 | CA | SER | 778 | 27.227 | −3.542 | −5.143 | 1.00 | 28.59 |
| ATOM | 856 | CB | SER | 778 | 26.574 | −2.369 | −4.408 | 1.00 | 28.41 |
| ATOM | 857 | OG | SER | 778 | 25.199 | −2.621 | −4.172 | 1.00 | 27.42 |
| ATOM | 858 | C | SER | 778 | 27.043 | −4.820 | −4.323 | 1.00 | 29.24 |
| ATOM | 859 | O | SER | 778 | 27.756 | −5.039 | −3.352 | 1.00 | 29.39 |
| ATOM | 860 | N | ARG | 779 | 26.078 | −5.645 | −4.733 | 1.00 | 29.69 |
| ATOM | 861 | CA | ARG | 779 | 25.739 | −6.904 | −4.081 | 1.00 | 30.16 |
| ATOM | 862 | CB | ARG | 779 | 26.998 | −7.730 | −3.817 | 1.00 | 30.77 |
| ATOM | 863 | CG | ARG | 779 | 27.686 | −8.208 | −5.085 | 1.00 | 30.83 |
| ATOM | 864 | CD | ARG | 779 | 28.959 | −8.974 | −4.796 | 1.00 | 31.77 |
| ATOM | 865 | NE | ARG | 779 | 29.699 | −9.207 | −6.030 | 1.00 | 33.22 |
| ATOM | 866 | CZ | ARG | 779 | 30.984 | −9.547 | −6.096 | 1.00 | 33.96 |
| ATOM | 867 | NH1 | ARG | 779 | 31.700 | −9.705 | −4.987 | 1.00 | 33.90 |
| ATOM | 868 | NH2 | ARG | 779 | 31.562 | −9.699 | −7.283 | 1.00 | 34.13 |
| ATOM | 869 | C | ARG | 779 | 24.942 | −6.698 | −2.790 | 1.00 | 30.89 |
| ATOM | 870 | O | ARG | 779 | 24.962 | −7.541 | −1.886 | 1.00 | 30.62 |
| ATOM | 871 | N | MET | 780 | 24.232 | −5.570 | −2.729 | 1.00 | 31.21 |
| ATOM | 872 | CA | MET | 780 | 23.384 | −5.221 | −1.592 | 1.00 | 31.28 |
| ATOM | 873 | CB | MET | 780 | 23.948 | −4.017 | −0.832 | 1.00 | 32.57 |
| ATOM | 874 | CG | MET | 780 | 25.288 | −4.215 | −0.172 | 1.00 | 34.02 |
| ATOM | 875 | SD | MET | 780 | 25.814 | −2.649 | 0.565 | 1.00 | 37.00 |
| ATOM | 876 | CE | MET | 780 | 26.603 | −1.893 | −0.815 | 1.00 | 34.95 |
| ATOM | 877 | C | MET | 780 | 22.010 | −4.839 | −2.137 | 1.00 | 30.81 |
| ATOM | 878 | O | MET | 780 | 21.414 | −3.841 | −1.718 | 1.00 | 31.05 |
| ATOM | 879 | N | TYR | 781 | 21.497 | −5.621 | −3.074 | 1.00 | 29.92 |
| ATOM | 880 | CA | TYR | 781 | 20.208 | −5.283 | −3.651 | 1.00 | 29.23 |
| ATOM | 881 | CB | TYR | 781 | 19.920 | −6.156 | −4.882 | 1.00 | 28.90 |
| ATOM | 882 | CG | TYR | 781 | 18.721 | −5.689 | −5.670 | 1.00 | 28.52 |
| ATOM | 883 | CD1 | TYR | 781 | 18.851 | −4.762 | −6.701 | 1.00 | 28.60 |
| ATOM | 884 | CE1 | TYR | 781 | 17.726 | −4.311 | −7.408 | 1.00 | 28.68 |
| ATOM | 885 | CD2 | TYR | 781 | 17.443 | −6.152 | −5.359 | 1.00 | 28.60 |
| ATOM | 886 | CE2 | TYR | 781 | 16.318 | −5.706 | −6.051 | 1.00 | 28.33 |
| ATOM | 887 | CZ | TYR | 781 | 16.461 | −4.791 | −7.071 | 1.00 | 28.53 |
| ATOM | 888 | OH | TYR | 781 | 15.337 | −4.364 | −7.748 | 1.00 | 28.76 |
| ATOM | 889 | C | TYR | 781 | 19.087 | −5.407 | −2.620 | 1.00 | 28.96 |
| ATOM | 890 | O | TYR | 781 | 18.246 | −4.513 | −2.513 | 1.00 | 28.45 |
| ATOM | 891 | N | SER | 782 | 19.068 | −6.504 | −1.862 | 1.00 | 28.78 |
| ATOM | 892 | CA | SER | 782 | 18.030 | −6.678 | −0.835 | 1.00 | 28.74 |
| ATOM | 893 | CB | SER | 782 | 18.209 | −8.004 | −0.100 | 1.00 | 29.02 |
| ATOM | 894 | OG | SER | 782 | 18.036 | −9.090 | −0.987 | 1.00 | 30.66 |
| ATOM | 895 | C | SER | 782 | 18.044 | −5.531 | 0.187 | 1.00 | 27.95 |
| ATOM | 896 | O | SER | 782 | 17.045 | −4.839 | 0.363 | 1.00 | 28.09 |
| ATOM | 897 | N | GLN | 783 | 19.170 | −5.325 | 0.855 | 1.00 | 27.40 |
| ATOM | 898 | CA | GLN | 783 | 19.249 | −4.244 | 1.836 | 1.00 | 27.42 |
| ATOM | 899 | CB | GLN | 783 | 20.669 | −4.113 | 2.397 | 1.00 | 27.83 |
| ATOM | 900 | CG | GLN | 783 | 21.268 | −5.393 | 2.978 | 1.00 | 28.33 |
| ATOM | 901 | CD | GLN | 783 | 21.844 | −6.302 | 1.919 | 1.00 | 29.14 |
| ATOM | 902 | OE1 | GLN | 783 | 22.658 | −7.184 | 2.215 | 1.00 | 29.90 |

TABLE A-continued

| | | | | | | | | |
|---|---|---|---|---|---|---|---|---|
| ATOM | 903 | NE2 | GLN | 783 | 21.426 | −6.099 | 0.672 | 1.00 | 28.96 |
| ATOM | 904 | C | GLN | 783 | 18.840 | −2.924 | 1.177 | 1.00 | 26.96 |
| ATOM | 905 | O | GLN | 783 | 18.124 | −2.114 | 1.781 | 1.00 | 26.53 |
| ATOM | 906 | N | CYS | 784 | 19.290 | −2.719 | −0.064 | 1.00 | 26.46 |
| ATOM | 907 | CA | CYS | 784 | 18.963 | −1.506 | −0.808 | 1.00 | 26.18 |
| ATOM | 908 | CB | CYS | 784 | 19.695 | −1.488 | −2.159 | 1.00 | 27.17 |
| ATOM | 909 | SG | CYS | 784 | 21.458 | −1.025 | −2.047 | 1.00 | 28.41 |
| ATOM | 910 | C | CYS | 784 | 17.452 | −1.389 | −1.002 | 1.00 | 25.21 |
| ATOM | 911 | O | CYS | 784 | 16.901 | −0.290 | −0.952 | 1.00 | 24.95 |
| ATOM | 912 | N | VAL | 785 | 16.789 | −2.524 | −1.210 | 1.00 | 24.67 |
| ATOM | 913 | CA | VAL | 785 | 15.330 | −2.554 | −1.351 | 1.00 | 24.38 |
| ATOM | 914 | CB | VAL | 785 | 14.821 | −3.960 | −1.738 | 1.00 | 24.36 |
| ATOM | 915 | CG1 | VAL | 785 | 13.455 | −4.230 | −1.081 | 1.00 | 24.20 |
| ATOM | 916 | CG2 | VAL | 785 | 14.705 | −4.055 | −3.247 | 1.00 | 23.60 |
| ATOM | 917 | C | VAL | 785 | 14.698 | −2.157 | −0.021 | 1.00 | 23.98 |
| ATOM | 918 | O | VAL | 785 | 13.705 | −1.441 | 0.020 | 1.00 | 23.63 |
| ATOM | 919 | N | ARG | 786 | 15.280 | −2.646 | 1.067 | 1.00 | 24.16 |
| ATOM | 920 | CA | ARG | 786 | 14.808 | −2.304 | 2.411 | 1.00 | 24.19 |
| ATOM | 921 | CB | ARG | 786 | 15.667 | −3.016 | 3.465 | 1.00 | 24.76 |
| ATOM | 922 | CG | ARG | 786 | 15.663 | −4.537 | 3.386 | 1.00 | 25.63 |
| ATOM | 923 | CD | ARG | 786 | 14.617 | −5.109 | 4.314 | 1.00 | 26.26 |
| ATOM | 924 | NE | ARG | 786 | 15.149 | −6.186 | 5.141 | 1.00 | 26.47 |
| ATOM | 925 | CZ | ARG | 786 | 14.769 | −6.414 | 6.396 | 1.00 | 26.71 |
| ATOM | 926 | NH1 | ARG | 786 | 13.861 | −5.637 | 6.970 | 1.00 | 26.62 |
| ATOM | 927 | NH2 | ARG | 786 | 15.283 | −7.426 | 7.074 | 1.00 | 26.60 |
| ATOM | 928 | C | ARG | 786 | 14.934 | −0.783 | 2.613 | 1.00 | 23.52 |
| ATOM | 929 | O | ARG | 786 | 14.015 | −0.128 | 3.087 | 1.00 | 23.13 |
| ATOM | 930 | N | MET | 787 | 16.079 | −0.227 | 2.236 | 1.00 | 23.46 |
| ATOM | 931 | CA | MET | 787 | 16.326 | 1.201 | 2.404 | 1.00 | 24.21 |
| ATOM | 932 | CB | MET | 787 | 17.799 | 1.506 | 2.153 | 1.00 | 24.32 |
| ATOM | 933 | CG | MET | 787 | 18.695 | 0.872 | 3.191 | 1.00 | 25.11 |
| ATOM | 934 | SD | MET | 787 | 20.411 | 1.249 | 2.977 | 1.00 | 26.06 |
| ATOM | 935 | CE | MET | 787 | 20.960 | −0.200 | 2.082 | 1.00 | 25.69 |
| ATOM | 936 | C | MET | 787 | 15.443 | 2.082 | 1.535 | 1.00 | 24.88 |
| ATOM | 937 | O | MET | 787 | 14.947 | 3.113 | 1.999 | 1.00 | 24.39 |
| ATOM | 938 | N | ARG | 788 | 15.260 | 1.675 | 0.278 | 1.00 | 25.61 |
| ATOM | 939 | CA | ARG | 788 | 14.399 | 2.394 | −0.651 | 1.00 | 26.64 |
| ATOM | 940 | CB | ARG | 788 | 14.361 | 1.661 | −2.003 | 1.00 | 27.51 |
| ATOM | 941 | CG | ARG | 788 | 13.561 | 2.371 | −3.089 | 1.00 | 28.69 |
| ATOM | 942 | CD | ARG | 788 | 14.374 | 2.537 | −4.378 | 1.00 | 29.41 |
| ATOM | 943 | NE | ARG | 788 | 14.059 | 1.556 | −5.419 | 1.00 | 29.78 |
| ATOM | 944 | CZ | ARG | 788 | 14.634 | 1.548 | −6.626 | 1.00 | 31.03 |
| ATOM | 945 | NH1 | ARG | 788 | 15.549 | 2.465 | −6.935 | 1.00 | 30.51 |
| ATOM | 946 | NH2 | ARG | 788 | 14.298 | 0.631 | −7.532 | 1.00 | 30.16 |
| ATOM | 947 | C | ARG | 788 | 13.016 | 2.401 | 0.007 | 1.00 | 26.84 |
| ATOM | 948 | O | ARG | 788 | 12.328 | 3.418 | 0.047 | 1.00 | 26.40 |
| ATOM | 949 | N | HIS | 789 | 12.632 | 1.251 | 0.545 | 1.00 | 27.75 |
| ATOM | 950 | CA | HIS | 789 | 11.359 | 1.104 | 1.233 | 1.00 | 29.39 |
| ATOM | 951 | CB | HIS | 789 | 11.238 | −0.300 | 1.811 | 1.00 | 30.70 |
| ATOM | 952 | CG | HIS | 789 | 9.968 | −0.996 | 1.447 | 1.00 | 32.08 |
| ATOM | 953 | CD2 | HIS | 789 | 8.916 | −1.387 | 2.205 | 1.00 | 32.40 |
| ATOM | 954 | ND1 | HIS | 789 | 9.685 | −1.396 | 0.157 | 1.00 | 32.78 |
| ATOM | 955 | CE1 | HIS | 789 | 8.513 | −2.009 | 0.139 | 1.00 | 33.40 |
| ATOM | 956 | NE2 | HIS | 789 | 8.026 | −2.017 | 1.369 | 1.00 | 33.45 |
| ATOM | 957 | C | HIS | 789 | 11.275 | 2.120 | 2.373 | 1.00 | 29.90 |
| ATOM | 958 | O | HIS | 789 | 10.274 | 2.829 | 2.513 | 1.00 | 29.93 |
| ATOM | 959 | N | LEU | 790 | 12.328 | 2.173 | 3.192 | 1.00 | 30.02 |
| ATOM | 960 | CA | LEU | 790 | 12.390 | 3.115 | 4.307 | 1.00 | 30.13 |
| ATOM | 961 | CB | LEU | 790 | 13.775 | 3.071 | 4.956 | 1.00 | 30.30 |
| ATOM | 962 | CG | LEU | 790 | 14.142 | 4.222 | 5.896 | 1.00 | 30.27 |
| ATOM | 963 | CD1 | LEU | 790 | 13.147 | 4.322 | 7.029 | 1.00 | 30.03 |
| ATOM | 964 | CD2 | LEU | 790 | 15.536 | 3.978 | 6.445 | 1.00 | 31.35 |
| ATOM | 965 | C | LEU | 790 | 12.107 | 4.533 | 3.836 | 1.00 | 30.25 |
| ATOM | 966 | O | LEU | 790 | 11.194 | 5.189 | 4.325 | 1.00 | 30.14 |
| ATOM | 967 | N | SER | 791 | 12.911 | 5.000 | 2.890 | 1.00 | 30.62 |
| ATOM | 968 | CA | SER | 791 | 12.759 | 6.334 | 2.338 | 1.00 | 31.31 |
| ATOM | 969 | CB | SER | 791 | 13.661 | 6.504 | 1.123 | 1.00 | 31.61 |
| ATOM | 970 | OG | SER | 791 | 13.224 | 5.654 | 0.082 | 1.00 | 32.91 |
| ATOM | 971 | C | SER | 791 | 11.318 | 6.603 | 1.920 | 1.00 | 31.63 |
| ATOM | 972 | O | SER | 791 | 10.747 | 7.626 | 2.290 | 1.00 | 32.03 |
| ATOM | 973 | N | GLN | 792 | 10.734 | 5.696 | 1.138 | 1.00 | 31.71 |
| ATOM | 974 | CA | GLN | 792 | 9.354 | 5.873 | 0.687 | 1.00 | 31.71 |
| ATOM | 975 | CB | GLN | 792 | 8.909 | 4.666 | −0.150 | 1.00 | 31.94 |
| ATOM | 976 | CG | GLN | 792 | 9.637 | 4.593 | −1.492 | 1.00 | 32.57 |
| ATOM | 977 | CD | GLN | 792 | 9.418 | 3.282 | −2.223 | 1.00 | 33.30 |
| ATOM | 978 | OE1 | GLN | 792 | 8.385 | 3.073 | −2.860 | 1.00 | 33.62 |
| ATOM | 979 | NE2 | GLN | 792 | 10.394 | 2.384 | −2.128 | 1.00 | 33.08 |
| ATOM | 980 | C | GLN | 792 | 8.417 | 6.107 | 1.870 | 1.00 | 31.60 |
| ATOM | 981 | O | GLN | 792 | 7.459 | 6.881 | 1.766 | 1.00 | 31.38 |

TABLE A-continued

| | | | | | | | | | |
|---|---|---|---|---|---|---|---|---|---|
| ATOM | 982 | N | GLU | 793 | 8.706 | 5.455 | 2.997 | 1.00 | 31.29 |
| ATOM | 983 | CA | GLU | 793 | 7.913 | 5.629 | 4.216 | 1.00 | 30.78 |
| ATOM | 984 | CB | GLU | 793 | 8.490 | 4.782 | 5.353 | 1.00 | 31.16 |
| ATOM | 985 | CG | GLU | 793 | 8.422 | 3.301 | 5.099 | 1.00 | 31.63 |
| ATOM | 986 | CD | GLU | 793 | 7.024 | 2.753 | 5.256 | 1.00 | 32.41 |
| ATOM | 987 | OE1 | GLU | 793 | 6.056 | 3.549 | 5.178 | 1.00 | 32.89 |
| ATOM | 988 | OE2 | GLU | 793 | 6.892 | 1.523 | 5.447 | 1.00 | 32.77 |
| ATOM | 989 | C | GLU | 793 | 7.927 | 7.101 | 4.630 | 1.00 | 30.41 |
| ATOM | 990 | O | GLU | 793 | 6.959 | 7.609 | 5.202 | 1.00 | 30.34 |
| ATOM | 991 | N | PHE | 794 | 9.032 | 7.787 | 4.355 | 1.00 | 29.94 |
| ATOM | 992 | CA | PHE | 794 | 9.119 | 9.195 | 4.703 | 1.00 | 29.89 |
| ATOM | 993 | CB | PHE | 794 | 10.498 | 9.762 | 4.367 | 1.00 | 29.61 |
| ATOM | 994 | CG | PHE | 794 | 11.586 | 9.331 | 5.316 | 1.00 | 29.83 |
| ATOM | 995 | CD1 | PHE | 794 | 11.472 | 9.567 | 6.683 | 1.00 | 29.77 |
| ATOM | 996 | CD2 | PHE | 794 | 12.722 | 8.684 | 4.848 | 1.00 | 29.90 |
| ATOM | 997 | CE1 | PHE | 794 | 12.466 | 9.161 | 7.561 | 1.00 | 29.72 |
| ATOM | 998 | CE2 | PHE | 794 | 13.722 | 8.274 | 5.726 | 1.00 | 30.02 |
| ATOM | 999 | CZ | PHE | 794 | 13.592 | 8.513 | 7.083 | 1.00 | 29.58 |
| ATOM | 1000 | C | PHE | 794 | 8.057 | 9.943 | 3.922 | 1.00 | 30.47 |
| ATOM | 1001 | O | PHE | 794 | 7.721 | 11.075 | 4.248 | 1.00 | 30.71 |
| ATOM | 1002 | N | GLY | 795 | 7.532 | 9.296 | 2.883 | 1.00 | 31.23 |
| ATOM | 1003 | CA | GLY | 795 | 6.513 | 9.910 | 2.053 | 1.00 | 31.91 |
| ATOM | 1004 | C | GLY | 795 | 5.101 | 9.482 | 2.410 | 1.00 | 32.71 |
| ATOM | 1005 | O | GLY | 795 | 4.219 | 10.322 | 2.557 | 1.00 | 32.69 |
| ATOM | 1006 | N | TRP | 796 | 4.875 | 8.181 | 2.557 | 1.00 | 33.17 |
| ATOM | 1007 | CA | TRP | 796 | 3.539 | 7.701 | 2.897 | 1.00 | 34.04 |
| ATOM | 1008 | CB | TRP | 796 | 3.490 | 6.176 | 2.820 | 1.00 | 33.54 |
| ATOM | 1009 | CG | TRP | 796 | 3.880 | 5.642 | 1.484 | 1.00 | 33.47 |
| ATOM | 1010 | CD2 | TRP | 796 | 4.706 | 4.499 | 1.223 | 1.00 | 33.26 |
| ATOM | 1011 | CE2 | TRP | 796 | 4.779 | 4.347 | −0.183 | 1.00 | 32.92 |
| ATOM | 1012 | CE3 | TRP | 796 | 5.391 | 3.587 | 2.039 | 1.00 | 33.53 |
| ATOM | 1013 | CD1 | TRP | 796 | 3.497 | 6.125 | 0.259 | 1.00 | 33.23 |
| ATOM | 1014 | NE1 | TRP | 796 | 4.033 | 5.351 | −0.743 | 1.00 | 32.89 |
| ATOM | 1015 | CZ2 | TRP | 796 | 5.509 | 3.320 | −0.793 | 1.00 | 32.88 |
| ATOM | 1016 | CZ3 | TRP | 796 | 6.124 | 2.556 | 1.426 | 1.00 | 33.73 |
| ATOM | 1017 | CH2 | TRP | 796 | 6.172 | 2.438 | 0.022 | 1.00 | 33.34 |
| ATOM | 1018 | C | TRP | 796 | 3.079 | 8.168 | 4.283 | 1.00 | 34.95 |
| ATOM | 1019 | O | TRP | 796 | 1.883 | 8.130 | 4.596 | 1.00 | 35.51 |
| ATOM | 1020 | N | LEU | 797 | 4.026 | 8.620 | 5.105 | 1.00 | 35.59 |
| ATOM | 1021 | CA | LEU | 797 | 3.712 | 9.097 | 6.451 | 1.00 | 35.60 |
| ATOM | 1022 | CB | LEU | 797 | 4.672 | 8.487 | 7.466 | 1.00 | 35.55 |
| ATOM | 1023 | CG | LEU | 797 | 4.539 | 6.978 | 7.667 | 1.00 | 35.46 |
| ATOM | 1024 | CD1 | LEU | 797 | 5.745 | 6.465 | 8.443 | 1.00 | 35.46 |
| ATOM | 1025 | CD2 | LEU | 797 | 3.232 | 6.671 | 8.390 | 1.00 | 35.11 |
| ATOM | 1026 | C | LEU | 797 | 3.794 | 10.610 | 6.545 | 1.00 | 35.92 |
| ATOM | 1027 | O | LEU | 797 | 3.574 | 11.182 | 7.612 | 1.00 | 36.29 |
| ATOM | 1028 | N | GLN | 798 | 4.103 | 11.257 | 5.427 | 1.00 | 36.20 |
| ATOM | 1029 | CA | GLN | 798 | 4.224 | 12.711 | 5.397 | 1.00 | 36.28 |
| ATOM | 1030 | CB | GLN | 798 | 2.830 | 13.377 | 5.366 | 1.00 | 37.02 |
| ATOM | 1031 | CG | GLN | 798 | 2.233 | 13.503 | 3.939 | 1.00 | 38.04 |
| ATOM | 1032 | CD | GLN | 798 | 0.757 | 13.919 | 3.908 | 1.00 | 38.46 |
| ATOM | 1033 | OE1 | GLN | 798 | −0.113 | 13.231 | 4.458 | 1.00 | 39.04 |
| ATOM | 1034 | NE2 | GLN | 798 | 0.472 | 15.036 | 3.247 | 1.00 | 38.17 |
| ATOM | 1035 | C | GLN | 798 | 5.033 | 13.185 | 6.598 | 1.00 | 35.87 |
| ATOM | 1036 | O | GLN | 798 | 4.637 | 14.099 | 7.321 | 1.00 | 36.50 |
| ATOM | 1037 | N | ILE | 799 | 6.179 | 12.543 | 6.794 | 1.00 | 35.08 |
| ATOM | 1038 | CA | ILE | 799 | 7.084 | 12.869 | 7.885 | 1.00 | 34.09 |
| ATOM | 1039 | CB | ILE | 799 | 8.205 | 11.824 | 7.982 | 1.00 | 33.96 |
| ATOM | 1040 | CG2 | ILE | 799 | 9.294 | 12.288 | 8.934 | 1.00 | 33.52 |
| ATOM | 1041 | CG1 | ILE | 799 | 7.598 | 10.504 | 8.439 | 1.00 | 34.19 |
| ATOM | 1042 | CD1 | ILE | 799 | 8.575 | 9.407 | 8.549 | 1.00 | 35.01 |
| ATOM | 1043 | C | ILE | 799 | 7.691 | 14.247 | 7.694 | 1.00 | 33.51 |
| ATOM | 1044 | O | ILE | 799 | 8.244 | 14.547 | 6.645 | 1.00 | 33.24 |
| ATOM | 1045 | N | THR | 800 | 7.587 | 15.074 | 8.728 | 1.00 | 33.31 |
| ATOM | 1046 | CA | THR | 800 | 8.102 | 16.436 | 8.700 | 1.00 | 33.05 |
| ATOM | 1047 | CB | THR | 800 | 7.351 | 17.341 | 9.717 | 1.00 | 33.44 |
| ATOM | 1048 | OG1 | THR | 800 | 7.803 | 17.043 | 11.048 | 1.00 | 33.14 |
| ATOM | 1049 | CG2 | THR | 800 | 5.840 | 17.113 | 9.636 | 1.00 | 32.47 |
| ATOM | 1050 | C | THR | 800 | 9.582 | 16.515 | 9.050 | 1.00 | 33.21 |
| ATOM | 1051 | O | THR | 800 | 10.166 | 15.577 | 9.599 | 1.00 | 33.40 |
| ATOM | 1052 | N | PRO | 801 | 10.214 | 17.644 | 8.719 | 1.00 | 33.07 |
| ATOM | 1053 | CD | PRO | 801 | 9.726 | 18.642 | 7.748 | 1.00 | 33.01 |
| ATOM | 1054 | CA | PRO | 801 | 11.630 | 17.858 | 9.007 | 1.00 | 32.90 |
| ATOM | 1055 | CB | PRO | 801 | 11.891 | 19.229 | 8.386 | 1.00 | 32.72 |
| ATOM | 1056 | CG | PRO | 801 | 11.012 | 19.196 | 7.189 | 1.00 | 32.68 |
| ATOM | 1057 | C | PRO | 801 | 11.886 | 17.841 | 10.521 | 1.00 | 32.91 |
| ATOM | 1058 | O | PRO | 801 | 12.899 | 17.314 | 10.995 | 1.00 | 33.12 |
| ATOM | 1059 | N | GLN | 802 | 10.967 | 18.426 | 11.281 | 1.00 | 32.37 |
| ATOM | 1060 | CA | GLN | 802 | 11.117 | 18.458 | 12.729 | 1.00 | 31.71 |

TABLE A-continued

| | | | | | | | | |
|---|---|---|---|---|---|---|---|---|
| ATOM | 1061 | CB | GLN | 802 | 10.090 | 19.425 | 13.340 | 1.00 | 32.11 |
| ATOM | 1062 | CG | GLN | 802 | 10.276 | 20.925 | 12.948 | 1.00 | 32.69 |
| ATOM | 1063 | CD | GLN | 802 | 9.954 | 21.244 | 11.464 | 1.00 | 33.21 |
| ATOM | 1064 | OE1 | GLN | 802 | 8.898 | 20.871 | 10.943 | 1.00 | 33.11 |
| ATOM | 1065 | NE2 | GLN | 802 | 10.865 | 21.956 | 10.798 | 1.00 | 33.53 |
| ATOM | 1066 | C | GLN | 802 | 10.987 | 17.045 | 13.338 | 1.00 | 31.06 |
| ATOM | 1067 | O | GLN | 802 | 11.680 | 16.711 | 14.305 | 1.00 | 31.17 |
| ATOM | 1068 | N | GLU | 803 | 10.109 | 16.217 | 12.775 | 1.00 | 29.88 |
| ATOM | 1069 | CA | GLU | 803 | 9.935 | 14.849 | 13.269 | 1.00 | 28.79 |
| ATOM | 1070 | CB | GLU | 803 | 8.750 | 14.154 | 12.587 | 1.00 | 29.29 |
| ATOM | 1071 | CG | GLU | 803 | 7.378 | 14.677 | 12.936 | 1.00 | 30.44 |
| ATOM | 1072 | CD | GLU | 803 | 6.286 | 13.977 | 12.145 | 1.00 | 30.78 |
| ATOM | 1073 | OE1 | GLU | 803 | 6.277 | 14.099 | 10.905 | 1.00 | 29.94 |
| ATOM | 1074 | OE2 | GLU | 803 | 5.440 | 13.295 | 12.766 | 1.00 | 32.29 |
| ATOM | 1075 | C | GLU | 803 | 11.198 | 14.058 | 12.940 | 1.00 | 27.63 |
| ATOM | 1076 | O | GLU | 803 | 11.743 | 13.358 | 13.783 | 1.00 | 27.67 |
| ATOM | 1077 | N | PHE | 804 | 11.644 | 14.167 | 11.694 | 1.00 | 25.86 |
| ATOM | 1078 | CA | PHE | 804 | 12.835 | 13.472 | 11.252 | 1.00 | 24.53 |
| ATOM | 1079 | CB | PHE | 804 | 13.176 | 13.850 | 9.803 | 1.00 | 23.88 |
| ATOM | 1080 | CG | PHE | 804 | 14.603 | 13.578 | 9.439 | 1.00 | 23.21 |
| ATOM | 1081 | CD1 | PHE | 804 | 15.098 | 12.280 | 9.449 | 1.00 | 22.70 |
| ATOM | 1082 | CD2 | PHE | 804 | 15.475 | 14.625 | 9.164 | 1.00 | 23.07 |
| ATOM | 1083 | CE1 | PHE | 804 | 16.436 | 12.031 | 9.199 | 1.00 | 22.58 |
| ATOM | 1084 | CE2 | PHE | 804 | 16.823 | 14.384 | 8.909 | 1.00 | 22.21 |
| ATOM | 1085 | CZ | PHE | 804 | 17.303 | 13.091 | 8.929 | 1.00 | 22.63 |
| ATOM | 1086 | C | PHE | 804 | 14.044 | 13.755 | 12.146 | 1.00 | 23.92 |
| ATOM | 1087 | O | PHE | 804 | 14.797 | 12.841 | 12.480 | 1.00 | 23.49 |
| ATOM | 1088 | N | LEU | 805 | 14.242 | 15.013 | 12.517 | 1.00 | 23.43 |
| ATOM | 1089 | CA | LEU | 805 | 15.377 | 15.360 | 13.362 | 1.00 | 23.07 |
| ATOM | 1090 | CB | LEU | 805 | 15.572 | 16.881 | 13.432 | 1.00 | 22.40 |
| ATOM | 1091 | CG | LEU | 805 | 15.862 | 17.582 | 12.100 | 1.00 | 22.11 |
| ATOM | 1092 | CD1 | LEU | 805 | 16.020 | 19.075 | 12.339 | 1.00 | 22.35 |
| ATOM | 1093 | CD2 | LEU | 805 | 17.104 | 17.007 | 11.441 | 1.00 | 21.68 |
| ATOM | 1094 | C | LEU | 805 | 15.240 | 14.791 | 14.761 | 1.00 | 23.01 |
| ATOM | 1095 | O | LEU | 805 | 16.231 | 14.404 | 15.358 | 1.00 | 23.29 |
| ATOM | 1096 | N | CYS | 806 | 14.028 | 14.731 | 15.301 | 1.00 | 23.32 |
| ATOM | 1097 | CA | CYS | 806 | 13.872 | 14.151 | 16.638 | 1.00 | 23.74 |
| ATOM | 1098 | CB | CYS | 806 | 12.469 | 14.379 | 17.179 | 1.00 | 24.34 |
| ATOM | 1099 | SG | CYS | 806 | 12.141 | 16.076 | 17.527 | 1.00 | 30.40 |
| ATOM | 1100 | C | CYS | 806 | 14.145 | 12.649 | 16.605 | 1.00 | 22.67 |
| ATOM | 1101 | O | CYS | 806 | 14.877 | 12.117 | 17.447 | 1.00 | 22.58 |
| ATOM | 1102 | N | MET | 807 | 13.543 | 11.971 | 15.637 | 1.00 | 21.64 |
| ATOM | 1103 | CA | MET | 807 | 13.724 | 10.532 | 15.503 | 1.00 | 21.18 |
| ATOM | 1104 | CB | MET | 807 | 12.919 | 9.991 | 14.313 | 1.00 | 22.00 |
| ATOM | 1105 | CG | MET | 807 | 11.403 | 10.114 | 14.463 | 1.00 | 23.29 |
| ATOM | 1106 | SD | MET | 807 | 10.507 | 9.386 | 13.019 | 1.00 | 25.08 |
| ATOM | 1107 | CE | MET | 807 | 10.295 | 10.783 | 12.018 | 1.00 | 24.91 |
| ATOM | 1108 | C | MET | 807 | 15.204 | 10.193 | 15.330 | 1.00 | 19.80 |
| ATOM | 1109 | O | MET | 807 | 15.698 | 9.267 | 15.950 | 1.00 | 19.29 |
| ATOM | 1110 | N | LYS | 808 | 15.900 | 10.950 | 14.488 | 1.00 | 18.78 |
| ATOM | 1111 | CA | LYS | 808 | 17.321 | 10.730 | 14.250 | 1.00 | 18.18 |
| ATOM | 1112 | CB | LYS | 808 | 17.877 | 11.789 | 13.284 | 1.00 | 17.70 |
| ATOM | 1113 | CG | LYS | 808 | 19.376 | 11.652 | 13.044 | 1.00 | 18.55 |
| ATOM | 1114 | CD | LYS | 808 | 19.775 | 11.948 | 11.583 | 1.00 | 18.83 |
| ATOM | 1115 | CE | LYS | 808 | 19.711 | 13.425 | 11.271 | 1.00 | 17.98 |
| ATOM | 1116 | NZ | LYS | 808 | 20.547 | 14.166 | 12.258 | 1.00 | 18.71 |
| ATOM | 1117 | C | LYS | 808 | 18.063 | 10.786 | 15.588 | 1.00 | 17.76 |
| ATOM | 1118 | O | LYS | 808 | 18.823 | 9.880 | 15.921 | 1.00 | 16.45 |
| ATOM | 1119 | N | ALA | 809 | 17.829 | 11.853 | 16.347 | 1.00 | 17.98 |
| ATOM | 1120 | CA | ALA | 809 | 18.443 | 12.011 | 17.661 | 1.00 | 18.61 |
| ATOM | 1121 | CB | ALA | 809 | 17.950 | 13.283 | 18.321 | 1.00 | 18.30 |
| ATOM | 1122 | C | ALA | 809 | 18.105 | 10.786 | 18.532 | 1.00 | 18.88 |
| ATOM | 1123 | O | ALA | 809 | 18.986 | 10.210 | 19.167 | 1.00 | 18.79 |
| ATOM | 1124 | N | LEU | 810 | 16.842 | 10.369 | 18.533 | 1.00 | 19.30 |
| ATOM | 1125 | CA | LEU | 810 | 16.432 | 9.204 | 19.321 | 1.00 | 19.68 |
| ATOM | 1126 | CB | LEU | 810 | 14.917 | 9.033 | 19.242 | 1.00 | 19.80 |
| ATOM | 1127 | CG | LEU | 810 | 14.250 | 8.133 | 20.290 | 1.00 | 21.07 |
| ATOM | 1128 | CD1 | LEU | 810 | 14.607 | 8.601 | 21.706 | 1.00 | 21.00 |
| ATOM | 1129 | CD2 | LEU | 810 | 12.736 | 8.168 | 20.094 | 1.00 | 20.91 |
| ATOM | 1130 | C | LEU | 810 | 17.137 | 7.924 | 18.837 | 1.00 | 19.90 |
| ATOM | 1131 | O | LEU | 810 | 17.497 | 7.051 | 19.631 | 1.00 | 19.94 |
| ATOM | 1132 | N | LEU | 811 | 17.347 | 7.824 | 17.530 | 1.00 | 20.06 |
| ATOM | 1133 | CA | LEU | 811 | 18.010 | 6.665 | 16.949 | 1.00 | 20.23 |
| ATOM | 1134 | CB | LEU | 811 | 18.125 | 6.825 | 15.424 | 1.00 | 19.95 |
| ATOM | 1135 | CG | LEU | 811 | 17.498 | 5.720 | 14.561 | 1.00 | 20.82 |
| ATOM | 1136 | CD1 | LEU | 811 | 17.661 | 6.059 | 13.079 | 1.00 | 20.39 |
| ATOM | 1137 | CD2 | LEU | 811 | 18.139 | 4.380 | 14.874 | 1.00 | 20.09 |
| ATOM | 1138 | C | LEU | 811 | 19.407 | 6.447 | 17.555 | 1.00 | 20.02 |
| ATOM | 1139 | O | LEU | 811 | 19.889 | 5.326 | 17.622 | 1.00 | 20.87 |

TABLE A-continued

| | | | | | | | | |
|---|---|---|---|---|---|---|---|---|
| ATOM | 1140 | N | LEU | 812 | 20.060 | 7.513 | 17.992 | 1.00 | 19.93 |
| ATOM | 1141 | CA | LEU | 812 | 21.389 | 7.380 | 18.581 | 1.00 | 19.94 |
| ATOM | 1142 | CB | LEU | 812 | 22.041 | 8.753 | 18.753 | 1.00 | 19.93 |
| ATOM | 1143 | CG | LEU | 812 | 23.309 | 8.740 | 19.607 | 1.00 | 19.48 |
| ATOM | 1144 | CD1 | LEU | 812 | 24.523 | 8.421 | 18.748 | 1.00 | 19.57 |
| ATOM | 1145 | CD2 | LEU | 812 | 23.467 | 10.068 | 20.272 | 1.00 | 19.85 |
| ATOM | 1146 | C | LEU | 812 | 21.355 | 6.692 | 19.940 | 1.00 | 19.79 |
| ATOM | 1147 | O | LEU | 812 | 22.383 | 6.237 | 20.414 | 1.00 | 19.89 |
| ATOM | 1148 | N | PHE | 813 | 20.182 | 6.638 | 20.564 | 1.00 | 20.27 |
| ATOM | 1149 | CA | PHE | 813 | 20.025 | 6.011 | 21.872 | 1.00 | 20.89 |
| ATOM | 1150 | CB | PHE | 813 | 19.334 | 6.988 | 22.830 | 1.00 | 21.71 |
| ATOM | 1151 | CG | PHE | 813 | 20.049 | 8.309 | 22.964 | 1.00 | 22.53 |
| ATOM | 1152 | CD1 | PHE | 813 | 21.296 | 8.381 | 23.575 | 1.00 | 22.94 |
| ATOM | 1153 | CD2 | PHE | 813 | 19.483 | 9.475 | 22.452 | 1.00 | 22.60 |
| ATOM | 1154 | CE1 | PHE | 813 | 21.974 | 9.600 | 23.676 | 1.00 | 23.67 |
| ATOM | 1155 | CE2 | PHE | 813 | 20.143 | 10.698 | 22.543 | 1.00 | 23.12 |
| ATOM | 1156 | CZ | PHE | 813 | 21.392 | 10.764 | 23.156 | 1.00 | 24.01 |
| ATOM | 1157 | C | PHE | 813 | 19.233 | 4.706 | 21.814 | 1.00 | 21.29 |
| ATOM | 1158 | O | PHE | 813 | 18.573 | 4.327 | 22.780 | 1.00 | 20.70 |
| ATOM | 1159 | N | SER | 814 | 19.304 | 4.013 | 20.680 | 1.00 | 22.24 |
| ATOM | 1160 | CA | SER | 814 | 18.571 | 2.762 | 20.526 | 1.00 | 22.82 |
| ATOM | 1161 | CB | SER | 814 | 17.604 | 2.870 | 19.352 | 1.00 | 23.27 |
| ATOM | 1162 | OG | SER | 814 | 16.529 | 3.731 | 19.689 | 1.00 | 25.04 |
| ATOM | 1163 | C | SER | 814 | 19.402 | 1.502 | 20.387 | 1.00 | 22.78 |
| ATOM | 1164 | O | SER | 814 | 18.901 | 0.486 | 19.933 | 1.00 | 23.31 |
| ATOM | 1165 | N | ILE | 815 | 20.664 | 1.554 | 20.792 | 1.00 | 23.17 |
| ATOM | 1166 | CA | ILE | 815 | 21.519 | 0.388 | 20.715 | 1.00 | 24.25 |
| ATOM | 1167 | CB | ILE | 815 | 22.260 | 0.339 | 19.361 | 1.00 | 25.14 |
| ATOM | 1168 | CG2 | ILE | 815 | 22.988 | 1.640 | 19.099 | 1.00 | 25.51 |
| ATOM | 1169 | CG1 | ILE | 815 | 23.222 | −0.849 | 19.343 | 1.00 | 26.20 |
| ATOM | 1170 | CD1 | ILE | 815 | 22.524 | −2.177 | 19.315 | 1.00 | 26.03 |
| ATOM | 1171 | C | ILE | 815 | 22.500 | 0.376 | 21.888 | 1.00 | 24.71 |
| ATOM | 1172 | O | ILE | 815 | 23.306 | 1.292 | 22.065 | 1.00 | 24.79 |
| ATOM | 1173 | N | ILE | 816 | 22.417 | −0.671 | 22.700 | 1.00 | 25.36 |
| ATOM | 1174 | CA | ILE | 816 | 23.263 | −0.784 | 23.887 | 1.00 | 26.22 |
| ATOM | 1175 | CB | ILE | 816 | 22.595 | −0.092 | 25.081 | 1.00 | 25.90 |
| ATOM | 1176 | CG2 | ILE | 816 | 22.537 | 1.422 | 24.853 | 1.00 | 25.91 |
| ATOM | 1177 | CG1 | ILE | 816 | 21.202 | −0.690 | 25.282 | 1.00 | 25.62 |
| ATOM | 1178 | CD1 | ILE | 816 | 20.460 | −0.144 | 26.481 | 1.00 | 26.47 |
| ATOM | 1179 | C | ILE | 816 | 23.570 | −2.220 | 24.328 | 1.00 | 26.59 |
| ATOM | 1180 | O | ILE | 816 | 22.807 | −3.142 | 24.048 | 1.00 | 26.12 |
| ATOM | 1181 | N | PRO | 817 | 24.694 | −2.413 | 25.041 | 1.00 | 27.17 |
| ATOM | 1182 | CD | PRO | 817 | 25.758 | −1.427 | 25.304 | 1.00 | 27.29 |
| ATOM | 1183 | CA | PRO | 817 | 25.085 | −3.742 | 25.525 | 1.00 | 27.80 |
| ATOM | 1184 | CB | PRO | 817 | 26.384 | −3.474 | 26.284 | 1.00 | 27.15 |
| ATOM | 1185 | CG | PRO | 817 | 26.958 | −2.313 | 25.557 | 1.00 | 27.61 |
| ATOM | 1186 | C | PRO | 817 | 24.010 | −4.324 | 26.435 | 1.00 | 28.43 |
| ATOM | 1187 | O | PRO | 817 | 23.380 | −3.600 | 27.212 | 1.00 | 27.45 |
| ATOM | 1188 | N | VAL | 818 | 23.808 | −5.634 | 26.312 | 1.00 | 29.98 |
| ATOM | 1189 | CA | VAL | 818 | 22.833 | −6.380 | 27.108 | 1.00 | 31.48 |
| ATOM | 1190 | CB | VAL | 818 | 22.947 | −7.891 | 26.825 | 1.00 | 31.98 |
| ATOM | 1191 | CG1 | VAL | 818 | 24.335 | −8.377 | 27.215 | 1.00 | 33.11 |
| ATOM | 1192 | CG2 | VAL | 818 | 21.879 | −8.665 | 27.590 | 1.00 | 32.85 |
| ATOM | 1193 | C | VAL | 818 | 23.032 | −6.163 | 28.609 | 1.00 | 32.15 |
| ATOM | 1194 | O | VAL | 818 | 22.069 | −6.152 | 29.364 | 1.00 | 32.43 |
| ATOM | 1195 | N | ASP | 819 | 24.276 | −5.997 | 29.046 | 1.00 | 33.13 |
| ATOM | 1196 | CA | ASP | 819 | 24.536 | −5.786 | 30.466 | 1.00 | 34.13 |
| ATOM | 1197 | CB | ASP | 819 | 25.707 | −6.662 | 30.932 | 1.00 | 35.28 |
| ATOM | 1198 | CG | ASP | 819 | 27.024 | −6.302 | 30.258 | 1.00 | 36.52 |
| ATOM | 1199 | OD1 | ASP | 819 | 27.991 | −7.091 | 30.403 | 1.00 | 37.48 |
| ATOM | 1200 | OD2 | ASP | 819 | 27.097 | −5.242 | 29.591 | 1.00 | 37.03 |
| ATOM | 1201 | C | ASP | 819 | 24.798 | −4.315 | 30.798 | 1.00 | 34.30 |
| ATOM | 1202 | O | ASP | 819 | 25.668 | −3.989 | 31.610 | 1.00 | 33.84 |
| ATOM | 1203 | N | GLY | 820 | 24.026 | −3.440 | 30.150 | 1.00 | 34.60 |
| ATOM | 1204 | CA | GLY | 820 | 24.125 | −2.005 | 30.361 | 1.00 | 34.11 |
| ATOM | 1205 | C | GLY | 820 | 25.477 | −1.375 | 30.121 | 1.00 | 33.97 |
| ATOM | 1206 | O | GLY | 820 | 26.474 | −2.068 | 29.945 | 1.00 | 33.92 |
| ATOM | 1207 | N | LEU | 821 | 25.493 | −0.042 | 30.133 | 1.00 | 34.32 |
| ATOM | 1208 | CA | LEU | 821 | 26.693 | 0.768 | 29.925 | 1.00 | 34.47 |
| ATOM | 1209 | CB | LEU | 821 | 26.330 | 2.053 | 29.191 | 1.00 | 34.92 |
| ATOM | 1210 | CG | LEU | 821 | 25.887 | 2.042 | 27.733 | 1.00 | 35.26 |
| ATOM | 1211 | CD1 | LEU | 821 | 25.251 | 3.398 | 27.420 | 1.00 | 35.53 |
| ATOM | 1212 | CD2 | LEU | 821 | 27.080 | 1.769 | 26.819 | 1.00 | 34.91 |
| ATOM | 1213 | C | LEU | 821 | 27.348 | 1.154 | 31.242 | 1.00 | 34.74 |
| ATOM | 1214 | O | LEU | 821 | 26.836 | 0.841 | 32.313 | 1.00 | 34.48 |
| ATOM | 1215 | N | LYS | 822 | 28.476 | 1.855 | 31.148 | 1.00 | 35.36 |
| ATOM | 1216 | CA | LYS | 822 | 29.211 | 2.316 | 32.325 | 1.00 | 36.27 |
| ATOM | 1217 | CB | LYS | 822 | 30.384 | 3.204 | 31.903 | 1.00 | 36.87 |
| ATOM | 1218 | CG | LYS | 822 | 31.286 | 2.590 | 30.856 | 1.00 | 37.44 |

TABLE A-continued

| | | | | | | | | |
|---|---|---|---|---|---|---|---|---|
| ATOM | 1219 | CD | LYS | 822 | 31.934 | 1.317 | 31.361 | 1.00 | 38.01 |
| ATOM | 1220 | CE | LYS | 822 | 32.921 | 0.770 | 30.343 | 1.00 | 38.61 |
| ATOM | 1221 | NZ | LYS | 822 | 34.065 | 1.699 | 30.117 | 1.00 | 39.07 |
| ATOM | 1222 | C | LYS | 822 | 28.296 | 3.112 | 33.263 | 1.00 | 36.51 |
| ATOM | 1223 | O | LYS | 822 | 28.440 | 3.056 | 34.480 | 1.00 | 36.71 |
| ATOM | 1224 | N | ASN | 823 | 27.359 | 3.859 | 32.690 | 1.00 | 36.69 |
| ATOM | 1225 | CA | ASN | 823 | 26.424 | 4.644 | 33.483 | 1.00 | 36.49 |
| ATOM | 1226 | CB | ASN | 823 | 26.893 | 6.098 | 33.529 | 1.00 | 37.62 |
| ATOM | 1227 | CG | ASN | 823 | 28.271 | 6.239 | 34.150 | 1.00 | 39.08 |
| ATOM | 1228 | OD1 | ASN | 823 | 29.251 | 5.668 | 33.658 | 1.00 | 39.96 |
| ATOM | 1229 | ND2 | ASN | 823 | 28.356 | 7.000 | 35.244 | 1.00 | 39.54 |
| ATOM | 1230 | C | ASN | 823 | 25.009 | 4.550 | 32.908 | 1.00 | 35.90 |
| ATOM | 1231 | O | ASN | 823 | 24.470 | 5.523 | 32.380 | 1.00 | 35.84 |
| ATOM | 1232 | N | GLN | 824 | 24.410 | 3.371 | 33.026 | 1.00 | 35.27 |
| ATOM | 1233 | CA | GLN | 824 | 23.064 | 3.128 | 32.512 | 1.00 | 34.89 |
| ATOM | 1234 | CB | GLN | 824 | 22.544 | 1.759 | 32.968 | 1.00 | 35.03 |
| ATOM | 1235 | CG | GLN | 824 | 22.418 | 0.736 | 31.853 | 1.00 | 35.35 |
| ATOM | 1236 | CD | GLN | 824 | 21.877 | 1.332 | 30.573 | 1.00 | 36.02 |
| ATOM | 1237 | OE1 | GLN | 824 | 20.725 | 1.789 | 30.507 | 1.00 | 36.30 |
| ATOM | 1238 | NE2 | GLN | 824 | 22.713 | 1.341 | 29.538 | 1.00 | 36.24 |
| ATOM | 1239 | C | GLN | 824 | 22.016 | 4.159 | 32.879 | 1.00 | 34.22 |
| ATOM | 1240 | O | GLN | 824 | 21.240 | 4.589 | 32.029 | 1.00 | 34.41 |
| ATOM | 1241 | N | LYS | 825 | 21.980 | 4.534 | 34.150 | 1.00 | 33.69 |
| ATOM | 1242 | CA | LYS | 825 | 20.989 | 5.478 | 34.645 | 1.00 | 33.20 |
| ATOM | 1243 | CB | LYS | 825 | 21.240 | 5.765 | 36.120 | 1.00 | 33.85 |
| ATOM | 1244 | CG | LYS | 825 | 20.044 | 6.323 | 36.860 | 1.00 | 34.71 |
| ATOM | 1245 | CD | LYS | 825 | 18.931 | 5.304 | 36.990 | 1.00 | 35.57 |
| ATOM | 1246 | CE | LYS | 825 | 17.744 | 5.903 | 37.732 | 1.00 | 36.43 |
| ATOM | 1247 | NZ | LYS | 825 | 18.151 | 6.447 | 39.063 | 1.00 | 37.01 |
| ATOM | 1248 | C | LYS | 825 | 20.929 | 6.788 | 33.870 | 1.00 | 32.38 |
| ATOM | 1249 | O | LYS | 825 | 19.857 | 7.329 | 33.656 | 1.00 | 32.60 |
| ATOM | 1250 | N | PHE | 826 | 22.077 | 7.299 | 33.453 | 1.00 | 31.31 |
| ATOM | 1251 | CA | PHE | 826 | 22.094 | 8.543 | 32.709 | 1.00 | 30.15 |
| ATOM | 1252 | CB | PHE | 826 | 23.496 | 9.152 | 32.709 | 1.00 | 30.44 |
| ATOM | 1253 | CG | PHE | 826 | 24.003 | 9.506 | 34.076 | 1.00 | 31.16 |
| ATOM | 1254 | CD1 | PHE | 826 | 25.088 | 10.364 | 34.226 | 1.00 | 32.02 |
| ATOM | 1255 | CD2 | PHE | 826 | 23.415 | 8.973 | 35.219 | 1.00 | 31.65 |
| ATOM | 1256 | CE1 | PHE | 826 | 25.579 | 10.682 | 35.496 | 1.00 | 31.86 |
| ATOM | 1257 | CE2 | PHE | 826 | 23.900 | 9.285 | 36.490 | 1.00 | 31.49 |
| ATOM | 1258 | CZ | PHE | 826 | 24.983 | 10.140 | 36.624 | 1.00 | 31.58 |
| ATOM | 1259 | C | PHE | 826 | 21.618 | 8.307 | 31.283 | 1.00 | 28.87 |
| ATOM | 1260 | O | PHE | 826 | 20.921 | 9.142 | 30.720 | 1.00 | 28.43 |
| ATOM | 1261 | N | PHE | 827 | 21.989 | 7.166 | 30.708 | 1.00 | 27.44 |
| ATOM | 1262 | CA | PHE | 827 | 21.568 | 6.833 | 29.354 | 1.00 | 26.53 |
| ATOM | 1263 | CB | PHE | 827 | 22.122 | 5.476 | 28.935 | 1.00 | 25.44 |
| ATOM | 1264 | CG | PHE | 827 | 21.708 | 5.061 | 27.556 | 1.00 | 24.15 |
| ATOM | 1265 | CD1 | PHE | 827 | 22.592 | 5.157 | 26.493 | 1.00 | 23.63 |
| ATOM | 1266 | CD2 | PHE | 827 | 20.425 | 4.599 | 27.312 | 1.00 | 23.97 |
| ATOM | 1267 | CE1 | PHE | 827 | 22.202 | 4.800 | 25.203 | 1.00 | 23.50 |
| ATOM | 1268 | CE2 | PHE | 827 | 20.026 | 4.241 | 26.016 | 1.00 | 23.68 |
| ATOM | 1269 | CZ | PHE | 827 | 20.913 | 4.342 | 24.968 | 1.00 | 22.72 |
| ATOM | 1270 | C | PHE | 827 | 20.045 | 6.788 | 29.340 | 1.00 | 26.44 |
| ATOM | 1271 | O | PHE | 827 | 19.406 | 7.407 | 28.492 | 1.00 | 26.04 |
| ATOM | 1272 | N | ASP | 828 | 19.475 | 6.052 | 30.296 | 1.00 | 26.33 |
| ATOM | 1273 | CA | ASP | 828 | 18.022 | 5.931 | 30.436 | 1.00 | 26.22 |
| ATOM | 1274 | CB | ASP | 828 | 17.669 | 5.082 | 31.654 | 1.00 | 27.34 |
| ATOM | 1275 | CG | ASP | 828 | 18.195 | 3.673 | 31.567 | 1.00 | 28.47 |
| ATOM | 1276 | OD1 | ASP | 828 | 18.511 | 3.119 | 32.644 | 1.00 | 29.17 |
| ATOM | 1277 | OD2 | ASP | 828 | 18.281 | 3.117 | 30.448 | 1.00 | 28.69 |
| ATOM | 1278 | C | ASP | 828 | 17.332 | 7.288 | 30.601 | 1.00 | 25.75 |
| ATOM | 1279 | O | ASP | 828 | 16.266 | 7.506 | 30.052 | 1.00 | 25.47 |
| ATOM | 1280 | N | GLU | 829 | 17.915 | 8.191 | 31.382 | 1.00 | 25.59 |
| ATOM | 1281 | CA | GLU | 829 | 17.292 | 9.494 | 31.559 | 1.00 | 26.44 |
| ATOM | 1282 | CB | GLU | 829 | 18.006 | 10.303 | 32.650 | 1.00 | 28.25 |
| ATOM | 1283 | CG | GLU | 829 | 17.415 | 11.696 | 32.898 | 1.00 | 30.25 |
| ATOM | 1284 | CD | GLU | 829 | 18.210 | 12.499 | 33.925 | 1.00 | 32.25 |
| ATOM | 1285 | OE1 | GLU | 829 | 19.432 | 12.719 | 33.717 | 1.00 | 33.52 |
| ATOM | 1286 | OE2 | GLU | 829 | 17.618 | 12.918 | 34.946 | 1.00 | 33.33 |
| ATOM | 1287 | C | GLU | 829 | 17.343 | 10.233 | 30.223 | 1.00 | 25.94 |
| ATOM | 1288 | O | GLU | 829 | 16.342 | 10.797 | 29.777 | 1.00 | 25.19 |
| ATOM | 1289 | N | LEU | 830 | 18.506 | 10.208 | 29.575 | 1.00 | 25.30 |
| ATOM | 1290 | CA | LEU | 830 | 18.645 | 10.859 | 28.282 | 1.00 | 25.23 |
| ATOM | 1291 | CB | LEU | 830 | 20.072 | 10.736 | 27.761 | 1.00 | 26.02 |
| ATOM | 1292 | CG | LEU | 830 | 20.940 | 11.959 | 28.038 | 1.00 | 27.07 |
| ATOM | 1293 | CD1 | LEU | 830 | 21.096 | 12.139 | 29.555 | 1.00 | 28.25 |
| ATOM | 1294 | CD2 | LEU | 830 | 22.298 | 11.793 | 27.362 | 1.00 | 27.32 |
| ATOM | 1295 | C | LEU | 830 | 17.678 | 10.249 | 27.279 | 1.00 | 25.12 |
| ATOM | 1296 | O | LEU | 830 | 16.943 | 10.966 | 26.606 | 1.00 | 24.67 |
| ATOM | 1297 | N | ARG | 831 | 17.668 | 8.922 | 27.188 | 1.00 | 25.07 |

TABLE A-continued

| | | | | | | | | |
|---|---|---|---|---|---|---|---|---|
| ATOM | 1298 | CA | ARG | 831 | 16.768 | 8.253 | 26.261 | 1.00 | 25.48 |
| ATOM | 1299 | CB | ARG | 831 | 16.913 | 6.732 | 26.358 | 1.00 | 25.48 |
| ATOM | 1300 | CG | ARG | 831 | 15.953 | 5.993 | 25.441 | 1.00 | 25.24 |
| ATOM | 1301 | CD | ARG | 831 | 16.261 | 4.499 | 25.357 | 1.00 | 25.58 |
| ATOM | 1302 | NE | ARG | 831 | 15.158 | 3.781 | 24.719 | 1.00 | 25.78 |
| ATOM | 1303 | CZ | ARG | 831 | 14.822 | 3.879 | 23.436 | 1.00 | 25.10 |
| ATOM | 1304 | NH1 | ARG | 831 | 15.507 | 4.661 | 22.617 | 1.00 | 24.95 |
| ATOM | 1305 | NH2 | ARG | 831 | 13.774 | 3.213 | 22.982 | 1.00 | 25.49 |
| ATOM | 1306 | C | ARG | 831 | 15.319 | 8.654 | 26.526 | 1.00 | 25.51 |
| ATOM | 1307 | O | ARG | 831 | 14.559 | 8.929 | 25.590 | 1.00 | 25.14 |
| ATOM | 1308 | N | MET | 832 | 14.948 | 8.697 | 27.804 | 1.00 | 25.71 |
| ATOM | 1309 | CA | MET | 832 | 13.591 | 9.070 | 28.202 | 1.00 | 26.13 |
| ATOM | 1310 | CB | MET | 832 | 13.393 | 8.855 | 29.706 | 1.00 | 26.07 |
| ATOM | 1311 | CG | MET | 832 | 12.280 | 9.683 | 30.316 | 1.00 | 25.80 |
| ATOM | 1312 | SD | MET | 832 | 11.876 | 9.192 | 32.002 | 1.00 | 28.43 |
| ATOM | 1313 | CE | MET | 832 | 12.867 | 10.272 | 32.995 | 1.00 | 26.55 |
| ATOM | 1314 | C | MET | 832 | 13.255 | 10.518 | 27.847 | 1.00 | 25.99 |
| ATOM | 1315 | O | MET | 832 | 12.114 | 10.828 | 27.518 | 1.00 | 26.12 |
| ATOM | 1316 | N | ASN | 833 | 14.241 | 11.403 | 27.916 | 1.00 | 26.07 |
| ATOM | 1317 | CA | ASN | 833 | 13.996 | 12.800 | 27.590 | 1.00 | 26.18 |
| ATOM | 1318 | CB | ASN | 833 | 15.129 | 13.668 | 28.126 | 1.00 | 26.83 |
| ATOM | 1319 | CG | ASN | 833 | 15.026 | 13.874 | 29.625 | 1.00 | 27.86 |
| ATOM | 1320 | OD1 | ASN | 833 | 16.004 | 14.206 | 30.297 | 1.00 | 28.97 |
| ATOM | 1321 | ND2 | ASN | 833 | 13.827 | 13.682 | 30.156 | 1.00 | 27.93 |
| ATOM | 1322 | C | ASN | 833 | 13.795 | 13.021 | 26.099 | 1.00 | 26.03 |
| ATOM | 1323 | O | ASN | 833 | 12.989 | 13.856 | 25.701 | 1.00 | 25.96 |
| ATOM | 1324 | N | TYR | 834 | 14.513 | 12.267 | 25.277 | 1.00 | 25.89 |
| ATOM | 1325 | CA | TYR | 834 | 14.375 | 12.385 | 23.835 | 1.00 | 26.53 |
| ATOM | 1326 | CB | TYR | 834 | 15.572 | 11.732 | 23.142 | 1.00 | 25.95 |
| ATOM | 1327 | CG | TYR | 834 | 16.759 | 12.670 | 23.114 | 1.00 | 25.75 |
| ATOM | 1328 | CD1 | TYR | 834 | 17.008 | 13.471 | 22.004 | 1.00 | 25.23 |
| ATOM | 1329 | CE1 | TYR | 834 | 18.028 | 14.418 | 22.017 | 1.00 | 25.38 |
| ATOM | 1330 | CD2 | TYR | 834 | 17.566 | 12.839 | 24.239 | 1.00 | 25.31 |
| ATOM | 1331 | CE2 | TYR | 834 | 18.584 | 13.784 | 24.260 | 1.00 | 24.66 |
| ATOM | 1332 | CZ | TYR | 834 | 18.813 | 14.569 | 23.149 | 1.00 | 24.63 |
| ATOM | 1333 | OH | TYR | 834 | 19.831 | 15.496 | 23.153 | 1.00 | 24.47 |
| ATOM | 1334 | C | TYR | 834 | 13.054 | 11.784 | 23.364 | 1.00 | 27.63 |
| ATOM | 1335 | O | TYR | 834 | 12.385 | 12.338 | 22.493 | 1.00 | 27.51 |
| ATOM | 1336 | N | ILE | 835 | 12.668 | 10.655 | 23.948 | 1.00 | 28.57 |
| ATOM | 1337 | CA | ILE | 835 | 11.404 | 10.044 | 23.586 | 1.00 | 29.73 |
| ATOM | 1338 | CB | ILE | 835 | 11.131 | 8.765 | 24.404 | 1.00 | 29.44 |
| ATOM | 1339 | CG2 | ILE | 835 | 9.640 | 8.458 | 24.415 | 1.00 | 29.00 |
| ATOM | 1340 | CG1 | ILE | 835 | 11.940 | 7.598 | 23.828 | 1.00 | 29.23 |
| ATOM | 1341 | CD1 | ILE | 835 | 11.798 | 6.295 | 24.604 | 1.00 | 28.37 |
| ATOM | 1342 | C | ILE | 835 | 10.294 | 11.053 | 23.861 | 1.00 | 31.03 |
| ATOM | 1343 | O | ILE | 835 | 9.354 | 11.171 | 23.084 | 1.00 | 30.89 |
| ATOM | 1344 | N | LYS | 836 | 10.410 | 11.777 | 24.971 | 1.00 | 32.73 |
| ATOM | 1345 | CA | LYS | 836 | 9.411 | 12.772 | 25.335 | 1.00 | 34.47 |
| ATOM | 1346 | CB | LYS | 836 | 9.613 | 13.246 | 26.781 | 1.00 | 35.12 |
| ATOM | 1347 | CG | LYS | 836 | 9.220 | 12.210 | 27.845 | 1.00 | 36.26 |
| ATOM | 1348 | CD | LYS | 836 | 9.047 | 12.853 | 29.226 | 1.00 | 36.96 |
| ATOM | 1349 | CE | LYS | 836 | 8.689 | 11.822 | 30.292 | 1.00 | 37.93 |
| ATOM | 1350 | NZ | LYS | 836 | 7.331 | 11.205 | 30.106 | 1.00 | 38.44 |
| ATOM | 1351 | C | LYS | 836 | 9.411 | 13.974 | 24.401 | 1.00 | 35.36 |
| ATOM | 1352 | O | LYS | 836 | 8.401 | 14.663 | 24.288 | 1.00 | 35.57 |
| ATOM | 1353 | N | GLU | 837 | 10.533 | 14.232 | 23.730 | 1.00 | 36.74 |
| ATOM | 1354 | CA | GLU | 837 | 10.605 | 15.360 | 22.801 | 1.00 | 37.88 |
| ATOM | 1355 | CB | GLU | 837 | 12.056 | 15.750 | 22.516 | 1.00 | 38.02 |
| ATOM | 1356 | CG | GLU | 837 | 12.811 | 16.300 | 23.720 | 1.00 | 38.61 |
| ATOM | 1357 | CD | GLU | 837 | 12.171 | 17.552 | 24.298 | 1.00 | 38.88 |
| ATOM | 1358 | OE1 | GLU | 837 | 12.694 | 18.080 | 25.301 | 1.00 | 38.97 |
| ATOM | 1359 | OE2 | GLU | 837 | 11.145 | 18.011 | 23.751 | 1.00 | 39.85 |
| ATOM | 1360 | C | GLU | 837 | 9.902 | 14.995 | 21.502 | 1.00 | 39.04 |
| ATOM | 1361 | O | GLU | 837 | 9.248 | 15.837 | 20.883 | 1.00 | 39.39 |
| ATOM | 1362 | N | LEU | 838 | 10.035 | 13.737 | 21.089 | 1.00 | 40.19 |
| ATOM | 1363 | CA | LEU | 838 | 9.377 | 13.283 | 19.873 | 1.00 | 41.66 |
| ATOM | 1364 | CB | LEU | 838 | 9.745 | 11.840 | 19.551 | 1.00 | 40.92 |
| ATOM | 1365 | CG | LEU | 838 | 9.059 | 11.325 | 18.283 | 1.00 | 40.71 |
| ATOM | 1366 | CD1 | LEU | 838 | 9.337 | 12.287 | 17.131 | 1.00 | 40.13 |
| ATOM | 1367 | CD2 | LEU | 838 | 9.549 | 9.921 | 17.961 | 1.00 | 40.28 |
| ATOM | 1368 | C | LEU | 838 | 7.882 | 13.376 | 20.098 | 1.00 | 43.18 |
| ATOM | 1369 | O | LEU | 838 | 7.117 | 13.684 | 19.187 | 1.00 | 43.33 |
| ATOM | 1370 | N | ASP | 839 | 7.469 | 13.105 | 21.329 | 1.00 | 45.15 |
| ATOM | 1371 | CA | ASP | 839 | 6.063 | 13.176 | 21.679 | 1.00 | 47.48 |
| ATOM | 1372 | CB | ASP | 839 | 5.852 | 12.690 | 23.109 | 1.00 | 47.71 |
| ATOM | 1373 | CG | ASP | 839 | 4.409 | 12.777 | 23.538 | 1.00 | 48.24 |
| ATOM | 1374 | CD1 | ASP | 839 | 3.575 | 12.016 | 22.996 | 1.00 | 48.44 |
| ATOM | 1375 | OD2 | ASP | 839 | 4.108 | 13.617 | 24.411 | 1.00 | 48.69 |
| ATOM | 1376 | C | ASP | 839 | 5.565 | 14.617 | 21.539 | 1.00 | 48.74 |

TABLE A-continued

| | | | | | | | | |
|---|---|---|---|---|---|---|---|---|
| ATOM | 1377 | O | ASP | 839 | 4.525 | 14.866 | 20.938 | 1.00 | 48.83 |
| ATOM | 1378 | N | ARG | 840 | 6.314 | 15.566 | 22.086 | 1.00 | 50.51 |
| ATOM | 1379 | CA | ARG | 840 | 5.922 | 16.965 | 21.999 | 1.00 | 52.38 |
| ATOM | 1380 | CB | ARG | 840 | 6.739 | 17.805 | 22.985 | 1.00 | 52.53 |
| ATOM | 1381 | CG | ARG | 840 | 6.330 | 17.586 | 24.444 | 1.00 | 53.33 |
| ATOM | 1382 | CD | ARG | 840 | 7.033 | 18.548 | 25.395 | 1.00 | 53.67 |
| ATOM | 1383 | NE | ARG | 840 | 8.378 | 18.110 | 25.759 | 1.00 | 53.99 |
| ATOM | 1384 | CZ | ARG | 840 | 9.318 | 18.922 | 26.232 | 1.00 | 54.20 |
| ATOM | 1385 | NH1 | ARG | 840 | 9.057 | 20.214 | 26.388 | 1.00 | 54.27 |
| ATOM | 1386 | NH2 | ARG | 840 | 10.513 | 18.447 | 26.558 | 1.00 | 54.13 |
| ATOM | 1387 | C | ARG | 840 | 6.041 | 17.534 | 20.585 | 1.00 | 53.55 |
| ATOM | 1388 | O | ARG | 840 | 5.293 | 18.436 | 20.211 | 1.00 | 53.71 |
| ATOM | 1389 | N | ILE | 841 | 6.979 | 17.021 | 19.796 | 1.00 | 54.98 |
| ATOM | 1390 | CA | ILE | 841 | 7.120 | 17.511 | 18.433 | 1.00 | 56.52 |
| ATOM | 1391 | CB | ILE | 841 | 8.440 | 17.040 | 17.784 | 1.00 | 56.31 |
| ATOM | 1392 | CG2 | ILE | 841 | 8.442 | 15.540 | 17.629 | 1.00 | 56.61 |
| ATOM | 1393 | CG1 | ILE | 841 | 8.600 | 17.678 | 16.405 | 1.00 | 56.35 |
| ATOM | 1394 | CD1 | ILE | 841 | 8.600 | 19.187 | 16.425 | 1.00 | 56.59 |
| ATOM | 1395 | C | ILE | 841 | 5.927 | 16.955 | 17.659 | 1.00 | 57.71 |
| ATOM | 1396 | O | ILE | 841 | 5.593 | 17.414 | 16.564 | 1.00 | 57.95 |
| ATOM | 1397 | N | ILE | 842 | 5.285 | 15.955 | 18.247 | 1.00 | 59.05 |
| ATOM | 1398 | CA | ILE | 842 | 4.115 | 15.345 | 17.644 | 1.00 | 60.55 |
| ATOM | 1399 | CB | ILE | 842 | 3.929 | 13.899 | 18.145 | 1.00 | 60.34 |
| ATOM | 1400 | CG2 | ILE | 842 | 2.539 | 13.386 | 17.786 | 1.00 | 60.36 |
| ATOM | 1401 | CG1 | ILE | 842 | 5.014 | 13.002 | 17.552 | 1.00 | 60.28 |
| ATOM | 1402 | CD1 | ILE | 842 | 4.968 | 12.899 | 16.046 | 1.00 | 60.36 |
| ATOM | 1403 | C | ILE | 842 | 2.886 | 16.173 | 18.021 | 1.00 | 61.84 |
| ATOM | 1404 | O | ILE | 842 | 2.077 | 16.521 | 17.165 | 1.00 | 62.01 |
| ATOM | 1405 | N | ALA | 843 | 2.768 | 16.503 | 19.304 | 1.00 | 63.28 |
| ATOM | 1406 | CA | ALA | 843 | 1.636 | 17.274 | 19.811 | 1.00 | 64.93 |
| ATOM | 1407 | CB | ALA | 843 | 1.202 | 16.719 | 21.168 | 1.00 | 64.96 |
| ATOM | 1408 | C | ALA | 843 | 1.921 | 18.770 | 19.931 | 1.00 | 66.08 |
| ATOM | 1409 | O | ALA | 843 | 2.657 | 19.346 | 19.125 | 1.00 | 66.22 |
| ATOM | 1410 | N | CYS | 844 | 1.327 | 19.393 | 20.946 | 1.00 | 67.46 |
| ATOM | 1411 | CA | CYS | 844 | 1.499 | 20.825 | 21.187 | 1.00 | 68.93 |
| ATOM | 1412 | CB | CYS | 844 | 0.818 | 21.235 | 22.496 | 1.00 | 69.02 |
| ATOM | 1413 | SG | CYS | 844 | 1.052 | 22.983 | 22.913 | 1.00 | 69.96 |
| ATOM | 1414 | C | CYS | 844 | 2.965 | 21.264 | 21.224 | 1.00 | 69.69 |
| ATOM | 1415 | O | CYS | 844 | 3.734 | 20.858 | 22.103 | 1.00 | 69.75 |
| ATOM | 1416 | N | ALA | 845 | 3.331 | 22.104 | 20.260 | 1.00 | 70.51 |
| ATOM | 1417 | CA | ALA | 845 | 4.685 | 22.631 | 20.138 | 1.00 | 71.20 |
| ATOM | 1418 | CB | ALA | 845 | 5.697 | 21.488 | 20.150 | 1.00 | 71.12 |
| ATOM | 1419 | C | ALA | 845 | 4.805 | 23.418 | 18.837 | 1.00 | 71.67 |
| ATOM | 1420 | O | ALA | 845 | 5.173 | 24.599 | 18.838 | 1.00 | 71.61 |
| ATOM | 1421 | N | ALA | 846 | 4.473 | 22.754 | 17.732 | 1.00 | 72.18 |
| ATOM | 1422 | CA | ALA | 846 | 4.555 | 23.359 | 16.411 | 1.00 | 72.76 |
| ATOM | 1423 | CB | ALA | 846 | 5.743 | 22.785 | 15.670 | 1.00 | 72.64 |
| ATOM | 1424 | C | ALA | 846 | 3.291 | 23.178 | 15.572 | 1.00 | 73.29 |
| ATOM | 1425 | O | ALA | 846 | 2.639 | 24.157 | 15.204 | 1.00 | 73.45 |
| ATOM | 1426 | N | LYS | 847 | 2.949 | 21.925 | 15.273 | 1.00 | 73.74 |
| ATOM | 1427 | CA | LYS | 847 | 1.780 | 21.617 | 14.450 | 1.00 | 74.06 |
| ATOM | 1428 | CB | LYS | 847 | 1.558 | 20.100 | 14.383 | 1.00 | 74.11 |
| ATOM | 1429 | CG | LYS | 847 | 2.498 | 19.384 | 13.412 | 1.00 | 74.21 |
| ATOM | 1430 | CD | LYS | 847 | 2.359 | 19.953 | 12.002 | 1.00 | 74.15 |
| ATOM | 1431 | CE | LYS | 847 | 3.331 | 19.313 | 11.026 | 1.00 | 74.04 |
| ATOM | 1432 | NZ | LYS | 847 | 3.206 | 19.907 | 9.662 | 1.00 | 73.48 |
| ATOM | 1433 | C | LYS | 847 | 0.478 | 22.307 | 14.842 | 1.00 | 74.24 |
| ATOM | 1434 | O | LYS | 847 | 0.203 | 22.539 | 16.021 | 1.00 | 74.15 |
| ATOM | 1435 | N | ALA | 848 | −0.311 | 22.632 | 13.820 | 1.00 | 74.54 |
| ATOM | 1436 | CA | ALA | 848 | −1.600 | 23.296 | 13.981 | 1.00 | 74.71 |
| ATOM | 1437 | CB | ALA | 848 | −1.786 | 24.350 | 12.885 | 1.00 | 74.65 |
| ATOM | 1438 | C | ALA | 848 | −2.755 | 22.289 | 13.948 | 1.00 | 74.78 |
| ATOM | 1439 | O | ALA | 848 | −3.691 | 22.386 | 14.746 | 1.00 | 75.01 |
| ATOM | 1440 | N | PRO | 849 | −2.715 | 21.318 | 13.016 | 1.00 | 74.70 |
| ATOM | 1441 | CD | PRO | 849 | −1.791 | 21.178 | 11.874 | 1.00 | 74.87 |
| ATOM | 1442 | CA | PRO | 849 | −3.789 | 20.320 | 12.936 | 1.00 | 74.53 |
| ATOM | 1443 | CB | PRO | 849 | −3.627 | 19.756 | 11.529 | 1.00 | 74.63 |
| ATOM | 1444 | CG | PRO | 849 | −2.143 | 19.803 | 11.336 | 1.00 | 74.79 |
| ATOM | 1445 | C | PRO | 849 | −3.632 | 19.250 | 14.014 | 1.00 | 74.18 |
| ATOM | 1446 | O | PRO | 849 | −2.519 | 18.800 | 14.286 | 1.00 | 74.25 |
| ATOM | 1447 | N | THR | 850 | −4.746 | 18.848 | 14.621 | 1.00 | 73.78 |
| ATOM | 1448 | CA | THR | 850 | −4.736 | 17.840 | 15.682 | 1.00 | 73.31 |
| ATOM | 1449 | CB | THR | 850 | −6.180 | 17.441 | 16.067 | 1.00 | 73.45 |
| ATOM | 1450 | OG1 | THR | 850 | −6.144 | 16.387 | 17.038 | 1.00 | 73.57 |
| ATOM | 1451 | CG2 | THR | 850 | −6.961 | 16.990 | 14.832 | 1.00 | 73.61 |
| ATOM | 1452 | C | THR | 850 | −3.933 | 16.578 | 15.329 | 1.00 | 72.80 |
| ATOM | 1453 | O | THR | 850 | −4.467 | 15.613 | 14.771 | 1.00 | 72.81 |
| ATOM | 1454 | N | SER | 851 | −2.648 | 16.591 | 15.675 | 1.00 | 71.96 |
| ATOM | 1455 | CA | SER | 851 | −1.751 | 15.471 | 15.393 | 1.00 | 71.07 |

TABLE A-continued

| | | | | | | | | |
|---|---|---|---|---|---|---|---|---|
| ATOM | 1456 | CB | SER | 851 | −0.664 | 15.924 | 14.405 | 1.00 | 71.04 |
| ATOM | 1457 | OG | SER | 851 | 0.243 | 14.881 | 14.097 | 1.00 | 70.59 |
| ATOM | 1458 | C | SER | 851 | −1.099 | 14.932 | 16.670 | 1.00 | 70.34 |
| ATOM | 1459 | O | SER | 851 | −0.015 | 15.370 | 17.047 | 1.00 | 70.40 |
| ATOM | 1460 | N | CYS | 852 | −1.759 | 13.982 | 17.333 | 1.00 | 69.35 |
| ATOM | 1461 | CA | CYS | 852 | −1.225 | 13.395 | 18.565 | 1.00 | 68.12 |
| ATOM | 1462 | CB | CYS | 852 | −1.375 | 14.384 | 19.735 | 1.00 | 68.59 |
| ATOM | 1463 | SG | CYS | 852 | −3.043 | 15.096 | 19.978 | 1.00 | 69.59 |
| ATOM | 1464 | C | CYS | 852 | −1.854 | 12.050 | 18.944 | 1.00 | 66.82 |
| ATOM | 1465 | O | CYS | 852 | −1.848 | 11.662 | 20.113 | 1.00 | 66.81 |
| ATOM | 1466 | N | SER | 853 | −2.382 | 11.334 | 17.956 | 1.00 | 65.27 |
| ATOM | 1467 | CA | SER | 853 | −3.007 | 10.041 | 18.211 | 1.00 | 63.60 |
| ATOM | 1468 | CB | SER | 853 | −4.373 | 9.970 | 17.514 | 1.00 | 63.93 |
| ATOM | 1469 | OG | SER | 853 | −4.272 | 10.324 | 16.148 | 1.00 | 63.97 |
| ATOM | 1470 | C | SER | 853 | −2.134 | 8.862 | 17.778 | 1.00 | 62.15 |
| ATOM | 1471 | O | SER | 853 | −1.316 | 8.371 | 18.562 | 1.00 | 62.22 |
| ATOM | 1472 | N | ARG | 854 | −2.305 | 8.411 | 16.537 | 1.00 | 60.15 |
| ATOM | 1473 | CA | ARG | 854 | −1.532 | 7.282 | 16.021 | 1.00 | 58.00 |
| ATOM | 1474 | CB | ARG | 854 | −2.376 | 6.455 | 15.035 | 1.00 | 58.75 |
| ATOM | 1475 | CG | ARG | 854 | −2.622 | 7.112 | 13.680 | 1.00 | 59.49 |
| ATOM | 1476 | CD | ARG | 854 | −3.460 | 6.203 | 12.778 | 1.00 | 60.59 |
| ATOM | 1477 | NE | ARG | 854 | −3.671 | 6.744 | 11.429 | 1.00 | 61.32 |
| ATOM | 1478 | CZ | ARG | 854 | −4.324 | 7.873 | 11.150 | 1.00 | 61.65 |
| ATOM | 1479 | NH1 | ARG | 854 | −4.848 | 8.611 | 12.124 | 1.00 | 61.58 |
| ATOM | 1480 | NH2 | ARG | 854 | −4.454 | 8.267 | 9.887 | 1.00 | 61.67 |
| ATOM | 1481 | C | ARG | 854 | −0.241 | 7.730 | 15.339 | 1.00 | 55.94 |
| ATOM | 1482 | O | ARG | 854 | 0.411 | 6.952 | 14.653 | 1.00 | 55.60 |
| ATOM | 1483 | N | ARG | 855 | 0.129 | 8.987 | 15.540 | 1.00 | 53.73 |
| ATOM | 1484 | CA | ARG | 855 | 1.342 | 9.528 | 14.946 | 1.00 | 51.51 |
| ATOM | 1485 | CB | ARG | 855 | 1.337 | 11.051 | 15.063 | 1.00 | 50.74 |
| ATOM | 1486 | CG | ARG | 855 | 2.404 | 11.739 | 14.247 | 1.00 | 49.65 |
| ATOM | 1487 | CD | ARG | 855 | 2.238 | 11.446 | 12.760 | 1.00 | 48.66 |
| ATOM | 1488 | NE | ARG | 855 | 3.212 | 12.183 | 11.966 | 1.00 | 46.95 |
| ATOM | 1489 | CZ | ARG | 855 | 3.327 | 12.088 | 10.650 | 1.00 | 46.55 |
| ATOM | 1490 | NH1 | ARG | 855 | 2.526 | 11.280 | 9.967 | 1.00 | 45.80 |
| ATOM | 1491 | NH2 | ARG | 855 | 4.248 | 12.802 | 10.020 | 1.00 | 46.32 |
| ATOM | 1492 | C | ARG | 855 | 2.580 | 8.955 | 15.642 | 1.00 | 50.40 |
| ATOM | 1493 | O | ARG | 855 | 3.633 | 8.777 | 15.026 | 1.00 | 50.15 |
| ATOM | 1494 | N | PHE | 856 | 2.448 | 8.669 | 16.933 | 1.00 | 48.68 |
| ATOM | 1495 | CA | PHE | 856 | 3.554 | 8.117 | 17.694 | 1.00 | 46.90 |
| ATOM | 1496 | CB | PHE | 856 | 3.327 | 8.325 | 19.196 | 1.00 | 47.21 |
| ATOM | 1497 | CG | PHE | 856 | 4.461 | 7.836 | 20.058 | 1.00 | 47.24 |
| ATOM | 1498 | CD1 | PHE | 856 | 5.710 | 8.448 | 20.004 | 1.00 | 47.28 |
| ATOM | 1499 | CD2 | PHE | 856 | 4.278 | 6.766 | 20.930 | 1.00 | 47.12 |
| ATOM | 1500 | CE1 | PHE | 856 | 6.761 | 8.000 | 20.811 | 1.00 | 47.48 |
| ATOM | 1501 | CE2 | PHE | 856 | 5.324 | 6.312 | 21.743 | 1.00 | 47.30 |
| ATOM | 1502 | CZ | PHE | 856 | 6.566 | 6.929 | 21.684 | 1.00 | 47.08 |
| ATOM | 1503 | C | PHE | 856 | 3.705 | 6.633 | 17.393 | 1.00 | 45.50 |
| ATOM | 1504 | O | PHE | 856 | 4.825 | 6.122 | 17.331 | 1.00 | 45.41 |
| ATOM | 1505 | N | TYR | 857 | 2.584 | 5.940 | 17.196 | 1.00 | 43.60 |
| ATOM | 1506 | CA | TYR | 857 | 2.643 | 4.511 | 16.910 | 1.00 | 41.70 |
| ATOM | 1507 | CB | TYR | 857 | 1.249 | 3.880 | 16.893 | 1.00 | 42.01 |
| ATOM | 1508 | CG | TYR | 857 | 1.271 | 2.393 | 16.574 | 1.00 | 42.12 |
| ATOM | 1509 | CD1 | TYR | 857 | 1.713 | 1.462 | 17.512 | 1.00 | 42.35 |
| ATOM | 1510 | CE1 | TYR | 857 | 1.785 | 0.100 | 17.206 | 1.00 | 42.40 |
| ATOM | 1511 | CD2 | TYR | 857 | 0.895 | 1.923 | 15.315 | 1.00 | 42.37 |
| ATOM | 1512 | CE2 | TYR | 857 | 0.967 | 0.562 | 14.997 | 1.00 | 42.18 |
| ATOM | 1513 | CZ | TYR | 857 | 1.414 | −0.341 | 15.946 | 1.00 | 42.56 |
| ATOM | 1514 | OH | TYR | 857 | 1.516 | −1.681 | 15.629 | 1.00 | 42.93 |
| ATOM | 1515 | C | TYR | 857 | 3.323 | 4.222 | 15.582 | 1.00 | 40.32 |
| ATOM | 1516 | O | TYR | 857 | 4.092 | 3.266 | 15.478 | 1.00 | 40.51 |
| ATOM | 1517 | N | GLN | 858 | 3.047 | 5.023 | 14.558 | 1.00 | 38.44 |
| ATOM | 1518 | CA | GLN | 858 | 3.682 | 4.764 | 13.271 | 1.00 | 36.90 |
| ATOM | 1519 | CB | GLN | 858 | 2.888 | 5.372 | 12.104 | 1.00 | 37.28 |
| ATOM | 1520 | CG | GLN | 858 | 2.188 | 6.677 | 12.379 | 1.00 | 37.76 |
| ATOM | 1521 | CD | GLN | 858 | 0.934 | 6.820 | 11.536 | 1.00 | 38.54 |
| ATOM | 1522 | OE1 | GLN | 858 | 0.165 | 5.862 | 11.391 | 1.00 | 38.69 |
| ATOM | 1523 | NE2 | GLN | 858 | 0.712 | 8.012 | 10.982 | 1.00 | 38.73 |
| ATOM | 1524 | C | GLN | 858 | 5.134 | 5.201 | 13.210 | 1.00 | 35.37 |
| ATOM | 1525 | O | GLN | 858 | 5.949 | 4.501 | 12.612 | 1.00 | 35.14 |
| ATOM | 1526 | N | LEU | 859 | 5.471 | 6.330 | 13.834 | 1.00 | 33.65 |
| ATOM | 1527 | CA | LEU | 859 | 6.859 | 6.782 | 13.826 | 1.00 | 32.33 |
| ATOM | 1528 | CB | LEU | 859 | 6.995 | 8.191 | 14.412 | 1.00 | 32.33 |
| ATOM | 1529 | CG | LEU | 859 | 6.425 | 9.362 | 13.596 | 1.00 | 32.70 |
| ATOM | 1530 | CD1 | LEU | 859 | 6.736 | 10.688 | 14.294 | 1.00 | 32.82 |
| ATOM | 1531 | CD2 | LEU | 859 | 7.017 | 9.368 | 12.210 | 1.00 | 32.87 |
| ATOM | 1532 | C | LEU | 859 | 7.743 | 5.806 | 14.607 | 1.00 | 31.28 |
| ATOM | 1533 | O | LEU | 859 | 8.844 | 5.475 | 14.174 | 1.00 | 30.56 |
| ATOM | 1534 | N | THR | 860 | 7.264 | 5.339 | 15.754 | 1.00 | 30.60 |

TABLE A-continued

| | | | | | | | | |
|---|---|---|---|---|---|---|---|---|
| ATOM | 1535 | CA | THR | 860 | 8.043 | 4.389 | 16.550 | 1.00 | 30.04 |
| ATOM | 1536 | CB | THR | 860 | 7.398 | 4.142 | 17.938 | 1.00 | 30.12 |
| ATOM | 1537 | OG1 | THR | 860 | 6.024 | 3.776 | 17.777 | 1.00 | 30.74 |
| ATOM | 1538 | CG2 | THR | 860 | 7.472 | 5.403 | 18.780 | 1.00 | 29.71 |
| ATOM | 1539 | C | THR | 860 | 8.162 | 3.083 | 15.764 | 1.00 | 29.10 |
| ATOM | 1540 | O | THR | 860 | 9.114 | 2.329 | 15.926 | 1.00 | 28.88 |
| ATOM | 1541 | N | LYS | 861 | 7.191 | 2.839 | 14.893 | 1.00 | 28.36 |
| ATOM | 1542 | CA | LYS | 861 | 7.202 | 1.659 | 14.039 | 1.00 | 27.61 |
| ATOM | 1543 | CB | LYS | 861 | 5.855 | 1.517 | 13.334 | 1.00 | 28.44 |
| ATOM | 1544 | CG | LYS | 861 | 5.025 | 0.365 | 13.819 | 1.00 | 29.58 |
| ATOM | 1545 | CD | LYS | 861 | 5.650 | −0.948 | 13.420 | 1.00 | 30.16 |
| ATOM | 1546 | CE | LYS | 861 | 4.869 | −2.106 | 13.998 | 1.00 | 30.39 |
| ATOM | 1547 | NZ | LYS | 861 | 5.567 | −3.402 | 13.771 | 1.00 | 31.31 |
| ATOM | 1548 | C | LYS | 861 | 8.291 | 1.885 | 12.991 | 1.00 | 26.55 |
| ATOM | 1549 | O | LYS | 861 | 9.097 | 1.002 | 12.680 | 1.00 | 26.06 |
| ATOM | 1550 | N | LEU | 862 | 8.300 | 3.088 | 12.439 | 1.00 | 25.35 |
| ATOM | 1551 | CA | LEU | 862 | 9.288 | 3.421 | 11.439 | 1.00 | 24.93 |
| ATOM | 1552 | CB | LEU | 862 | 9.030 | 4.818 | 10.891 | 1.00 | 24.31 |
| ATOM | 1553 | CG | LEU | 862 | 10.060 | 5.242 | 9.855 | 1.00 | 24.36 |
| ATOM | 1554 | CD1 | LEU | 862 | 9.948 | 4.337 | 8.645 | 1.00 | 23.62 |
| ATOM | 1555 | CD2 | LEU | 862 | 9.846 | 6.687 | 9.484 | 1.00 | 23.25 |
| ATOM | 1556 | C | LEU | 862 | 10.692 | 3.332 | 12.038 | 1.00 | 24.54 |
| ATOM | 1557 | O | LEU | 862 | 11.581 | 2.748 | 11.433 | 1.00 | 24.21 |
| ATOM | 1558 | N | LEU | 863 | 10.894 | 3.901 | 13.227 | 1.00 | 24.64 |
| ATOM | 1559 | CA | LEU | 863 | 12.216 | 3.843 | 13.868 | 1.00 | 24.87 |
| ATOM | 1560 | CB | LEU | 863 | 12.216 | 4.613 | 15.188 | 1.00 | 24.73 |
| ATOM | 1561 | CG | LEU | 863 | 12.307 | 6.129 | 15.049 | 1.00 | 25.00 |
| ATOM | 1562 | CD1 | LEU | 863 | 12.356 | 6.762 | 16.428 | 1.00 | 24.84 |
| ATOM | 1563 | CD2 | LEU | 863 | 13.554 | 6.483 | 14.240 | 1.00 | 25.12 |
| ATOM | 1564 | C | LEU | 863 | 12.689 | 2.402 | 14.105 | 1.00 | 24.37 |
| ATOM | 1565 | O | LEU | 863 | 13.837 | 2.068 | 13.826 | 1.00 | 24.46 |
| ATOM | 1566 | N | ASP | 864 | 11.815 | 1.549 | 14.622 | 1.00 | 24.20 |
| ATOM | 1567 | CA | ASP | 864 | 12.190 | 0.154 | 14.835 | 1.00 | 24.33 |
| ATOM | 1568 | CB | ASP | 864 | 11.014 | −0.626 | 15.438 | 1.00 | 25.03 |
| ATOM | 1569 | CG | ASP | 864 | 10.670 | −0.189 | 16.878 | 1.00 | 26.02 |
| ATOM | 1570 | OD1 | ASP | 864 | 11.490 | 0.519 | 17.518 | 1.00 | 25.80 |
| ATOM | 1571 | OD2 | ASP | 864 | 9.578 | −0.573 | 17.367 | 1.00 | 25.23 |
| ATOM | 1572 | C | ASP | 864 | 12.598 | −0.511 | 13.499 | 1.00 | 24.21 |
| ATOM | 1573 | O | ASP | 864 | 13.473 | −1.383 | 13.460 | 1.00 | 24.29 |
| ATOM | 1574 | N | SER | 865 | 11.966 | −0.090 | 12.404 | 1.00 | 23.73 |
| ATOM | 1575 | CA | SER | 865 | 12.237 | −0.682 | 11.098 | 1.00 | 23.19 |
| ATOM | 1576 | CB | SER | 865 | 11.217 | −0.194 | 10.052 | 1.00 | 22.65 |
| ATOM | 1577 | OG | SER | 865 | 11.527 | 1.099 | 9.565 | 1.00 | 21.98 |
| ATOM | 1578 | C | SER | 865 | 13.659 | −0.432 | 10.611 | 1.00 | 23.12 |
| ATOM | 1579 | O | SER | 865 | 14.149 | −1.138 | 9.738 | 1.00 | 23.62 |
| ATOM | 1580 | N | VAL | 866 | 14.331 | 0.562 | 11.178 | 1.00 | 22.48 |
| ATOM | 1581 | CA | VAL | 866 | 15.708 | 0.839 | 10.786 | 1.00 | 21.73 |
| ATOM | 1582 | CB | VAL | 866 | 16.190 | 2.188 | 11.345 | 1.00 | 20.85 |
| ATOM | 1583 | CG1 | VAL | 866 | 17.665 | 2.377 | 11.012 | 1.00 | 20.74 |
| ATOM | 1584 | CG2 | VAL | 866 | 15.354 | 3.317 | 10.784 | 1.00 | 19.44 |
| ATOM | 1585 | C | VAL | 866 | 16.653 | −0.236 | 11.338 | 1.00 | 21.81 |
| ATOM | 1586 | O | VAL | 866 | 17.656 | −0.598 | 10.723 | 1.00 | 22.06 |
| ATOM | 1587 | N | GLN | 867 | 16.327 | −0.744 | 12.512 | 1.00 | 21.74 |
| ATOM | 1588 | CA | GLN | 867 | 17.178 | −1.722 | 13.153 | 1.00 | 21.73 |
| ATOM | 1589 | CB | GLN | 867 | 16.607 | −2.055 | 14.527 | 1.00 | 22.18 |
| ATOM | 1590 | CG | GLN | 867 | 16.498 | −0.829 | 15.412 | 1.00 | 22.59 |
| ATOM | 1591 | CD | GLN | 867 | 17.837 | −0.158 | 15.638 | 1.00 | 22.57 |
| ATOM | 1592 | OE1 | GLN | 867 | 18.826 | −0.819 | 15.953 | 1.00 | 23.51 |
| ATOM | 1593 | NE2 | GLN | 867 | 17.873 | 1.158 | 15.497 | 1.00 | 22.55 |
| ATOM | 1594 | C | GLN | 867 | 17.481 | −2.994 | 12.372 | 1.00 | 21.37 |
| ATOM | 1595 | O | GLN | 867 | 18.650 | −3.330 | 12.187 | 1.00 | 21.44 |
| ATOM | 1596 | N | PRO | 868 | 16.448 | −3.733 | 11.923 | 1.00 | 21.04 |
| ATOM | 1597 | CD | PRO | 868 | 14.989 | −3.550 | 12.037 | 1.00 | 21.82 |
| ATOM | 1598 | CA | PRO | 868 | 16.770 | −4.948 | 11.175 | 1.00 | 20.68 |
| ATOM | 1599 | CB | PRO | 868 | 15.390 | −5.545 | 10.841 | 1.00 | 20.96 |
| ATOM | 1600 | CG | PRO | 868 | 14.468 | −4.383 | 10.884 | 1.00 | 21.59 |
| ATOM | 1601 | C | PRO | 868 | 17.617 | −4.622 | 9.950 | 1.00 | 20.19 |
| ATOM | 1602 | O | PRO | 868 | 18.479 | −5.403 | 9.551 | 1.00 | 20.47 |
| ATOM | 1603 | N | ILE | 869 | 17.383 | −3.455 | 9.362 | 1.00 | 19.77 |
| ATOM | 1604 | CA | ILE | 869 | 18.175 | −3.037 | 8.216 | 1.00 | 18.93 |
| ATOM | 1605 | CB | ILE | 869 | 17.656 | −1.698 | 7.649 | 1.00 | 18.67 |
| ATOM | 1606 | CG2 | ILE | 869 | 18.605 | −1.185 | 6.545 | 1.00 | 18.45 |
| ATOM | 1607 | CG1 | ILE | 869 | 16.235 | −1.890 | 7.121 | 1.00 | 18.20 |
| ATOM | 1608 | CD1 | ILE | 869 | 15.597 | −0.642 | 6.543 | 1.00 | 17.92 |
| ATOM | 1609 | C | ILE | 869 | 19.641 | −2.881 | 8.665 | 1.00 | 18.84 |
| ATOM | 1610 | O | ILE | 869 | 20.551 | −3.408 | 8.023 | 1.00 | 17.81 |
| ATOM | 1611 | N | ALA | 870 | 19.863 | −2.169 | 9.773 | 1.00 | 18.50 |
| ATOM | 1612 | CA | ALA | 870 | 21.221 | −1.964 | 10.280 | 1.00 | 19.01 |
| ATOM | 1613 | CB | ALA | 870 | 21.207 | −1.118 | 11.563 | 1.00 | 17.32 |

TABLE A-continued

| ATOM | 1614 | C | ALA | 870 | 21.898 | −3.305 | 10.541 | 1.00 | 19.42 |
| --- | --- | --- | --- | --- | --- | --- | --- | --- | --- |
| ATOM | 1615 | O | ALA | 870 | 23.104 | −3.452 | 10.329 | 1.00 | 19.55 |
| ATOM | 1616 | N | ARG | 871 | 21.116 | −4.286 | 10.981 | 1.00 | 20.41 |
| ATOM | 1617 | CA | ARG | 871 | 21.654 | −5.615 | 11.274 | 1.00 | 21.54 |
| ATOM | 1618 | CB | ARG | 871 | 20.619 | −6.462 | 12.038 | 1.00 | 21.89 |
| ATOM | 1619 | CG | ARG | 871 | 21.042 | −7.895 | 12.307 | 1.00 | 23.32 |
| ATOM | 1620 | CD | ARG | 871 | 22.427 | −7.959 | 12.926 | 1.00 | 25.37 |
| ATOM | 1621 | NE | ARG | 871 | 22.888 | −9.331 | 13.146 | 1.00 | 26.95 |
| ATOM | 1622 | CZ | ARG | 871 | 22.292 | −10.205 | 13.953 | 1.00 | 26.98 |
| ATOM | 1623 | NH1 | ARG | 871 | 21.202 | −9.854 | 14.617 | 1.00 | 27.28 |
| ATOM | 1624 | NH2 | ARG | 871 | 22.803 | −11.420 | 14.116 | 1.00 | 26.87 |
| ATOM | 1625 | C | ARG | 871 | 22.096 | −6.316 | 9.992 | 1.00 | 22.03 |
| ATOM | 1626 | O | ARG | 871 | 23.135 | −6.976 | 9.970 | 1.00 | 22.91 |
| ATOM | 1627 | N | GLU | 872 | 21.316 | −6.171 | 8.922 | 1.00 | 21.94 |
| ATOM | 1628 | CA | GLU | 872 | 21.683 | −6.772 | 7.647 | 1.00 | 21.84 |
| ATOM | 1629 | CB | GLU | 872 | 20.613 | −6.515 | 6.578 | 1.00 | 23.42 |
| ATOM | 1630 | CG | GLU | 872 | 19.305 | −7.281 | 6.758 | 1.00 | 25.54 |
| ATOM | 1631 | CD | GLU | 872 | 18.418 | −7.213 | 5.518 | 1.00 | 27.28 |
| ATOM | 1632 | OE1 | GLU | 872 | 17.294 | −7.766 | 5.553 | 1.00 | 28.13 |
| ATOM | 1633 | OE2 | GLU | 872 | 18.845 | −6.612 | 4.503 | 1.00 | 27.83 |
| ATOM | 1634 | C | GLU | 872 | 23.005 | −6.198 | 7.161 | 1.00 | 21.22 |
| ATOM | 1635 | O | GLU | 872 | 23.888 | −6.941 | 6.742 | 1.00 | 21.80 |
| ATOM | 1636 | N | LEU | 873 | 23.140 | −4.873 | 7.222 | 1.00 | 20.38 |
| ATOM | 1637 | CA | LEU | 873 | 24.353 | −4.198 | 6.773 | 1.00 | 19.25 |
| ATOM | 1638 | CB | LEU | 873 | 24.115 | −2.677 | 6.674 | 1.00 | 19.83 |
| ATOM | 1639 | CG | LEU | 873 | 23.051 | −2.181 | 5.675 | 1.00 | 19.60 |
| ATOM | 1640 | CD1 | LEU | 873 | 23.053 | −0.665 | 5.635 | 1.00 | 20.16 |
| ATOM | 1641 | CD2 | LEU | 873 | 23.330 | −2.726 | 4.279 | 1.00 | 19.48 |
| ATOM | 1642 | C | LEU | 873 | 25.530 | −4.489 | 7.690 | 1.00 | 19.03 |
| ATOM | 1643 | O | LEU | 873 | 26.670 | −4.505 | 7.252 | 1.00 | 18.60 |
| ATOM | 1644 | N | HIS | 874 | 25.264 | −4.720 | 8.972 | 1.00 | 18.94 |
| ATOM | 1645 | CA | HIS | 874 | 26.354 | −5.037 | 9.880 | 1.00 | 18.94 |
| ATOM | 1646 | CB | HIS | 874 | 25.881 | −5.078 | 11.337 | 1.00 | 18.69 |
| ATOM | 1647 | CG | HIS | 874 | 25.715 | −3.729 | 11.956 | 1.00 | 17.78 |
| ATOM | 1648 | CD2 | HIS | 874 | 26.460 | −2.605 | 11.855 | 1.00 | 17.59 |
| ATOM | 1649 | ND1 | HIS | 874 | 24.703 | −3.440 | 12.843 | 1.00 | 17.53 |
| ATOM | 1650 | CE1 | HIS | 874 | 24.835 | −2.196 | 13.267 | 1.00 | 17.42 |
| ATOM | 1651 | NE2 | HIS | 874 | 25.894 | −1.667 | 12.685 | 1.00 | 17.13 |
| ATOM | 1652 | C | HIS | 874 | 26.879 | −6.396 | 9.482 | 1.00 | 18.68 |
| ATOM | 1653 | O | HIS | 874 | 28.084 | −6.611 | 9.418 | 1.00 | 18.92 |
| ATOM | 1654 | N | GLN | 875 | 25.971 | −7.313 | 9.202 | 1.00 | 19.13 |
| ATOM | 1655 | CA | GLN | 875 | 26.374 | −8.654 | 8.810 | 1.00 | 20.22 |
| ATOM | 1656 | CB | GLN | 875 | 25.141 | −9.518 | 8.582 | 1.00 | 20.38 |
| ATOM | 1657 | CG | GLN | 875 | 25.441 | −10.988 | 8.502 | 1.00 | 21.65 |
| ATOM | 1658 | CD | GLN | 875 | 26.165 | −11.480 | 9.742 | 1.00 | 21.80 |
| ATOM | 1659 | OE1 | GLN | 875 | 27.387 | −11.562 | 9.765 | 1.00 | 22.35 |
| ATOM | 1660 | NE2 | GLN | 875 | 25.408 | −11.787 | 10.786 | 1.00 | 21.86 |
| ATOM | 1661 | C | GLN | 875 | 27.226 | −8.609 | 7.536 | 1.00 | 20.68 |
| ATOM | 1662 | O | GLN | 875 | 28.321 | −9.185 | 7.475 | 1.00 | 20.84 |
| ATOM | 1663 | N | PHE | 876 | 26.728 | −7.904 | 6.527 | 1.00 | 21.33 |
| ATOM | 1664 | CA | PHE | 876 | 27.432 | −7.778 | 5.257 | 1.00 | 21.58 |
| ATOM | 1665 | CB | PHE | 876 | 26.563 | −7.003 | 4.258 | 1.00 | 22.76 |
| ATOM | 1666 | CG | PHE | 876 | 27.324 | −6.426 | 3.099 | 1.00 | 23.48 |
| ATOM | 1667 | CD1 | PHE | 876 | 27.981 | −5.211 | 3.220 | 1.00 | 24.12 |
| ATOM | 1668 | CD2 | PHE | 876 | 27.354 | −7.084 | 1.876 | 1.00 | 24.70 |
| ATOM | 1669 | CE1 | PHE | 876 | 28.658 | −4.646 | 2.139 | 1.00 | 25.07 |
| ATOM | 1670 | CE2 | PHE | 876 | 28.028 | −6.535 | 0.780 | 1.00 | 25.33 |
| ATOM | 1671 | CZ | PHE | 876 | 28.684 | −5.305 | 0.913 | 1.00 | 25.56 |
| ATOM | 1672 | C | PHE | 876 | 28.782 | −7.104 | 5.404 | 1.00 | 21.53 |
| ATOM | 1673 | O | PHE | 876 | 29.788 | −7.616 | 4.917 | 1.00 | 21.91 |
| ATOM | 1674 | N | THR | 877 | 28.806 | −5.952 | 6.063 | 1.00 | 21.43 |
| ATOM | 1675 | CA | THR | 877 | 30.063 | −5.220 | 6.249 | 1.00 | 22.00 |
| ATOM | 1676 | CB | THR | 877 | 29.824 | −3.884 | 7.014 | 1.00 | 20.78 |
| ATOM | 1677 | CG2 | THR | 877 | 31.108 | −3.079 | 7.227 | 1.00 | 15.00 |
| ATOM | 1678 | OG1 | THR | 877 | 28.924 | −3.062 | 6.286 | 1.00 | 15.00 |
| ATOM | 1679 | C | THR | 877 | 31.088 | −6.071 | 6.987 | 1.00 | 21.87 |
| ATOM | 1680 | O | THR | 877 | 32.265 | −6.025 | 6.661 | 1.00 | 21.92 |
| ATOM | 1681 | N | PHE | 878 | 30.648 | −6.834 | 7.984 | 1.00 | 22.33 |
| ATOM | 1682 | CA | PHE | 878 | 31.568 | −7.694 | 8.727 | 1.00 | 23.05 |
| ATOM | 1683 | CB | PHE | 878 | 30.867 | −8.381 | 9.899 | 1.00 | 22.33 |
| ATOM | 1684 | CG | PHE | 878 | 31.666 | −9.513 | 10.495 | 1.00 | 21.73 |
| ATOM | 1685 | CD1 | PHE | 878 | 32.782 | −9.254 | 11.288 | 1.00 | 21.25 |
| ATOM | 1686 | CD2 | PHE | 878 | 31.317 | −10.838 | 10.241 | 1.00 | 21.33 |
| ATOM | 1687 | CE1 | PHE | 878 | 33.538 | −10.301 | 11.822 | 1.00 | 20.86 |
| ATOM | 1688 | CE2 | PHE | 878 | 32.069 | −11.889 | 10.771 | 1.00 | 21.01 |
| ATOM | 1689 | CZ | PHE | 878 | 33.181 | −11.618 | 11.562 | 1.00 | 21.09 |
| ATOM | 1690 | C | PHE | 878 | 32.092 | −8.766 | 7.775 | 1.00 | 23.92 |
| ATOM | 1691 | O | PHE | 878 | 33.307 | −8.936 | 7.618 | 1.00 | 23.91 |
| ATOM | 1692 | N | ASP | 879 | 31.166 | −9.503 | 7.160 | 1.00 | 24.70 |

TABLE A-continued

| | | | | | | | | |
|---|---|---|---|---|---|---|---|---|
| ATOM | 1693 | CA | ASP | 879 | 31.545 | −10.540 | 6.203 | 1.00 | 25.62 |
| ATOM | 1694 | CB | ASP | 879 | 30.318 | −11.110 | 5.483 | 1.00 | 26.61 |
| ATOM | 1695 | CG | ASP | 879 | 29.466 | −12.011 | 6.373 | 1.00 | 28.26 |
| ATOM | 1696 | OD1 | ASP | 879 | 29.869 | −12.286 | 7.532 | 1.00 | 29.19 |
| ATOM | 1697 | OD2 | ASP | 879 | 28.388 | −12.446 | 5.903 | 1.00 | 28.52 |
| ATOM | 1698 | C | ASP | 879 | 32.485 | −9.937 | 5.161 | 1.00 | 25.71 |
| ATOM | 1699 | O | ASP | 879 | 33.446 | −10.586 | 4.743 | 1.00 | 25.95 |
| ATOM | 1700 | N | LEU | 880 | 32.224 | −8.690 | 4.759 | 1.00 | 25.33 |
| ATOM | 1701 | CA | LEU | 880 | 33.050 | −8.038 | 3.740 | 1.00 | 25.14 |
| ATOM | 1702 | CB | LEU | 880 | 32.420 | −6.706 | 3.288 | 1.00 | 24.49 |
| ATOM | 1703 | CG | LEU | 880 | 33.171 | −5.970 | 2.157 | 1.00 | 24.36 |
| ATOM | 1704 | CD1 | LEU | 880 | 33.263 | −6.890 | 0.941 | 1.00 | 24.34 |
| ATOM | 1705 | CD2 | LEU | 880 | 32.486 | −4.669 | 1.777 | 1.00 | 23.43 |
| ATOM | 1706 | C | LEU | 880 | 34.494 | −7.800 | 4.174 | 1.00 | 24.87 |
| ATOM | 1707 | O | LEU | 880 | 35.414 | −7.954 | 3.384 | 1.00 | 24.35 |
| ATOM | 1708 | N | LEU | 881 | 34.672 | −7.424 | 5.433 | 1.00 | 25.68 |
| ATOM | 1709 | CA | LEU | 881 | 35.984 | −7.151 | 6.010 | 1.00 | 26.42 |
| ATOM | 1710 | CB | LEU | 881 | 35.823 | −6.684 | 7.459 | 1.00 | 26.13 |
| ATOM | 1711 | CG | LEU | 881 | 37.124 | −6.552 | 8.247 | 1.00 | 25.98 |
| ATOM | 1712 | CD1 | LEU | 881 | 37.921 | −5.392 | 7.676 | 1.00 | 25.56 |
| ATOM | 1713 | CD2 | LEU | 881 | 36.828 | −6.335 | 9.726 | 1.00 | 26.07 |
| ATOM | 1714 | C | LEU | 881 | 36.905 | −8.358 | 5.988 | 1.00 | 27.40 |
| ATOM | 1715 | O | LEU | 881 | 38.030 | −8.284 | 5.498 | 1.00 | 27.41 |
| ATOM | 1716 | N | ILE | 882 | 36.416 | −9.466 | 6.532 | 1.00 | 28.64 |
| ATOM | 1717 | CA | ILE | 882 | 37.187 | −10.694 | 6.610 | 1.00 | 30.19 |
| ATOM | 1718 | CB | ILE | 882 | 36.353 | −11.858 | 7.171 | 1.00 | 29.99 |
| ATOM | 1719 | CG2 | ILE | 882 | 37.279 | −13.022 | 7.499 | 1.00 | 30.50 |
| ATOM | 1720 | CG1 | ILE | 882 | 35.594 | −11.420 | 8.431 | 1.00 | 29.82 |
| ATOM | 1721 | CD1 | ILE | 882 | 36.488 | −10.926 | 9.537 | 1.00 | 28.87 |
| ATOM | 1722 | C | ILE | 882 | 37.734 | −11.143 | 5.270 | 1.00 | 31.79 |
| ATOM | 1723 | O | ILE | 882 | 38.813 | −11.731 | 5.212 | 1.00 | 32.60 |
| ATOM | 1724 | N | LYS | 883 | 36.997 | −10.886 | 4.192 | 1.00 | 33.37 |
| ATOM | 1725 | CA | LYS | 883 | 37.456 | −11.298 | 2.873 | 1.00 | 35.08 |
| ATOM | 1726 | CB | LYS | 883 | 36.473 | −12.298 | 2.254 | 1.00 | 35.22 |
| ATOM | 1727 | CG | LYS | 883 | 35.030 | −12.122 | 2.676 | 1.00 | 35.39 |
| ATOM | 1728 | CD | LYS | 883 | 34.263 | −13.428 | 2.488 | 1.00 | 35.67 |
| ATOM | 1729 | CE | LYS | 883 | 33.018 | −13.508 | 3.387 | 1.00 | 35.63 |
| ATOM | 1730 | NZ | LYS | 883 | 33.347 | −13.507 | 4.849 | 1.00 | 34.49 |
| ATOM | 1731 | C | LYS | 883 | 37.729 | −10.165 | 1.901 | 1.00 | 36.23 |
| ATOM | 1732 | O | LYS | 883 | 37.951 | −10.409 | 0.720 | 1.00 | 36.16 |
| ATOM | 1733 | N | SER | 884 | 37.735 | −8.929 | 2.394 | 1.00 | 38.01 |
| ATOM | 1734 | CA | SER | 884 | 38.010 | −7.781 | 1.535 | 1.00 | 39.99 |
| ATOM | 1735 | CB | SER | 884 | 37.908 | −6.480 | 2.331 | 1.00 | 39.82 |
| ATOM | 1736 | OG | SER | 884 | 38.779 | −6.500 | 3.445 | 1.00 | 40.42 |
| ATOM | 1737 | C | SER | 884 | 39.421 | −7.946 | 0.991 | 1.00 | 41.45 |
| ATOM | 1738 | O | SER | 884 | 39.857 | −7.222 | 0.100 | 1.00 | 41.65 |
| ATOM | 1739 | N | HIS | 885 | 40.129 | −8.916 | 1.552 | 1.00 | 43.33 |
| ATOM | 1740 | CA | HIS | 885 | 41.485 | −9.216 | 1.146 | 1.00 | 45.27 |
| ATOM | 1741 | CB | HIS | 885 | 42.079 | −10.274 | 2.085 | 1.00 | 46.21 |
| ATOM | 1742 | CG | HIS | 885 | 41.975 | −9.918 | 3.539 | 1.00 | 47.51 |
| ATOM | 1743 | CD2 | HIS | 885 | 42.927 | −9.619 | 4.457 | 1.00 | 47.92 |
| ATOM | 1744 | ND1 | HIS | 885 | 40.765 | −9.800 | 4.193 | 1.00 | 47.61 |
| ATOM | 1745 | CE1 | HIS | 885 | 40.977 | −9.443 | 5.448 | 1.00 | 47.80 |
| ATOM | 1746 | NE2 | HIS | 885 | 42.280 | −9.326 | 5.635 | 1.00 | 48.03 |
| ATOM | 1747 | C | HIS | 885 | 41.482 | −9.732 | −0.291 | 1.00 | 46.02 |
| ATOM | 1748 | O | HIS | 885 | 42.195 | −9.210 | −1.145 | 1.00 | 46.12 |
| ATOM | 1749 | N | MET | 886 | 40.650 | −10.739 | −0.545 | 1.00 | 46.78 |
| ATOM | 1750 | CA | MET | 886 | 40.542 | −11.377 | −1.856 | 1.00 | 47.47 |
| ATOM | 1751 | CB | MET | 886 | 40.210 | −12.861 | −1.660 | 1.00 | 48.40 |
| ATOM | 1752 | CG | MET | 886 | 40.207 | −13.696 | −2.934 | 1.00 | 49.75 |
| ATOM | 1753 | SD | MET | 886 | 39.580 | −15.376 | −2.674 | 1.00 | 51.35 |
| ATOM | 1754 | CE | MET | 886 | 37.809 | −15.116 | −2.950 | 1.00 | 50.99 |
| ATOM | 1755 | C | MET | 886 | 39.533 | −10.762 | −2.842 | 1.00 | 47.47 |
| ATOM | 1756 | O | MET | 886 | 39.399 | −11.242 | −3.966 | 1.00 | 47.36 |
| ATOM | 1757 | N | VAL | 887 | 38.821 | −9.713 | −2.441 | 1.00 | 47.33 |
| ATOM | 1758 | CA | VAL | 887 | 37.851 | −9.109 | −3.351 | 1.00 | 46.96 |
| ATOM | 1759 | CB | VAL | 887 | 36.451 | −9.054 | −2.723 | 1.00 | 47.00 |
| ATOM | 1760 | CG1 | VAL | 887 | 35.425 | −8.807 | −3.799 | 1.00 | 47.21 |
| ATOM | 1761 | CG2 | VAL | 887 | 36.149 | −10.356 | −2.003 | 1.00 | 47.16 |
| ATOM | 1762 | C | VAL | 887 | 38.271 | −7.702 | −3.772 | 1.00 | 46.99 |
| ATOM | 1763 | O | VAL | 887 | 37.553 | −7.017 | −4.511 | 1.00 | 46.75 |
| ATOM | 1764 | N | SER | 888 | 39.435 | −7.279 | −3.283 | 1.00 | 46.66 |
| ATOM | 1765 | CA | SER | 888 | 40.008 | −5.982 | −3.617 | 1.00 | 46.35 |
| ATOM | 1766 | CB | SER | 888 | 40.275 | −5.926 | −5.123 | 1.00 | 46.40 |
| ATOM | 1767 | OG | SER | 888 | 41.043 | −7.042 | −5.542 | 1.00 | 45.75 |
| ATOM | 1768 | C | SER | 888 | 39.180 | −4.765 | −3.200 | 1.00 | 46.54 |
| ATOM | 1769 | O | SER | 888 | 38.840 | −3.922 | −4.038 | 1.00 | 46.44 |
| ATOM | 1770 | N | VAL | 889 | 38.876 | −4.666 | −1.907 | 1.00 | 46.50 |
| ATOM | 1771 | CA | VAL | 889 | 38.104 | −3.546 | −1.375 | 1.00 | 46.35 |

TABLE A-continued

| | | | | | | | | |
|---|---|---|---|---|---|---|---|---|
| ATOM | 1772 | CB | VAL | 889 | 36.750 | −4.024 | −0.836 | 1.00 | 46.08 |
| ATOM | 1773 | CG1 | VAL | 889 | 35.952 | −2.849 | −0.321 | 1.00 | 46.13 |
| ATOM | 1774 | CG2 | VAL | 889 | 35.986 | −4.742 | −1.925 | 1.00 | 46.06 |
| ATOM | 1775 | C | VAL | 889 | 38.864 | −2.854 | −0.243 | 1.00 | 46.74 |
| ATOM | 1776 | O | VAL | 889 | 39.218 | −3.490 | 0.751 | 1.00 | 46.95 |
| ATOM | 1777 | N | ASP | 890 | 39.117 | −1.554 | −0.391 | 1.00 | 46.98 |
| ATOM | 1778 | CA | ASP | 890 | 39.834 | −0.804 | 0.640 | 1.00 | 47.18 |
| ATOM | 1779 | CB | ASP | 890 | 40.261 | 0.589 | 0.145 | 1.00 | 48.23 |
| ATOM | 1780 | CG | ASP | 890 | 40.782 | 0.586 | −1.275 | 1.00 | 49.20 |
| ATOM | 1781 | OD1 | ASP | 890 | 41.642 | −0.261 | −1.600 | 1.00 | 50.24 |
| ATOM | 1782 | OD2 | ASP | 890 | 40.339 | 1.452 | −2.065 | 1.00 | 49.63 |
| ATOM | 1783 | C | ASP | 890 | 38.946 | −0.595 | 1.863 | 1.00 | 46.72 |
| ATOM | 1784 | O | ASP | 890 | 37.725 | −0.488 | 1.748 | 1.00 | 46.63 |
| ATOM | 1785 | N | PHE | 891 | 39.568 | −0.534 | 3.033 | 1.00 | 46.21 |
| ATOM | 1786 | CA | PHE | 891 | 38.850 | −0.284 | 4.274 | 1.00 | 45.79 |
| ATOM | 1787 | CB | PHE | 891 | 38.739 | −1.551 | 5.129 | 1.00 | 44.93 |
| ATOM | 1788 | CG | PHE | 891 | 37.417 | −2.260 | 5.003 | 1.00 | 43.95 |
| ATOM | 1789 | CD1 | PHE | 891 | 37.284 | −3.385 | 4.192 | 1.00 | 43.65 |
| ATOM | 1790 | CD2 | PHE | 891 | 36.300 | −1.795 | 5.683 | 1.00 | 43.28 |
| ATOM | 1791 | CE1 | PHE | 891 | 36.060 | −4.032 | 4.064 | 1.00 | 43.03 |
| ATOM | 1792 | CE2 | PHE | 891 | 35.071 | −2.437 | 5.561 | 1.00 | 42.87 |
| ATOM | 1793 | CZ | PHE | 891 | 34.952 | −3.557 | 4.750 | 1.00 | 42.99 |
| ATOM | 1794 | C | PHE | 891 | 39.647 | 0.764 | 5.028 | 1.00 | 46.31 |
| ATOM | 1795 | O | PHE | 891 | 40.804 | 0.535 | 5.376 | 1.00 | 46.19 |
| ATOM | 1796 | N | PRO | 892 | 39.056 | 1.945 | 5.258 | 1.00 | 46.87 |
| ATOM | 1797 | CD | PRO | 892 | 37.779 | 2.479 | 4.761 | 1.00 | 47.03 |
| ATOM | 1798 | CA | PRO | 892 | 39.800 | 2.973 | 5.989 | 1.00 | 47.86 |
| ATOM | 1799 | CB | PRO | 892 | 38.777 | 4.100 | 6.126 | 1.00 | 47.55 |
| ATOM | 1800 | CG | PRO | 892 | 38.002 | 3.981 | 4.856 | 1.00 | 47.27 |
| ATOM | 1801 | C | PRO | 892 | 40.272 | 2.421 | 7.337 | 1.00 | 48.77 |
| ATOM | 1802 | O | PRO | 892 | 39.559 | 1.660 | 7.994 | 1.00 | 48.53 |
| ATOM | 1803 | N | GLU | 893 | 41.478 | 2.804 | 7.737 | 1.00 | 49.95 |
| ATOM | 1804 | CA | GLU | 893 | 42.069 | 2.330 | 8.987 | 1.00 | 50.96 |
| ATOM | 1805 | CB | GLU | 893 | 43.278 | 3.194 | 9.349 | 1.00 | 51.80 |
| ATOM | 1806 | CG | GLU | 893 | 44.243 | 2.521 | 10.314 | 1.00 | 53.18 |
| ATOM | 1807 | CD | GLU | 893 | 44.688 | 1.145 | 9.833 | 1.00 | 53.98 |
| ATOM | 1808 | OE1 | GLU | 893 | 43.850 | 0.215 | 9.823 | 1.00 | 54.56 |
| ATOM | 1809 | OE2 | GLU | 893 | 45.874 | 0.995 | 9.461 | 1.00 | 54.43 |
| ATOM | 1810 | C | GLU | 893 | 41.108 | 2.267 | 10.177 | 1.00 | 50.91 |
| ATOM | 1811 | O | GLU | 893 | 41.006 | 1.232 | 10.834 | 1.00 | 51.08 |
| ATOM | 1812 | N | MET | 894 | 40.415 | 3.368 | 10.454 | 1.00 | 50.86 |
| ATOM | 1813 | CA | MET | 894 | 39.468 | 3.418 | 11.567 | 1.00 | 50.94 |
| ATOM | 1814 | CB | MET | 894 | 38.942 | 4.846 | 11.768 | 1.00 | 51.97 |
| ATOM | 1815 | CG | MET | 894 | 39.769 | 5.723 | 12.688 | 1.00 | 53.43 |
| ATOM | 1816 | SD | MET | 894 | 39.094 | 7.410 | 12.777 | 1.00 | 55.12 |
| ATOM | 1817 | CE | MET | 894 | 40.330 | 8.326 | 11.783 | 1.00 | 54.74 |
| ATOM | 1818 | C | MET | 894 | 38.278 | 2.495 | 11.337 | 1.00 | 50.28 |
| ATOM | 1819 | O | MET | 894 | 37.617 | 2.069 | 12.287 | 1.00 | 50.13 |
| ATOM | 1820 | N | MET | 895 | 38.007 | 2.204 | 10.068 | 1.00 | 49.44 |
| ATOM | 1821 | CA | MET | 895 | 36.885 | 1.351 | 9.682 | 1.00 | 48.35 |
| ATOM | 1822 | CB | MET | 895 | 36.715 | 1.388 | 8.155 | 1.00 | 49.15 |
| ATOM | 1823 | CG | MET | 895 | 35.410 | 0.824 | 7.630 | 1.00 | 49.68 |
| ATOM | 1824 | SD | MET | 895 | 34.001 | 1.826 | 8.121 | 1.00 | 51.13 |
| ATOM | 1825 | CE | MET | 895 | 34.136 | 3.188 | 6.979 | 1.00 | 50.63 |
| ATOM | 1826 | C | MET | 895 | 37.094 | −0.089 | 10.152 | 1.00 | 46.87 |
| ATOM | 1827 | O | MET | 895 | 36.336 | −0.597 | 10.975 | 1.00 | 46.59 |
| ATOM | 1828 | N | ALA | 896 | 38.136 | −0.729 | 9.634 | 1.00 | 45.22 |
| ATOM | 1829 | CA | ALA | 896 | 38.442 | −2.113 | 9.977 | 1.00 | 43.83 |
| ATOM | 1830 | CB | ALA | 896 | 39.706 | −2.563 | 9.247 | 1.00 | 43.37 |
| ATOM | 1831 | C | ALA | 896 | 38.601 | −2.324 | 11.481 | 1.00 | 42.67 |
| ATOM | 1832 | O | ALA | 896 | 38.473 | −3.440 | 11.976 | 1.00 | 42.42 |
| ATOM | 1833 | N | GLU | 897 | 38.872 | −1.243 | 12.200 | 1.00 | 41.32 |
| ATOM | 1834 | CA | GLU | 897 | 39.058 | −1.306 | 13.640 | 1.00 | 39.88 |
| ATOM | 1835 | CB | GLU | 897 | 39.828 | −0.058 | 14.101 | 1.00 | 40.74 |
| ATOM | 1836 | CG | GLU | 897 | 40.690 | −0.236 | 15.353 | 1.00 | 41.25 |
| ATOM | 1837 | CD | GLU | 897 | 41.768 | 0.849 | 15.491 | 1.00 | 41.90 |
| ATOM | 1838 | OE1 | GLU | 897 | 42.665 | 0.918 | 14.619 | 1.00 | 41.86 |
| ATOM | 1839 | OE2 | GLU | 897 | 41.723 | 1.632 | 16.468 | 1.00 | 42.21 |
| ATOM | 1840 | C | GLU | 897 | 37.685 | −1.390 | 14.313 | 1.00 | 38.68 |
| ATOM | 1841 | O | GLU | 897 | 37.346 | −2.397 | 14.944 | 1.00 | 38.45 |
| ATOM | 1842 | N | ILE | 898 | 36.889 | −0.339 | 14.159 | 1.00 | 36.89 |
| ATOM | 1843 | CA | ILE | 898 | 35.558 | −0.308 | 14.745 | 1.00 | 35.29 |
| ATOM | 1844 | CB | ILE | 898 | 34.799 | 0.981 | 14.366 | 1.00 | 35.18 |
| ATOM | 1845 | CG2 | ILE | 898 | 33.459 | 1.003 | 15.063 | 1.00 | 34.79 |
| ATOM | 1846 | CG1 | ILE | 898 | 35.614 | 2.212 | 14.782 | 1.00 | 35.43 |
| ATOM | 1847 | CD1 | ILE | 898 | 34.990 | 3.555 | 14.378 | 1.00 | 34.84 |
| ATOM | 1848 | C | ILE | 898 | 34.728 | −1.513 | 14.307 | 1.00 | 33.92 |
| ATOM | 1849 | O | ILE | 898 | 33.926 | −2.034 | 15.087 | 1.00 | 33.92 |
| ATOM | 1850 | N | ILE | 899 | 34.912 | −1.951 | 13.064 | 1.00 | 32.03 |

TABLE A-continued

| | | | | | | | | |
|---|---|---|---|---|---|---|---|---|
| ATOM | 1851 | CA | ILE | 899 | 34.173 | −3.108 | 12.566 | 1.00 | 30.47 |
| ATOM | 1852 | CB | ILE | 899 | 34.485 | −3.404 | 11.099 | 1.00 | 30.35 |
| ATOM | 1853 | CG2 | ILE | 899 | 33.746 | −4.653 | 10.663 | 1.00 | 29.70 |
| ATOM | 1854 | CG1 | ILE | 899 | 34.090 | −2.222 | 10.221 | 1.00 | 30.03 |
| ATOM | 1855 | CD1 | ILE | 899 | 34.481 | −2.407 | 8.775 | 1.00 | 29.09 |
| ATOM | 1856 | C | ILE | 899 | 34.528 | −4.370 | 13.343 | 1.00 | 29.56 |
| ATOM | 1857 | O | ILE | 899 | 33.668 | −5.007 | 13.934 | 1.00 | 29.56 |
| ATOM | 1858 | N | SER | 900 | 35.809 | −4.717 | 13.339 | 1.00 | 28.34 |
| ATOM | 1859 | CA | SER | 900 | 36.283 | −5.916 | 14.007 | 1.00 | 27.55 |
| ATOM | 1860 | CB | SER | 900 | 37.767 | −6.124 | 13.711 | 1.00 | 27.86 |
| ATOM | 1861 | OG | SER | 900 | 38.539 | −5.030 | 14.182 | 1.00 | 29.18 |
| ATOM | 1862 | C | SER | 900 | 36.072 | −5.940 | 15.511 | 1.00 | 26.83 |
| ATOM | 1863 | O | SER | 900 | 35.911 | −7.016 | 16.108 | 1.00 | 26.70 |
| ATOM | 1864 | N | VAL | 901 | 36.066 | −4.761 | 16.122 | 1.00 | 25.47 |
| ATOM | 1865 | CA | VAL | 901 | 35.914 | −4.669 | 17.565 | 1.00 | 24.36 |
| ATOM | 1866 | CB | VAL | 901 | 36.810 | −3.539 | 18.132 | 1.00 | 24.53 |
| ATOM | 1867 | CG1 | VAL | 901 | 36.613 | −3.401 | 19.635 | 1.00 | 24.63 |
| ATOM | 1868 | CG2 | VAL | 901 | 38.261 | −3.838 | 17.826 | 1.00 | 24.17 |
| ATOM | 1869 | C | VAL | 901 | 34.489 | −4.457 | 18.052 | 1.00 | 23.82 |
| ATOM | 1870 | O | VAL | 901 | 34.056 | −5.107 | 18.998 | 1.00 | 23.59 |
| ATOM | 1871 | N | GLN | 902 | 33.754 | −3.565 | 17.404 | 1.00 | 23.25 |
| ATOM | 1872 | CA | GLN | 902 | 32.396 | −3.264 | 17.836 | 1.00 | 23.10 |
| ATOM | 1873 | CB | GLN | 902 | 32.128 | −1.771 | 17.652 | 1.00 | 23.43 |
| ATOM | 1874 | CG | GLN | 902 | 33.026 | −0.856 | 18.468 | 1.00 | 24.40 |
| ATOM | 1875 | CD | GLN | 902 | 32.724 | −0.898 | 19.960 | 1.00 | 25.11 |
| ATOM | 1876 | OE1 | GLN | 902 | 32.836 | 0.108 | 20.652 | 1.00 | 25.82 |
| ATOM | 1877 | NE2 | GLN | 902 | 32.353 | −2.070 | 20.463 | 1.00 | 26.55 |
| ATOM | 1878 | C | GLN | 902 | 31.285 | −4.062 | 17.150 | 1.00 | 22.80 |
| ATOM | 1879 | O | GLN | 902 | 30.330 | −4.488 | 17.802 | 1.00 | 22.81 |
| ATOM | 1880 | N | VAL | 903 | 31.409 | −4.260 | 15.840 | 1.00 | 21.89 |
| ATOM | 1881 | CA | VAL | 903 | 30.397 | −4.985 | 15.083 | 1.00 | 21.01 |
| ATOM | 1882 | CB | VAL | 903 | 30.753 | −4.987 | 13.568 | 1.00 | 20.43 |
| ATOM | 1883 | CG1 | VAL | 903 | 29.811 | −5.891 | 12.783 | 1.00 | 20.60 |
| ATOM | 1884 | CG2 | VAL | 903 | 30.625 | −3.572 | 13.033 | 1.00 | 19.46 |
| ATOM | 1885 | C | VAL | 903 | 30.118 | −6.404 | 15.594 | 1.00 | 20.85 |
| ATOM | 1886 | O | VAL | 903 | 28.962 | −6.798 | 15.710 | 1.00 | 19.49 |
| ATOM | 1887 | N | PRO | 904 | 31.172 | −7.182 | 15.925 | 1.00 | 21.30 |
| ATOM | 1888 | CD | PRO | 904 | 32.614 | −6.943 | 15.734 | 1.00 | 20.97 |
| ATOM | 1889 | CA | PRO | 904 | 30.941 | −8.545 | 16.421 | 1.00 | 21.34 |
| ATOM | 1890 | CB | PRO | 904 | 32.356 | −9.114 | 16.548 | 1.00 | 20.99 |
| ATOM | 1891 | CG | PRO | 904 | 33.120 | −8.353 | 15.512 | 1.00 | 21.65 |
| ATOM | 1892 | C | PRO | 904 | 30.175 | −8.585 | 17.750 | 1.00 | 22.05 |
| ATOM | 1893 | O | PRO | 904 | 29.548 | −9.600 | 18.077 | 1.00 | 22.76 |
| ATOM | 1894 | N | LYS | 905 | 30.234 | −7.503 | 18.524 | 1.00 | 21.69 |
| ATOM | 1895 | CA | LYS | 905 | 29.512 | −7.464 | 19.791 | 1.00 | 22.05 |
| ATOM | 1896 | CB | LYS | 905 | 29.823 | −6.183 | 20.577 | 1.00 | 22.91 |
| ATOM | 1897 | CG | LYS | 905 | 31.236 | −6.070 | 21.145 | 1.00 | 23.84 |
| ATOM | 1898 | CD | LYS | 905 | 31.333 | −4.835 | 22.041 | 1.00 | 24.82 |
| ATOM | 1899 | CE | LYS | 905 | 32.692 | −4.710 | 22.736 | 1.00 | 25.65 |
| ATOM | 1900 | NZ | LYS | 905 | 32.716 | −3.560 | 23.693 | 1.00 | 25.72 |
| ATOM | 1901 | C | LYS | 905 | 28.023 | −7.491 | 19.477 | 1.00 | 21.85 |
| ATOM | 1902 | O | LYS | 905 | 27.208 | −7.982 | 20.255 | 1.00 | 21.42 |
| ATOM | 1903 | N | ILE | 906 | 27.675 | −6.929 | 18.330 | 1.00 | 21.67 |
| ATOM | 1904 | CA | ILE | 906 | 26.286 | −6.873 | 17.903 | 1.00 | 21.52 |
| ATOM | 1905 | CB | ILE | 906 | 26.078 | −5.742 | 16.827 | 1.00 | 21.27 |
| ATOM | 1906 | CG2 | ILE | 906 | 24.655 | −5.766 | 16.313 | 1.00 | 20.46 |
| ATOM | 1907 | CG1 | ILE | 906 | 26.442 | −4.380 | 17.434 | 1.00 | 20.69 |
| ATOM | 1908 | CD1 | ILE | 906 | 26.272 | −3.193 | 16.517 | 1.00 | 21.16 |
| ATOM | 1909 | C | ILE | 906 | 25.865 | −8.226 | 17.331 | 1.00 | 21.33 |
| ATOM | 1910 | O | ILE | 906 | 24.902 | −8.827 | 17.800 | 1.00 | 21.55 |
| ATOM | 1911 | N | LEU | 907 | 26.607 | −8.715 | 16.342 | 1.00 | 20.88 |
| ATOM | 1912 | CA | LEU | 907 | 26.274 | −9.990 | 15.717 | 1.00 | 21.31 |
| ATOM | 1913 | CB | LEU | 907 | 27.244 | −10.280 | 14.561 | 1.00 | 19.40 |
| ATOM | 1914 | CG | LEU | 907 | 27.380 | −9.060 | 13.634 | 1.00 | 18.63 |
| ATOM | 1915 | CD1 | LEU | 907 | 28.333 | −9.370 | 12.509 | 1.00 | 17.46 |
| ATOM | 1916 | CD2 | LEU | 907 | 26.008 | −8.646 | 13.092 | 1.00 | 17.25 |
| ATOM | 1917 | C | LEU | 907 | 26.225 | −11.165 | 16.695 | 1.00 | 21.62 |
| ATOM | 1918 | O | LEU | 907 | 25.360 | −12.037 | 16.563 | 1.00 | 22.68 |
| ATOM | 1919 | N | SER | 908 | 27.118 | −11.177 | 17.685 | 1.00 | 21.63 |
| ATOM | 1920 | CA | SER | 908 | 27.150 | −12.266 | 18.664 | 1.00 | 22.10 |
| ATOM | 1921 | CB | SER | 908 | 28.564 | −12.433 | 19.238 | 1.00 | 21.84 |
| ATOM | 1922 | OG | SER | 908 | 28.952 | −11.279 | 19.949 | 1.00 | 22.32 |
| ATOM | 1923 | C | SER | 908 | 26.146 | −12.060 | 19.802 | 1.00 | 22.09 |
| ATOM | 1924 | O | SER | 908 | 26.086 | −12.862 | 20.740 | 1.00 | 22.15 |
| ATOM | 1925 | N | GLY | 909 | 25.376 | −10.976 | 19.730 | 1.00 | 22.11 |
| ATOM | 1926 | CA | GLY | 909 | 24.361 | −10.718 | 20.743 | 1.00 | 22.44 |
| ATOM | 1927 | C | GLY | 909 | 24.707 | −9.946 | 22.006 | 1.00 | 22.41 |
| ATOM | 1928 | O | GLY | 909 | 23.843 | −9.735 | 22.854 | 1.00 | 22.66 |
| ATOM | 1929 | N | LYS | 910 | 25.950 | −9.519 | 22.152 | 1.00 | 22.78 |

TABLE A-continued

| | | | | | | | | |
|---|---|---|---|---|---|---|---|---|
| ATOM | 1930 | CA | LYS | 910 | 26.332 | −8.773 | 23.344 | 1.00 | 23.71 |
| ATOM | 1931 | CB | LYS | 910 | 27.838 | −8.650 | 23.410 | 1.00 | 24.13 |
| ATOM | 1932 | CG | LYS | 910 | 28.521 | −9.978 | 23.588 | 1.00 | 25.11 |
| ATOM | 1933 | CD | LYS | 910 | 30.006 | −9.783 | 23.775 | 1.00 | 25.46 |
| ATOM | 1934 | CE | LYS | 910 | 30.613 | −11.053 | 24.288 | 1.00 | 26.49 |
| ATOM | 1935 | NZ | LYS | 910 | 29.764 | −11.585 | 25.391 | 1.00 | 27.68 |
| ATOM | 1936 | C | LYS | 910 | 25.702 | −7.381 | 23.438 | 1.00 | 24.13 |
| ATOM | 1937 | O | LYS | 910 | 25.442 | −6.880 | 24.540 | 1.00 | 23.96 |
| ATOM | 1938 | N | VAL | 911 | 25.465 | −6.769 | 22.278 | 1.00 | 24.03 |
| ATOM | 1939 | CA | VAL | 911 | 24.869 | −5.445 | 22.182 | 1.00 | 24.31 |
| ATOM | 1940 | CB | VAL | 911 | 25.868 | −4.413 | 21.588 | 1.00 | 24.16 |
| ATOM | 1941 | CG1 | VAL | 911 | 26.588 | −5.010 | 20.444 | 1.00 | 25.18 |
| ATOM | 1942 | CG2 | VAL | 911 | 25.142 | −3.180 | 21.086 | 1.00 | 24.84 |
| ATOM | 1943 | C | VAL | 911 | 23.672 | −5.582 | 21.272 | 1.00 | 24.68 |
| ATOM | 1944 | O | VAL | 911 | 23.781 | −6.139 | 20.185 | 1.00 | 25.01 |
| ATOM | 1945 | N | LYS | 912 | 22.527 | −5.081 | 21.710 | 1.00 | 24.92 |
| ATOM | 1946 | CA | LYS | 912 | 21.322 | −5.192 | 20.910 | 1.00 | 25.57 |
| ATOM | 1947 | CB | LYS | 912 | 20.429 | −6.297 | 21.470 | 1.00 | 26.08 |
| ATOM | 1948 | CG | LYS | 912 | 21.049 | −7.676 | 21.478 | 1.00 | 26.96 |
| ATOM | 1949 | CD | LYS | 912 | 20.221 | −8.591 | 22.357 | 1.00 | 28.27 |
| ATOM | 1950 | CE | LYS | 912 | 20.096 | −7.986 | 23.747 | 1.00 | 28.84 |
| ATOM | 1951 | NZ | LYS | 912 | 21.426 | −7.849 | 24.424 | 1.00 | 28.86 |
| ATOM | 1952 | C | LYS | 912 | 20.516 | −3.903 | 20.836 | 1.00 | 25.87 |
| ATOM | 1953 | O | LYS | 912 | 20.561 | −3.069 | 21.742 | 1.00 | 25.78 |
| ATOM | 1954 | N | PRO | 913 | 19.763 | −3.731 | 19.742 | 1.00 | 26.36 |
| ATOM | 1955 | CD | PRO | 913 | 19.645 | −4.672 | 18.615 | 1.00 | 26.55 |
| ATOM | 1956 | CA | PRO | 913 | 18.927 | −2.550 | 19.520 | 1.00 | 26.76 |
| ATOM | 1957 | CB | PRO | 913 | 18.356 | −2.777 | 18.118 | 1.00 | 26.68 |
| ATOM | 1958 | CG | PRO | 913 | 19.296 | −3.755 | 17.493 | 1.00 | 27.35 |
| ATOM | 1959 | C | PRO | 913 | 17.808 | −2.527 | 20.549 | 1.00 | 27.50 |
| ATOM | 1960 | O | PRO | 913 | 17.435 | −3.571 | 21.088 | 1.00 | 27.19 |
| ATOM | 1961 | N | ILE | 914 | 17.288 | −1.335 | 20.826 | 1.00 | 28.15 |
| ATOM | 1962 | CA | ILE | 914 | 16.168 | −1.190 | 21.743 | 1.00 | 28.95 |
| ATOM | 1963 | CB | ILE | 914 | 16.344 | 0.020 | 22.690 | 1.00 | 29.11 |
| ATOM | 1964 | CG2 | ILE | 914 | 15.077 | 0.212 | 23.525 | 1.00 | 28.84 |
| ATOM | 1965 | CG1 | ILE | 914 | 17.563 | −0.195 | 23.598 | 1.00 | 29.16 |
| ATOM | 1966 | CD1 | ILE | 914 | 17.882 | 0.986 | 24.507 | 1.00 | 29.16 |
| ATOM | 1967 | C | ILE | 914 | 14.955 | −0.942 | 20.848 | 1.00 | 29.58 |
| ATOM | 1968 | O | ILE | 914 | 14.896 | 0.069 | 20.148 | 1.00 | 30.48 |
| ATOM | 1969 | N | TYR | 915 | 14.010 | −1.879 | 20.844 | 1.00 | 29.76 |
| ATOM | 1970 | CA | TYR | 915 | 12.791 | −1.759 | 20.042 | 1.00 | 29.79 |
| ATOM | 1971 | CB | TYR | 915 | 12.344 | −3.133 | 19.514 | 1.00 | 29.35 |
| ATOM | 1972 | CG | TYR | 915 | 13.194 | −3.687 | 18.405 | 1.00 | 29.23 |
| ATOM | 1973 | CD1 | TYR | 915 | 14.242 | −4.574 | 18.667 | 1.00 | 29.36 |
| ATOM | 1974 | CE1 | TYR | 915 | 15.055 | −5.047 | 17.641 | 1.00 | 29.21 |
| ATOM | 1975 | CD2 | TYR | 915 | 12.981 | −3.289 | 17.092 | 1.00 | 29.29 |
| ATOM | 1976 | CE2 | TYR | 915 | 13.785 | −3.749 | 16.064 | 1.00 | 29.70 |
| ATOM | 1977 | CZ | TYR | 915 | 14.818 | −4.626 | 16.340 | 1.00 | 29.95 |
| ATOM | 1978 | OH | TYR | 915 | 15.597 | −5.080 | 15.296 | 1.00 | 31.15 |
| ATOM | 1979 | C | TYR | 915 | 11.641 | −1.180 | 20.861 | 1.00 | 29.93 |
| ATOM | 1980 | O | TYR | 915 | 11.549 | −1.412 | 22.060 | 1.00 | 30.36 |
| ATOM | 1981 | N | PHE | 916 | 10.765 | −0.426 | 20.217 | 1.00 | 29.99 |
| ATOM | 1982 | CA | PHE | 916 | 9.610 | 0.105 | 20.917 | 1.00 | 30.60 |
| ATOM | 1983 | CB | PHE | 916 | 9.025 | 1.319 | 20.191 | 1.00 | 30.23 |
| ATOM | 1984 | CG | PHE | 916 | 9.744 | 2.602 | 20.478 | 1.00 | 30.62 |
| ATOM | 1985 | CD1 | PHE | 916 | 9.659 | 3.192 | 21.731 | 1.00 | 30.55 |
| ATOM | 1986 | CD2 | PHE | 916 | 10.503 | 3.226 | 19.494 | 1.00 | 30.58 |
| ATOM | 1987 | CE1 | PHE | 916 | 10.315 | 4.381 | 22.000 | 1.00 | 30.34 |
| ATOM | 1988 | CE2 | PHE | 916 | 11.163 | 4.417 | 19.757 | 1.00 | 30.86 |
| ATOM | 1989 | CZ | PHE | 916 | 11.068 | 4.994 | 21.010 | 1.00 | 30.74 |
| ATOM | 1990 | C | PHE | 916 | 8.564 | −1.014 | 20.982 | 1.00 | 31.09 |
| ATOM | 1991 | O | PHE | 916 | 7.976 | −1.259 | 22.038 | 1.00 | 31.66 |
| ATOM | 1992 | N | HIS | 917 | 8.345 | −1.696 | 19.858 | 1.00 | 31.14 |
| ATOM | 1993 | CA | HIS | 917 | 7.373 | −2.782 | 19.802 | 1.00 | 31.46 |
| ATOM | 1994 | CB | HIS | 917 | 6.375 | −2.579 | 18.651 | 1.00 | 30.70 |
| ATOM | 1995 | CG | HIS | 917 | 5.843 | −1.185 | 18.534 | 1.00 | 29.89 |
| ATOM | 1996 | CD2 | HIS | 917 | 4.695 | −0.628 | 18.984 | 1.00 | 29.89 |
| ATOM | 1997 | ND1 | HIS | 917 | 6.514 | −0.188 | 17.863 | 1.00 | 29.93 |
| ATOM | 1998 | CE1 | HIS | 917 | 5.800 | 0.924 | 17.899 | 1.00 | 29.50 |
| ATOM | 1999 | NE2 | HIS | 917 | 4.691 | 0.683 | 18.574 | 1.00 | 29.71 |
| ATOM | 2000 | C | HIS | 917 | 8.093 | −4.099 | 19.590 | 1.00 | 32.03 |
| ATOM | 2001 | O | HIS | 917 | 9.218 | −4.116 | 19.102 | 1.00 | 33.01 |
| ATOM | 2002 | N | ALA | 918 | 7.442 | −5.201 | 19.949 | 1.00 | 32.62 |
| ATOM | 2003 | CA | ALA | 918 | 8.025 | −6.529 | 19.777 | 1.00 | 32.98 |
| ATOM | 2004 | CB | ALA | 918 | 7.769 | −7.382 | 21.013 | 1.00 | 33.52 |
| ATOM | 2005 | C | ALA | 918 | 7.421 | −7.201 | 18.551 | 1.00 | 33.16 |
| ATOM | 2006 | O | ALA | 918 | 7.922 | −7.049 | 17.432 | 1.00 | 33.55 |

What is claimed is:

1. A method for inhibiting the growth of hormone-dependent tumor cells in a patient in need thereof, comprising administering to said patient a selective androgen receptor modulator compound in an amount effective therefor, wherein:

said selective androgen receptor modulator compound exhibits antagonist activity inhibiting growth of said hormone-dependent tumor; and wherein said selective androgen receptor modulator compound exhibits no activity or agonist activity against other, nontumor tissues containing the androgen receptor, wherein said no activity is maintaining at least one of average normal bone density, average normal muscle mass, average normal reproductive function, and average normal libido seen in ugonadal warm-blooded male mammals, wherein said agonist activity is having an activation effect greater than 5% in vivo as compared to control animals on the weights of at least one of ventral prostate, seminal vesicles, levator ani, and luteinizing hormone serum levels, and wherein said selective androgen receptor modulator compound binds to an androgen receptor ligand binding domain having the structural coordinates of Table A.

2. The method of claim 1, wherein said tumor cells are prostate tumor cells and wherein, in addition to exhibiting antagonist activity in said tumor cells and no activity or agonist activity against other, nontumor tissues containing the androgen receptor, said selective androgen receptor modulator compound further exhibits agonist, antagonist or no activity in normal prostate tissue.

3. The method of claim 1, wherein said selective androgen receptor modulator compound exhibits agonist activity against other, nontumor tissues containing the androgen receptor.

4. The method of claim 1, wherein said selective androgen receptor modulator compound exhibits no activity against other, nontumor tissues containing the androgen receptor.

5. The method of claim 1, wherein said hormone-dependent tumor is prostate cancer.

6. The method of claim 1, wherein said other, nontumor tissue containing the androgen receptor comprises one or more of the following tissues: seminal vesicles, male and female genitalia, skin, testis, ovary, cartilage, sebaceous glands, hair follicles, sweat glands, muscle, gastrointestinal vesicular cells, thyroid follicular cells, adrenal cortex, liver, pineal, bone, stromal cells, kidney tubules, urinary bladder and/or brain cortical and subcortical regions.

7. The method of claim 6, wherein said other, nontumor tissue containing the androgen receptor comprises one or more of the following tissues: cardiac muscle, skeletal muscle and/or smooth muscle.

8. A method for inhibiting the growth of hormone-dependent tumor cells in a patient in need thereof, comprising administering to said patient a selective androgen receptor modulator compound in an amount effective therefor, wherein:

said selective androgen receptor modulator compound exhibits antagonist activity inhibiting growth of said hormone-dependent tumor;

wherein said selective androgen receptor modulator compound exhibits agonist activity against other, nontumor tissues containing the androgen receptor, and wherein said selective androgen receptor modulator compound binds to an androgen receptor ligand binding domain having the structural coordinates of Table A.

* * * * *

SEQUENCE LISTING

<160> NUMBER OF SEQ ID NOS: 2

<210> SEQ ID NO 1
<211> LENGTH: 246
<212> TYPE: PRT
<213> ORGANISM: Homo sapiens

<400> SEQUENCE: 1

```
Ile Phe Leu Asn Val Leu Glu Ala Ile Glu Pro Val Val Cys Ala
 1               5                  10                  15

Gly His Asp Asn Ala Gln Pro Asp Ser Phe Ala Ala Leu Leu Ser Ser
                20                  25                  30

Leu Asn Glu Leu Gly Glu Arg Gln Leu Val His Val Val Lys Trp Ala
            35                  40                  45

Lys Ala Leu Pro Gly Phe Arg Asn Leu His Val Asp Asp Gln Met Ala
        50                  55                  60

Val Ile Gln Tyr Ser Trp Met Gly Leu Met Val Phe Ala Met Gly Trp
65                  70                  75                  80

Arg Ser Phe Thr Asn Val Asn Ser Arg Met Leu Tyr Phe Ala Pro Asp
                85                  90                  95

Leu Val Phe Asn Glu Tyr Arg Met His Lys Ser Arg Met Tyr Ser Gln
            100                 105                 110

Cys Val Arg Met Arg His Leu Ser Gln Glu Phe Gly Trp Leu Gln Ile
        115                 120                 125

Thr Pro Gln Glu Phe Leu Cys Met Lys Ala Leu Leu Leu Phe Ser Ile
    130                 135                 140

Ile Pro Val Asp Gly Leu Lys Asn Gln Lys Phe Phe Asp Glu Leu Arg
145                 150                 155                 160

Met Asn Tyr Ile Lys Glu Leu Asp Arg Ile Ile Ala Cys Ala Ala Ala
                165                 170                 175

Ala Ala Ala Ser Cys Ser Arg Arg Phe Tyr Gln Leu Thr Lys Leu Leu
            180                 185                 190

Asp Ser Val Gln Pro Ile Ala Arg Glu Leu His Gln Phe Thr Phe Asp
        195                 200                 205

Leu Leu Ile Lys Ser His Met Val Ser Val Asp Phe Pro Glu Met Met
    210                 215                 220

Ala Glu Ile Ile Ser Val Gln Val Pro Lys Ile Leu Ser Gly Lys Val
225                 230                 235                 240

Lys Pro Ile Tyr Phe His
                245
```

<210> SEQ ID NO 2
<211> LENGTH: 235
<212> TYPE: PRT
<213> ORGANISM: Homo sapiens

<400> SEQUENCE: 2

```
Ser Leu Ala Leu Ser Leu Thr Ala Asp Gln Met Val Ser Ala Leu Leu
 1               5                  10                  15

Asp Ala Glu Pro Pro Ile Leu Tyr Ser Glu Phe Ser Glu Ala Ser Met
                20                  25                  30

Met Gly Leu Leu Thr Asn Leu Ala Asp Arg Glu Leu Val His Met Ile
            35                  40                  45

Asn Trp Ala Lys Arg Val Pro Gly Phe Val Asp Leu Thr Leu His Asp
        50                  55                  60
```

```
Gln Val His Leu Leu Glu Cys Ala Trp Leu Glu Ile Leu Met Ile Gly
 65                  70                  75                  80

Leu Val Trp Arg Ser Met Glu His Pro Gly Lys Leu Leu Phe Ala Pro
             85                  90                  95

Asn Leu Leu Leu Asp Arg Asn Gln Gly Lys Cys Val Glu Gly Met Val
            100                 105                 110

Glu Ile Phe Asp Met Leu Leu Ala Thr Ser Ser Arg Phe Arg Met Met
        115                 120                 125

Asn Leu Gln Gly Glu Glu Phe Val Cys Leu Lys Ser Ile Ile Leu Leu
        130                 135                 140

Asn Ser Gly Val Tyr Thr Phe Thr Leu Lys Ser Leu Glu Glu Lys Asp
145                 150                 155                 160

His Ile His Arg Val Leu Asp Lys Ile Thr Asp Thr Leu Ile His Leu
            165                 170                 175

Met Ala Lys Ala Gly Leu Thr Leu Gln Gln Gln His Gln Arg Leu Ala
            180                 185                 190

Gln Leu Leu Leu Ile Leu Ser His Ile Arg His Met Ser Asn Lys Gly
        195                 200                 205

Met Glu His Leu Tyr Ser Met Lys Cys Lys Asn Val Val Pro Leu Tyr
    210                 215                 220

Asp Leu Leu Leu Glu Met Leu Asp Ala His Arg
225                 230                 235
```